US008952131B2

(12) United States Patent
Berasi et al.

(10) Patent No.: US 8,952,131 B2

(45) Date of Patent: Feb. 10, 2015

(54) DESIGNER OSTEOGENIC PROTEINS

(75) Inventors: Stephen Berasi, Arlington, MA (US); Robert Vincent Martinez, Carlisle, MA (US); Michael John Cain, Exeter, NH (US); John Wozney, Hudson, MA (US); Howard Seeherman, Cambridge, MA (US); Z. Sean Juo, Cambridge, MA (US); Valerie P. Calabro, Carro (FR); Christopher Todd Brown, Chelmsford, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 13/211,755

(22) Filed: Aug. 17, 2011

(65) Prior Publication Data

US 2012/0046227 A1 Feb. 23, 2012

Related U.S. Application Data

(60) Provisional application No. 61/375,636, filed on Aug. 20, 2010.

(51) Int. Cl.

| | |
|---|---|
| ***C07K 14/51*** | (2006.01) |
| ***C07H 21/04*** | (2006.01) |
| ***A61K 38/18*** | (2006.01) |
| ***A61P 19/08*** | (2006.01) |
| *A61K 38/00* | (2006.01) |

(52) U.S. Cl.

CPC *C07K 14/51* (2013.01); *A61K 38/00* (2013.01)

USPC .......... 530/350; 536/23.5; 435/69.1; 514/8.8; 514/16.7

(58) Field of Classification Search

None

See application file for complete search history.

(56) References Cited

U.S. PATENT DOCUMENTS

| | | | |
|---|---|---|---|
| 5,141,905 | A | 8/1992 | Rosen et al. |
| 5,543,394 | A | 8/1996 | Wozney et al. |
| 5,688,678 | A | 11/1997 | Hewick et al. |
| 5,703,043 | A | 12/1997 | Celeste et al. |
| 5,733,757 | A | 3/1998 | Barbas, III et al. |
| 5,827,733 | A | 10/1998 | Lee et al. |
| 5,849,686 | A | 12/1998 | Kuberasampath et al. |
| 5,854,071 | A | 12/1998 | Oppermann et al. |
| 5,994,094 | A | 11/1999 | Hotten et al. |
| 6,025,475 | A | 2/2000 | Lee et al. |
| 6,027,919 | A | 2/2000 | Celeste et al. |
| 6,034,229 | A | 3/2000 | Celeste et al. |
| 6,177,406 | B1 | 1/2001 | Wang et al. |
| 6,204,047 | B1 | 3/2001 | Lee et al. |
| 6,245,889 | B1 | 6/2001 | Wang et al. |
| 6,287,816 | B1 | 9/2001 | Rosen et al. |
| 6,331,612 | B1 | 12/2001 | Celeste et al. |
| 6,407,060 | B1 | 6/2002 | Charette et al. |
| 6,437,111 | B1 | 8/2002 | Wozney et al. |
| 6,506,729 | B1 | 1/2003 | Rueger et al. |
| 6,613,744 | B2 | 9/2003 | Wozney et al. |
| 6,800,603 | B2 | 10/2004 | Rueger et al. |
| 6,846,906 | B1 | 1/2005 | Oppermann et al. |
| 6,861,404 | B1 | 3/2005 | Cohen et al. |
| 6,949,505 | B1 | 9/2005 | Rueger et al. |
| 7,435,260 | B2 | 10/2008 | Ferree |
| 7,563,455 | B2 | 7/2009 | McKay |
| 7,575,751 | B2 | 8/2009 | Vale |
| 7,601,685 | B2 | 10/2009 | Hubbell |
| 7,612,186 | B2 | 11/2009 | Rooslid |
| 7,671,014 | B2 | 3/2010 | Beals |
| 7,749,268 | B2 | 7/2010 | Trieu |
| 7,786,080 | B2 | 8/2010 | Muller |
| 7,910,552 | B2 | 3/2011 | Birr |
| RE42,954 | E | 11/2011 | Vukicevic |
| 8,147,862 | B2 | 4/2012 | McKay |
| 8,226,729 | B2 | 7/2012 | McKay |
| 8,372,801 | B2 | 2/2013 | Roosild |
| 2004/0039162 | A1 | 2/2004 | Lee |
| 2007/0293425 | A1 | 12/2007 | Muller et al. |
| 2009/0098130 | A1 | 4/2009 | Bradshaw et al. |

FOREIGN PATENT DOCUMENTS

| | | |
|---|---|---|
| EP | 1571159 | 7/2005 |
| WO | 0192298 | 12/2001 |
| WO | 2005118635 | 12/2005 |
| WO | 2008051526 | 5/2008 |
| WO | 2009/086131 A1 | 7/2009 |
| WO | 2009086131 | 7/2009 |
| WO | 2010099219 | 9/2010 |

OTHER PUBLICATIONS

Alaoui-Ismaili MH, Falb D. Design of second generation therapeutic recombinant bone morphogenetic proteins. Cytokine Growth Factor Rev. Oct.-Dec. 2009;20(5-6):501-7.*

Guo et al. Protein tolerance to random amino acid change. Proc Natl Acad Sci U S A. Jun. 22, 2004;101(25):9205-10. Epub Jun. 14, 2004.*

Thies et al., Growth Factors 18:251-259 (2001).

Manning et al., Science 298:1912-34 (2002).

McDonnell, Curr. Opin. Chem. Biol. 5:572-577 (2001).

De Crescenzo et al., J. Biol. Chem., 276:29632-29643 (2001).

De Crescenzo et al., J. Mol. Biol. 328:1173-1183 (2003).

Wang and Hirschberg, J. Biol. Chem., 279:23200- 23206 (2004).

Lander et al, Nature, 409:860-921 (2001).

Nickel et al., Cytokine Growth Factor Rev 20:367-77 (2009).

Heinecke et al., BMC Biol 7:59 (2009).

Kirsch et al., EMBO J. 19:3314-3324 (2000).

Groppe et al., Nature 420:636-642 (2002).

Nickel et al., J. Bone Joint Surg. Am. 83:7-14 (2001).

(Continued)

*Primary Examiner* — David Romeo

(74) *Attorney, Agent, or Firm* — Kacvinsky Daisak Bluni PLLC

(57) ABSTRACT

The invention relates to novel designer osteogenic proteins having altered affinity for a cognate receptor, nucleic acids encoding the same, and methods of use therefor. More preferably, the novel designer osteogenic proteins are designer BMPs and have altered affinity for a cognate BMP receptor. The designer BMPs demonstrate altered biological characteristics and provide potential useful novel therapeutics.

10 Claims, 29 Drawing Sheets

(56) References Cited

OTHER PUBLICATIONS

Weber et al., BMC Structural Biol. 7:6 (2007).
Kotzsch et al., EMBO J 28:937-47 (2009).
Isaacs et al., Mol. Endocrinol. 24:1469-1477 (2010).
Lane et al., J. Bone Min. Res. 18:2105-2115 (2003).
Weiskirchen et al., Frontiers in Biosci. 14:4992-5012 (2009).
Loureiro et al., Nephrol. Dial. Transplant 25:1098-1108 (2010).
Pegorier et al., Resp. Res. 11:85 (2010).
Keller et al., Nat Struct Mol Biol 11:481-488 (2004).

* cited by examiner

Type II Binding Domain A

Type I

Type II Binding Domain B wt BMP2 : 293-KSSCKRHP wt BMP6 : 409-KTACRKHE

A
Cellufine-SO4 Capture
B
BMP-E Cellufine Sulfate Capture
Non-Reduced
Reduced
F16 F17 F18 F19 F20
F16 F17 F18 F19 F20
C
Reversed Phase
D
BMP-E Reversed Phase
Non-Reduced
Reduced
F13 F15 F16 F17 F18
F13 F15 F16 F17 F18

A
* p < .01 by T-test
mg HA
0
1
2
3
4
5
BMP2,.1 ug
BMP2,.5 ug
BMPE,.1 ug
BMPE,.5ug
BMP2/6,.1 ug
BMP2/6,.5 ug
B
* p < .05 by T-test
** p < .01 by T-test
mg HA
0
1
2
3
4
BMP2,.1 ug
BMP2,.5ug
BMPG,.1ug
BMPG,.5ug
BMPA,.1ug
BMPA,.5 ug
BMPF,.1ug
BMPF,.5ug 4 week Radiographs
5304
5604
8104
9804
16204
17504
22506
1
2
3
4
5
6
7
8
9
10
11
12
13
14
E
BMP2

4 week Radiographs
6204
6606
18004
19204
20204
22906
23106
G
BMP2
1
2
3
4
5
6
7
8
9
10
11
12
13
14

8 week Radiographs
6204
6606
18004
19204
20204
2290
23106
G
BMP2
1
2
3
4
5
6
7
8
9
10
11
12
13
14

A
Max torque (N-m)
1.5
1.0
0.5
BMP-2
BMP-GER
21% Average
increase over
BMP-2 treatment
Paired t-test: p =0.0168
B
Rotational Stiffness (Nm/deg)
0.08
0.06
0.04
0.02
BMP-2
BMP-GER
24% Average
increase over
BMP-2 treatment
Paired t-test: p =0.0041
C
Callus Volume (mm$^3$)
2000
1500
1000
500
BMP-2
BMP-GER
55% Average
increase over
BMP-2 treatment
Paired t-test: p = 0.0018

NHP #1

GER

BMP-2

NHP #2

GER

BMP-2

NHP #3

GER

BMP-2

Bone Score
0
1
2
3
4
BMP-GER .125 ug
BMP-GER .25 ug
BMP-GER .5 ug
BMP-GER 1.0 ug
BMP-GER-NR .125 ug
BMP-GER-NR .25 ug
BMP-GER-NR .5 ug
BMP-GER-NR 1.0 ug Bone Score
0
1
2
3
4
BMP-E .125 ug
BMP-E .25 ug
BMP-E .5 ug
BMP-E 1.0 ug
BMP-E-NR .125 ug
BMP-E-NR .25 ug
BMP-E-NR .5 ug
BMP-E-NR 1.0 ug

SEQUENCE LISTING

```
<160> NUMBER OF SEQ ID NOS: 139

<210> SEQ ID NO 1
<211> LENGTH: 114
<212> TYPE: PRT
<213> ORGANISM: Homo sapiens

<400> SEQUENCE: 1

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
```

```
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 2
<211> LENGTH: 116
<212> TYPE: PRT
<213> ORGANISM: Homo sapiens

<400> SEQUENCE: 2

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115


<210> SEQ ID NO 3
<211> LENGTH: 138
<212> TYPE: PRT
<213> ORGANISM: Homo sapiens

<400> SEQUENCE: 3

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
            20                  25                  30

Gln Lys Gln Ala Cys Lys Lys His Glu Leu Tyr Val Ser Phe Arg Asp
        35                  40                  45

Leu Gly Trp Gln Asp Trp Ile Ile Ala Pro Glu Gly Tyr Ala Ala Phe
    50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
            100                 105                 110

Val Leu Tyr Phe Asp Asp Ser Ser Asn Val Ile Leu Lys Lys Tyr Arg
        115                 120                 125
```

```
Asn Met Val Val Arg Ser Cys Gly Cys His
    130                 135


<210> SEQ ID NO 4
<211> LENGTH: 139
<212> TYPE: PRT
<213> ORGANISM: Homo sapiens

<400> SEQUENCE: 4

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135


<210> SEQ ID NO 5
<211> LENGTH: 139
<212> TYPE: PRT
<213> ORGANISM: Homo sapiens

<400> SEQUENCE: 5

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135


<210> SEQ ID NO 6
<211> LENGTH: 139
<212> TYPE: PRT
<213> ORGANISM: Homo sapiens
```

<400> SEQUENCE: 6

```
Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Met Pro
                85                  90                  95

Asp Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135
```

<210> SEQ ID NO 7
<211> LENGTH: 110
<212> TYPE: PRT
<213> ORGANISM: Homo sapiens

<400> SEQUENCE: 7

```
Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110
```

<210> SEQ ID NO 8
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 8

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Asn Tyr Cys His Gly Glu Cys Pro
        35                  40                  45
```

```
Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 9
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Lys Leu Asn Ala Ile Ser Val Leu Tyr Phe Asp Asp Asn Ser
                85                  90                  95

Asn Val Ile Leu Lys Asn Tyr Gln Asp Met Val Val Glu Gly Cys Gly
            100                 105                 110

Cys Arg


<210> SEQ ID NO 10
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Asn Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Lys Leu Asn Ala Ile Ser Val Leu Tyr Phe Asp Asp Asn Ser
                85                  90                  95
```

```
Asn Val Ile Leu Lys Asn Tyr Gln Asp Met Val Val Glu Gly Cys Gly
            100                 105                 110

Cys Arg


<210> SEQ ID NO 11
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Asn Ala His Met Asn Ala Thr Asn His Ala Ile Val Gln
    50                  55                  60

Thr Leu Val His Leu Met Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 12
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110

Gly Cys Arg
        115


<210> SEQ ID NO 13
```

<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 14
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Asp Asn Ser
                85                  90                  95

Asn Val Ile Leu Lys Asn Tyr Gln Asp Met Val Val Glu Gly Cys Gly
            100                 105                 110

Cys Arg
```

<210> SEQ ID NO 15
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Glu Asn Ser
                85                  90                  95

Asn Val Val Leu Lys Lys Tyr Gln Asp Met Val Val Arg Gly Cys Gly
            100                 105                 110

Cys Arg


<210> SEQ ID NO 16
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Ala Lys His Lys Gln Arg Lys Arg Leu Lys Ser Ser Cys Lys Arg
1               5                   10                  15

His Glu Leu Tyr Val Ser Phe Gln Asp Leu Gly Trp Gln Asp Trp Ile
            20                  25                  30

Ile Ala Pro Lys Gly Tyr Ala Ala Asn Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Asp Asn Ser
                85                  90                  95

Asn Val Ile Leu Lys Lys Tyr Arg Asn Met Val Val Arg Ala Cys Gly
            100                 105                 110

Cys Arg


<210> SEQ ID NO 17
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr His Ala Phe Tyr Cys Asp Gly Glu Cys Ser
        35                  40                  45
```

```
Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Glu Asn
                85                  90                  95

Ser Asn Val Val Leu Lys Lys Tyr Gln Asp Met Val Val Arg Gly Cys
            100                 105                 110

Gly Cys Arg
        115


<210> SEQ ID NO 18
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Lys His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 19
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Thr His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
```

```
                85                  90                  95

Lys Val Val Leu Lys Asn Tyr Gln Asp Met Val Val Glu Gly Cys Gly
            100                 105                 110

Cys Arg


<210> SEQ ID NO 20
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Pro Gly Tyr Ala Ala Asn Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 21
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Arg Gly Tyr Ala Ala Asn Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 22
```

<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Asn Tyr Cys His Gly Glu Cys Pro
        35                  40                  45

Phe Pro Leu Ala Asp His Leu Asn Ser Thr Lys His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 23
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Asn Tyr Cys His Gly Glu Cys Pro
        35                  40                  45

Phe Pro Leu Ala Asp His Leu Asn Ser Thr Thr His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 24
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Gln Ala Lys His Lys Gln Arg Lys Arg Leu Lys Ser Ser Cys Lys Arg
1 5 10 15

His Pro Leu Tyr Val Asp Phe Ser Asp Val Gly Trp Asn Asp Trp Ile
20 25 30

Val Ala Pro Pro Gly Tyr His Ala Phe Tyr Cys His Gly Glu Cys Pro
35 40 45

Phe Pro Leu Asn Ala His Met Asn Ala Thr Asn His Ala Ile Val Gln
50 55 60

Thr Leu Val His Leu Met Asn Pro Ser Lys Ile Pro Lys Ala Cys Cys
65 70 75 80

Val Pro Thr Glu Leu Ser Ala Ile Ser Met Leu Tyr Leu Asp Glu Asn
85 90 95

Glu Lys Val Val Leu Lys Asn Tyr Gln Asp Met Val Val Glu Gly Cys
100 105 110

Gly Cys Arg
115

<210> SEQ ID NO 25
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

Gln Ala Lys His Lys Gln Arg Lys Arg Leu Lys Ser Ser Cys Lys Arg
1 5 10 15

His Pro Leu Tyr Val Asp Phe Ser Asp Val Gly Trp Asn Asp Trp Ile
20 25 30

Val Ala Pro Pro Gly Tyr His Ala Phe Tyr Cys Lys Gly Gly Cys Phe
35 40 45

Phe Pro Leu Ala Asp Asp Val Thr Pro Thr Lys His Ala Ile Val Gln
50 55 60

Thr Leu Val His Leu Lys Phe Pro Thr Lys Val Gly Lys Ala Cys Cys
65 70 75 80

Val Pro Thr Glu Leu Ser Ala Ile Ser Met Leu Tyr Leu Asp Glu Asn
85 90 95

Glu Lys Val Val Leu Lys Asn Tyr Gln Asp Met Val Val Glu Gly Cys
100 105 110

Gly Cys Arg
115

<210> SEQ ID NO 26
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Gln Ala Lys His Lys Gln Arg Lys Arg Leu Lys Ser Ser Cys Lys Arg
1 5 10 15

His Pro Leu Tyr Val Asp Phe Ser Asp Val Gly Trp Asn Asp Trp Ile
20 25 30

```
Val Ala Pro Pro Gly Tyr His Ala Phe Tyr Cys Arg Gly Val Cys Asn
        35                  40                  45

Tyr Pro Leu Ala Glu His Leu Thr Pro Thr Lys His Ala Ile Ile Gln
    50                  55                  60

Ala Leu Val His Leu Lys Asn Ser Gln Lys Ala Ser Lys Ala Cys Cys
65                  70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110

Gly Cys Arg
        115


<210> SEQ ID NO 27
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Asp Gly Glu Cys Ser
        35                  40                  45

Phe Pro Leu Asn Ala His Met Asn Ala Thr Lys His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110

Gly Cys Arg
        115


<210> SEQ ID NO 28
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Asp Gly Glu Cys Ser
        35                  40                  45

Phe Pro Leu Asn Ala His Met Asn Ala Thr Thr His Ala Ile Val Gln
    50                  55                  60

Thr Leu Val His Leu Met Asn Pro Glu Tyr Val Pro Lys Pro Cys Cys
```

```
65                  70                  75                  80

Ala Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110

Gly Cys Arg
        115


<210> SEQ ID NO 29
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Arg Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 30
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Glu Gly Leu Cys Glu
        35                  40                  45

Phe Pro Leu Arg Ser His Leu Glu Pro Thr Asn His Ala Val Ile Gln
    50                  55                  60

Thr Leu Met Asn Ser Met Asp Pro Glu Ser Thr Pro Pro Thr Cys Cys
65                  70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110
```

Gly Cys Arg
115

<210> SEQ ID NO 31
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Arg Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

<210> SEQ ID NO 32
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Pro Gly Tyr Ala Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Asp Asn Ser
                85                  90                  95

Asn Val Ile Leu Lys Asn Tyr Gln Asp Met Val Val Glu Gly Cys Gly
            100                 105                 110

Cys Arg
```

<210> SEQ ID NO 33
<211> LENGTH: 114
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 33

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Arg Gly Tyr Ala Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Asp Asn Ser
                85                  90                  95

Asn Val Ile Leu Lys Asn Tyr Gln Asp Met Val Val Glu Gly Cys Gly
            100                 105                 110

Cys Arg
```

<210> SEQ ID NO 34
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Phe Tyr Cys His Gly Glu Cys Pro
        35                  40                  45

Phe Pro Leu Ala Asp His Leu Asn Ser Thr Lys His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Asp Asn Ser
                85                  90                  95

Asn Val Ile Leu Lys Asn Tyr Gln Asp Met Val Val Glu Gly Cys Gly
            100                 105                 110

Cys Arg
```

<210> SEQ ID NO 35
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Gln Ala Lys His Lys Gln Arg Lys Arg Leu Lys Ser Ser Cys Lys Arg
1               5                   10                  15
```

```
His Pro Leu Tyr Val Asp Phe Ser Asp Val Gly Trp Asn Asp Trp Ile
            20                  25                  30

Ile Ala Pro Lys Gly Tyr Ala Ala Phe Tyr Cys His Gly Glu Cys Pro
        35                  40                  45

Phe Pro Leu Ala Asp His Leu Asn Ser Thr Thr His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Asn Ala Ile Ser Val Leu Tyr Phe Asp Asp Asn Ser
                85                  90                  95

Asn Val Ile Leu Lys Asn Tyr Gln Asp Met Val Val Glu Gly Cys Gly
            100                 105                 110

Cys Arg


<210> SEQ ID NO 36
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr Ala Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Asp Asn
                85                  90                  95

Ser Asn Val Ile Leu Lys Asn Tyr Gln Asp Met Val Val Glu Gly Cys
            100                 105                 110

Gly Cys Arg
        115


<210> SEQ ID NO 37
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Arg Gly Tyr Ala Ala Phe Tyr Cys Asp Gly Glu Cys Ser
        35                  40                  45

Phe Pro Leu Asn Ala His Met Asn Ala Thr Asn His Ala Ile Val Gln
    50                  55                  60
```

```
Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Asp Asn
                85                  90                  95

Ser Asn Val Ile Leu Lys Asn Tyr Gln Asp Met Val Val Glu Gly Cys
            100                 105                 110

Gly Cys Arg
        115


<210> SEQ ID NO 38
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Pro Gly Tyr His Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Glu Asn
                85                  90                  95

Ser Asn Val Val Leu Lys Lys Tyr Gln Asp Met Val Val Arg Gly Cys
            100                 105                 110

Gly Cys Arg
        115


<210> SEQ ID NO 39
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Arg Gly Tyr His Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Glu Asn
                85                  90                  95
```

```
Ser Asn Val Val Leu Lys Lys Tyr Gln Asp Met Val Val Arg Gly Cys
            100                 105                 110

Gly Cys Arg
        115


<210> SEQ ID NO 40
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr His Ala Phe Tyr Cys Asp Gly Glu Cys Ser
        35                  40                  45

Phe Pro Leu Asn Ala His Met Asn Ala Thr Lys His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Glu Asn
                85                  90                  95

Ser Asn Val Val Leu Lys Lys Tyr Gln Asp Met Val Val Arg Gly Cys
            100                 105                 110

Gly Cys Arg
        115


<210> SEQ ID NO 41
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Gly Tyr His Ala Phe Tyr Cys Asp Gly Glu Cys Ser
        35                  40                  45

Phe Pro Leu Asn Ala His Met Asn Ala Thr Thr His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Asn Ala Ile Ser Val Leu Tyr Phe Asp Glu Asn
                85                  90                  95

Ser Asn Val Val Leu Lys Lys Tyr Gln Asp Met Val Val Arg Gly Cys
            100                 105                 110

Gly Cys Arg
        115
```

```
<210> SEQ ID NO 42
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Glu Tyr Glu Ala Tyr Glu Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg


<210> SEQ ID NO 43
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Pro Ile Ser Val Leu Tyr Lys Asp Asp Met Gly
                85                  90                  95

Val Pro Thr Leu Lys Asn Tyr Gln Asp Met Val Val Glu Gly Cys Gly
            100                 105                 110

Cys Arg


<210> SEQ ID NO 44
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 44

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Glu Leu Ser Pro Ile Ser Val Leu Tyr Lys Asp Asp Met
                85                  90                  95

Gly Val Pro Thr Leu Lys Asn Tyr Gln Asp Met Val Val Glu Gly Cys
            100                 105                 110

Gly Cys Arg
        115
```

<210> SEQ ID NO 45
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Lys Glu Tyr Glu Ala Tyr Glu Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Pro Ile Ser Val Leu Tyr Lys Asp Asp Met Gly
                85                  90                  95

Val Pro Thr Leu Lys Asn Tyr Gln Asp Met Val Val Glu Gly Cys Gly
            100                 105                 110

Cys Arg
```

<210> SEQ ID NO 46
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Gln Ala Lys His Lys Gln Arg Lys Arg Leu Lys Ser Ser Cys Gln Lys
1               5                   10                  15

Thr Ser Leu Arg Val Asn Phe Glu Asp Ile Gly Trp Asp Ser Trp Ile
            20                  25                  30
```

```
Ile Ala Pro Lys Glu Tyr Glu Ala Tyr Glu Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Lys Leu Ser Pro Ile Ser Val Leu Tyr Lys Asp Asp Met Gly
                85                  90                  95

Val Pro Thr Leu Lys Tyr His Tyr Glu Gly Met Ser Val Ala Glu Cys
            100                 105                 110

Gly Cys Arg
        115


<210> SEQ ID NO 47
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Ala Lys His Lys Gln Arg Lys Arg Leu Lys Ser Ser Cys Gln Lys
1               5                   10                  15

Thr Ser Leu Arg Val Asn Phe Glu Asp Ile Gly Trp Asp Ser Trp Ile
            20                  25                  30

Ile Ala Pro Lys Glu Tyr Glu Ala Tyr Glu Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Val Pro Thr Lys Leu Ser Pro Ile Ser Val Leu Tyr Lys Asp Asp Met
                85                  90                  95

Gly Val Pro Thr Leu Lys Tyr His Tyr Glu Gly Met Ser Val Ala Glu
            100                 105                 110

Cys Gly Cys Arg
        115


<210> SEQ ID NO 48
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Ala Lys His Lys Gln Arg Lys Arg Leu Lys Ser Ser Cys Gln Lys
1               5                   10                  15

Thr Ser Leu Arg Val Asn Phe Glu Asp Ile Gly Trp Asp Ser Trp Ile
            20                  25                  30

Ile Ala Pro Lys Glu Tyr Glu Ala Tyr Glu Cys Lys Gly Gly Cys Phe
        35                  40                  45

Phe Pro Leu Ala Asp Asp Val Thr Pro Thr Lys His Ala Ile Val Gln
    50                  55                  60

Thr Leu Val His Leu Lys Phe Pro Thr Lys Val Gly Lys Ala Cys Cys
```

65 70 75 80

Val Pro Thr Lys Leu Ser Pro Ile Ser Val Leu Tyr Lys Asp Asp Met
85 90 95

Gly Val Pro Thr Leu Lys Tyr His Tyr Glu Gly Met Ser Val Ala Glu
100 105 110

Cys Gly Cys Arg
115

<210> SEQ ID NO 49
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Gln Ala Lys His Lys Gln Arg Lys Arg Leu Lys Ser Ser Ser Ala Gly
1 5 10 15

Ala Gly Ser His Cys Gln Lys Thr Ser Leu Arg Val Asn Phe Glu Asp
20 25 30

Ile Gly Trp Asp Ser Trp Ile Ile Ala Pro Lys Glu Tyr Glu Ala Tyr
35 40 45

Glu Cys Lys Gly Gly Cys Phe Phe Pro Leu Ala Asp Asp Val Thr Pro
50 55 60

Thr Lys His Ala Ile Val Gln Thr Leu Val His Leu Lys Phe Pro Thr
65 70 75 80

Lys Val Gly Lys Ala Cys Cys Val Pro Thr Lys Leu Ser Pro Ile Ser
85 90 95

Val Leu Tyr Lys Asp Asp Met Gly Val Pro Thr Leu Lys Tyr His Tyr
100 105 110

Glu Gly Met Ser Val Ala Glu Cys Gly Cys Arg
115 120

<210> SEQ ID NO 50
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Gln Ala Lys His Lys Gln Arg Lys Arg Leu Lys Ser Ser Cys Lys Arg
1 5 10 15

His Pro Leu Tyr Val Asp Phe Ser Asp Val Gly Trp Asn Asp Trp Ile
20 25 30

Ile Ala Pro Pro Gly Tyr Ala Ala Phe Tyr Cys Asp Gly Glu Cys Ser
35 40 45

Phe Pro Leu Asn Ala His Met Asn Ala Thr Asn His Ala Ile Val Gln
50 55 60

Thr Leu Val His Leu Met Asn Pro Glu Tyr Val Pro Lys Pro Cys Cys
65 70 75 80

Ala Pro Thr Glu Leu Asn Ala Ile Ser Val Leu Tyr Phe Asp Asp Asn
85 90 95

Ser Asn Val Ile Leu Lys Asn Tyr Gln Asp Met Val Val Glu Gly Cys
100 105 110

```
Gly Cys Arg
        115


<210> SEQ ID NO 51
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala Ala Met Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115


<210> SEQ ID NO 52
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala His Leu Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115


<210> SEQ ID NO 53
<211> LENGTH: 139
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

Ser Ala Ser Ser Arg Arg Arg Gln Gln Ser Arg Asn Arg Ser Thr Gln
1 5 10 15

Ser Gln Asp Val Ala Arg Val Ser Ser Ala Ser Asp Tyr Asn Ser Ser
20 25 30

Glu Leu Lys Thr Ala Cys Arg Lys His Glu Leu Tyr Val Ser Phe Gln
35 40 45

Asp Leu Gly Trp Gln Asp Trp Ile Ile Ala Pro Lys Gly Tyr Ala Ala
50 55 60

Asn Tyr Cys Asp Gly Glu Cys Ser Phe Pro Leu Ala Asp His Leu Asn
65 70 75 80

Ser Thr Asn His Ala Ile Val Gln Thr Leu Val Asn Ser Val Asn Pro
85 90 95

Glu Tyr Val Pro Lys Pro Cys Cys Ala Pro Thr Lys Leu Asn Ala Ile
100 105 110

Ser Val Leu Tyr Phe Asp Asp Asn Ser Asn Val Ile Leu Lys Lys Tyr
115 120 125

Arg Asn Met Val Val Arg Ala Cys Gly Cys His
130 135

<210> SEQ ID NO 54
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Ser Ala Ser Ser Arg Arg Arg Gln Gln Ser Arg Asn Arg Ser Thr Gln
1 5 10 15

Ser Gln Asp Val Ala Arg Val Ser Ser Ala Ser Asp Tyr Asn Ser Ser
20 25 30

Glu Leu Lys Thr Ala Cys Arg Lys His Glu Leu Tyr Val Ser Phe Gln
35 40 45

Asp Leu Gly Trp Gln Asp Trp Ile Ile Ala Pro Lys Gly Tyr Ala Ala
50 55 60

Asn Tyr Cys His Gly Glu Cys Pro Phe Pro Leu Ala Asp His Leu Asn
65 70 75 80

Ser Thr Asn His Ala Ile Val Gln Thr Leu Val Asn Ser Val Asn Ser
85 90 95

Lys Ile Pro Lys Ala Cys Cys Val Pro Thr Lys Leu Asn Ala Ile Ser
100 105 110

Val Leu Tyr Phe Asp Asp Asn Ser Asn Val Ile Leu Lys Lys Tyr Arg
115 120 125

Asn Met Val Val Arg Ala Cys Gly Cys His
130 135

<210> SEQ ID NO 55
<211> LENGTH: 139
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Val Ala Pro Pro Gly Tyr His Ala
    50                  55                  60

Phe Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135


<210> SEQ ID NO 56
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Glu Leu Ser Ala Ile Ser
            100                 105                 110

Met Leu Tyr Leu Asp Glu Asn Glu Lys Val Val Leu Lys Lys Tyr Arg
        115                 120                 125

Asn Met Val Val Arg Ala Cys Gly Cys His
    130                 135


<210> SEQ ID NO 57
<211> LENGTH: 117
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 57

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Ala Asp His Leu Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115


<210> SEQ ID NO 58
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Val Ser Ser Ala Ser Asp Tyr Asn Ser Ser Glu Leu Lys Thr Ala Cys
1               5                   10                  15

Lys Arg His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala His Met Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115


<210> SEQ ID NO 59
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59
```

```
Val Ser Ser Ala Ser Asp Tyr Asn Ser Ser Glu Leu Lys Thr Ala Cys
1               5                   10                  15

Lys Arg His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Ala Asp His Leu Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115
```

<210> SEQ ID NO 60
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Lys Arg His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Ala Asp His Leu Asn
65                  70                  75                  80

Ser Thr Asn His Ala Ile Val Gln Thr Leu Val Asn Ser Val Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135
```

<210> SEQ ID NO 61
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
```

```
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Ala Asp His Leu Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135


<210> SEQ ID NO 62
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Lys Arg His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Ala Asp His Leu Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135


<210> SEQ ID NO 63
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30
```

```
Glu Leu Lys Thr Ala Cys Lys Arg His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135


<210> SEQ ID NO 64
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Lys Arg His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys His Gly Glu Cys Pro Phe Pro Leu Ala Asp His Leu Asn
65                  70                  75                  80

Ser Thr Asn His Ala Ile Val Gln Thr Leu Val Asn Ser Val Asn Ser
                85                  90                  95

Lys Ile Pro Lys Ala Cys Cys Val Pro Thr Lys Leu Asn Ala Ile Ser
            100                 105                 110

Val Leu Tyr Phe Asp Asp Asn Ser Asn Val Ile Leu Lys Lys Tyr Arg
        115                 120                 125

Asn Met Val Val Arg Ala Cys Gly Cys His
    130                 135


<210> SEQ ID NO 65
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Arg Glu Lys Arg Ser Ala Gly Ala Gly Ser His Cys Gln Lys Thr Ser
1               5                   10                  15

Leu Arg Val Asn Phe Glu Asp Ile Gly Trp Asp Ser Trp Ile Ile Ala
            20                  25                  30
```

```
Pro Lys Glu Tyr Glu Ala Tyr Glu Cys His Gly Glu Cys Pro Phe Pro
        35                  40                  45

Leu Ala Asp His Leu Asn Ser Thr Asn His Ala Ile Val Gln Thr Leu
    50                  55                  60

Val Asn Ser Val Asn Ser Lys Ile Pro Lys Ala Cys Cys Val Pro Thr
65                  70                  75                  80

Lys Leu Ser Pro Ile Ser Val Leu Tyr Lys Asp Asp Met Gly Val Pro
                85                  90                  95

Thr Leu Lys Tyr His Tyr Glu Gly Met Ser Val Ala Glu Cys Gly Cys
            100                 105                 110

Arg


<210> SEQ ID NO 66
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Asp Gly Glu Cys Ser Phe Pro Leu Asn Ala His
        35                  40                  45

Met Asn Ala Thr Asn His Ala Ile Val Gln Thr Leu Val His Leu Met
    50                  55                  60

Asn Pro Glu Tyr Val Pro Lys Pro Cys Cys Ala Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110


<210> SEQ ID NO 67
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala His Met Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95
```

```
Asp Asn Ser Asn Val Ile Leu Lys Lys Tyr Arg Asn Met Val Val Arg
            100                 105                 110

Ala Cys Gly Cys His
        115


<210> SEQ ID NO 68
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala Ala Met Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115


<210> SEQ ID NO 69
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala His Leu Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

Ala Cys Gly Cys His
        115
```

<210> SEQ ID NO 70
<211> LENGTH: 115
<212> TYPE: PRT
<213> ORGANISM: Artificial Sequence
<220> FEATURE:
<221> NAME/KEY: source
<223> OTHER INFORMATION: BMP-E-NR amended

<400> SEQUENCE: 70

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Lys Leu Arg Pro Met Ser Met Leu Tyr Tyr Asp Asp Gly
                85                  90                  95

Gln Asn Ile Ile Lys Lys Asp Ile Gln Asn Met Ile Val Glu Glu Cys
            100                 105                 110

Gly Cys Ser
        115
```

<210> SEQ ID NO 71
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 71

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Arg Gly Tyr Ala Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Lys Leu Arg Pro Met Ser Met Leu Tyr Tyr Asp Asp Gly
                85                  90                  95

Gln Asn Ile Ile Lys Lys Asp Ile Gln Asn Met Ile Val Glu Glu Cys
            100                 105                 110

Gly Cys Ser
        115
```

<210> SEQ ID NO 72
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 72

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Lys Leu Asn Ala Ile Ser Val Leu Tyr Phe Asp Asp Asn
                85                  90                  95

Ser Asn Val Ile Leu Lys Lys Tyr Arg Asn Met Val Val Arg Ala Cys
            100                 105                 110

Gly Cys His
        115
```

<210> SEQ ID NO 73
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Ile Ala Pro Arg Gly Tyr Ala Ala Phe Tyr Cys Asp Gly Glu Cys Ser
        35                  40                  45

Phe Pro Leu Asn Ala His Met Asn Ala Thr Asn His Ala Ile Val Gln
    50                  55                  60

Thr Leu Val His Leu Met Asn Pro Glu Tyr Val Pro Lys Pro Cys Cys
65                  70                  75                  80

Ala Pro Thr Lys Leu Asn Ala Ile Ser Val Leu Tyr Phe Asp Asp Asn
                85                  90                  95

Ser Asn Val Ile Leu Lys Lys Tyr Arg Asn Met Val Val Arg Ala Cys
            100                 105                 110

Gly Cys His
        115
```

<210> SEQ ID NO 74
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120
```

```
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
ttaggaaaca atagcagttt ccatcaccga attaatattt atgaaatcat aaaacctgca    540
acagccaact cgaaattccc cgtgaccaga cttttggaca ccaggttggt gaatcagaat    600
gcaagcaggt gggaaagttt tgatgtcacc cccgctgtga tgcggtggac tgcacaggga    660
cacgccaacc atggattcgt ggtggaagtg gcccacttgg aggagaaaca aggtgtctcc    720
aagagacatg ttaggataag caggtctttg caccaagatg aacacagctg gtcacagata    780
aggccattgc tagtaacttt tggccatgat ggaaaagggc atcctctcca caaaagagaa    840
aaacgtcaag ccaaacacaa acagcggaaa cgccttaagt ccagctgtaa gagacaccct    900
ttgtacgtgg acttcagtga cgtggggtgg aatgactgga ttattgcacc caagggctat    960
gctgccaatt actgccacgg agaatgccct tttcctctgg ctgatcatct gaactccact   1020
aatcatgcca ttgttcagac gttggtcaac tctgttaact ctaagattcc taaggcatgc   1080
tgtgtcccga cagaactcag tgctatctcg atgctgtacc ttgacgagaa tgaaaaggtt   1140
gtattaaaga actatcagga catggttgtg gagggttgtg ggtgtcgctg a            1191
```

<210> SEQ ID NO 75
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
atggtggccg ggacccgctg tcttctagcg ttgctgcttc cccaggtcct cctgggcggc     60
gcggctggcc tcgttccgga gctgggccgc aggaagttcg cggcggcgtc gtcgggccgc    120
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
ttaggaaaca atagcagttt ccatcaccga attaatattt atgaaatcat aaaacctgca    540
acagccaact cgaaattccc cgtgaccaga cttttggaca ccaggttggt gaatcagaat    600
gcaagcaggt gggaaagttt tgatgtcacc cccgctgtga tgcggtggac tgcacaggga    660
cacgccaacc atggattcgt ggtggaagtg gcccacttgg aggagaaaca aggtgtctcc    720
aagagacatg ttaggataag caggtctttg caccaagatg aacacagctg gtcacagata    780
aggccattgc tagtaacttt tggccatgat ggaaaagggc atcctctcca caaaagagaa    840
aaacgtcaag ccaaacacaa acagcggaaa cgccttaagt ccagctgtaa gagacaccct    900
```

```
ttgtacgtgg acttcagtga cgtggggtgg aatgactgga ttgtggctcc cccggggtat    960

cacgcctttt actgccacgg agaatgccct tttcctctgg ctgatcatct gaactccact   1020

aatcatgcca ttgttcagac gttggtcaac tctgttaact ctaagattcc taaggcatgc   1080

tgtgtcccga caaagctaaa tgccatctcg gttctttact ttgatgacaa ctccaatgtc   1140

attttaaaga actatcagga catggttgtg gagggttgtg ggtgtcgctg a            1191
```

<210> SEQ ID NO 76
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc caagggctat    960

gctgccaatt actgccacgg agaatgccct tttcctctgg ctgatcatct gaactccact   1020

aatcatgcca ttgttcagac gttggtcaac tctgttaact ctaagattcc taaggcatgc   1080

tgtgtcccga caaagctaaa tgccatctcg gttctttact ttgatgacaa ctccaatgtc   1140

attttaaaga actatcagga catggttgtg gagggttgtg ggtgtcgctg a            1191
```

<210> SEQ ID NO 77
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180
```

```
ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgccacgg agaatgccct tttccactca acgcacacat gaatgcaacc   1020

aaccacgcga ttgtgcagac cttggttcac cttatgaact ctaagattcc taaggcatgc   1080

tgtgtcccga cagaactcag tgctatctcg atgctgtacc ttgacgagaa tgaaaaggtt   1140

gtattaaaga actatcagga catggttgtg gagggttgtg ggtgtcgctg a            1191
```

```
<210> SEQ ID NO 78
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
```

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960
```

```
cacgcctttt actgcgatgg agaatgctcc ttcccactca acgcacacat gaatgcaacc   1020

aaccacgcga ttgtgcagac cttggttcac cttatgaacc ccgagtatgt ccccaaaccg   1080

tgctgtgcgc cgacagaact cagtgctatc tcgatgctgt accttgacga gaatgaaaag   1140

gttgtattaa agaactatca ggacatggtt gtggagggtt gtgggtgtcg ctga         1194
```

<210> SEQ ID NO 79
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc caagggctat    960

gctgcctttt actgccacgg agaatgccct ttcctctgg ctgatcatct gaactccact    1020

aatcatgcca ttgttcagac gttggtcaac tctgttaact ctaagattcc taaggcatgc   1080

tgtgtcccga cagaactcag tgctatctcg atgctgtacc ttgacgagaa tgaaaaggtt   1140

gtattaaaga actatcagga catggttgtg gagggttgtg ggtgtcgctg a            1191
```

<210> SEQ ID NO 80
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240
```

```
gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc caagggctat    960

gctgcctttt actgccacgg agaatgccct ttcctctgg ctgatcatct gaactccact   1020

aatcatgcca ttgttcagac gttggtcaac tctgttaact ctaagattcc taaggcatgc   1080

tgtgtcccga cagaactcaa tgccatctcg gttctttact ttgatgacaa ctccaatgtc   1140

attttaaaga actatcagga catggttgtg gagggttgtg ggtgtcgctg a            1191
```

<210> SEQ ID NO 81
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgctcc caaggggtat    960

cacgcctttt actgccacgg agaatgccct ttcctctgg ctgatcatct gaactccact   1020
```

```
aatcatgcca ttgttcagac gttggtcaac tctgttaact ctaagattcc taaggcatgc   1080

tgtgtcccga cagaactcaa tgctatctcg gttctgtact ttgacgagaa ttccaatgtt   1140

gtattaaaga aatatcagga catggttgtg agaggttgtg ggtgtcgctg a            1191
```

<210> SEQ ID NO 82
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacacgag    900

ctgtatgtga gtttccaaga cctgggatgg caggactgga tcattgcacc caagggctat    960

gctgccaatt actgccacgg agaatgccct ttcctctggg ctgatcatct gaactccact   1020

aatcatgcca ttgttcagac gttggtcaac tctgttaact ctaagattcc taaggcatgc   1080

tgtgtcccga cagaactaaa tgccatctcg gttctttact ttgatgacaa ctccaatgtc   1140

attctgaaaa aatacaggaa tatggttgta agagcttgtg ggtgtcgctg a            1191
```

<210> SEQ ID NO 83
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300
```

```
agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgctcc caaggggtat    960

cacgcctttt actgcgatgg agaatgctcc ttcccactca acgcacacat gaatgcaacc   1020

aaccacgcga ttgtgcagac cttggttcac cttatgaacc ccgagtatgt ccccaaaccg   1080

tgctgtgcgc cgacagaact caatgctatc tcggttctgt actttgacga gaattccaat   1140

gttgtattaa agaaatatca ggacatggtt gtgagaggtt gtgggtgtcg ctga         1194
```

<210> SEQ ID NO 84
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 84

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgccacgg agaatgccct tttcctctgg ctgatcatct gaactccact   1020

aaacatgcca ttgttcagac gttggtcaac tctgttaact ctaagattcc taaggcatgc   1080
```

tgtgtcccga cagaactcag tgctatctcg atgctgtacc ttgacgagaa tgaaaaggtt 1140
gtattaaaga actatcagga catggttgtg gagggttgtg ggtgtcgcta g 1191

<210> SEQ ID NO 85
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 85
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360
ctaccagaaa cgagtgggaa aacaacccgg agattcttct ttaatttaag ttctatcccc 420
acggaggagt ttatcacctc agcagagctt caggttttcc gagaacagat gcaagatgct 480
ttaggaaaca atagcagttt ccatcaccga attaatattt atgaaatcat aaaacctgca 540
acagccaact cgaaattccc cgtgaccaga cttttggaca ccaggttggt gaatcagaat 600
gcaagcaggt gggaaagttt tgatgtcacc cccgctgtga tgcggtggac tgcacaggga 660
cacgccaacc atggattcgt ggtggaagtg gcccacttgg aggagaaaca aggtgtctcc 720
aagagacatg ttaggataag caggtctttg caccaagatg aacacagctg gtcacagata 780
aggccattgc tagtaacttt tggccatgat ggaaaagggc atcctctcca caaaagagaa 840
aaacgtcaag ccaaacacaa acagcggaaa cgccttaagt ccagctgtaa gagacaccct 900
ttgtacgtgg acttcagtga cgtggggtgg aatgactgga ttgtggctcc cccggggtat 960
cacgcctttt actgccacgg agaatgccct tttcctctgg ctgatcatct gaactccact 1020
actcatgcca ttgttcagac gttggtcaac tctgttaact ctaagattcc taaggcatgc 1080
tgtgtcccga cagaactcag tgctatctcg atgctgtacc ttgacgagaa tgaaaaggtt 1140
gtattaaaga actatcagga catggttgtg gagggttgtg ggtgtcgcta g 1191

<210> SEQ ID NO 86
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360

```
ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc cccgggctat    960

gctgccaatt actgccacgg agaatgccct tttcctctgg ctgatcatct gaactccact   1020

aatcatgcca ttgttcagac gttggtcaac tctgttaact ctaagattcc taaggcatgc   1080

tgtgtcccga cagaactcag tgctatctcg atgctgtacc ttgacgagaa tgaaaaggtt   1140

gtattaaaga actatcagga catggttgtg gagggttgtg ggtgtcgctg a            1191
```

<210> SEQ ID NO 87
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc caggggctat    960

gctgccaatt actgccacgg agaatgccct tttcctctgg ctgatcatct gaactccact   1020

aatcatgcca ttgttcagac gttggtcaac tctgttaact ctaagattcc taaggcatgc   1080

tgtgtcccga cagaactcag tgctatctcg atgctgtacc ttgacgagaa tgaaaaggtt   1140
```

gtattaaaga actatcagga catggttgtg gagggttgtg ggtgtcgctg a 1191

<210> SEQ ID NO 88
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360
ctaccagaaa cgagtgggaa aacaacccgg agattcttct ttaatttaag ttctatcccc 420
acggaggagt ttatcacctc agcagagctt caggttttcc gagaacagat gcaagatgct 480
ttaggaaaca atagcagttt ccatcaccga attaatattt atgaaatcat aaaacctgca 540
acagccaact cgaaattccc cgtgaccaga cttttggaca ccaggttggt gaatcagaat 600
gcaagcaggt gggaaagttt tgatgtcacc cccgctgtga tgcggtggac tgcacaggga 660
cacgccaacc atggattcgt ggtggaagtg gcccacttgg aggagaaaca aggtgtctcc 720
aagagacatg ttaggataag caggtctttg caccaagatg aacacagctg gtcacagata 780
aggccattgc tagtaacttt tggccatgat ggaaaagggc atcctctcca caaaagagaa 840
aaacgtcaag ccaaacacaa acagcggaaa cgccttaagt ccagctgtaa gagacaccct 900
ttgtacgtgg acttcagtga cgtggggtgg aatgactgga ttattgcacc caagggctat 960
gctgccaatt actgccacgg agaatgccct tttcctctgg ctgatcatct gaactccact 1020
aaacatgcca ttgttcagac gttggtcaac tctgttaact ctaagattcc taaggcatgc 1080
tgtgtcccga cagaactcag tgctatctcg atgctgtacc ttgacgagaa tgaaaaggtt 1140
gtattaaaga actatcagga catggttgtg gagggttgtg ggtgtcgctg a 1191

<210> SEQ ID NO 89
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360
ctaccagaaa cgagtgggaa aacaacccgg agattcttct ttaatttaag ttctatcccc 420

```
acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc caagggctat    960

gctgccaatt actgccacgg agaatgccct ttcctctgg ctgatcatct gaactccact   1020

actcatgcca ttgttcagac gttggtcaac tctgttaact ctaagattcc taaggcatgc   1080

tgtgtcccga cagaactcag tgctatctcg atgctgtacc ttgacgagaa tgaaaaggtt   1140

gtattaaaga actatcagga catggttgtg gagggttgtg ggtgtcgctg a             1191
```

<210> SEQ ID NO 90
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgccacgg agaatgccct tttccactca acgcacacat gaatgcaacc   1020

aaccacgcga ttgtgcagac cttggttcac cttatgaacc cctctaagat tcctaaggca   1080

tgctgtgtcc cgacagaact cagtgctatc tcgatgctgt accttgacga gaatgaaaag   1140

gttgtattaa agaactatca ggacatggtt gtggagggtt gtgggtgtcg ctga         1194
```

<210> SEQ ID NO 91
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 91

```
atggtggccg ggacccgctg tcttctagcg ttgctgcttc cccaggtcct cctgggcggc     60
gcggctggcc tcgttccgga gctgggccgc aggaagttcg cggcggcgtc gtcgggccgc    120
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
ttaggaaaca atagcagttt ccatcaccga attaatattt atgaaatcat aaaacctgca    540
acagccaact cgaaattccc cgtgaccaga cttttggaca ccaggttggt gaatcagaat    600
gcaagcaggt gggaaagttt tgatgtcacc cccgctgtga tgcggtggac tgcacaggga    660
cacgccaacc atggattcgt ggtggaagtg gcccacttgg aggagaaaca aggtgtctcc    720
aagagacatg ttaggataag caggtctttg caccaagatg aacacagctg gtcacagata    780
aggccattgc tagtaacttt tggccatgat ggaaaagggc atcctctcca caaaagagaa    840
aaacgtcaag ccaaacacaa acagcggaaa cgccttaagt ccagctgtaa gagacaccct    900
ttgtacgtgg acttcagtga cgtggggtgg aatgactgga ttgtggctcc cccggggtat    960
cacgcctttt actgcaaggg cggctgcttc ttccccttgg ctgacgatgt gacgccgacg   1020
aaacacgcta tcgtgcagac cctggtgcat ctcaagttcc ccacaaaggt gggcaaggcc   1080
tgctgtgtcc cgacagaact cagtgctatc tcgatgctgt accttgacga gaatgaaaag   1140
gttgtattaa agaactatca ggacatggtt gtggagggtt gtgggtgtcg ctag         1194
```

<210> SEQ ID NO 92
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
atggtggccg ggacccgctg tcttctagcg ttgctgcttc cccaggtcct cctgggcggc     60
gcggctggcc tcgttccgga gctgggccgc aggaagttcg cggcggcgtc gtcgggccgc    120
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
```

```
ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgccgtgg tgtttgtaac taccccctgg cagagcatct cacacccaca   1020

aagcatgcaa ttatccaggc cttggtccac ctcaagaatt cccagaaagc ttccaaagcc   1080

tgctgtgtcc cgacagaact cagtgctatc tcgatgctgt accttgacga gaatgaaaag   1140

gttgtattaa agaactatca ggacatggtt gtggagggtt gtgggtgtcg ctag         1194
```

<210> SEQ ID NO 93
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgcgatgg agaatgctcc ttcccactca acgcacacat gaatgcaacc   1020

aaacacgcga ttgtgcagac cttggttcac cttatgaacc ccgagtatgt ccccaaaccg   1080

tgctgtgcgc cgacagaact cagtgctatc tcgatgctgt accttgacga gaatgaaaag   1140

gttgtattaa agaactatca ggacatggtt gtggagggtt gtgggtgtcg ctga         1194
```

<210> SEQ ID NO 94

<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgcgatgg agaatgctcc ttcccactca acgcacacat gaatgcaacc   1020

acccacgcga ttgtgcagac cttggttcac cttatgaacc ccgagtatgt ccccaaaccg   1080

tgctgtgcgc cgacagaact cagtgctatc tcgatgctgt accttgacga gaatgaaaag   1140

gttgtattaa agaactatca ggacatggtt gtggagggtt gtgggtgtcg ctga         1194
```

<210> SEQ ID NO 95
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540
```

```
acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc caggggggtat    960

cacgcctttt actgccacgg agaatgccct tttcctctgg ctgatcatct gaactccact   1020

aatcatgcca ttgttcagac gttggtcaac tctgttaact ctaagattcc taaggcatgc   1080

tgtgtcccga cagaactcag tgctatctcg atgctgtacc ttgacgagaa tgaaaaggtt   1140

gtattaaaga actatcagga catggttgtg gagggttgtg ggtgtcgcta g            1191
```

<210> SEQ ID NO 96
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgcgaggg gctgtgcgag ttcccattgc gctcccacct ggagcccacg   1020

aatcatgcag tcatccagac cctgatgaac tccatggacc ccgagtccac accacccacc   1080

tgctgtgtcc cgacagaact cagtgctatc tcgatgctgt accttgacga gaatgaaaag   1140

gttgtattaa agaactatca ggacatggtt gtggagggtt gtgggtgtcg ctag         1194
```

<210> SEQ ID NO 97
<211> LENGTH: 1194
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97

```
atggtggccg ggacccgctg tcttctagcg ttgctgcttc cccaggtcct cctgggcggc     60
gcggctggcc tcgttccgga gctgggccgc aggaagttcg cggcggcgtc gtcgggccgc    120
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
ttaggaaaca atagcagttt ccatcaccga attaatattt atgaaatcat aaaacctgca    540
acagccaact cgaaattccc cgtgaccaga cttttggaca ccaggttggt gaatcagaat    600
gcaagcaggt gggaaagttt tgatgtcacc cccgctgtga tgcggtggac tgcacaggga    660
cacgccaacc atggattcgt ggtggaagtg gcccacttgg aggagaaaca aggtgtctcc    720
aagagacatg ttaggataag caggtctttg caccaagatg aacacagctg gtcacagata    780
aggccattgc tagtaacttt tggccatgat ggaaaagggc atcctctcca caaaagagaa    840
aaacgtcaag ccaaacacaa acagcggaaa cgccttaagt ccagctgtaa gagacaccct    900
ttgtacgtgg acttcagtga cgtggggtgg aatgactgga ttgtggctcc caggggggtat    960
cacgcctttt actgcgatgg agaatgctcc ttcccactca acgcacacat gaatgcaacc   1020
aaccacgcga ttgtgcagac cttggttcac cttatgaacc ccgagtatgt ccccaaaccg   1080
tgctgtgcgc cgacagaact cagtgctatc tcgatgctgt accttgacga gaatgaaaag   1140
gttgtattaa agaactatca ggacatggtt gtggagggtt gtgggtgtcg ctga         1194
```

<210> SEQ ID NO 98
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 98

```
atggtggccg ggacccgctg tcttctagcg ttgctgcttc cccaggtcct cctgggcggc     60
gcggctggcc tcgttccgga gctgggccgc aggaagttcg cggcggcgtc gtcgggccgc    120
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
ttaggaaaca atagcagttt ccatcaccga attaatattt atgaaatcat aaaacctgca    540
acagccaact cgaaattccc cgtgaccaga cttttggaca ccaggttggt gaatcagaat    600
```

```
gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc cccgggctat    960

gctgcctttt actgccacgg agaatgccct ttcctctgg ctgatcatct gaactccact    1020

aatcatgcca ttgttcagac gttggtcaac tctgttaact ctaagattcc taaggcatgc    1080

tgtgtcccga cagaactcaa tgccatctcg gttctttact ttgatgacaa ctccaatgtc    1140

attttaaaga actatcagga catggttgtg gagggttgtg ggtgtcgctg a             1191
```

<210> SEQ ID NO 99
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
atggtggccg ggacccgctg tcttctagcg ttgctgcttc cccaggtcct cctgggcggc      60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgcacc caggggctat    960

gctgcctttt actgccacgg agaatgccct ttcctctgg ctgatcatct gaactccact    1020

aatcatgcca ttgttcagac gttggtcaac tctgttaact ctaagattcc taaggcatgc    1080

tgtgtcccga cagaactcaa tgccatctcg gttctttact ttgatgacaa ctccaatgtc    1140

attttaaaga actatcagga catggttgtg gagggttgtg ggtgtcgctg a             1191
```

<210> SEQ ID NO 100
<211> LENGTH: 1191
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 100

```
atggtggccg ggacccgctg tcttctagcg ttgctgcttc cccaggtcct cctgggcggc      60

gcggctggcc tcgttccgga gctgggccgc aggaagttcg cggcggcgtc gtcgggccgc     120

ccctcatccc agccctctga cgaggtcctg agcgagttcg agttgcggct gctcagcatg     180

ttcggcctga aacagagacc cacccccagc agggacgccg tggtgccccc ctacatgcta     240

gacctgtatc gcaggcactc aggtcagccg ggctcacccg ccccagacca ccggttggag     300

agggcagcca gccgagccaa cactgtgcgc agcttccacc atgaagaatc tttggaagaa     360

ctaccagaaa cgagtgggaa aacaacccgg agattcttct ttaatttaag ttctatcccc     420

acggaggagt ttatcacctc agcagagctt caggttttcc gagaacagat gcaagatgct     480

ttaggaaaca atagcagttt ccatcaccga attaatattt atgaaatcat aaaacctgca     540

acagccaact cgaaattccc cgtgaccaga cttttggaca ccaggttggt gaatcagaat     600

gcaagcaggt gggaaagttt tgatgtcacc cccgctgtga tgcggtggac tgcacaggga     660

cacgccaacc atggattcgt ggtggaagtg gcccacttgg aggagaaaca aggtgtctcc     720

aagagacatg ttaggataag caggtctttg caccaagatg aacacagctg gtcacagata     780

aggccattgc tagtaacttt tggccatgat ggaaaagggc atcctctcca caaaagagaa     840

aaacgtcaag ccaaacacaa acagcggaaa cgccttaagt ccagctgtaa gagacaccct     900

ttgtacgtgg acttcagtga cgtggggtgg aatgactgga ttattgcacc caagggctat     960

gctgcctttt actgccacgg agaatgccct tttcctctgg ctgatcatct gaactccact    1020

aaacatgcca ttgttcagac gttggtcaac tctgttaact ctaagattcc taaggcatgc    1080

tgtgtcccga cagaactcaa tgccatctcg gttctttact ttgatgacaa ctccaatgtc    1140

attttaaaga actatcagga catggttgtg gagggttgtg ggtgtcgctg a             1191
```

<210> SEQ ID NO 101
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

```
atggtggccg ggacccgctg tcttctagcg ttgctgcttc cccaggtcct cctgggcggc      60

gcggctggcc tcgttccgga gctgggccgc aggaagttcg cggcggcgtc gtcgggccgc     120

ccctcatccc agccctctga cgaggtcctg agcgagttcg agttgcggct gctcagcatg     180

ttcggcctga aacagagacc cacccccagc agggacgccg tggtgccccc ctacatgcta     240

gacctgtatc gcaggcactc aggtcagccg ggctcacccg ccccagacca ccggttggag     300

agggcagcca gccgagccaa cactgtgcgc agcttccacc atgaagaatc tttggaagaa     360

ctaccagaaa cgagtgggaa aacaacccgg agattcttct ttaatttaag ttctatcccc     420

acggaggagt ttatcacctc agcagagctt caggttttcc gagaacagat gcaagatgct     480

ttaggaaaca atagcagttt ccatcaccga attaatattt atgaaatcat aaaacctgca     540

acagccaact cgaaattccc cgtgaccaga cttttggaca ccaggttggt gaatcagaat     600

gcaagcaggt gggaaagttt tgatgtcacc cccgctgtga tgcggtggac tgcacaggga     660
```

cacgccaacc atggattcgt ggtggaagtg gcccacttgg aggagaaaca aggtgtctcc 720
aagagacatg ttaggataag caggtctttg caccaagatg aacacagctg gtcacagata 780
aggccattgc tagtaacttt tggccatgat ggaaaagggc atcctctcca caaaagagaa 840
aaacgtcaag ccaaacacaa acagcggaaa cgccttaagt ccagctgtaa gagacaccct 900
ttgtacgtgg acttcagtga cgtggggtgg aatgactgga ttattgcacc caagggctat 960
gctgcctttt actgccacgg agaatgccct tttcctctgg ctgatcatct gaactccact 1020
actcatgcca ttgttcagac gttggtcaac tctgttaact ctaagattcc taaggcatgc 1080
tgtgtcccga cagaactcaa tgccatctcg gttctttact ttgatgacaa ctccaatgtc 1140
attttaaaga actatcagga catggttgtg gagggttgtg ggtgtcgctg a 1191

<210> SEQ ID NO 102
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102
atggtggctg gcaccagatg tctgctggcc ctgctgctgc cccaggtgct gctgggcgga 60
gctgctggac tggtgcccga gctgggcaga agaaagttcg ccgctgcctc ctctggccgg 120
ccttccagcc agccttccga cgaggtgctg tccgagttcg agctgcggct gctgtccatg 180
ttcggcctga agcagcggcc cacccccttct agggacgccg tggtgccccc ctacatgctg 240
gacctgtacc ggcggcactc cggccagcct ggatctcctg cccccgacca cagactggaa 300
agagccgcct cccgggccaa caccgtgcgg tctttccacc acgaggaatc cctggaagaa 360
ctgcccgaga catccggcaa gaccacccgg cggttctttt tcaacctgtc atccatcccc 420
accgaagagt tcatcacctc cgccgagctg caggtgttcc gcgagcagat gcaggacgcc 480
ctgggcaaca actcctcctt ccaccaccgg atcaacatct acgagatcat caagcccgcc 540
accgccaact ccaagttccc cgtgacccgg ctgctggaca cccggctggt gaaccagaac 600
gcctccagat gggagtcctt cgacgtgacc cctgccgtga tgagatggac cgcccagggc 660
cacgccaacc acggctttgt ggtggaagtg gcccacctgg aagagaagca gggcgtgtcc 720
aagcggcacg tgcggatctc tcggtccctg caccaggacg agcacagctg gtcccagatc 780
cggcccctgc tggtgacatt cggccacgat ggcaagggcc acccccctgca caagagagag 840 aagcggcagg ccaagcacaa gcagcggaag cggctgaagt cctcctgcaa gcggcacccc 900
ctgtacgtgg acttctccga cgtgggctgg aacgactgga tcattgcccc caagggctac 960
gccgccttct actgcgacgg cgagtgctcc ttcccccctga acgcccacat gaacgccacc 1020
aaccacgcca tcgtgcagac cctggtgcac ctgatgaacc ccgagtacgt gcccaagcct 1080
tgttgcgccc ccaccgagct gaacgccatc tccgtgctgt acttcgacga caactccaac 1140
gtgatcctga agaactacca ggacatggtg gtcgaaggct gcggctgtag atga 1194

<210> SEQ ID NO 103
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 103
atggtggctg gcaccagatg tctgctggcc ctgctgctgc cccaggtgct gctgggcgga 60
gctgctggac tggtgcccga gctgggcaga agaaagttcg ccgctgcctc ctctggccgg 120
ccttccagcc agccttccga cgaggtgctg tccgagttcg agctgcggct gctgtccatg 180
ttcggcctga agcagcggcc cacccccttct agggacgccg tggtgccccc ctacatgctg 240
gacctgtacc ggcggcactc cggccagcct ggatctcctg cccccgacca cagactggaa 300
agagccgcct cccgggccaa caccgtgcgg tctttccacc acgaggaatc cctggaagaa 360
ctgcccgaga catccggcaa gaccacccgg cggttctttt tcaacctgtc atccatcccc 420
accgaagagt tcatcacctc cgccgagctg caggtgttcc gcgagcagat gcaggacgcc 480
ctgggcaaca actcctcctt ccaccaccgg atcaacatct acgagatcat caagcccgcc 540
accgccaact ccaagttccc cgtgacccgg ctgctggaca cccggctggt gaaccagaac 600
gcctccagat gggagtcctt cgacgtgacc cctgccgtga tgagatggac cgcccagggc 660
cacgccaacc acggctttgt ggtggaagtg gcccacctgg aagagaagca gggcgtgtcc 720
aagcggcacg tgcggatctc tcggtccctg caccaggacg agcacagctg gtcccagatc 780
cggcccctgc tggtgacatt cggccacgat ggcaagggcc acccccctgca caagagagag 840 aagcggcagg ccaagcacaa gcagcggaag cggctgaagt cctcctgcaa gcggcacccc 900
ctgtacgtgg acttctccga cgtgggctgg aacgactgga tyrtkgcycc caggggstay 960
smcgccttyt actgcgacgg cgagtgctcc ttcccccctga acgcccacat gaacgccacc 1020
aaccacgcca tcgtgcagac cctggtgcac ctgatgaacc ccgagtacgt gcccaagcct 1080
tgttgcgccc ccaccgagct gaacgccatc tccgtgctgt acttcgacga caactccaac 1140
gtgatcctga agaactacca ggacatggtg gtcgaaggct gcggctgtag atga 1194

<210> SEQ ID NO 104
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360
ctaccagaaa cgagtgggaa aacaacccgg agattcttct ttaatttaag ttctatcccc 420
acggaggagt ttatcacctc agcagagctt caggttttcc gagaacagat gcaagatgct 480
ttaggaaaca atagcagttt ccatcaccga attaatattt atgaaatcat aaaacctgca 540
acagccaact cgaaattccc cgtgaccaga cttttggaca ccaggttggt gaatcagaat 600
gcaagcaggt gggaaagttt tgatgtcacc cccgctgtga tgcggtggac tgcacaggga 660
cacgccaacc atggattcgt ggtggaagtg gcccacttgg aggagaaaca aggtgtctcc 720

```
aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgctcc cccggggtat    960

cacgcctttt actgcgatgg agaatgctcc ttcccactca acgcacacat gaatgcaacc   1020

aaccacgcga ttgtgcagac cttggttcac cttatgaacc ccgagtatgt ccccaaaccg   1080

tgctgtgcgc cgacagaact caatgctatc tcggttctgt actttgacga gaattccaat   1140

gttgtattaa agaaatatca ggacatggtt gtgagaggtt gtgggtgtcg ctga         1194
```

```
<210> SEQ ID NO 105
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105

atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840

aaacgtcaag ccaaacacaa acagcggaaa cgccttaagt ccagctgtaa gagacaccct    900

ttgtacgtgg acttcagtga cgtggggtgg aatgactgga ttattgctcc caggggggtat   960

cacgcctttt actgcgatgg agaatgctcc ttcccactca acgcacacat gaatgcaacc   1020

aaccacgcga ttgtgcagac cttggttcac cttatgaacc ccgagtatgt ccccaaaccg   1080

tgctgtgcgc cgacagaact caatgctatc tcggttctgt actttgacga gaattccaat   1140

gttgtattaa agaaatatca ggacatggtt gtgagaggtt gtgggtgtcg ctga         1194
```

```
<210> SEQ ID NO 106
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 106
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360
ctaccagaaa cgagtgggaa aacaacccgg agattcttct ttaatttaag ttctatcccc 420
acggaggagt ttatcacctc agcagagctt caggttttcc gagaacagat gcaagatgct 480
ttaggaaaca atagcagttt ccatcaccga attaatattt atgaaatcat aaaacctgca 540
acagccaact cgaaattccc cgtgaccaga cttttggaca ccaggttggt gaatcagaat 600
gcaagcaggt gggaaagttt tgatgtcacc cccgctgtga tgcggtggac tgcacaggga 660
cacgccaacc atggattcgt ggtggaagtg gcccacttgg aggagaaaca aggtgtctcc 720
aagagacatg ttaggataag caggtctttg caccaagatg aacacagctg gtcacagata 780
aggccattgc tagtaacttt tggccatgat ggaaaagggc atcctctcca caaaagagaa 840
aaacgtcaag ccaaacacaa acagcggaaa cgccttaagt ccagctgtaa gagacaccct 900
ttgtacgtgg acttcagtga cgtggggtgg aatgactgga ttattgctcc caaggggtat 960
cacgcctttt actgcgatgg agaatgctcc ttcccactca acgcacacat gaatgcaacc 1020
aaacacgcga ttgtgcagac cttggttcac cttatgaacc ccgagtatgt ccccaaaccg 1080
tgctgtgcgc cgacagaact caatgctatc tcggttctgt actttgacga gaattccaat 1140
gttgtattaa agaaatatca ggacatggtt gtgagaggtt gtgggtgtcg ctga 1194

<210> SEQ ID NO 107
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 107
atggtggccg ggacccgctg tcttctagcg ttgctgcttc cccaggtcct cctgggcggc 60
gcggctggcc tcgttccgga gctgggccgc aggaagttcg cggcggcgtc gtcgggccgc 120
ccctcatccc agccctctga cgaggtcctg agcgagttcg agttgcggct gctcagcatg 180
ttcggcctga aacagagacc cacccccagc agggacgccg tggtgccccc ctacatgcta 240
gacctgtatc gcaggcactc aggtcagccg ggctcacccg ccccagacca ccggttggag 300
agggcagcca gccgagccaa cactgtgcgc agcttccacc atgaagaatc tttggaagaa 360
ctaccagaaa cgagtgggaa aacaacccgg agattcttct ttaatttaag ttctatcccc 420
acggaggagt ttatcacctc agcagagctt caggttttcc gagaacagat gcaagatgct 480
ttaggaaaca atagcagttt ccatcaccga attaatattt atgaaatcat aaaacctgca 540
acagccaact cgaaattccc cgtgaccaga cttttggaca ccaggttggt gaatcagaat 600
gcaagcaggt gggaaagttt tgatgtcacc cccgctgtga tgcggtggac tgcacaggga 660
cacgccaacc atggattcgt ggtggaagtg gcccacttgg aggagaaaca aggtgtctcc 720
aagagacatg ttaggataag caggtctttg caccaagatg aacacagctg gtcacagata 780

```
aggccattgc tagtaacttt tggccatgat ggaaaagggc atcctctcca caaaagagaa    840

aaacgtcaag ccaaacacaa acagcggaaa cgccttaagt ccagctgtaa gagacacccct   900

ttgtacgtgg acttcagtga cgtggggtgg aatgactgga ttattgctcc caaggggtat    960

cacgcctttt actgcgatgg agaatgctcc ttcccactca acgcacacat gaatgcaacc   1020

acccacgcga ttgtgcagac cttggttcac cttatgaacc ccgagtatgt ccccaaaccg   1080

tgctgtgcgc cgacagaact caatgctatc tcggttctgt actttgacga gaattccaat   1140

gttgtattaa agaaatatca ggacatggtt gtgagaggtt gtgggtgtcg ctga         1194
```

<210> SEQ ID NO 108
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 108

```
atggtggctg gcaccagatg tctgctggcc ctgctgctgc cccaggtgct gctgggcgga     60

gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc cacccccttct agggacgccg tggtgccccc ctacatgctg   240

gacctgtacc ggcggcactc cggacagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc ctccatcccc    420

accgaagagt tcatcacctc cgccgagctg caggtgttcc gcgagcagat gcaggacgcc    480

ctgggcaaca actcctcctt ccaccatcgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc acccccctgca caagagagag   840

aagcggcagg ccaagcacaa gcagcggaag cggctgaagt cctcctgcaa gcggcacccc    900

ctgtacgtgg acttctccga cgtgggctgg aacgactgga tcattgcccc caaagagtac    960

gaggcctacg agtgccacgg cgagtgccct ttcccccctgg ccgaccacct gaactccacc   1020

aaccacgcca tcgtgcagac cctggtgaac tccgtgaaca gcaagatccc caaggcctgc   1080

tgcgtgccca ccgagctgtc cgccatctcc atgctgtacc tggacgagaa cgagaaggtg   1140

gtgctgaaga actaccagga catggtggtc gaaggctgcg gctgtcggtg a            1191
```

<210> SEQ ID NO 109
<211> LENGTH: 1176
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 109

```
atggtggctg gcaccagatg tctgctggcc ctgctgctgc cccaggtgct gctgggcgga     60

gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc cacccccttct agggacgccg tggtgccccc ctacatgctg    240

gacctgtacc ggcggcactc cggacagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc ctccatcccc    420

accgaagagt tcatcacctc cgccgagctg caggtgttcc gcgagcagat gcaggacgcc    480

ctgggcaaca actcctcctt ccaccatcgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc acccccctgca caagagagag    840

aagcggcagg ccaagcacaa gcagcggaag cggctgaagt cctcctgcaa gcggcacccc    900

ctgtacgtgg acttctccga cgtgggctgg aacgactgga tcgtggcccc tcccggctac    960

cacggcgagt gccctttccc cctggccgac cacctgaact ccaccaacca cgccatcgtg   1020

cagaccctgg tgaactccgt gaacagcaag atccccaagg cctgctgcgt gcccaccgag   1080

ctgtccccca tctccgtgct gtacaaggac gacatgggcg tgcccaccct gaagaactac   1140

caggacatgg tggtcgaagg ctgcggctgt cggtga                             1176
```

```
<210> SEQ ID NO 110
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110

atggtggctg gcaccagatg tctgctggcc ctgctgctgc cccaggtgct gctgggcgga     60

gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc cacccccttct agggacgccg tggtgccccc ctacatgctg    240

gacctgtacc ggcggcactc cggacagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc ctccatcccc    420

accgaagagt tcatcacctc cgccgagctg caggtgttcc gcgagcagat gcaggacgcc    480

ctgggcaaca actcctcctt ccaccatcgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc acccccctgca caagagagag    840
```

```
aagcggcagg ccaagcacaa gcagcggaag cggctgaagt cctcctgcaa gcggcacccc    900

ctgtacgtgg acttctccga cgtgggctgg aacgactgga tcgtggcccc tcccggctac    960

cacgccttct actgcgacgg cgagtgctcc ttcccccctga acgcccacat gaacgccacc   1020

aaccacgcca tcgtgcagac cctggtgcac ctgatgaacc ccgagtacgt gcccaagccc   1080

tgctgcgccc ccaccgagct gtcccccatc tccgtgctgt acaaggacga catgggcgtg   1140

cccaccctga agaactacca ggacatggtg gtcgaaggct gcggctgtcg gtga         1194
```

<210> SEQ ID NO 111
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111

```
atggtggctg gcaccagatg tctgctggcc ctgctgctgc cccaggtgct gctgggcgga     60

gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc cacccccttct agggacgccg tggtgccccc ctacatgctg    240

gacctgtacc ggcggcactc cggacagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc ctccatcccc    420

accgaagagt tcatcacctc cgccgagctg caggtgttcc gcgagcagat gcaggacgcc    480

ctgggcaaca actcctcctt ccaccatcgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc accccctgca caagagagag    840

aagcggcagg ccaagcacaa gcagcggaag cggctgaagt cctcctgcaa gcggcacccc    900

ctgtacgtgg acttctccga cgtgggctgg aacgactgga tcatcgcccc taaggagtac    960

gaggcctacg agtgccacgg cgagtgccct ttcccccctgg ccgaccacct gaactccacc   1020

aaccacgcca tcgtgcagac cctggtgaac tccgtgaaca gcaagatccc caaggcctgc   1080

tgcgtgccca ccgagctgtc ccccatctcc gtgctgtaca aggacgacat gggcgtgccc   1140

accctgaaga actaccagga catggtggtc gaaggctgcg gctgtcggtg a             1191
```

<210> SEQ ID NO 112
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 112

```
atggtggctg gcaccagatg tctgctggcc ctgctgctgc cccaggtgct gctgggcgga     60
```

```
gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc cacccccttct agggacgccg tggtgccccc ctacatgctg    240

gacctgtacc ggcggcactc cggacagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc ctccatcccc    420

accgaagagt tcatcacctc cgccgagctg caggtgttcc gcgagcagat gcaggacgcc    480

ctgggcaaca actcctcctt ccaccatcgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc acccccctgca caagagagag    840

aagcggcagg ccaagcacaa gcagcggaag cggctgaagt cctcctgcca gaaaacctcc    900

ctgcgggtga acttcgagga tatcggctgg gactcctgga tcatcgcccc taaggagtac    960

gaggcctacg agtgccacgg cgagtgccct ttccccctgg ccgaccacct gaactccacc   1020

aaccacgcca tcgtgcagac cctggtgaac tccgtgaaca gcaagatccc caaggcctgc   1080

tgcgtgccca ccaagctgtc ccccatctcc gtgctgtaca aggacgacat gggcgtgccc   1140

accctgaagt accactacga gggcatgtcc gtcgccgagt gcggctgtcg gtga         1194
```

<210> SEQ ID NO 113
<211> LENGTH: 1197
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 113

```
atggtggctg gcaccagatg tctgctggcc ctgctgctgc cccaggtgct gctgggcgga     60

gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc cacccccttct agggacgccg tggtgccccc ctacatgctg    240

gacctgtacc ggcggcactc cggacagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc ctccatcccc    420

accgaagagt tcatcacctc cgccgagctg caggtgttcc gcgagcagat gcaggacgcc    480

ctgggcaaca actcctcctt ccaccatcgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc acccccctgca caagagagag    840

aagcggcagg ccaagcacaa gcagcggaag cggctgaagt cctcctgcca gaaaacctcc    900
```

```
ctgcgggtga acttcgagga tatcggctgg gactcctgga tcatcgcccc taaggagtac    960

gaggcctacg agtgcgacgg cgagtgctcc ttcccctga acgcccacat gaacgccacc    1020

aaccacgcca tcgtgcagac cctggtgcac ctgatgaacc ccgagtacgt gcccaagccc    1080

tgctgcgtcc ccaccaagct gtcccccatc tccgtgctgt acaaggacga catgggcgtg    1140

cccaccctga agtaccacta cgagggcatg tccgtcgccg agtgcggctg tcggtga       1197
```

<210> SEQ ID NO 114
<211> LENGTH: 1308
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114

```
atgtgtcctg gcgctctgtg ggtggccctg cctctgctgt ctctgctggc cggcagcctg      60

cagggcaagc ctctgcagtc ctggggcaga ggctccgctg gcggcaatgc tcacagccct     120

ctgggagtgc ctggcggcgg actgcccgag cacaccttca acctgaagat gttcctggaa     180

aacgtgaagg tggacttcct gcggtccctg aacctgtccg gcgtgcccag ccaggacaag     240

acccgggtgg aaccccccca gtacatgatc gacctgtaca accggtacac ctccgacaag     300

tccaccaccc ccgcctccaa catcgtgcgg tccttcagca tggaagatgc catctccatt     360

accgccaccg aggacttccc atttcagaag cacatcctgc tgttcaacat ctccatcccc     420

cggcacgagc agatcaccag agccgagctg cggctgtacg tgtcctgcca gaaccacgtg     480

gacccctccc acgacctgaa gggctccgtg gtgatctacg acgtgctgga cggcaccgac     540

gcctgggact ccgctaccga gacaaagacc ttcctggtgt cccaggatat ccaggacgag     600

ggctgggaga cactggaagt gtcctccgcc gtgaagagat gggtgcgatc cgactccacc     660

aagtccaaga acaagctgga agtgaccgtg gaatcccacc ggaagggctg cgacaccctg     720

gacatctccg tgcccccctgg ctcccggaac ctgcccttct tcgtggtgtt ctccaacgac     780

cactcctccg gcaccaaaga gacacggctg gaactgagag agatgatctc ccacgagcag     840

gaatccgtcc tgaagaagct gtccaaggac ggctccaccg aggccggcga gtcctctcac     900

gaagaggaca ccgacggcca cgtggcagct ggctctaccc tggccagacg gaagcggcag     960

gccaagcaca agcagcggaa gcggctgaag tccagctgcc agaaaacctc cctgagagtg    1020

aacttcgagg acatcggctg ggacagctgg atcattgccc ccaaagagta cgaggcctac    1080

gagtgcaagg gcggctgctt cttcccccctg gccgacgacg tgacccccac caagcacgcc    1140

atcgtgcaga ccctggtgca cctgaagttc ccccaccaaag tgggcaaggc ctgctgcgtg    1200

cccaccaagc tgtcccccat cagcgtgctg tacaaggacg acatgggcgt gccaaccctg    1260

aagtaccact acgagggcat gtccgtggcc gagtgtggct gccggtga                 1308
```

<210> SEQ ID NO 115
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115

```
atgtgtcctg gcgctctgtg ggtggccctg cctctgctgt ctctgctggc cggcagcctg     60
cagggcaagc ctctgcagtc ctggggcaga ggctccgctg gcggcaatgc tcacagccct    120
ctgggagtgc ctggcggcgg actgcccgag cacaccttca acctgaagat gttcctggaa    180
aacgtgaagg tggacttcct gcggtccctg aacctgtccg gcgtgcccag ccaggacaag    240
acccgggtgg aacccccca gtacatgatc gacctgtaca accggtacac ctccgacaag    300
tccaccaccc ccgcctccaa catcgtgcgg tccttcagca tggaagatgc catctccatt    360
accgccaccg aggacttccc atttcagaag cacatcctgc tgttcaacat ctccatcccc    420
cggcacgagc agatcaccag agccgagctg cggctgtacg tgtcctgcca gaaccacgtg    480
gacccctccc acgacctgaa gggctccgtg gtgatctacg acgtgctgga cggcaccgac    540
gcctgggact ccgctaccga gacaaagacc ttcctggtgt cccaggatat ccaggacgag    600
ggctgggaga cactggaagt gtcctccgcc gtgaagagat gggtgcgatc cgactccacc    660
aagtccaaga acaagctgga agtgaccgtg gaatcccacc ggaagggctg cgacaccctg    720
gacatctccg tgccccctgg ctcccggaac ctgcccttct tcgtggtgtt ctccaacgac    780
cactcctccg gcaccaaaga gacacggctg gaactgagag agatgatctc ccacgagcag    840
gaatccgtcc tgaagaagct gtccaaggac ggctccaccg aggccggcga gtcctctcac    900
gaagaggaca ccgacggcca cgtggcagct ggctctaccc tggccagacg gaagcggcag    960
gccaagcaca agcagcggaa gcggctgaag tccagctccg ctggcgcagg ctcccactgc   1020
cagaaaacct ccctgagagt gaacttcgag gacatcggct gggacagctg gatcattgcc   1080
cccaaagagt acgaggccta cgagtgcaag ggcggctgct tcttcccccct ggccgacgac   1140
gtgaccccca ccaagcacgc catcgtgcag accctggtgc acctgaagtt ccccaccaaa   1200
gtgggcaagg cctgctgcgt gcccaccaag ctgtccccca tcagcgtgct gtacaaggac   1260
gacatgggcg tgccaaccct gaagtaccac tacgagggca tgtccgtggc cgagtgtggc   1320
tgccggtga                                                            1329
```

```
<210> SEQ ID NO 116
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116
```

```
atgtgtcctg gcgctctgtg ggtggccctg cctctgctgt ctctgctggc cggcagcctg     60
cagggcaagc ctctgcagtc ctggggcaga ggctccgctg gcggcaatgc tcacagccct    120
ctgggagtgc ctggcggcgg actgcccgag cacaccttca acctgaagat gttcctggaa    180
aacgtgaagg tggacttcct gcggtccctg aacctgtccg gcgtgcccag ccaggacaag    240
acccgggtgg aacccccca gtacatgatc gacctgtaca accggtacac ctccgacaag    300
tccaccaccc ccgcctccaa catcgtgcgg tccttcagca tggaagatgc catctccatt    360
accgccaccg aggacttccc atttcagaag cacatcctgc tgttcaacat ctccatcccc    420
cggcacgagc agatcaccag agccgagctg cggctgtacg tgtcctgcca gaaccacgtg    480
gacccctccc acgacctgaa gggctccgtg gtgatctacg acgtgctgga cggcaccgac    540
gcctgggact ccgctaccga gacaaagacc ttcctggtgt cccaggatat ccaggacgag    600
ggctgggaga cactggaagt gtcctccgcc gtgaagagat gggtgcgatc cgactccacc    660
```

```
aagtccaaga acaagctgga agtgaccgtg gaatcccacc ggaagggctg cgacaccctg    720

gacatctccg tgcccctgg ctcccggaac ctgcccttct tcgtggtgtt ctccaacgac    780

cactcctccg gcaccaaaga gacacggctg gaactgagag agatgatctc ccacgagcag    840

gaatccgtcc tgaagaagct gtccaaggac ggctccaccg aggccggcga gtcctctcac    900

gaagaggaca ccgacggcca cgtggcagct ggctctaccc tggccagacg gaagcggcag    960

gccaagcaca agcagcggaa gcggctgaag tccagctccg ctggcgcagg ctcccactgc   1020

cagaaaacct ccctgagagt gaacttcgag gacatcggct gggacagctg gatcattgcc   1080

cccaaagagt acgaggccta cgagtgcaag ggcggctgct tcttcccct ggccgacgac   1140

gtgaccccca ccaagcacgc catcgtgcag accctggtgc acctgaagtt ccccaccaaa   1200

gtgggcaagg cctgctgcgt gcccaccaag ctgtccccca tcagcgtgct gtacaaggac   1260

gacatgggcg tgccaaccct gaagtaccac tacgagggca tgtccgtggc cgagtgtggc   1320

tgccggtga                                                           1329
```

<210> SEQ ID NO 117
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 117

```
atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260
```

```
ttccaagacc tgggatggca ggactggatc attgcaccca agggctatgc tgccaattac   1320

tgtgatggag aatgctcctt cccactcaac gcagccatga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

```
<210> SEQ ID NO 118
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260

ttccaagacc tgggatggca ggactggatc attgcaccca agggctatgc tgccaattac   1320

tgtgatggag aatgctcctt cccactcaac gcacacctga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

```
<210> SEQ ID NO 119
<211> LENGTH: 1542
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic polynucleotide"

<400> SEQUENCE: 119

```
atgccggggc tggggcggag ggcgcagtgg ctgtgctggt ggtgggggct gctgtgcagc     60
tgctgcgggc ccccgccgct gcggccgccc ttgcccgctg ccgcggccgc cgccgccggg    120
gggcagctgc tgggggacgg cgggagcccc ggccgcacgg agcagccgcc gccgtcrccg    180
cagtcctcct cgggcttcct gtaccggcgg ctcaagacgc aggagaagcg ggagatgcag    240
aaggagatct tgtcggtgct ggggctcccg caccggcccc ggcccctgca cggcctccaa    300
cagccgcagc ccccggcgct ccggcagcag gaggagcagc agcagcagca gcagctgcct    360
cgcggagagc cccctcccgg gcgactgaag tccgcgcccc tcttcatgct ggatctgtac    420
aacgccctgt ccgccgacaa cgacgaggac ggggcgtcgg agggggagag gcagcagtcc    480
tggccccacg aagcagccag ctcgtcccag cgtcggcagc cgcccccggg cgccgcgcac    540
ccgctcaacc gcaagagcct tctggccccc ggatctggca gcggcggcgc gtccccactg    600
accagcgcgc aggacagcgc cttcctcaac gacgcggaca tggtcatgag ctttgtgaac    660
ctggtggagt acgacaagga gttctcccct cgtcagcgac accacaaaga gttcaagttc    720
aacttatccc agattcctga gggtgaggtg gtgacggctg cagaattccg catctacaag    780
gactgtgtta tggggagttt taaaaaccaa acttttctta tcagcattta tcaagtctta    840
caggagcatc agcacagaga ctctgacctg tttttgttgg acacccgtgt agtatgggcc    900
tcagaagaag gctggctgga atttgacatc acggccacta gcaatctgtg ggttgtgact    960
ccacagcata acatggggct tcagctgagc gtggtgacaa gggatggagt ccacgtccac   1020
ccccgagccg caggcctggt gggcagagac ggcccttacg ataagcagcc cttcatggtg   1080
gctttcttca aagtgagtga ggtccacgtg cgcaccacca ggtcagcctc cagccggcgc   1140
cgacaacaga gtcgtaatcg ctctacccag tcccaggacg tggcgcgggt ctccagtgct   1200
tcagattaca acagcagtga attgaaaaca gcctgcagga agcatgagct gtatgtgagt   1260
ttccaagacc tgggatggca ggactggatc attgcaccca agggctatgc tgccaattac   1320
tgtgatggag aatgctcctt ccctctggct gatcatctga actccactaa tcatgccatt   1380
gtgcagacct tggttaactc tgttaacccc gagtatgtcc ccaaaccgtg ctgtgcgcca   1440
actaagctaa atgccatctc ggttctttac tttgatgaca actccaatgt cattctgaaa   1500
aaatacagga atatggttgt aagagcttgt ggatgccact aa                       1542
```

<210> SEQ ID NO 120
<211> LENGTH: 1539
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120

```
atgccggggc tggggcggag ggcgcagtgg ctgtgctggt ggtgggggct gctgtgcagc     60
tgctgcgggc ccccgccgct gcggccgccc ttgcccgctg ccgcggccgc cgccgccggg    120
gggcagctgc tgggggacgg cgggagcccc ggccgcacgg agcagccgcc gccgtcgccg    180
cagtcctcct cgggcttcct gtaccggcgg ctcaagacgc aggagaagcg ggagatgcag    240
```

```
aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg ataagcagcc cttcatggtg   1080

gctttcttca aagtgagtga ggtccacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260

ttccaagacc tgggatggca ggactggatc attgcaccca agggctatgc tgccaattac   1320

tgtcacggag aatgcccttt tcctctggct gatcatctga actccactaa tcatgccatt   1380

gtgcagacct tggttaactc tgttaactct aagattccta aggcatgctg tgtcccaact   1440

aagctaaatg ccatctcggt tctttacttt gatgacaact ccaatgtcat tctgaaaaaa   1500

tacaggaata tggttgtaag agcttgtgga tgccactaa                          1539
```

<210> SEQ ID NO 121
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 121

```
atgccggggc tggggcggag ggcgcagtgg ctgtgctggt ggtgggggct gctgtgcagc     60

tgctgcgggc cccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720
```

```
aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260

ttccaagacc tgggatggca ggactggatc gtggctcctc cggggtatca cgccttttac   1320

tgtgatggag aatgctcctt cccactcaac gcacacatga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

<210> SEQ ID NO 122
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122

```
atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140
```

cgacaacaga gtcgtaatcg ctctacccag tcccaggacg tggcgcgggt ctccagtgct 1200
tcagattaca acagcagtga attgaaaaca gcctgcagga agcatgagct gtatgtgagt 1260
ttccaagacc tgggatggca ggactggatc gtggctcctc cggggtatca cgccttttac 1320
tgtgatggag aatgctcctt cccactcaac gcacacatga atgcaaccaa ccacgcgatt 1380
gtgcagacct tggttcacct tatgaacccc gagtatgtcc ccaaaccgtg ctgtgcgcca 1440
actgaactca gtgctatctc gatgctgtac cttgacgaga atgaaaaggt tgtactgaaa 1500
aaatacagga atatggttgt aagagcttgt ggatgccact aa 1542

<210> SEQ ID NO 123
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 123
atgccggggc tggggcggag ggcgcagtgg ctgtgctggt ggtgggggct gctgtgcagc 60
tgctgcgggc ccccgccgct gcggccgccc ttgcccgctg ccgcggccgc cgccgccggg 120
gggcagctgc tgggggacgg cgggagcccc ggccgcacgg agcagccgcc gccgtcgccg 180
cagtcctcct cgggcttcct gtaccggcgg ctcaagacgc aggagaagcg ggagatgcag 240
aaggagatct tgtcggtgct ggggctcccg caccggcccc ggcccctgca cggcctccaa 300
cagccgcagc cccggcgct ccggcagcag gaggagcagc agcagcagca gcagctgcct 360
cgcggagagc cccctcccgg gcgactgaag tccgcgcccc tcttcatgct ggatctgtac 420
aacgccctgt ccgccgacaa cgacgaggac ggggcgtcgg agggggagag gcagcagtcc 480
tggccccacg aagcagccag ctcgtcccag cgtcggcagc cgcccccggg cgccgcgcac 540
ccgctcaacc gcaagagcct tctggccccc ggatctggca gcggcggcgc gtccccactg 600
accagcgcgc aggacagcgc cttcctcaac gacgcggaca tggtcatgag ctttgtgaac 660
ctggtggagt acgacaagga gttctcccct cgtcagcgac accacaaaga gttcaagttc 720
aacttatccc agattcctga gggtgaggtg gtgacggctg cagaattccg catctacaag 780
gactgtgtta tggggagttt taaaaaccaa acttttctta tcagcattta tcaagtctta 840
caggagcatc agcacagaga ctctgacctg tttttgttgg acacccgtgt agtatgggcc 900
tcagaagaag gctggctgga atttgacatc acggccacta gcaatctgtg ggttgtgact 960
ccacagcata acatggggct tcagctgagc gtggtgacaa gggatggagt ccacgtccac 1020
ccccgagccg caggcctggt gggcagagac ggcccttacg acaagcagcc cttcatggtg 1080
gctttcttca aagtgagtga ggtgcacgtg cgcaccacca ggtcagcctc cagccggcgc 1140
cgacaacaga gtcgtaatcg ctctacccag tcccaggacg tggcgcgggt ctccagtgct 1200
tcagattaca acagcagtga attgaaaaca gcctgcagga agcatgagct gtatgtgagt 1260
ttccaagacc tgggatggca ggactggatc attgcaccca agggctatgc tgccaattac 1320
tgtgatggag aatgctcctt cccactcgcc gatcacctga atgcaaccaa ccacgcgatt 1380
gtgcagacct tggttcacct tatgaacccc gagtatgtcc ccaaaccgtg ctgtgcgcca 1440
actaagctaa atgccatctc ggttctttac tttgatgaca actccaatgt cattctgaaa 1500
aaatacagga atatggttgt aagagcttgt ggatgccact aa 1542

```
<210> SEQ ID NO 124
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124

atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc cccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcaaga ggcatgagct gtatgtgagt   1260

ttccaagacc tgggatggca ggactggatc attgcaccca agggctatgc tgccaattac   1320

tgtgatggag aatgctcctt cccactcaac gcacacatga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542


<210> SEQ ID NO 125
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 125

atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120
```

```
gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcaaga ggcatgagct gtatgtgagt   1260

ttccaagacc tgggatggca ggactggatc attgcaccca agggctatgc tgccaattac   1320

tgtgatggag aatgctcctt cccactcgcc gatcacctga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

<210> SEQ ID NO 126
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126

```
atgccggggc tggggcggag ggcgcagtgg ctgtgctggt ggtgggggct gctgtgcagc     60

tgctgcgggc cccgccgct gcggccgccc ttgcccgctg ccgcggccgc cgccgccggg    120

gggcagctgc tgggggacgg cgggagcccc ggccgcacgg agcagccgcc gccgtcrccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600
```

```
accagcgcgc aggacagcgc cttcctcaac gacgcggaca tggtcatgag ctttgtgaac    660
ctggtggagt acgacaagga gttctcccct cgtcagcgac accacaaaga gttcaagttc    720
aacttatccc agattcctga gggtgaggtg gtgacggctg cagaattccg catctacaag    780
gactgtgtta tggggagttt taaaaaccaa acttttctta tcagcattta tcaagtctta    840
caggagcatc agcacagaga ctctgacctg tttttgttgg acacccgtgt agtatgggcc    900
tcagaagaag gctggctgga atttgacatc acggccacta gcaatctgtg ggttgtgact    960
ccacagcata acatggggct tcagctgagc gtggtgacaa gggatggagt ccacgtccac   1020
ccccgagccg caggcctggt gggcagagac ggcccttacg ataagcagcc cttcatggtg   1080
gctttcttca aagtgagtga ggtccacgtg cgcaccacca ggtcagcctc cagccggcgc   1140
cgacaacaga gtcgtaatcg ctctacccag tcccaggacg tggcgcgggt ctccagtgct   1200
tcagattaca acagcagtga attgaaaaca gcctgcaaga ggcatgagct gtatgtgagt   1260
ttccaagacc tgggatggca ggactggatc attgcaccca agggctatgc tgccaattac   1320
tgtgatggag aatgctcctt ccctctggct gatcatctga actccactaa tcatgccatt   1380
gtgcagacct tggttaactc tgttaacccc gagtatgtcc ccaaaccgtg ctgtgcgcca   1440
actaagctaa atgccatctc ggttctttac tttgatgaca actccaatgt cattctgaaa   1500
aaatacagga atatggttgt aagagcttgt ggatgccact aa                      1542
```

<210> SEQ ID NO 127
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127

```
atgccggggc tggggcggag ggcgcagtgg ctgtgctggt ggtgggggct gctgtgcagc     60
tgctgcgggc ccccgccgct gcggccgccc ttgcccgctg ccgcggccgc cgccgccggg    120
gggcagctgc tgggggacgg cgggagcccc ggccgcacgg agcagccgcc gccgtcgccg    180
cagtcctcct cgggcttcct gtaccggcgg ctcaagacgc aggagaagcg ggagatgcag    240
aaggagatct tgtcggtgct ggggctcccg caccggcccc ggcccctgca cggcctccaa    300
cagccgcagc cccggcgct ccggcagcag gaggagcagc agcagcagca gcagctgcct    360
cgcggagagc cccctcccgg gcgactgaag tccgcgcccc tcttcatgct ggatctgtac    420
aacgccctgt ccgccgacaa cgacgaggac ggggcgtcgg agggggagag gcagcagtcc    480
tggccccacg aagcagccag ctcgtcccag cgtcggcagc cgcccccggg cgccgcgcac    540
ccgctcaacc gcaagagcct tctggccccc ggatctggca gcggcggcgc gtccccactg    600
accagcgcgc aggacagcgc cttcctcaac gacgcggaca tggtcatgag ctttgtgaac    660
ctggtggagt acgacaagga gttctcccct cgtcagcgac accacaaaga gttcaagttc    720
aacttatccc agattcctga gggtgaggtg gtgacggctg cagaattccg catctacaag    780
gactgtgtta tggggagttt taaaaaccaa acttttctta tcagcattta tcaagtctta    840
caggagcatc agcacagaga ctctgacctg tttttgttgg acacccgtgt agtatgggcc    900
tcagaagaag gctggctgga atttgacatc acggccacta gcaatctgtg ggttgtgact    960
ccacagcata acatggggct tcagctgagc gtggtgacaa gggatggagt ccacgtccac   1020
```

```
ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260

ttccaagacc tgggatggca ggactggatc attgcaccca agggctatgc tgccaattac   1320

tgtgatggag aatgctcctt cccactcgcc gatcacctga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

```
<210> SEQ ID NO 128
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128
```

```
atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc cccggcgct ccggcagcag gaggagcagc agcagcagca gcagctgcct     360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcaaga ggcatgagct gtatgtgagt   1260

ttccaagacc tgggatggca ggactggatc attgcaccca agggctatgc tgccaattac   1320

tgtgatggag aatgctcctt cccactcgcc gatcacctga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500
```

```
aaatacagga atatggttgt aagagcttgt ggatgccact aa                    1542


<210> SEQ ID NO 129
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

atgccggggc tggggcggag ggcgcagtgg ctgtgctggt ggtgggggct gctgtgcagc     60

tgctgcgggc ccccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg acaagcagcc cttcatggtg   1080

gctttcttca aagtgagtga ggtgcacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcaaga ggcatgagct gtatgtgagt   1260

ttccaagacc tgggatggca ggactggatc attgcaccca agggctatgc tgccaattac   1320

tgtgatggag aatgctcctt cccactcaac gcacacatga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                    1542


<210> SEQ ID NO 130
<211> LENGTH: 1539
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
```

```
atgccggggc tggggcggag ggcgcagtgg ctgtgctggt ggtgggggct gctgtgcagc      60
tgctgcgggc ccccgccgct gcggccgccc ttgcccgctg ccgcggccgc cgccgccggg     120
gggcagctgc tgggggacgg cgggagcccc ggccgcacgg agcagccgcc gccgtcgccg     180
cagtcctcct cgggcttcct gtaccggcgg ctcaagacgc aggagaagcg ggagatgcag     240
aaggagatct tgtcggtgct ggggctcccg caccggcccc ggcccctgca cggcctccaa     300
cagccgcagc cccggcgct ccggcagcag gaggagcagc agcagcagca gcagctgcct     360
cgcggagagc cccctcccgg gcgactgaag tccgcgcccc tcttcatgct ggatctgtac     420
aacgccctgt ccgccgacaa cgacgaggac ggggcgtcgg agggggagag gcagcagtcc     480
tggccccacg aagcagccag ctcgtcccag cgtcggcagc cgcccccggg cgccgcgcac     540
ccgctcaacc gcaagagcct tctggccccc ggatctggca gcggcggcgc gtccccactg     600
accagcgcgc aggacagcgc cttcctcaac gacgcggaca tggtcatgag ctttgtgaac     660
ctggtggagt acgacaagga gttctcccct cgtcagcgac accacaaaga gttcaagttc     720
aacttatccc agattcctga gggtgaggtg gtgacggctg cagaattccg catctacaag     780
gactgtgtta tggggagttt taaaaaccaa acttttctta tcagcattta tcaagtctta     840
caggagcatc agcacagaga ctctgacctg tttttgttgg acacccgtgt agtatgggcc     900
tcagaagaag gctggctgga atttgacatc acggccacta gcaatctgtg ggttgtgact     960
ccacagcata acatggggct tcagctgagc gtggtgacaa gggatggagt ccacgtccac    1020
ccccgagccg caggcctggt gggcagagac ggcccttacg ataagcagcc cttcatggtg    1080
gctttcttca aagtgagtga ggtccacgtg cgcaccacca ggtcagcctc cagccggcgc    1140
cgacaacaga gtcgtaatcg ctctacccag tcccaggacg tggcgcgggt ctccagtgct    1200
tcagattaca acagcagtga attgaaaaca gcctgcaaga ggcatgagct gtatgtgagt    1260
ttccaagacc tgggatggca ggactggatc attgcaccca agggctatgc tgccaattac    1320
tgtcacggag aatgcccttt tcctctggct gatcatctga actccactaa tcatgccatt    1380
gtgcagacct tggttaactc tgttaactct aagattccta aggcatgctg tgtcccaact    1440
aagctaaatg ccatctcggt tctttacttt gatgacaact ccaatgtcat tctgaaaaaa    1500
tacaggaata tggttgtaag agcttgtgga tgccactaa                            1539
```

```
<210> SEQ ID NO 131
<211> LENGTH: 1287
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
```

```
atgtgtcctg gcgctctgtg ggtggccctg cctctgctgt ctctgctggc cggcagcctg      60
cagggcaagc ctctgcagtc ctggggcaga ggctccgctg gcggcaatgc tcacagccct     120
ctgggagtgc ctggcggcgg actgcccgag cacaccttca acctgaagat gttcctggaa     180
aacgtgaagg tggacttcct gcggtccctg aacctgtccg gcgtgcccag ccaggacaag     240
acccgggtgg aacccccca gtacatgatc gacctgtaca accggtacac ctccgacaag     300
tccaccaccc ccgcctccaa catcgtgcgg tccttcagca tggaagatgc catctccatt     360
accgccaccg aggacttccc atttcagaag cacatcctgc tgttcaacat ctccatcccc     420
cggcacgagc agatcaccag agccgagctg cggctgtacg tgtcctgcca gaaccacgtg     480
```

```
gacccctccc acgacctgaa gggctccgtg gtgatctacg acgtgctgga cggcaccgac    540

gcctgggact ccgctaccga gacaaagacc ttcctggtgt cccaggatat ccaggacgag    600

ggctgggaga cactggaagt gtcctccgcc gtgaagagat gggtgcgatc cgactccacc    660

aagtccaaga acaagctgga agtgaccgtg gaatcccacc ggaagggctg cgacaccctg    720

gacatctccg tgcccccctgg ctcccggaac ctgcccttct tcgtggtgtt ctccaacgac    780

cactcctccg gcaccaaaga gacacggctg gaactgagag agatgatctc ccacgagcag    840

gaatccgtcc tgaagaagct gtccaaggac ggctccaccg aggccggcga gtcctctcac    900

gaagaggaca cagacggcca cgtggcagct ggctctaccc tggccagacg gaagcggtcc    960

gccggagctg gctcccactg ccagaaaacc tccctgagag tgaacttcga ggacatcggc   1020

tgggacagct ggatcattgc ccccaaagag tacgaggcct acgagtgcca cggcgagtgc   1080

cccttccccc tggccgacca cctgaactcc accaaccacg ccatcgtgca gaccctggtg   1140

aactccgtga actccaaaat ccccaaggcc tgctgcgtgc ccaccaagct gtcccccatc   1200

agcgtgctgt acaaggacga catgggcgtg ccaaccctga agtaccacta cgagggcatg   1260

tccgtggccg agtgtggctg ccggtga                                       1287
```

```
<210> SEQ ID NO 132
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132

atgtgtcctg gcgctctgtg ggtggccctg cctctgctgt ctctgctggc cggcagcctg     60

cagggcaagc ctctgcagtc ctggggcaga ggctccgctg gcggcaatgc tcacagccct    120

ctgggagtgc ctggcggcgg actgcccgag cacaccttca acctgaagat gttcctggaa    180

aacgtgaagg tggacttcct gcggtccctg aacctgtccg gcgtgcccag ccaggacaag    240

acccgggtgg aacccccccca gtacatgatc gacctgtaca accggtacac ctccgacaag    300

tccaccaccc ccgcctccaa catcgtgcgg tccttcagca tggaagatgc catctccatt    360

accgccaccg aggacttccc atttcagaag cacatcctgc tgttcaacat ctccatcccc    420

cggcacgagc agatcaccag agccgagctg cggctgtacg tgtcctgcca gaaccacgtg    480

gacccctccc acgacctgaa gggctccgtg gtgatctacg acgtgctgga cggcaccgac    540

gcctgggact ccgctaccga gacaaagacc ttcctggtgt cccaggatat ccaggacgag    600

ggctgggaga cactggaagt gtcctccgcc gtgaagagat gggtgcgatc cgactccacc    660

aagtccaaga acaagctgga agtgaccgtg gaatcccacc ggaagggctg cgacaccctg    720

gacatctccg tgcccccctgg ctcccggaac ctgcccttct tcgtggtgtt ctccaacgac    780

cactcctccg gcaccaaaga gacacggctg gaactgagag agatgatctc ccacgagcag    840

gaatccgtcc tgaagaagct gtccaaggac ggctccaccg aggccggcga gtcctctcac    900

gaagaggaca cagacggcca cgtggcagct ggctctaccc tggccagacg gaagcggtcc    960

gccggagctg gctcccactg ccagaaaacc tccctgagag tgaacttcga ggacatcggc   1020

tgggacagct ggatcattgc ccccaaagag tacgaggcct acgagtgcga cggcgagtgc   1080

tccttccccc tgaacgccca catgaacgcc accaaccacg ccatcgtgca gaccctggtg   1140
```

```
cacctgatga accccgagta cgtgcccaag ccctgctgcg cccccaccaa gctgtccccc   1200

atcagcgtgc tgtacaagga cgacatgggc gtgccaaccc tgaagtacca ctacgagggc   1260

atgtccgtgg ccgagtgtgg ctgccggtga                                    1290
```

<210> SEQ ID NO 133
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 133

```
atgccggggc tggggcggag ggcgcagtgg ctgtgctggt ggtgggggct gctgtgcagc     60

tgctgcgggc cccgccgct gcggccgccc ttgcccgctg ccgcggccgc cgccgccggg    120

gggcagctgc tgggggacgg cgggagcccc ggccgcacgg agcagccgcc gccgtcgccg    180

cagtcctcct cgggcttcct gtaccggcgg ctcaagacgc aggagaagcg ggagatgcag    240

aaggagatct tgtcggtgct ggggctcccg caccggcccc ggcccctgca cggcctccaa    300

cagccgcagc ccccggcgct ccggcagcag gaggagcagc agcagcagca gcagctgcct    360

cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgccccgggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg ataagcagcc cttcatggtg   1080

gctttcttca aagtgagtga ggtccacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260

ttccaagacc tgggatggca ggactggatc attgcaccca agggctatgc tgccaattac   1320

tgtgatggag aatgctcctt cccactcaac gcacacatga atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

<210> SEQ ID NO 134
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134

```
atgccggggc tggggcggag ggcgcagtgg ctgtgctggt ggtgggggct gctgtgcagc     60
tgctgcgggc ccccgccgct gcggccgccc ttgcccgctg ccgcggccgc cgccgccggg    120
gggcagctgc tgggggacgg cgggagcccc ggccgcacgg agcagccgcc gccgtcgccg    180
cagtcctcct cgggcttcct gtaccggcgg ctcaagacgc aggagaagcg ggagatgcag    240
aaggagatct tgtcggtgct ggggctcccg caccggcccc ggcccctgca cggcctccaa    300
cagccgcagc ccccggcgct ccggcagcag gaggagcagc agcagcagca gcagctgcct    360
cgcggagagc cccctcccgg gcgactgaag tccgcgcccc tcttcatgct ggatctgtac    420
aacgccctgt ccgccgacaa cgacgaggac ggggcgtcgg agggggagag gcagcagtcc    480
tggccccacg aagcagccag ctcgtcccag cgtcggcagc cgcccccggg cgccgcgcac    540
ccgctcaacc gcaagagcct tctggccccc ggatctggca gcggcggcgc gtccccactg    600
accagcgcgc aggacagcgc cttcctcaac gacgcggaca tggtcatgag ctttgtgaac    660
ctggtggagt acgacaagga gttctcccct cgtcagcgac accacaaaga gttcaagttc    720
aacttatccc agattcctga gggtgaggtg gtgacggctg cagaattccg catctacaag    780
gactgtgtta tggggagttt taaaaaccaa acttttctta tcagcattta tcaagtctta    840
caggagcatc agcacagaga ctctgacctg tttttgttgg acacccgtgt agtatgggcc    900
tcagaagaag gctggctgga atttgacatc acggccacta gcaatctgtg ggttgtgact    960
ccacagcata acatggggct tcagctgagc gtggtgacaa gggatggagt ccacgtccac   1020
cccccgagccg caggcctggt gggcagagac ggcccttacg ataagcagcc cttcatggtg  1080
gctttcttca aagtgagtga ggtccacgtg cgcaccacca ggtcagcctc cagccggcgc   1140
cgacaacaga gtcgtaatcg ctctacccag tcccaggacg tggcgcgggt ctccagtgct   1200
tcagattaca acagcagtga attgaaaaca gcctgcagga agcatgagct gtatgtgagt   1260
ttccaagacc tgggatggca ggactggatc attgcaccca agggctatgc tgccaattac   1320
tgtgatggag aatgctcctt cccactcaac gcagccatga atgcaaccaa ccacgcgatt   1380
gtgcagacct tggttcacct tatgaacccc gagtatgtcc ccaaaccgtg ctgtgcgcca   1440
actaagctaa atgccatctc ggttctttac tttgatgaca actccaatgt cattctgaaa   1500
aaatacagga atatggttgt aagagcttgt ggatgccact aa                      1542
```

<210> SEQ ID NO 135
<211> LENGTH: 1542
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 135

```
atgccggggc tggggcggag ggcgcagtgg ctgtgctggt ggtgggggct gctgtgcagc     60
tgctgcgggc ccccgccgct gcggccgccc ttgcccgctg ccgcggccgc cgccgccggg    120
gggcagctgc tgggggacgg cgggagcccc ggccgcacgg agcagccgcc gccgtcgccg    180
cagtcctcct cgggcttcct gtaccggcgg ctcaagacgc aggagaagcg ggagatgcag    240
aaggagatct tgtcggtgct ggggctcccg caccggcccc ggcccctgca cggcctccaa    300
cagccgcagc ccccggcgct ccggcagcag gaggagcagc agcagcagca gcagctgcct    360
```

```
cgcggagagc cccctcccgg gcgactgaag tccgcgcccc tcttcatgct ggatctgtac    420

aacgccctgt ccgccgacaa cgacgaggac ggggcgtcgg agggggagag gcagcagtcc    480

tggccccacg aagcagccag ctcgtcccag cgtcggcagc cgcccccggg cgccgcgcac    540

ccgctcaacc gcaagagcct tctggccccc ggatctggca gcggcggcgc gtccccactg    600

accagcgcgc aggacagcgc cttcctcaac gacgcggaca tggtcatgag ctttgtgaac    660

ctggtggagt acgacaagga gttctcccct cgtcagcgac accacaaaga gttcaagttc    720

aacttatccc agattcctga gggtgaggtg gtgacggctg cagaattccg catctacaag    780

gactgtgtta tggggagttt taaaaaccaa acttttctta tcagcattta tcaagtctta    840

caggagcatc agcacagaga ctctgacctg tttttgttgg acacccgtgt agtatgggcc    900

tcagaagaag gctggctgga atttgacatc acggccacta gcaatctgtg ggttgtgact    960

ccacagcata acatggggct tcagctgagc gtggtgacaa gggatggagt ccacgtccac   1020

ccccgagccg caggcctggt gggcagagac ggcccttacg ataagcagcc cttcatggtg   1080

gctttcttca aagtgagtga ggtccacgtg cgcaccacca ggtcagcctc cagccggcgc   1140

cgacaacaga gtcgtaatcg ctctacccag tcccaggacg tggcgcgggt ctccagtgct   1200

tcagattaca acagcagtga attgaaaaca gcctgcagga agcatgagct gtatgtgagt   1260

ttccaagacc tgggatggca ggactggatc attgcaccca agggctatgc tgccaattac   1320

tgtgatggag aatgctcctt cccactcaac gcacacctca atgcaaccaa ccacgcgatt   1380

gtgcagacct tggttcacct tatgaacccc gagtatgtcc ccaaaccgtg ctgtgcgcca   1440

actaagctaa atgccatctc ggttctttac tttgatgaca actccaatgt cattctgaaa   1500

aaatacagga atatggttgt aagagcttgt ggatgccact aa                      1542
```

<210> SEQ ID NO 136
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 136

```
atggtggccg ggacccgctg tcttctagcg ttgctgcttc cccaggtcct cctgggcggc     60

gcggctggcc tcgttccgga gctgggccgc aggaagttcg cggcggcgtc gtcgggccgc    120

ccctcatccc agccctctga cgaggtcctg agcgagttcg agttgcggct gctcagcatg    180

ttcggcctga aacagagacc cacccccagc agggacgccg tggtgccccc ctacatgcta    240

gacctgtatc gcaggcactc aggtcagccg ggctcacccg ccccagacca ccggttggag    300

agggcagcca gccgagccaa cactgtgcgc agcttccacc atgaagaatc tttggaagaa    360

ctaccagaaa cgagtgggaa aacaacccgg agattcttct ttaatttaag ttctatcccc    420

acggaggagt ttatcacctc agcagagctt caggttttcc gagaacagat gcaagatgct    480

ttaggaaaca atagcagttt ccatcaccga attaatattt atgaaatcat aaaacctgca    540

acagccaact cgaaattccc cgtgaccaga cttttggaca ccaggttggt gaatcagaat    600

gcaagcaggt gggaaagttt tgatgtcacc cccgctgtga tgcggtggac tgcacaggga    660

cacgccaacc atggattcgt ggtggaagtg gcccacttgg aggagaaaca aggtgtctcc    720

aagagacatg ttaggataag caggtctttg caccaagatg aacacagctg gtcacagata    780

aggccattgc tagtaacttt tggccatgat ggaaaagggc atcctctcca caaaagagaa    840
```

```
aaacgtcaag ccaaacacaa acagcggaaa cgccttaagt ccagctgtaa gagacaccct    900

ttgtacgtgg acttcagtga cgtggggtgg aatgactgga ttgtggctcc cccggggtat    960

cacgcctttt actgcgatgg agaatgctcc ttcccactca acgcacacat gaatgcaacc   1020

aaccacgcga ttgtgcagac cttggttcac cttatgaacc ccgagtatgt ccccaaaccg   1080

tgctgtgcgc ccaccaagct gagacccatg tccatgttgt actatgatga tggtcaaaac   1140

atcatcaaaa aggacattca gaacatgatc gtggaggagt gtgggtgctc atag         1194
```

<210> SEQ ID NO 137
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 137

```
atggtggctg gcaccagatg tctgctggcc ctgctgctgc cccaggtgct gctgggcgga     60

gctgctggac tggtgcccga gctgggcaga agaaagttcg ccgctgcctc ctctggccgg    120

ccttccagcc agccttccga cgaggtgctg tccgagttcg agctgcggct gctgtccatg    180

ttcggcctga agcagcggcc caccccttct agggacgccg tggtgccccc ctacatgctg    240

gacctgtacc ggcggcactc cggccagcct ggatctcctg cccccgacca cagactggaa    300

agagccgcct cccgggccaa caccgtgcgg tctttccacc acgaggaatc cctggaagaa    360

ctgcccgaga catccggcaa gaccacccgg cggttctttt tcaacctgtc atccatcccc    420

accgaagagt tcatcacctc cgccgagctg caggtgttcc gcgagcagat gcaggacgcc    480

ctgggcaaca actcctcctt ccaccaccgg atcaacatct acgagatcat caagcccgcc    540

accgccaact ccaagttccc cgtgacccgg ctgctggaca cccggctggt gaaccagaac    600

gcctccagat gggagtcctt cgacgtgacc cctgccgtga tgagatggac cgcccagggc    660

cacgccaacc acggctttgt ggtggaagtg gcccacctgg aagagaagca gggcgtgtcc    720

aagcggcacg tgcggatctc tcggtccctg caccaggacg agcacagctg gtcccagatc    780

cggcccctgc tggtgacatt cggccacgat ggcaagggcc acccccctgca caagagagag    840

aagcggcagg ccaagcacaa gcagcggaag cggctgaagt cctcctgcaa gcggcacccc    900

ctgtacgtgg acttctccga cgtgggctgg aacgactgga tcattgcccc caggggctac    960

gccgccttct actgcgacgg cgagtgctcc ttccccctga acgcccacat gaacgccacc   1020

aaccacgcca tcgtgcagac cctggtgcac ctgatgaacc ccgagtacgt gcccaagcct   1080

tgttgcgccc ccaccaagct gagacccatg tccatgttgt actatgatga tggtcaaaac   1140

atcatcaaaa aggacattca gaacatgatc gtggaggagt gtgggtgctc atag         1194
```

<210> SEQ ID NO 138
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
atggtggccg ggacccgctg tcttctagcg ttgctgcttc cccaggtcct cctgggcggc     60
```

```
gcggctggcc tcgttccgga gctgggccgc aggaagttcg cggcggcgtc gtcgggccgc    120
ccctcatccc agccctctga cgaggtcctg agcgagttcg agttgcggct gctcagcatg    180
ttcggcctga aacagagacc cacccccagc agggacgccg tggtgccccc ctacatgcta    240
gacctgtatc gcaggcactc aggtcagccg ggctcacccg ccccagacca ccggttggag    300
agggcagcca gccgagccaa cactgtgcgc agcttccacc atgaagaatc tttggaagaa    360
ctaccagaaa cgagtgggaa aacaacccgg agattcttct ttaatttaag ttctatcccc    420
acggaggagt ttatcacctc agcagagctt caggttttcc gagaacagat gcaagatgct    480
ttaggaaaca atagcagttt ccatcaccga attaatattt atgaaatcat aaaacctgca    540
acagccaact cgaaattccc cgtgaccaga cttttggaca ccaggttggt gaatcagaat    600
gcaagcaggt gggaaagttt tgatgtcacc cccgctgtga tgcggtggac tgcacaggga    660
cacgccaacc atggattcgt ggtggaagtg gcccacttgg aggagaaaca aggtgtctcc    720
aagagacatg ttaggataag caggtctttg caccaagatg aacacagctg gtcacagata    780
aggccattgc tagtaacttt tggccatgat ggaaaagggc atcctctcca caaaagagaa    840
aaacgtcaag ccaaacacaa acagcggaaa cgccttaagt ccagctgtaa gagacaccct    900
ttgtacgtgg acttcagtga cgtggggtgg aatgactgga ttgtggctcc cccggggtat    960
cacgcctttt actgcgatgg agaatgctcc ttcccactca acgcacacat gaatgcaacc   1020
aaccacgcga ttgtgcagac cttggttcac cttatgaacc ccgagtatgt ccccaaaccg   1080
tgctgtgcgc caactaagct aaatgccatc tcggttcttt actttgatga caactccaat   1140
gtcattctga aaaaatacag gaatatggtt gtaagagctt gtggatgcca ctaa         1194
```

<210> SEQ ID NO 139
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 139

```
atggtggctg gcaccagatg tctgctggcc ctgctgctgc cccaggtgct gctgggcgga     60
gctgctggac tggtgcccga gctgggcaga agaaagttcg ccgctgcctc ctctggccgg    120
ccttccagcc agccttccga cgaggtgctg tccgagttcg agctgcggct gctgtccatg    180
ttcggcctga agcagcggcc cacccccttct agggacgccg tggtgccccc ctacatgctg    240
gacctgtacc ggcggcactc cggccagcct ggatctcctg cccccgacca cagactggaa    300
agagccgcct cccgggccaa caccgtgcgg tctttccacc acgaggaatc cctggaagaa    360
ctgcccgaga catccggcaa gaccacccgg cggttctttt tcaacctgtc atccatcccc    420
accgaagagt tcatcacctc cgccgagctg caggtgttcc gcgagcagat gcaggacgcc    480
ctgggcaaca actcctcctt ccaccaccgg atcaacatct acgagatcat caagcccgcc    540
accgccaact ccaagttccc cgtgacccgg ctgctggaca cccggctggt gaaccagaac    600
gcctccagat gggagtcctt cgacgtgacc cctgccgtga tgagatggac cgcccagggc    660
cacgccaacc acggctttgt ggtggaagtg gcccacctgg aagagaagca gggcgtgtcc    720
aagcggcacg tgcggatctc tcggtccctg caccaggacg agcacagctg gtcccagatc    780
cggcccctgc tggtgacatt cggccacgat ggcaagggcc accccctgca caagagagag    840
aagcggcagg ccaagcacaa gcagcggaag cggctgaagt cctcctgcaa gcggcacccc    900
```

-continued

```
ctgtacgtgg acttctccga cgtgggctgg aacgactgga tcattgcccc caggggctac     960

gccgccttct actgcgacgg cgagtgctcc ttcccccctga acgcccacat gaacgccacc   1020

aaccacgcca tcgtgcagac cctggtgcac ctgatgaacc ccgagtacgt gcccaagcct   1080

tgttgcgccc caactaagct aaatgccatc tcggttcttt actttgatga caactccaat   1140

gtcattctga aaaaatacag gaatatggtt gtaagagctt gtggatgcca ctaa         1194
```

DESIGNER OSTEOGENIC PROTEINS

CROSS-REFERENCE TO RELATED APPLICATIONS

This application claims the benefit of priority under 35 U.S.C. §119(e) to U.S. Provisional Patent Application No. 61/375,636, filed Aug. 20, 2010, which is herein incorporated in its entirety by reference.

SEQUENCE LISTING

The instant application contains a Sequence Listing which has been submitted electronically in ASCII format and is hereby incorporated by reference in its entirety. Said ASCII copy, created on Nov. 5, 2014, is named 7362172001_SL.txt and is 225,131 bytes in size.

FIELD OF THE INVENTION

This application relates to the field of osteogenic proteins, methods of making improved osteogenic proteins, and methods of treating patients with osteogenic proteins.

BACKGROUND OF THE INVENTION

The cystine knot cytokine superfamily is divided into subfamilies, which include, the transforming growth factor β (TGFβ) proteins, the glycoprotein hormones, the platelet-derived growth factor-like (PDGF-like) proteins, nerve growth factors (NGF), and the differential screening-selected gene aberrative in neuroblastoma (DAN) family (e.g., cerberus). In turn, the TGFβ superfamily comprises approximately 43 members, subdivided into three subfamilies: the TGFβs, the activins and the bone morphogenetic/growth differentiation factor proteins (BMP/GDF).

The TGF-β superfamily members contain the canonical cystine knot topology. That is, cystine knots are the result of an unusual arrangement of six cysteine residues. The knot consists of bonds between cysteines 1-4, cysteines 2-5, and the intervening sequence forming a ring, through which the disulfide bond between cysteines 3-6 passes. The active forms of these proteins are homodimers or heterodimers. In each case the monomer topology is stabilized by the cysteine knot and additional cysteines contribute to additional intrachain bonds and/or mediate dimerization with another protein unit. See Kingsley, 1994, Genes Dev. 8:133-146; Lander et al, 2001, Nature 409:860-921.

BMP/GDFs are the most numerous members of the TGF-β protein superfamily. The BMP/GDF subfamily includes, but is not limited to, BMP2, BMP3 (osteogenin), BMP3b (GDF-10), BMP4 (BMP2b), BMP5, BMP6, BMP7 (osteogenic protein-1 or OP1), BMP8 (OP2), BMP8B (OP3), BMP9 (GDF2), BMP10, BMP11 (GDF11), BMP12 (GDF7), BMP13 (GDF6, CDMP2), BMP15 (GDF9), BMP16, GDF1, GDF3, GDF5 (CDMP1; MP52), and GDF8 (myostatin). BMPs are sometimes referred to as Osteogenic Protein (OPs), Growth Differentiation Factors (GDFs), or Cartilage-Derived Morphogenetic Proteins (CDMPs). BMPs are also present in other animal species. Furthermore, there is some allelic variation in BMP sequences among different members of the human population.

BMPs are naturally expressed as pro-proteins comprising a long pro-domain, one or more cleavage sites, and a mature domain. This pro-protein is then processed by the cellular machinery to yield a dimeric mature BMP molecule. The pro-domain is believed to aid in the correct folding and processing of BMPs. Furthermore, in some but not all BMPs, the pro-domain may noncovalently bind the mature domain and may act as a chaperone; as well as an inhibitor (e.g.; Thies et al., Growth Factors 18:251-9 (2001)).

BMP signal transduction is initiated when a BMP dimer binds two type I and two type II serine/threonine kinase receptors. Type I receptors include, but are not limited to, ALK-1 (Activin receptor-Like Kinase 1), ALK-2 (also called ActRIa or ActRI); ALK-3 (also called BMPRIa), and ALK-6 (also called BMPRIb). Type II receptors include, but are not limited to, ActRIIa (also called ActRII). ActRIIb, and BMPRII. The human genome contains 12 members of the receptor serine/threonine kinase family, including 7 type I and 5 type II receptors, all of which are involved in TGF-β signaling (Manning et al., Science 298:1912-34 (2002)), the disclosures of which are hereby incorporated by reference). Thus, there are 12 receptors and 43 superfamily members, suggesting that at least some TGF-β superfamily members bind the same receptor(s). Following BMP binding, the type II receptors phosphorylate the type I receptors, the type I receptors phosphorylate members of the Smad family of transcription factors, and the Smads translocate to the nucleus and activate the expression of a number of genes.

BMPs are among the most numerous members of TGF-β superfamily, and control a diverse set of cellular and developmental processes, such as embryonic pattern formation and tissue specification as well as promoting wound healing and repair processes in adult tissues, BMPs were initially isolated by their ability to induce bone and cartilage formation. BMP signaling is inducible upon bone fracture and related tissue injury, leading to bone regeneration and repair, BMP molecules which have altered affinity for their receptors would have improved biological activity relative to the native proteins. Such BMPs include proteins with increased in vivo activity and may provide potential improved therapeutics for, among other things, tissue regeneration, repair, and the like, by providing greater or altered activity at lower protein levels thereby providing improved protein therapeutics.

SUMMARY OF THE INVENTION

The invention includes a designer BMP protein comprising at least one mutation in at least one type I or type II receptor binding domain, wherein the mutation confers altered binding to the type I or type II BMP receptor compared with the binding to the type I or type II receptor by a corresponding wild type BMP.

In one aspect, the protein is selected from the group consisting of BMP2, BMP4, BMP5, BMP6, BMP7, BMP8 and BMP9.

In another aspect; the protein comprises at least one mutation within: the type II binding domain A; the type II binding domain B; the type I binding domain; and any combination thereof.

The invention also includes a designer osteogenic protein comprising an amino acid sequence comprising at least one mutation in at least one type I or type II receptor binding domain, wherein the mutation confers altered binding to the type I or type II BMP receptor compared with the binding to the type I or type II receptor by wild type BMP2.

In one aspect, the mutation is a mutation within the type II binding domain A wherein said mutation is at least one mutation selected from the group consisting of a mutation at V33, P36, H39, and F41 with respect to the sequence of SEQ ID NO:1.

In another aspect, the is a mutation within the type II binding domain A wherein said mutation is at least one mutation selected from the group consisting of V33I, P36K, P36R, H39A, and F41N with respect to SEQ ID NO:1.

In yet another aspect, the mutation is a mutation within the type II binding domain B wherein said mutation is at least one mutation selected from the group consisting of a mutation at E83, S85, M89, L92, E94, E96, K97, and V99 with respect to the sequence of SEQ ID NO:1.

In a further aspect, the mutation is a mutation within the type II binding domain B wherein said mutation is at least one mutation selected from the group consisting of E83K, 385N, M89V, L92F, E94D, E963, K97N, and V99I with respect to of SEQ ID NO:1.

In another aspect, the mutation is a mutation within the type I binding domain wherein said mutation is at least one mutation selected from the group consisting of a mutation at H44, P48, A52, D53, L55, S57, N68, S69, V70, an insertion of a single amino acid after N71, S72, K73, I74, A77, and V80 with respect to the sequence of SEQ ID NO:1.

In yet another aspect, the mutation is a mutation within the type I binding domain wherein said mutation is at least one mutation selected from the group consisting of H44D, P48S, A52N, D53A, L55M, S57A, N68H, S69L, V70M, insertion of P after N71, S72E, K73Y, I74V, A77P, and V80A with respect to the sequence of SEQ ID NO:1.

In a further aspect, the protein comprises a mutation at each of amino acids H44, P48, A52, D53, L55, S57, N68, S69, V70, insertion of a single amino acid after N71, S72, K73, I74, A77, and V80 with respect to the sequence of SEQ ID NO:1.

In another aspect, the protein comprises a mutation at each of amino acids H44, P48, A52, D53, L55, S57, N68, S69, V70, insertion of a single amino acid after N71, S72, K73, I74, A77, and V80 with respect to the sequence of SEQ ID NO:1 wherein the mutations are H44D, P48S, A52N, D53A, L55M, S57A, N68H, S69L, V90M, insertion of a P after N71, S72E, K73Y, I74V, A77P, and V80A.

In yet another aspect, the protein comprises a mutation at each of amino acids V33, P36, H39, S85, M89, L92, E94, E96, K97, and V99 with respect to the sequence of SEQ ID NO:1.

In another aspect, the protein comprises a mutation at each of amino acids V33. P36, H39, S85, M89, L92, E94, E96, K97, and V99 with respect to the sequence of SEQ ID NO:1, wherein the mutations are V33I, P36K, H39A, S85N, M89, L92F, E94D, E96S, K97N, and V99I.

In a further aspect, the protein comprises a mutation at each of amino acids V33, P36, H39, H44, P48, A52, D53, L55, S57, N68, S69, V70, insertion of a single amino acid after N71, S72, K73, I74, A77, and V80, S85, M89, L92, E94, E96, K97, and V99 with respect to the sequence of SEQ ID NO:1.

In yet another aspect, the protein comprises a mutation at each of amino acids V33, P36, H39, H44, P48, A52, D53, L55, S57, N68, S69, V70, insertion of a single amino acid after N71, S72, K73, I74, A77, and V80, S85, M89, L92, E94, E96, K97, and V99 with respect to the sequence of SEQ. ID NO:1 wherein the mutations are V33I, P36K, H39A, H44D, P48S, A52N, D53A, L55M, S57A, N68H, S69L, V70M, insertion of a P after N71, S72E, K73Y, I74V, A77P, and V80A, S85N, M89, L92F, E94D, E96S, K97N, and V99I.

In yet another aspect, the protein comprises a mutation at each of amino acids V33, P36, H39, H44, P48, A52, D53, L55, S57, N68, S69, V70, insertion of a single amino acid after N71, S72, K73, I74, A77, and V80, S85, M89, L92, E94, E96, K97, and V99 with respect to the sequence of SEQ ID NO:1 wherein the mutations are V33I, P36R, H39A, H44D, P48S, A52N, D53A, L55M, S57A, N68H, S69L, V70M, insertion of a P after N71, S72E, K73Y, I74V, A77P, and V80A, S85N, M89, L92F, E94D, E96S, K97N, and V99I.

In another aspect, the protein binds: the ALK2 receptor with a $K_D$ not greater than about 2 nM; the ALK3 receptor with a $K_D$ not greater than about 2 nM; the ALK6 receptor with a $K_D$ not greater than about 1 nM; the ActRIIA receptor with a $K_D$ not greater than about 2 nM; the ActRIIB receptor with a $K_D$ not greater than about 0.5 nM; and the BMPRIIA receptor with a $K_D$ not greater than about 3.5 nM.

In one aspect, the protein further comprises 1, 2, 3, 4, 5, 6, 7, 8, 9, or 10 amino acid mutations not located within the type I or the type II binding regions.

The invention includes a designer osteogenic protein comprising the amino acid sequence of any one of SEQ ID NOs: 8-73.

The invention includes a designer osteogenic protein comprising the amino acid sequence of SEQ ID NO:12.

The invention includes a designer osteogenic protein comprising the amino acid sequence of SEQ ID NO:14.

The invention includes a designer osteogenic protein comprising the amino acid sequence of SEQ ID NO:36.

The invention includes a designer osteogenic protein comprising the amino acid sequence of SEQ ID NO:37.

The invention includes method of producing a designer BMP protein comprising at least one mutation in at least one type I or type II receptor binding domain, wherein the mutation confers altered binding to the type I or type II BMP receptor compared with the binding to the type I or type II receptor by a corresponding wild type BMP. The method comprises introducing a nucleic acid encoding the protein into a host cell, culturing the cell under conditions where the protein is produced, and purifying the protein.

In one aspect, the nucleic acid comprises a sequence selected from the nucleic acid sequence of any one of SEQ ID NOs:74-139.

The invention includes a designer BMP6 protein comprising an amino acid sequence comprising at least one mutation in at least one type I or type II receptor binding domain, wherein the mutation confers altered binding to the type I or type II BMP receptor compared with the binding to the type I or type II receptor by wild type BMP6.

In one aspect, the mutation is a mutation within the type II binding domain A wherein said mutation is at least one mutation selected from the group consisting of a mutation at I57, K60, G61, A63, N65, Y66, and D68 with respect to the sequence of SEQ ID NO:4.

In another aspect, the mutation is a mutation within the type II binding domain B wherein said mutation is at least one mutation selected from the group consisting of K108, N110, A111, V114, F117, D119, N120, S121, N122, V123, and I124 with respect to the sequence of SEQ ID NO:4.

In yet another aspect, the mutation is a mutation within the type I binding domain wherein said mutation is at least one mutation selected from the group consisting of a mutation at S72, N76, A77, H78, M79, N80, A81, N83, V87, T89, H92, L93, M94, N95, P96, E97, Y98, V99, and P100 with respect to the sequence of SEQ ID NO:4.

In another aspect, the mutation is a mutation at each of amino acid residues I57, K60, G61, A63, N65, Y66, and D68 with respect to the sequence of SEQ ID NO:4.

In a further aspect, the mutation is a mutation at each of amino acid residues K108, N110, A111, V114, F117, D119, N120, S121, N122, V123, and I124 with respect to the amino acid sequence of SEQ ID NO:4.

In yet another aspect, the mutation is a mutation at each of amino acid residues S72, N76, A77, H78, M79, N80, A81, N83, V87, T89, H92, L93, M94, N95, P96, E97, Y98, V99, or P100 with respect to the amino acid sequence of SEQ ID NO:4.

In another aspect, the designer BMP6 protein comprising an amino acid sequence comprising at least one mutation in at least one type I or type II receptor binding domain, wherein the mutation confers altered binding to the type I or type II BMP receptor compared with the binding to the type I or type II receptor by wild type BMP6 further comprises 1, 2, 3, 4, 5, 6, 7, 8, 9, or 10 amino acid mutations not located within the type I or the type II binding domains.

The invention includes an isolated nucleic acid molecule comprising a nucleotide sequence encoding an amino acid sequence selected from the group consisting of the sequence of SEQ ID NOs:8 to 73.

In one aspect, the nucleic acid encodes a protein comprising an amino acid sequence selected from the group consisting of the sequence of SEQ ID NO:12, SEQ ID NO:14, SEQ ID NO:36 and SEQ ID NO:37.

The invention includes an isolated nucleic acid molecule comprising a nucleotide sequence selected from the group consisting of SEQ ID NOs:74 to 139.

In one aspect, the nucleic acid comprises a nucleotide sequence selected from the group consisting of the sequence of SEQ ID NO:78, SEQ ID NO:80, SEQ ID NO:102, and SEQ ID NO:103.

The invention includes a method of producing the designer BMP6 protein comprising an amino acid sequence comprising at least one mutation in at least one type I or type II receptor binding domain, wherein the mutation confers altered binding to the type I or type II BMP receptor compared with the binding to the type I or type II receptor by wild type BMP6. The method comprises introducing a nucleic acid encoding said protein into a host cell, culturing said cell under conditions where said protein is produced, and purifying said protein.

The invention includes a method of treating a bone disease associated with bone loss in a patient in need thereof. The method comprises administering a therapeutically effective amount of a designer BMP protein comprising at least one mutation in at least one type I or type II receptor binding domain, wherein the mutation confers altered binding to the type I or type II BMP receptor compared with the binding to the type I or type II receptor by a corresponding wild type BMP protein to the patient, thereby treating bone disease in the patient.

The invention includes a method of treating fibrosis in a patient in need thereof. The method comprises administering a therapeutically effective amount of a designer BMP protein comprising at least one mutation in at least one type I or type II receptor binding domain, wherein the mutation confers altered binding to the type I or type II BMP receptor compared with the binding to the type I or type II receptor by a corresponding wild type BMP to the patient, thereby treating fibrosis.

The invention includes a method of inducing bone formation in a tissue. The method comprises contacting the tissue with a designer BMP protein comprising at least one mutation in at least one type I or type II receptor binding domain, wherein the mutation confers altered binding to the type I or type II BMP receptor compared with the binding to the type I or type II receptor by a corresponding wild type BMP, thereby inducing bone formation in said tissue.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

Figure 1A:
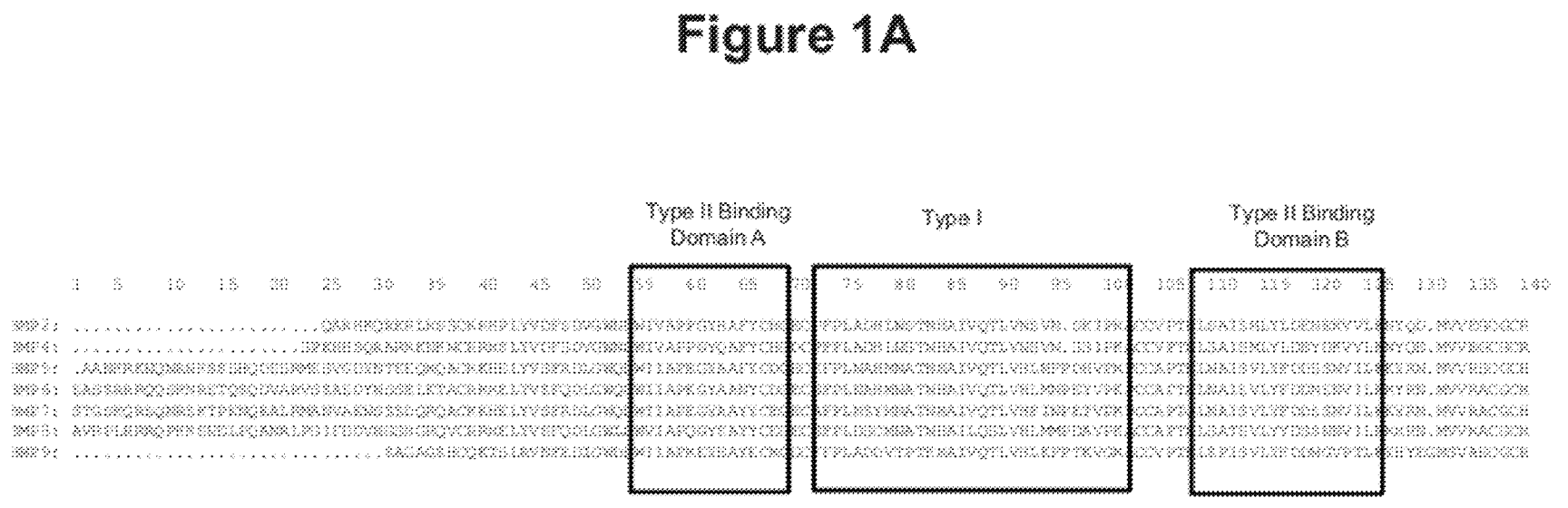
Figure 1B:
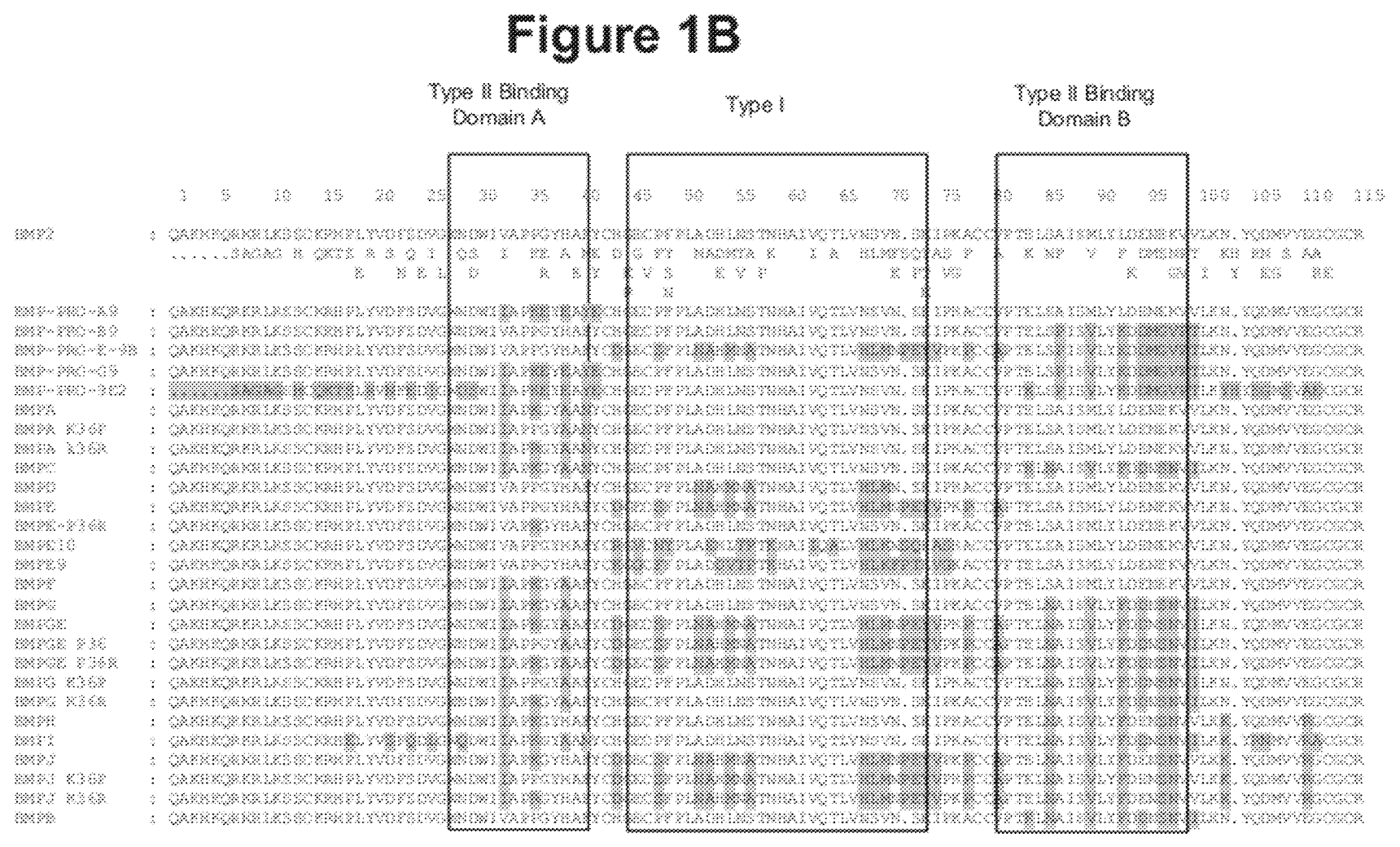

FIG. 1, comprising panels A-C, is a diagram showing the alignment of various wild type and designer BMP amino acid sequences and indicating (by being within a box) the regions of these proteins potentially involved in type I and type II receptor interactions. FIG. 1A shows the amino acid sequence alignment of wild type BMP2 (SEQ ID NO: 1), BMP4 (SEQ ID NO: 2), BMP5 (SEQ ID NO: 3), BMP6 (SEQ ID NO: 4), BMP7 (SEQ ID NO: 5), BMP8 (SEQ ID NO: 6) and BMP9 (SEQ ID NO: 7). FIG. 1B shows the amino acid sequence alignment of various designer BMPs where the corresponding wild type BMP is BMP2. FIG. 1B discloses SEQ ID NOS 1, 142 (consensus sequence), 42-45, 65, 8, 20-21, 10-12, 29, 26, 25, 13-14, 36, 50, 37, 32-33, 15-17, 38-39 and 9, respectively, in order of appearance. FIG. 1C discloses SEQ ID NOS 6, 143 (consensus sequence), 53-56, 67, 144-147, 68-69, 58, 158, 57, 62, 60, 64 and 149, respectively, in order of appearance.

FIG. 4A shows the glycan tether (N-linked glycan at N56) and histidine 54, in the non-doorstop orientation, as well as the interaction of the glycan tether with R16 all in CHO-produced BMP2. FIG. 4B shows the glycan tether (N-linked glycan at N80) and the histidine in the non-doorstop configuration at H78 in BMP6, as well as the R39 corresponding to R16 in BMP2. The sequence alignment of BMP2 (11-KSSCKRHP) (SEQ ID NO: 140) and BMP6 (35-KTACRKHE) (SEQ ID NO: 141) showing the corresponding amino acids between BMP2 and BMP6 is shown along the top of the figure.

FIG. 5A shows a chromatogram showing gradient elution of BMPs using a cellufine sulfate column. FIG. 5B is an image of a Coomassie stained SDS-PAGE (non-reduced on the left and reduced on the right side) gel containing samples of fractions from the cellufine sulfate column step. FIG. 5C shows a chromatogram showing the profile from preparative reversed phase purification step. FIG. 5D is an image of a Coomassie stained SDS-PAGE (non-reduced on the left and reduced on the right) gel of BMP containing samples of the fractions obtained by the preparative reversed phase purification step.

FIG. 9A is a graph showing the amount of ectopic bone (calculated as milligrams of hydroxyapatite; mg HA) as determined by μCT analysis for each limb which was implanted with the indicated BMP (BMP2, BMPE, and BMP2/6) at the dose indicated (0.1 or 0.5 μg). FIG. 9B is a graph showing the amount of ectopic bone (calculated as milligrams of hydroxyapatite) as determined by μCT analysis for each limb which was implanted with the indicated BMP (BMP2, BMPG, BMPA, and BMPF) the dose indicated (0.1 or 0.5 μg). The data presented are from 2 separate experiments.

FIG. 10, comprising panels A-D, shows images of radiographs showing the results of a non-human primate (NHP) fibula osteotomy model at 4 and 8 weeks. Radiographs are shown of the fibulas of 7 representative NHPs that received BMPE and BMPG, respectively, at 0.5 mg/ml (250 μl total BMP delivered/limb). Each NHP received WT BMP2 at the same dose in the contralateral limb.

FIG. 15A shows images of 5-week radiographs obtained in a NHP fibula wedge osteotomy model. FIG. 15A shows images of the fibulas of 4 representative NHPs which received BMP-GER in one limb and WT BMP-2 in the contralateral limb at 0.5 mg/ml (250 μG total BMP delivered/limb) at 5 weeks. FIG. 15B shows uCT images of the same limbs at 10 weeks showing the large calluses of the BMP-GER treated limbs compared with the BMP2-treated contralateral limbs for each animal.

FIG. 17, comprising panels A-C, shows radiographic images of the healing over time of 3 non-human primate's (NHP) fibulas treated with BMP-GER at 0.5 mg/ml and BMP-2 in the contra lateral limb at 1.5 mg/ml using a calcium phosphate based cement as a carrier following the wedge defect model. FIG. 17A, lower panel, shows results for NHP number 1 right arm treated with 1.5 mg/ml BMP-2 as follows: panels 1 and 2 show LAT (lateral) and AP (anterior-posterior) images; respectively, at the initial time point; panels 3 and 4 show LAT and AP images, respectively, at 2 weeks; panels 5 and 6 show LAT and AP images, respectively; at 4 weeks; panels 7 and 8 show LAT and AP images, respectively, at 6 weeks; panels 9 and 10 show LAT and AP images, respectively, at 7 weeks; panels 11 and 12 show LAT and AP images, respectively, at 8 weeks.

DETAILED DESCRIPTION OF THE INVENTION

Figure 1C:
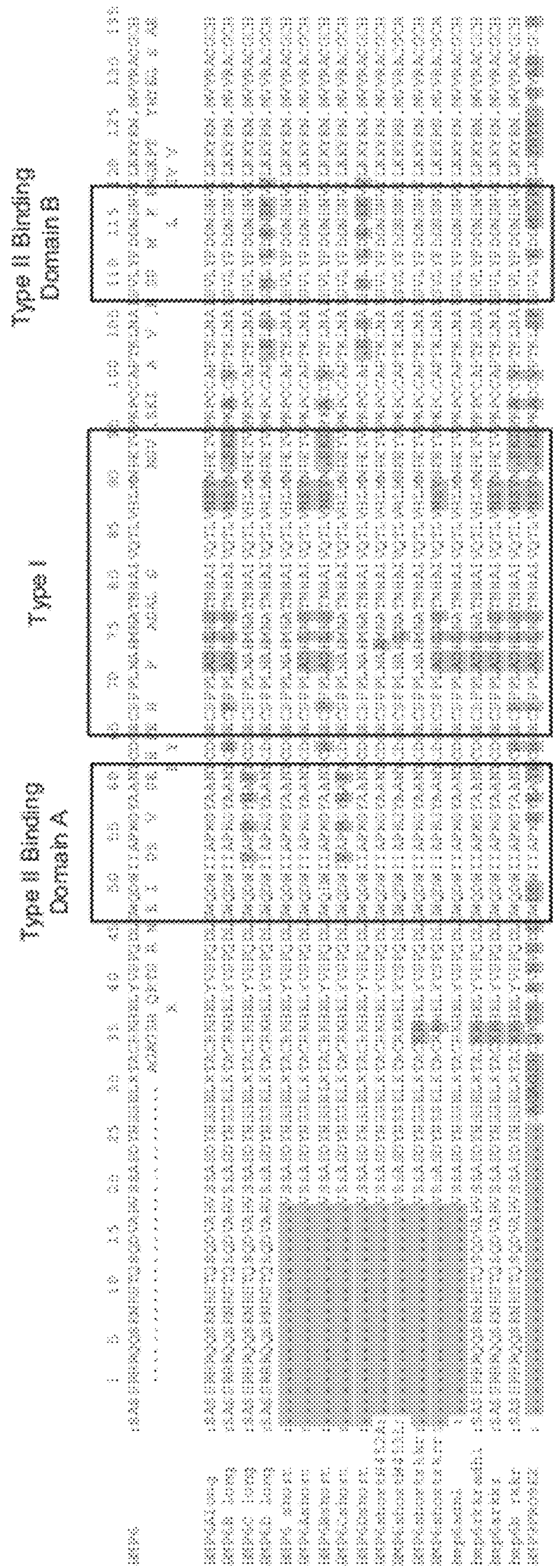
FIG. 1C shows the amino acid sequence alignment of various designer BMP6 molecules where the corresponding wild type BMP is BMP6.
Figure 2:
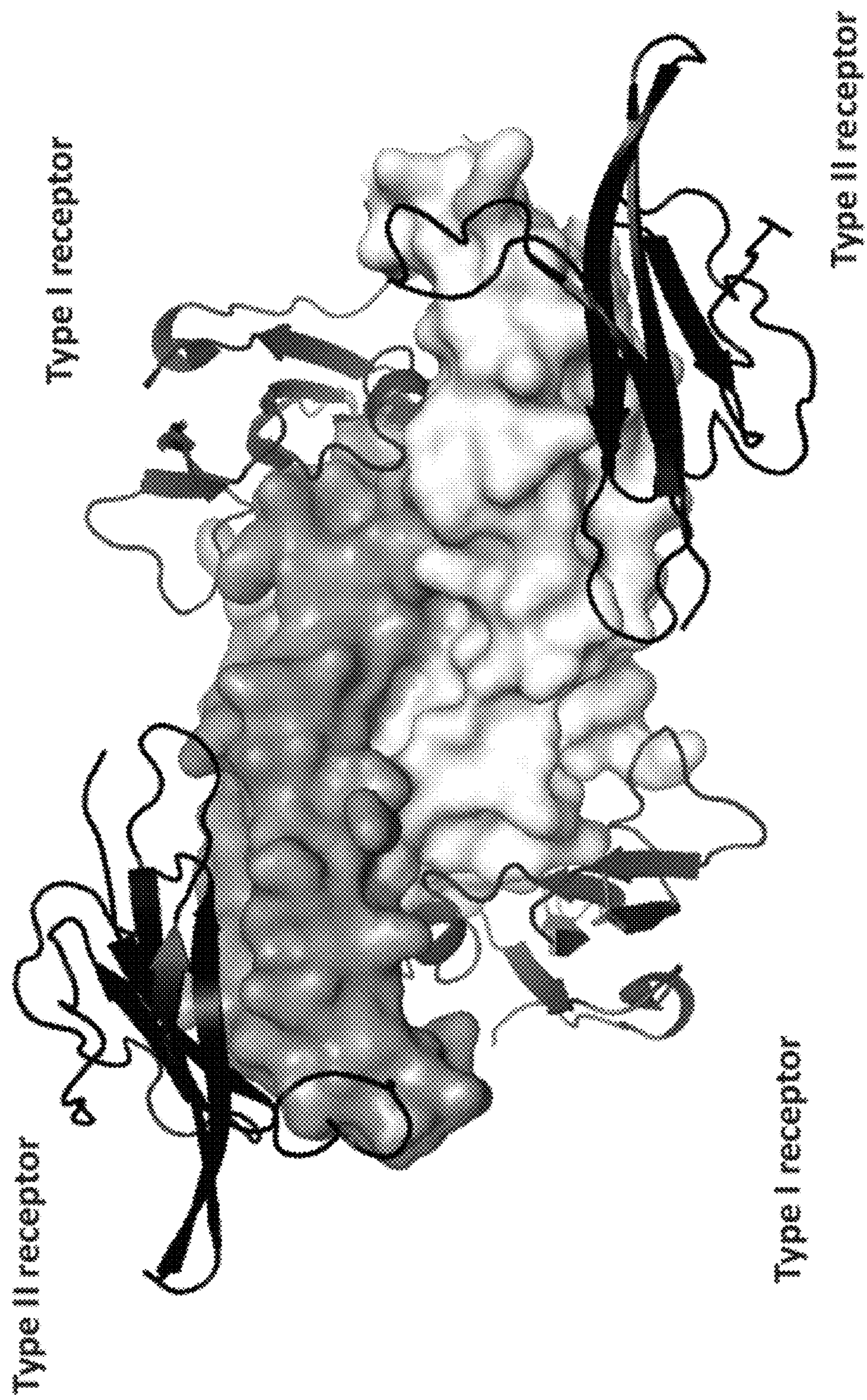
FIG. 2 is an illustration of a structural model showing a wild type BMP2 homodimer binding to two type I and two type II BMP receptors.

This invention relates a "designer" bone morphogenetic protein, referred to herein as "designer BMP," "designer osteogenic protein" and "designer protein." The designer BMPs of the invention may correspond to the amino acid sequences of wild type unmodified BMP, such as, but not limited to, BMP2, BMP4, BMP5, BMP6, BMP8, and BMP9. In particular embodiments, the designer BMPs show altered binding to a type I and/or type II BMP receptor when compared to its corresponding wild type BMP. In further embodiments, the designer BMP may be modified to have altered half-life, immunogenicity, or any pharmacokinetic/pharmacodynamic (PK/PD) parameter when compared to its corresponding BMP.

DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane, *Antibodies: A Laboratory Manual*, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

In this application, the use of "or" means "and/or" unless stated otherwise.

Conventional notation is used herein to portray polypeptide sequences; the left-hand end of a polypeptide sequence is the amino-terminus; the right-hand end of a polypeptide sequence is the carboxyl-terminus. As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference. As used herein, amino acids are represented by the full name thereof, by the three letter code corresponding thereto, or by the one-letter code corresponding thereto, as indicated as follows:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Gys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains; aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-1445 (1992), herein incorporated by reference. A "moderately conservative" replacement is any change having a nonnegative value in the PAM250 log-likelihood matrix.

Preferred amino acid substitutions are those which: (1) reduce susceptibility to proteolysis, (2) reduce susceptibility to oxidation, (3) alter binding affinity for forming protein complexes, and (4) confer modify other physicochemical or functional properties of such analogs. Analogs comprising substitutions, deletions, and/or insertions can include various muteins of a sequence other than the specified peptide sequence. For example, single or multiple amino acid substitutions (preferably conservative amino acid substitutions) may be made in the specified sequence (preferably in the portion of the polypeptide outside the domain(s) forming intermolecular contacts, e.g., outside of the CDRs or the type I or type II receptor binding sites). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W.H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), which are each incorporated herein by reference.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This also includes nucleic acids containing modified bases, for example, thio-uracil, thio-guanine, and fluoro-uracil, or containing carbohydrate, or lipids.

In the context of a nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence.

By "designer BMP nucleic acids," and grammatical equivalents herein is meant nucleic acids that encode designer BMPs.

The terms "protein" and "polypeptide" are used interchangeably herein. These terms refer to a sequential chain of amino acids linked together via peptide bonds. The terms include one or more proteins that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of multiple polypeptides that physically associate with one another, the term "protein" as used herein refers to the multiple polypeptides that are physically coupled and function together as the discrete unit. A protein to be expressed according to the present invention can be a protein therapeutic. A protein therapeutic is a protein that has a biological effect on a region in the body on which it acts or on a region of the body on which it remotely acts via intermediates. Examples of protein therapeutics are discussed in more detail below.

"Designer BMP," as the term is used herein, relates to a BMP protein comprising at least one amino acid mutation compared to a corresponding wild type BMP without the mutation, wherein the designer BMP has detectably altered binding for at least a type I receptor and/or at least one type II receptor compared with the binding of the corresponding wild type BMP for the type I and/or type II receptor.

By "corresponding wild type protein" it is meant the wild type version of the designer BMP prior to the introduction of any mutations. For example, if the designer BMP is a designer BMP2, the corresponding wild-type BMP is wild-type BMP2. Thus, in one embodiment, design of a designer BMP can, but need not, begin with a wild type BMP sequence wherein mutations (e.g., amino acid substitutions, deletions and/or insertion) are introduced into the wild type sequence. Therefore, the designer BMP can correspond with a wild type BMP, and the locations of the mutations can be said, for instance, to correspond with, be relative to and/or be respective with the amino acid sequence of the wild type corresponding or "reference" BMP sequence.

The proteins of the present invention include fragments, derivatives, analogs, or variants of the polypeptides described herein, and any combination thereof. The terms "fragment," "variant," "derivative" and "analog" when referring to proteins of the present invention include any proteins which retain at least some of the functional properties of the protein from which it was derived.

By the term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. Alternatively or additionally, the term as used herein also refers to any portion of a given polypeptide that includes at least an established sequence element found in the full-length polypeptide. In some embodiments, the sequence element spans at least about 4-5, 10, 15, 20, 25, 30, 35, 40, 45, 50 or more amino acids of the full-length polypeptide. Fragments of proteins of the present invention include proteolytic fragments, as well as deletion fragments.

Variants of the proteins of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant proteins may comprise conservative or non-conservative amino acid substitutions, deletions or additions.

The proteins of the invention include proteins having one or more residues chemically derivatized by reaction of a functional side group. Also included as proteins of the invention are polypeptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

"Recombinantly expressed polypeptide" and "recombinant polypeptide" as used herein refer to a polypeptide expressed from a host cell that has been manipulated to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, at least 40%, at least 50% or 60%, or at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=# of identical positions/total # of positions×100). The determination of percent homology between two sequences can be accomplished using a mathematical algorithm. A preferred, non-limiting example of a mathematical algorithm utilized for the comparison of two sequences is the algorithm of Karlin et al., *Proc Natl Acad Sci* USA 87:2264-8 (1990), modified as in Karlin et al., *Proc Natl Acad Sci* USA 90:5873-7 (1993). Such an algorithm is incorporated into the NBLAST and XBLAST programs of Altschul et al., *J Mol Biol* 215:403-10 (1990). BLAST nucleotide searches can be performed with the NBLAST program, score=100, wordlength=12.

BLAST protein searches can be performed with the XBLAST program, score=50, wordlength=3. To obtain gapped alignments for comparison purposes, Gapped BLAST can be utilized as described in Altschul et al., *Nucleic Acids Res* 253389-402 (1997). When utilizing BLAST and Gapped BLAST programs, the default parameters of the respective programs (e.g., XBLAST and NBLAST) can be used.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman-Wunsch algorithm (Needleman et al., J Mol Biol 48:443-53 (1970)) which has been incorporated into the GAP program in the GCG software package (available on at gcg.com), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available on the internee at gcg.com), using a NWSgapdna.CMP matrix and a gap weight of 40, 50, 60, 70, or 80 and a length weight of 1, 2, 3, 4, 5, or 6. One typical set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Myers and W. Miller (Myers et al., *Comput Appl Biosci* 4:11-7 (1988)) which has been incorporated into the ALIGN program (version 2.0), using a PAM120 weight residue table, a gap length penalty of 12 and a gap penalty of 4.

"Instructional material," as that term is used herein, includes a publication, a recording, a diagram, or any other medium of expression which can be used to communicate the usefulness of the compound, combination, and/or composition of the invention in the kit for affecting, alleviating or treating the various diseases or disorders recited herein. Optionally, or alternately, the instructional material can describe one or more methods of alleviating the diseases or disorders in a cell, a tissue, or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

Except when noted, the terms "patient" or "subject" are used interchangeably and refer to mammals such as human patients and non-human primates, as well as veterinary subjects such as rabbits, rats, and mice, and other animals. Preferably, patient refers to a human.

"Effective amount", or "therapeutically effective amount," as the terms are used interchangeably herein, is an amount that when administered to a tissue or a mammal, preferably a human, mediates a detectable therapeutic response compared to the response detected in the absence of the compound. A therapeutic response, such as, but not limited to, inhibition of and/or decreased fibrosis, increased bone mass or bone density, and the like, can be readily assessed by a plethora of art-recognized methods, including, e.g., such methods as disclosed herein.

The skilled artisan would understand that the effective amount of the compound or composition administered herein varies and can be readily determined based on a number of factors such as the disease or condition being treated, the stage of the disease, the age and health and physical condition of the mammal being treated, the severity of the disease, the particular compound being administered, and the like As used herein, to "treat" means reducing the frequency with which symptoms of a disease (e.g., decreased bone density, fracture, fibrosis, and the like) are experienced by a patient. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an BMP protein, an antibody or a peptide inhibitor which recognizes and binds a cognate receptor (e.g., a BMP type I or type II receptor, an antibody that binds with its cognate antigen, and the like) in a sample, but does not substantially recognize or bind other molecules in the sample. Thus, under designated assay conditions, the specified binding moiety (e.g., a BMP or a receptor binding fragment thereof) binds preferentially to a particular target molecule and does not bind in a significant amount to other components present in a test sample. A variety of assay formats may be used to select an antibody that specifically binds a molecule of interest. For example, solid-phase ELISA immunoassay, immunoprecipitation, BIAcore, FACS, Octet, and Western blot analysis are among many assays that may be used to identify a BMP that specifically reacts with a BMP receptor. Typically, a specific or selective reaction will be at least twice background signal or noise, more preferably, at least five-fold greater than background signal or noise, and more typically, more than 10 times background, even more specifically, a BMP is said to "specifically bind" a BMP receptor when the equilibrium dissociation constant ($K_D$) is ≤100 μM, more preferably ≤10 μM, even more preferably ≤1 μM, yet more preferably ≤100 nM and most preferably ≤10 nM.

The term "$K_D$" refers to the equilibrium dissociation constant of a particular ligand-receptor interaction.

"Binding affinity" generally refers to the strength of the sum total of noncovalent interactions between a binding site of a molecule (e.g., a BMP ligand) and its binding partner (e.g., a BMP type I or type II receptor). Unless indicated otherwise, as used herein, "binding affinity" refers to intrinsic binding affinity which reflects a 1:1 interaction between members of a binding pair (e.g., BMP and its cognate receptor). The affinity of a molecule X for its partner Y can generally be represented by the dissociation constant (Kd).

Affinity can be measured by common methods known in the art, including those described herein. Low-affinity BMPs generally bind a receptor slowly and tend to dissociate readily, whereas high-affinity BMPs generally bind a receptor faster and tend to remain bound longer. A variety of methods of measuring binding affinity are known in the art, any of which can be used for purposes of the present invention. Specific illustrative embodiments are described elsewhere herein.

The term "$k_{on}$", as used herein is intended to refer to the association or on rate constant, or specific reaction rate, of the forward, or complex-forming, reaction, measured in units: $M^{-1}$ $sec^{-1}$.

The term "$k_{off}$", as used herein, is intended to refer to the dissociation or off rate constant, or specific reaction rate, for dissociation of an antibody from the antibody/antigen complex, measured in units: $sec^{-1}$.

The term "$K_d$", as used herein, is intended to refer to the dissociation constant of a particular antibody-antigen interaction. It is calculated by the formula:

$$k_{off}/k_{on}=K_d$$

The term "altered binding" as used herein means the designer BMP comprises a different binding specificity for at least a type I receptor and/or a type II receptor when compared with the binding of a corresponding wild type BMP to the same type I and/or type II receptor. The designer BMP may bind with greater or lesser affinity with the receptor compared to the binding of the wild type BMP to that receptor. For instance, if the wild type BMP bound a certain type I receptor with a certain binding affinity, the corresponding designer BMP binds that receptor with greater or lesser affinity compared with the wild type BMP. It may even be that the designer BMP will specifically bind a receptor that the wild type BMP did not detectably bind and vice-a-versa where the designer BMP will no longer detectably bind a receptor that the wild type BMP binds. Thus, altered binding encompasses any detectable change in binding by a designer BMP to a type I or type II receptor compared with the binding of that receptor by the corresponding wild type BMP. It may be that the designer BMP has a greater or lesser $k_{on}$ value compared with the $k_{on}$ value for a corresponding wild type BMP and/or the designer BMP has a greater or lesser $k_{off}$ value compared with the $k_{off}$ value of the corresponding wild type BMP such that the Kd of the designer BMP is greater or lesser than the Kd of a corresponding wild type BMP for the same BMP receptor. Thus, any difference in a binding characteristic and/or affinity value between a designer BMP and a corresponding wild type BMP are encompassed by the term "altered binding" as used herein.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden, and Piscataway, N.J.). For further descriptions, see, e.g., Johnsson, et al., *Ann. Biol. Clin.* 51: 19-26 (1993); Johnsson, et al. *Biotechniques* 11: 620-627 (1991); Johnsson, et al., *J. Mol. Recognit.* 8: 125-131 (1995); and Johnnson, et al., *Anal. Biochem.* 198: 268-277 (1991).

As used herein, "substantially pure" means an object species is the predominant species present (i.e., on a molar basis it is more abundant than any other individual species in the composition), and preferably a substantially purified fraction is a composition wherein the object species (e.g., a designer BMP) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

DESCRIPTION

Bone Morphogenetic Proteins (BMPs)

As stated previously elsewhere herein, BMPs are members of the TGF-β protein superfamily all of which are characterized by six-conserved cysteine residues (Lander et al, (2001) Nature, 409:860-921. The BMP/GDF subfamily includes, but is not limited to, BMP2, BMP3 (osteogenin) (see, e.g., U.S. Pat. No. 6,177,406), BMP3b (GDF-10) (see, e.g., U.S. Pat. No. 6,204,047), BMP4 (BMP2b) (see, e.g., U.S. Pat. No. 6,245,889), BMP5 (see, e.g., U.S. Pat. No. 5,543,394), BMP6 (see, e.g., U.S. Pat. No. 6,613,744), BMP7 (osteogenic protein-1 or OP1) (see, e.g., U.S. Pat. No. 5,141,905), BMP8 (OP2) (see, e.g., U.S. Pat. No. 5,688,678), BMP8B (OP3) (see, e.g., U.S. Pat. No. 5,854,071), BMP9 (GDF2) (see, e.g., U.S. Pat. No. 6,287,816), BMP10 (see, e.g., U.S. Pat. No. 5,703,043), BMP11 (GDF11) (see, e.g., U.S. Pat. No. 6,437,111), BMP12 (GDF7) (see, e.g., U.S. Pat. No. 6,027,919), BMP13 (GDF6, CDMP2) (see, e.g., U.S. Pat. No. 6,027,919), BMP15 (GDF9) (see, e.g., U.S. Pat. No. 6,034,229), BMP16 (see, e.g., U.S. Pat. No. 6,331,612), GDF1 (see, e.g., US Application No. 2004/0039162), GDF3 (see, e.g., U.S. Pat. No. 6,025,475), GDF5 (CDMP1; MP52) (see, e.g., U.S. Pat. No. 5,994,094), and GDF8 (myostatin) (see, e.g., U.S. Pat. No. 5,827,733).

BMPs specifically bind their cognate receptors, which include Type I receptors: ALK-I, ALK-2 (also called ActRIa or ActRI), ALK-3 (also called BMPRIa), and ALK-6 (also called BMPRIb); and Type II receptors: ActRIIa (also called ActRII), ActRIIb, and BMPRII. The BMP-receptor binding interactions have been studied extensively, and the binding specificities of each wild type BMP for each type I and/or type II receptor is generally known in the art and are shown in Table 1. See, e.g., Nickel et al., *Cytokine Growth Factor Rev* 20:36 T-77 (2009); Heinecke et al., *BMC Biol* 7:59 (2009).

TABLE 1

| | ALK 1 | ALK 2 | ALK 3 | ALK 6 | ACTIIA | ACTIIB | BMPRII |
|---|---|---|---|---|---|---|---|
| BMP-2 | No Binding | No Binding | ++++ | ++++ | ++ | +++ | ++ |
| BMP-4 | No Binding | No Binding | ++++ | ++++ | ++ | ++ | ++ |
| BMP-6 | No Binding | No Binding | ++ | ++ | ++++ | ++++ | ++++ |
| BMP-7 | No Binding | No Binding | ++ | ++ | ++++ | ++++ | ++++ |
| BMP-9 | +++++ | No Binding | No Binding | No Binding | ++ | +++ | ++++ |

Designer Bone Morphogenetic Proteins with Improved Osteogenic Activity

This application is based, in part on the understanding that each BMP dimer binds to four BMP receptors two type I receptors and two type II receptors. The specificities of each BMP for each receptor are known in the art as shown above in Table 1. Also, the receptor binding regions of various BMPs that mediate binding of the BMP for each receptor have been mapped and are shown in Table 2. For instance, it is well established that wild type BMP2 and BMP4 bind type I BMP receptors Alk-3 and ALK-6 with high affinity and bind type II BMP receptors with lower affinity. On the other hand, wild type BMP6 and BMP7 are known to have bind type II receptors ActrIIA, ActrIIB, and BMPRII with high affinity but bind type I receptors with lower affinity than they do to type II. It is believed that the differing cellular responses from the approximately forty-three TGFβ superfamily members signaling through interaction with approximately twelve receptors is believed to be due to each ligand utilizing a specific repertoire of receptors with which it binds with differing affinities. The type I and II binding domains are described in Table 2.

TABLE 2

| BMP | Type II domain A amino acids | Type I domain amino acids | Type II domain B amino acids |
|---|---|---|---|
| BMP2 (SEQ ID NO 1) | 31-44 | 48-76 | 83-100 |
| BMP4 (SEQ ID NO: 2) | 33-46 | 50-78 | 85-102 |
| BMP5 (SEQ ID NO: 3) | 54-67 | 71-100 | 107-120 |
| BMP6 (SEQ ID NO: 4) | 55-69 | 73-102 | 108-126 |
| BMP7 (SEQ ID NO: 5) | 55-69 | 73-102 | 108-126 |
| BMP8 (SEQ ID NO: 6) | 55-69 | 73-102 | 108-126 |
| BMP9 (SEQ ID NO: 7) | 25-39 | 42-71 | 78-96 |

Rational Amino Acid Substitution to Alter Receptor Binding of Designer BMPs

In one embodiment, the invention comprises introducing an amino acid mutation in at least one receptor binding site thereby providing altered binding to type I and type II BMP receptors by designer BMPs compared to the binding of the corresponding wild type BMP to those receptors. That is, it is well known in the art that wild type BMP2 shows a relatively high affinity for type I receptors, while wild type BMP6 shows a high affinity for type II receptors. It is further known in the art that heterodimers of wild type BMP2 and BMP6 bind to both type I and type II receptors with relatively high affinity each BMP apparently providing the higher affinity binding site for each receptor. See Table 3, below. The BMP2/6 heterodimers are known to be more active that BMP2 or BMP6 alone or as homodimers, in both in vitro and in vivo bone formation assays. Table 3 shows an example of BMP2 and BMP6 binding affinities to type I and II receptors.

TABLE 3

| | Type I | | Type II | |
|---|---|---|---|---|
| Ligand | ALK3 $K_D$ (nM) | ALK6 $K_D$ (nM) | ActRIIA $K_D$ (nM) | ActRIIB $K_D$ (nM) |
| BMP2 | 0.69 | 0.17 | 141 | 42 |
| BMP6 | 150 | 102 | 0.73 | 2.0 |
| BMP2/6 | 1.67 | 0.43 | 2.56 | 1.15 |

Accordingly, it is an object of the invention to provide designer BMPs with improved binding to type I and/or type II receptors. As shown in FIG. 1A and Table 2, each BMP comprises three binding sites that contribute to receptor binding. From N- to C-terminus, each BMP comprises a type II receptor binding site A, a type I receptor binding site, and a second type II receptor binding site B. Although an exemplary alignment of wild type BMP2, BMP4, BMP5, BMP6, BMP7, BMP8, and BMP9 is illustrated in FIG. 1, the skilled artisan will appreciate that there are well-known alignments providing the relative positioning of various amino acids among the members of the TGFβ superfamily. Such alignments are provided, among others, in International Publication Nos. WO 2009/086131 (e.g., FIGS. 15-17, FIG. 31A), WO 2008/051526 (FIGS. 9-12), WO 2005/118636 (FIG. 6), WO 2005/118635, WO 2005/113585 (FIG. 3), WO 2001/92298 (FIG. 6A-6C), Kirsch et al., *EMBO J.* 19:3314-3324 (2000) (FIG. 1), US Patent Application Publication No., 2007/0293425 (FIG. 6), Groppe et al., *Nature* 420:636-642 (2002), Nickel et al., *J. Bone Joint Surg. Am.* 83:7-14 (2001), and Weber et al, *BMC Structural Biol.* 7:6 (2007). Thus, using protein sequence alignment algorithms and tools well-known in the art, including the alignments of the amino acid sequences of the various TGFβ superfamily members, as well as the disclosure provided herein, the corresponding amino acid in one BMP/GDF protein relative to the amino acid at any position in another BMP/GDF protein can be determined. In one embodiment, the corresponding amino acid residues in BMP-2, BMP-4, BMP-5, BMP-6, BMP-7, BMP-8 and BMP-9 are shown (see, e.g., FIG. 1A).

In some embodiments of the invention, the designer BMP comprises mutations in a type I binding domain or a type II binding domain, wherein the mutations confer altered binding to a type I or type II BMP receptor. In some embodiments, the designer BMP comprises one or more mutations in both a type I binding domain and a first (binding domain A) or second (binding domain B) type II binding domain. In other embodiments, the designer BMP comprises one or more mutations in both type II binding domains. In other embodiments, the designer BMP comprises one or more mutations in the first type II binding domain, in the second type II binding domain, and in the type I binding domain. In some embodiments, the designer BMP comprises one or more mutations in the type I binding domain.

In some embodiments, the mutations improve binding to a type I receptor. In other embodiments, the mutations improve binding to a type II receptor. In other embodiments, the mutations decrease binding to a type I or type II receptors. In some embodiments, the mutations create or destroy a glycan tether as more fully set forth below. In some embodiments, the mutations create or destroy a His doorstop as more fully set forth below.

Because BMPs are so well characterized and understood in the art, it would be understood, once provided with the disclosure provided herein, the location of possible mutations that can be made that do not further affect the activity of the designer BMPs would be understood. Accordingly, the designer BMPs of the invention encompass variant BMPs which differ from a corresponding wild type or designer BMP in that it contains additional insertions, deletions, or substitutions which do not affect the receptor binding affinity of the variant BMPs. In some non-limiting embodiments, those of skill in the art would understand that the cysteines involved in cysteine knot formation and amino acids involved in receptor interactions should not be mutated or should be changed with conservative substitutions, while other amino acids may be more freely substituted, inserted, or deleted without adversely affecting biological activity of the designer BMP.

It should be noted that unless otherwise stated, all positional numbering of designed or modified BMPs is based on the sequences of the mature native BMPs. Designer BMPs are characterized by the predetermined nature of the variation, a feature that sets them apart from naturally occurring allelic or interspecies variation of the BMP sequence. Variants of designer BMPs must retain at least 50% of the activity of the corresponding wild type or designer BMP activity in one or more cell types, as determined using an appropriate assay described below. Variants that retain at least 75%, 80%, 85%, 90% or 95% of wild type activity are more preferred, and variants that are more active than wild type are especially preferred. A designer BMP may contain insertions, deletions, and/or substitutions at the N-terminus, C-terminus, or internally. In a preferred embodiment, designed or modified BMPs have at least 1 residue that differs from the most similar human BMP sequence, with at least 2, 3, 4, 5, 6, 7, 8, 9, 10 or more different residues being more preferred.

Designer BMPs of the invention maintain at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity with the corresponding wild-type BMP protein sequence.

Designer BMPs of the invention may maintain at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity with the conserved cysteine domain of the C-terminal region of the corresponding wild-type BMP protein sequence.

Designer BMPs may contain further modifications, for instance mutations that alter additional protein properties such as stability or immunogenicity or which enable or prevent posttranslational modifications such as PEGylation or glycosylation. Designer BMPs may be subjected to co- or posttranslational modifications, including but not limited to synthetic derivatization of one or more side chains or termini, glycosylation. PEGylation, circular permutation, cyclization, fusion to proteins or protein domains, and addition of peptide tags or labels.

Due to the degeneracy of the genetic code, an extremely large number of nucleic acids may be made, all of which encode the designer BMPs of the present invention, by simply modifying the sequence of one or more codons in a way that does not change the amino acid sequence of the designer BMP. The designer BMPs of the invention do not comprise these sequences set forth in WO2008/051526 or WO2009/086131.

As described above. BMPs are naturally expressed as pro-proteins comprising a long pro-domain, one or more cleavage sites, and a mature domain. This pro-protein is then processed by the cellular machinery to yield a dimeric mature BMP molecule. In a preferred embodiment, the designer BMPs of the invention are produced in a similar manner. The pro-domain is believed to aid in the correct folding and processing of BMPs. Furthermore, in some but not all BMPs, the pro-domain may noncovalently bind the mature domain and may act as a chaperone, as well as an inhibitor (e.g. Thies et al. (2001) Growth Factors, 18:251-259). Preferably, the modified BMPs of the invention are produced and/or administered therapeutically in this form. Alternatively. BMPs may be produced in other forms, including, but not limited to, where the mature domain is produced directly or refolded from inclusion bodies, or comprises full-length intact pro protein. The designer BMPs of the invention will be useful in these and other forms.

In particular embodiments, the designer BMP of the invention comprises a backbone BMP, the wild type BMP, to which the designer BMP corresponds. In particular embodiments, this backbone BMP may be a wild type BMP2, BMP4, BMP5, BMP6, BMP7, BMP8, or BMP9 backbone.

In some embodiments of the invention, the designer BMP comprises at least one mutation in a type I binding domain and/or a type II binding domain, wherein the mutation confers altered binding to a type I or type II BMP receptor compared with the binding of a corresponding wild type BMP not comprising the mutation. In some embodiments, the designer BMP comprises at least one mutation in both a type I binding domain and at least one mutation in a type II binding domain. In other embodiments, the designer BMP comprises at least one mutation within the type II binding domain A and the type II binding domain B. In other embodiments, the designer BMP comprises at least one mutation in type II binding domain A, type II binding domain B, and a type I binding domain.

In certain embodiments, the mutation may comprise an amino or nucleic acid substitution, deletion and/or insertion. In a preferred embodiment, the mutation comprises an amino acid substitution.

In some embodiments, the backbone BMP is a wild type BMP and the mutations are one or more of the mutations listed in Tables 4 to 6. The designer BMP may contain any combination and any number of mutations listed in these tables.

In some embodiments, the backbone BMP is a wild type BMP and the mutations are one or more of the mutations listed in Tables 4 to 6. The designer BMP may contain a permutation and any and all of the mutations listed in these tables or disclosed elsewhere herein.

TABLE 4

Type I Binding Domain Mutations

| BMP2 | BMP4 | BMP5 | BMP6 | BMP7 | BMP8 | BMP9 | Possible mutations |
|---|---|---|---|---|---|---|---|
| P48 | P50 | S71 | S72 | A72 | S72 | F42 | F, S, N, A, P |
| F49 | F51 | F72 | F73 | F73 | F73 | F43 | Y |
| A52 | A54 | N75 | N76 | N76 | D76 | A46 | N, A |
| D53 | D55 | A76 | A77 | S77 | S77 | D47 | A, E, D |
| H54 | H56 | H77 | H78 | Y78 | C78 | D48 | D, C |
| L55 | L57 | M78 | M79 | M79 | M79 | V49 | M, V, L |
| N56 | N58 | N79 | N80 | N80 | N80 | T50 | T, N |
| S57 | S59 | A80 | A81 | A81 | A82 | P51 | A P |
| N59 | N61 | N82 | N83 | N83 | N83 | K53 | K, N |
| V63 | V65 | V86 | V87 | V87 | L87 | V57 | I, V, L |
| T65 | T67 | T88 | T89 | T89 | S89 | T59 | A, T, S |
| N68 | N70 | H91 | H92 | H92 | H92 | H62 | H, N |
| S69 | S71 | L92 | L93 | F93 | L93 | L63 | L, S, F |
| V70 | V72 | M93 | M94 | I94 | M94 | K64 | M, K, I, V |
| N71 | N73 | F94 | N95 | N95 | M95 | F65 | F, N, M |
| | | P95 | P96 | P96 | P96 | P66 | INSERT S, P; DELETE P |
| S72 | S74 | D96 | E97 | E97 | D97 | T67 | Q, T, E, D |
| K73 | S75 | H97 | Y98 | T98 | A98 | K68 | Y, H, T, A, K |
| I74 | I76 | V98 | V99 | V99 | V99 | V69 | A, V, I |
| P75 | P77 | P99 | P100 | P100 | P100 | G70 | S, G |

TABLE 5

Type II Binding Domain A Mutations

| BMP2 | BMP4 | BMP5 | BMP6 | BMP7 | BMP8 | BMP9 | Possible mutations |
|---|---|---|---|---|---|---|---|
| V33 | V35 | I56 | I57 | I57 | I57 | I27 | I, V |
| P36 | P38 | E59 | K60 | E60 | Q60 | K30 | K, R, P, E, Q |
| G37 | G39 | G60 | G61 | G61 | G61 | E31 | G, E |
| H39 | Q41 | A62 | A63 | A63 | S63 | E33 | A, E, S, Q |
| F41 | F43 | F64 | N65 | Y65 | Y65 | Y35 | N, Y, F |
| Y42 | Y44 | Y65 | Y66 | Y66 | Y66 | E36 | Y, E |
| H44 | H46 | D67 | D68 | E68 | E68 | K38 | H, D, K, R, E |

TABLE 6

| Type II Binding Domain B Mutations | | | | | | | |
|---|---|---|---|---|---|---|---|
| BMP2 | BMP4 | BMP5 | BMP6 | BMP7 | BMP8 | BMP9 | Possible mutations |
| E83 | E85 | K107 | K108 | Q108 | K108 | K78 | Q, K, E |
| S85 | S87 | N109 | N110 | N110 | S110 | S80 | N, S |
| A86 | A88 | A110 | A111 | A111 | A111 | P81 | P, A |
| M89 | M91 | V113 | V114 | V114 | V114 | V84 | M, V |
| L92 | L94 | F116 | F117 | F117 | Y117 | K87 | F, K, L, Y |
| E94 | E96 | D118 | D119 | D119 | D118 | D89 | D, E |
| N95 | Y97 | S119 | N120 | S120 | S119 | M90 | M, N, S |
| E96 | D98 | S120 | S121 | S121 | S120 | G91 | S, G, D |
| K97 | K99 | N121 | N122 | N122 | N121, N122 | V92 | N, V, K |
| V98 | V100 | V122 | V123 | V123 | V123 | P93 | P, V |
| V99 | V101 | I123 | I124 | I124 | I124 | T94 | T, I, V |

In some embodiments, the mutations improve binding to a type I receptor. In other embodiments improve binding to a type II receptor. In other embodiments, the mutations decrease binding to a type I or type II receptors.

Tables 4-6 above provide a non-limiting compilation of example mutations of the present invention where the position of the mutation is provided relative to the corresponding wild type BMP amino acid sequence. Thus, in some embodiments, the designer BMP comprises the following preferred combinations of mutations.

In certain embodiments, the corresponding wild type BMP to the designer BMP is BMP2. Further, the at least one mutation within the type II receptor binding domain A is a mutation selected from the group consisting of V33, P36, G37, H39, F41, Y42 AND H44.

In other embodiments, the designer BMP comprises at least one mutation within the type II receptor binding domain A and further comprises at least one additional mutation within a type I receptor binding domain. The mutation within the type I receptor binding domain is at least one mutation at P48, F49, A52, D53, H54, L55, N56, S57, N59, V63, T65, N68, S69, V70, N71, S72, K73, I74, and P75 with respect to the sequence of SEQ ID NO:1.

In yet further embodiments, the designer BMP comprises at least one mutation within a type II receptor binding domain A, at least one mutation within the type I receptor binding domain, and further comprises at least one additional mutation within a type IIB receptor binding domain. The mutation within the type II receptor binding domain B is at least one mutation at E83, S85, A86, M89, L92, E94, N95, E96, K97, V98, and V99 with respect to the sequence of SEQ ID NO:1.

In some embodiments, the designer BMP comprises mutations at each of amino acids H44, P48, A52, D53, L65, S57, N68, S69, V70, insertion of P after N71, S72, K73, I74, A77, and V80 with respect to the sequence of SEQ ID NO:1.

In one embodiment, the designer BMP comprises the following mutations: H44D, P48S, A52N, D53A, L55M, S57A, N68H, S69L, V70M, insertion of a P after N71, S72E, K73Y, I74V, A77P, and V80A with respect to the sequence of SEQ ID NO:1.

In some embodiments the designer BMP comprises mutations at each of amino acids V33, P36, H39, S85, M89, L92, E94, E96, K97, and V99 with respect to the sequence of SEQ ID NO:1.

In some embodiments, the designer BMP comprises mutations at each of amino acids V33I, P36K, H39A, S85N, M89, L92F, E94D, E96S, K97N, and V99I with respect to the sequence of SEQ ID NO:1.

In other embodiments, the designer BMP comprises the following mutations: V33I, P36K, H39A, H44D, P48S, A52N, L54M, S56M, N68H, V70M, S72E, K73E, insertion of a Y after K73, I74V, 77AP, S85N, M89V, L92F, E94D, E96S, K97N, and V99I with respect to the sequence of SEQ ID NO:1.

In yet other embodiments, the designer BMP comprises the following mutations: V33I, P36R, H39A, H44D, P48S, A52N, L54M, S56M, N68H, V70M, S72E, K73E, insertion of a Y after K73, I74V, 77AP, S85N, M89V, L92F, E94D, E96S, K97N, and V99I with respect to the sequence of SEQ ID NO:1.

In certain embodiments, the corresponding wild type BMP to the designer BMP is BMP4. In certain embodiments, the at least one mutation within the type II receptor binding domain A is at V35, P38, G39, Q41, F43, Y44, and H46 of SEQ ID NO:2.

In other embodiments, the designer BMP4 comprises at least one mutation within the type II receptor binding domain A and further comprises at least one additional mutation within a type I receptor binding domain. The mutation within the type I receptor binding domain is at least one mutation at P50, A54, D55, H56, L57, N58, S59, N61, V65, T67, N70, S71, V72, N73, S74, S75, I76, and P77 of SEQ ID NO:2.

In yet further embodiments, the designer BMP4 comprises at least one mutation within a type II receptor binding domain A, at least one mutation within the type I receptor binding domain, and further comprises at least one additional mutation within a type IIB receptor binding domain. The mutation within the type II receptor binding domain B is at least one mutation at E85, S87, A88, M91, L94, E96, K97, V98 and V99 of SEQ ID NO:2.

In certain embodiments, the corresponding wild type BMP to the designer BMP is BMP5. In certain embodiments, the mutation within the type II receptor binding domain A is at least one mutation at I56, E59, G60, A62, F64, Y65, or D67 of SEQ ID NO:3.

In other embodiments, the designer BMP comprises at least one mutation within the type II receptor binding domain A and further comprises at least one additional mutation within a type I receptor binding domain. The mutation within the type I receptor binding domain is at least one mutation at S71, F72, N75, A76, H77, M78, N79, A80, N82, V86, T88, H91, L92, M93, F94, P95, D96, H97, V98, or P99 of SEQ ID NO:3.

In yet further embodiments, the designer BMP comprises at least one mutation within a type II receptor binding domain A, at least one mutation within the type I receptor binding domain, and further comprises at least one additional mutation within a type IIB receptor binding domain. The mutation within the type II receptor binding domain B is at least one mutation at K107, N109, A110, V113, F116, D118, S119, S120, N121, V122, or I123 of SEQ ID NO:3.

In certain embodiments, the corresponding wild type BMP to the designer BMP is BMP6. In certain embodiments, the mutation within the type II receptor binding domain A is at least one mutation at I57, K60, G61, A63, N65, Y66, or D68 of SEQ ID NO:4.

In other embodiments, the designer BMP6 comprises at least one mutation within the type II receptor binding domain A and further comprises at east one additional mutation within a type I receptor binding domain. The mutation within the type I receptor binding domain is at least one mutation at S72, N76, A77, H78, M79, N80, A81, N83, V87, T89, H92, L93, M94, N95, P96, E97, Y98, V99, or P100 of SEQ. ID NO:4.

In yet further embodiments, the designer BMP6 comprises at least one mutation within a type II receptor binding domain A, at least one mutation within the type I receptor binding domain, and further comprises at least one additional mutation within a type IIB receptor binding domain. The mutation within the type II receptor binding domain B is at least one mutation at K108, N110, A111, V114, F117, D119, N120, S121, N122, V123, or I124 of SEQ ID NO:4.

In certain embodiments, the corresponding wild type BMP to the designer BMP is BMP7. In certain embodiments, the mutation within the type II receptor binding domain A is at least one mutation at I57, E60, G61, A63, Y65, Y66, or E68 of SEQ ID NO:5.

In other embodiments, the designer BMP7 comprises at least one mutation within the type II receptor binding domain A and further comprises at least one additional mutation within a type I receptor binding domain. The mutation within the type I receptor binding domain is at least one mutation at A72, F73, N76, S77, Y78, M79, N80, A81, N83, V87, T89, H92, F93, I94, N95, P96, E97, T98, V99, or P100 of SEQ ID NO:5.

In yet further embodiments, the designer BMP7 comprises at least one mutation within a type II receptor binding domain A, at least one mutation within the type I receptor binding domain, and further comprises at least one additional mutation within a type MB receptor binding domain. The mutation within the type II receptor binding domain B is at least one mutation at Q108, N110, A111, V114, F117, D119, S120, S121, N122, V123, or I124 of SEQ ID NO:5.

In certain embodiments, the corresponding wild type BMP to the designer BMP is BMP8. In certain embodiments, the mutation within the type II receptor binding domain A is at least one mutation at I57, Q60, G61, S63, Y65, Y66, or E68 of SEQ ID NO:6.

In other embodiments, the designer BMP8 comprises at least one mutation within the type II receptor binding domain A and further comprises at least one additional mutation within a type I receptor binding domain. The mutation within the type I receptor binding domain is at least one mutation at S72, F73, D76, S77, C78, M79, N80, A82, N83, L87, S89, H92, L93, M94, M95, P96, D97, A98, V99, or P100 of SEQ ID NO:6.

In yet further embodiments, the designer BMP8 comprises at least one mutation within a type II receptor binding domain A, at least one mutation within the type I receptor binding domain, and further comprises at least one additional mutation within a type MB receptor binding domain. The mutation within the type II receptor binding domain B is at least one mutation at K108, S110, A111, V114, Y117, D118, S119, S120, N121, N122, V123, or I124 or SEQ ID NO:6

In certain embodiments, the mutation within the type II receptor binding domain A is at least one mutation at I27, K30, E31, E33, Y35, or E36 of SEQ ID NO:7.

In other embodiments, the designer BMP9 comprises at least one mutation within the type II receptor binding domain A and further comprises at east one additional mutation within a type I receptor binding domain. The mutation within the type I receptor binding domain is at least one mutation at F42, F43, A46, D47, D48, V49, T50, P51, K53, V57, T59, H62, L63, K64, F65, P66. T67, K68, V69, or G70 of SEQ ID NO:7.

In yet further embodiments, the designer BMP9 comprises at least one mutation within a type II receptor binding domain A, at least one mutation within the type I receptor binding domain, and further comprises at least one additional mutation within a type IIB receptor binding domain. The mutation within the type II receptor binding domain B is at least one mutation at K78, S80, P81, V84, K87, D89, M90, G91, V92, P93, or T94 of SEQ ID NO:7.

Exemplary amino acid sequences of designer BMPs are set forth in Table 7, below. Table 7 shows the name and sequence of the designed molecules.

TABLE 7

| NAME | SEQUENCE | SEQ ID NO |
|---|---|---|
| BMP-A | QAKHKQRKRLKSSCKRHPLYVDFSDVGWNDWIIAPKGYAANYCHGECPFPLADHLNSTNHAIVQTLVN SVNSKIPKACCVPTELSAISMLYLDENEKVVLKNYQDMVVEGCGCR | 8 |
| BMP-B | QAKHKQRKRLKSSCKRHPLYVDFSDVGWNDWIVAPPGYHAFYCHGECPFPLADHLNSTNHAIVQTLVN SVNSKIPKACCVPTKLNAISVLYFDDNSNVILKNYQDMVVEGCGCR | 9 |
| BMP-C | QAKHKQRKRLKSSCKRHPLYVDFSDVGWNDWIIAPKGYAANYCHGECPFPLADHLNSTNHAIVQTLVN SVNSKIPKACCVPTKLNAISVLYFDDNSNVILKNYQDMVVEGCGCR | 10 |
| BMP-D | QAKHKQRKRLKSSCKRHPLYVDFSDVGWNDWIVAPPGYHAFYCHGECPFPLNAHMNATNHAIVQTLVH LMN-SKIPKACCVPTELSAISMLYLDENEKVVLKNYQDMVVEGCGCR | 11 |
| BMP-E | QAKHKQRKRLKSSCKRHPLYVDFSDVGWNDWIVAPPGYHAFYCDGECSFPLNAHMNATNHAIVQTLVH LMNPEYVPKPCCAPTELSAISMLYLDENEKVVLKNYQDMVVEGCGCR | 12 |
| BMP-F | QAKHKQRKRLKSSCKRHPLYVDFSDVGWNDWIIAPKGYAAFYCHGECPFPLADHLNSTNHAIVQTLVN SVNSKIPKACCVPTELSAISMLYLDENEKVVLKNYQDMVVEGCGCR | 13 |
| BMP-G | QAKHKQRKRLKSSCKRHPLYVDFSDVGWNDWIIAPKGYAAFYCHGECPFPLADHLNSTNHAIVQTLVN SVNSKIPKACCVPTELNAISVLYFDDNSNVILKNYQDMVVEGCGCR | 14 |

TABLE 7-continued

| NAME | SEQUENCE | SEQ ID NO |
|---|---|---|
| BMP-H | QAKHKQRKRLKSSCKRHPLYVDFSDVGWNDWIIAPKGYHAFYCHGECPFPLADHLNSTNHAIVQTLVN SVNSKIPKACCVPTELNAISVLYFDENSNVVLKKYQDMVVRGCGCR | 15 |
| BMP-I | QAKHKQRKRLKSSCKRHELYVSFQDLGWQDWIIAPKGYAANYCHGECPFPLADHLNSTNHAIVQTLVN SVNSKIPKACCVPTELNAISVLYFDDNSNVILKKYRNMVVRACGCR | 16 |
| BMP-J | QAKHKQRKRLKSSCKRHPLYVDFSDVGWNDWIIAPKGYHAFYCDGECSFPLNAHMNATNHAIVQTLVH LMNPEYVPKPCCAPTELNAISVLYFDENSNVVLKKYQDMVVRGCGCR | 17 |
| BMP-K | QAKHKQRKRLKSSCKRHPLYVDFSDVGWNDWIVAPPGYHAFYCHGECPFPLADHLNSTKHAIVQTLVN SVNSKIPKACCVPTELSAISMLYLDENEKVVLKNYQDMVVEGCGCR | 18 |
| BMP-T | QAKHKQRKRLKSSCKRHPLYVDFSDVGWNDWIVAPPGYHAFYCHGECPFPLADHLNSTTHAIVQTLVN SVNSKIPKACCVPTELSAISMLYLDENEKVVLKNYQDMVVEGCGCR | 19 |
| BMP-AP | QAKHKQRKRLKSSCKRHPLYVDFSDVGWNDWIIAPPGYAANYCHGECPFPLADHLNSTNHAIVQTLVN SVNSKIPKACCVPTELSAISMLYLDENEKVVLKNYQDMVVEGCGCR | 20 |
| BMP-AR | QAKHKQRKRLKSSCKRHPLYVDFSDVGWNDWIIAPRGYAANYCHGECPFPLADHLNSTNHAIVQTLVN SVNSKIPKACCVPTELSAISMLYLDENEKVVLKNYQDMVVEGCGCR | 21 |
| BMP-AK | QAKHKQRKRLKSSCKRHPLYVDFSDVGWNDWIIAPKGYAANYCHGECPFPLADHLNSTKHAIVQTLVN SVNSKIPKACCVPTELSAISMLYLDENEKVVLKNYQDMVVEGCGCR | 22 |
| BMP-AT | QAKHKQRKRLKSSCKRHPLYVDFSDVGWNDWIIAPKGYAANYCHGECPFPLADHLNSTTHAIVQTLVN SVNSKIPKACCVPTELSAISMLYLDENEKVVLKNYQDMVVEGCGCR | 23 |
| BMP-DP | QAKHKQRKRLKSSCKRHPLYVDFSDVGWNDWIVAPPGYHAFYCHGECPFPLNAHMNATNHAIVQTLVH LMNPSKIPKACCVPTELSAISMLYLDENEKVVLKNYQDMVVEGCGCR | 24 |
| BMP-E9 | QAKHKQRKRLKSSCKRHPLYVDFSDVGWNDWIVAPPGYHAFYCKGGCFFPLADDVTPTKHAIVQTLVH LKFPTKVGKACCVPTELSAISMLYLDENEKVVLKNYQDMVVEGCGCR | 25 |
| BMP-E10 | QAKHKQRKRLKSSCKRHPLYVDFSDVGWNDWIVAPPGYHAFYCRGVCNYPLAEHLTPTKHAIIQALVH LKNSQKASKACCVPTELSAISMLYLDENEKVVLKNYQDMVVEGCGCR | 26 |
| BMP-EK | QAKHKQRKRLKSSCKRHPLYVDFSDVGWNDWIVAPPGYHAFYCDGECSFPLNAHMNATKHAIVQTLVH LMNPEYVPKPCCAPTELSAISMLYLDENEKVVLKNYQDMVVEGCGCR | 27 |
| BMP-ET | QAKHKQRKRLKSSCKRHPLYVDFSDVGWNDWIVAPPGYHAFYCDGECSFPLNAHMNATTHAIVQTLVH LMNPEYVPKPCCAPTELSAISMLYLDENEKVVLKNYQDMVVEGCGCR | 28 |
| BMP-R | QAKHKQRKRLKSSCKRHPLYVDFSDVGWNDWIVAPRGYHAFYCHGECPFPLADHLNSTNHAIVQTLVN SVNSKIPKACCVPTELSAISMLYLDENEKVVLKNYQDMVVEGCGCR | 29 |
| BMP-G5 | QAKHKQRKRLKSSCKRHPLYVDFSDVGWNDWIVAPPGYHAFYCEGLCEFPLRSHLEPTNHAVIQTLMN SMDPESTPPTCCVPTELSAISMLYLDENEKVVLKNYQDMVVEGCGCR | 30 |
| BMP-ER | QAKHKQRKRLKSSCKRHPLYVDFSDVGWNDWIVAPRGYHAFYCHGECPFPLADHLNSTNHAIVQTLVN SVNSKIPKACCVPTELSAISMLYLDENEKVVLKNYQDMVVEGCGCR | 31 |
| BMP-GP | QAKHKQRKRLKSSCKRHPLYVDFSDVGWNDWIIAPPGYAAFYCHGECPFPLADHLNSTNHAIVQTLVN SVNSKIPKACCVPTELNAISVLYFDDNSNVILKNYQDMVVEGCGCR | 32 |
| BMP-GR | QAKHKQRKRLKSSCKRHPLYVDFSDVGWNDWIIAPRGYAAFYCHGECPFPLADHLNSTNHAIVQTLVN SVNSKIPKACCVPTELNAISVLYFDDNSNVILKNYQDMVVEGCGCR | 33 |
| BMP-GK | QAKHKQRKRLKSSCKRHPLYVDFSDVGWNDWIIAPKGYAAFYCHGECPFPLADHLNSTKHAIVQTLVN SVNSKIPKACCVPTELNAISVLYFDDNSNVILKNYQDMVVEGCGCR | 34 |
| BMP-GT | QAKHKQRKRLKSSCKRHPLYVDFSDVGWNDWIIAPKGYAAFYCHGECPFPLADHLNSTTHAIVQTLVN SVNSKIPKACCVPTELNAISVLYFDDNSNVILKNYQDMVVEGCGCR | 35 |
| BMP-GE | QAKHKQRKRLKSSCKRHPLYVDFSDVGWNDWIIAPKGYAAFYCDGECSFPLNAHMNATNHAIVQTLVH LMNPEYVPKPCCAPTELNAISVLYFDDNSNVILKNYQDMVVEGCGCR | 36 |
| BMP-GER | QAKHKQRKRLKSSCKRHPLYVDFSDVGWNDWIIAPRGYAAFYCDGECSFPLNAHMNATNHAIVQTLVH LMNPEYVPKPCCAPTELNAISVLYFDDNSNVILKNYQDMVVEGCGCR | 37 |
| BMP-JP | QAKHKQRKRLKSSCKRHPLYVDFSDVGWNDWIIAPPGYHAFYCDGECSFPLNAHMNATNHAIVQTLVH LMNPEYVPKPCCAPTELNAISVLYFDENSNVVLKKYQDMVVRGCGCR | 38 |
| BMP-JR | QAKHKQRKRLKSSCKRHPLYVDFSDVGWNDWIIAPRGYHAFYCDGECSFPLNAHMNATNHAIVQTLVH LMNPEYVPKPCCAPTELNAISVLYFDENSNVVLKKYQDMVVRGCGCR | 39 |
| BMP-JK | QAKHKQRKRLKSSCKRHPLYVDFSDVGWNDWIIAPKGYHAFYCDGECSFPLNAHMNATKHAIVQTLVH LMNPEYVPKPCCAPTELNAISVLYFDENSNVVLKKYQDMVVRGCGCR | 40 |

TABLE 7-continued

| NAME | SEQUENCE | SEQ ID NO |
|---|---|---|
| BMP-JT | QAKHKQRKRLKSSCKRHPLYVDFSDVGWNDWIIAPKGYHAFYCDGECSFPLNAHMNATTHAIVQTLVH LMNPEYVPKPCCAPTELNAISVLYFDENSNVVLKKYQDMVVRGCGCR | 41 |
| BMP-A9 | QAKHKQRKRLKSSCKRHPLYVDFSDVGWNDWIIAPKEYEAYECHGECPFPLADHLNSTNHAIVQTLVN SVNSKIPKACCVPTELSAISMLYLDENEKVVLKNYQDMVVEGCGCR | 42 |
| BMP-B9 | QAKHKQRKRLKSSCKRHPLYVDFSDVGWNDWIVAPPGYHAFYCHGECPFPLADHLNSTNHAIVQTLVN SVNSKIPKACCVPTELSPISVLYKDDMGVPTLKNYQDMVVEGCGCR | 43 |
| BMP-E9B | QAKHKQRKRLKSSCKRHPLYVDFSDVGWNDWIVAPPGYHAFYCDGECSFPLNAHMNATNHAIVQTLVH LMNPEYVPKPCCAPTELSPISVLYKDDMGVPTLKNYQDMVVEGCGCR. | 44 |
| BMP-G9 | QAKHKQRKRLKSSCKRHPLYVDFSDVGWNDWIIAPKEYEAYECHGECPFPLADHLNSTNHAIVQTLVN SVNSKIPKACCVPTELSPISVLYKDDMGVPTLKNYQDMVVEGCGCR | 45 |
| BMP929 | QAKHKQRKRLKSSCQKTSLRVNFEDIGWDSWIIAPKEYEAYECHGECPFPLADHLNSTNHAIVQTLVN SVNSKIPKACCVPTKLSPISVLYKDDMGVPTLKYHYEGMSVAECGCR | 46 |
| BMP969 | QAKHKQRKRLKSSCQKTSLRVNFEDIGWDSWIIAPKEYEAYECDGECSFPLNAHMNATNHAIVQTLVH LMNPEYVPKPCCVPTKLSPISVLYKDDMGVPTLKYHYEGMSVAECGCR | 47 |
| BMPQAK no SAGA | QAKHKQRKRLKSSCQKTSLRVNFEDIGWDSWIIAPKEYEAYECKGGCFFPLADDVTPTKHAIVQTLVH LKFPTKVGKACCVPTKLSPISVLYKDDMGVPTLKYHYEGMSVAECGCR | 48 |
| BMP-QAKSA GAC | QAKHKQRKRLKSSSAGAGSHCQKTSLRVNFEDIGWDSWIIAPKEYEAYECKGGCFFPLADDVTPTKHA IVQTLVHLKFPTKVGKACCVPTKLSPISVLYKDDMGVPTLKYHYEGMSVAECGCR | 49 |
| BMP-GEP | QAKHKQRKRLKSSCKRHPLYVDFSDVGWNDWIIAPPGYAAFYCDGECSFPLNAHMNATNHAIVQTLVH LMNPEYVPKPCCAPTELNAISVLYFDDNSNVILKNYQDMVVEGCGCR | 50 |
| BMP6-SA | VSSASDYNSSELKTACRKHELYVSFQDLGWQDWIIAPKGYAANYCDGECSFPLNAAMNATNHAIVQTL VHLMNPEYVPKPCCAPTKLNAISVLYFDDNSNVILKKYRNMVVRACGCH | 51 |
| BMP6-SL | VSSASDYNSSELKTACRKHELYVSFQDLGWQDWIIAPKGYAANYCDGECSFPLNAHLNATNHAIVQTL VHLMNPEYVPKPCCAPTKLNAISVLYFDDNSNVILKKYRNMVVRACGCH | 52 |
| BMP6A | SASSRRRQQSRNRSTQSQDVARVSSASDYNSSELKTACRKHELYVSFQDLGWQDWIIAPKGYAANYCD GECSFPLADHLNSTNHAIVQTLVNSVNPEYVPKPCCAPTKLNAISVLYFDDNSNVILKKYRNMVVRAC GCH. | 53 |
| BMP6B | SASSRRRQQSRNRSTQSQDVARVSSASDYNSSELKTACRKHELYVSFQDLGWQDWIIAPKGYAANYCH GECPFPLADHLNSTNHAIVQTLVNSVNSKIPKACCVPTKLNAISVLYFDDNSNVILKKYRNMVVRACG CH. | 54 |
| BMP6C | SASSRRRQQSRNRSTQSQDVARVSSASDYNSSELKTACRKHELYVSFQDLGWQDWIVAPPGYHAFYCD GECSFPLNAHMNATNHAIVQTLVHLMNPEYVPKPCCAPTKLNAISVLYFDDNSNVILKKYRNMVVRAC GCH. | 55 |
| BMP6D | SASSRRRQQSRNRSTQSQDVARVSSASDYNSSELKTACRKHELYVSFQDLGWQDWIIAPKGYAANYCD GECSFPLNAHMNATNHAIVQTLVHLMNPEYVPKPCCAPELSAISMLYLDENEKVVLKKYRNMVVRACG CH. | 56 |
| BMP6 ADHL | VSSASDYNSSELKTACRKHELYVSFQDLGWQDWIIAPKGYAANYCDGECSFPLADHLNATNHAIVQTL VHLMNPEYVPKPCCAPTKLNAISVLYFDDNSNVILKKYRNMVVRACGCH | 57 |
| BMP6-RK-KR | VSSASDYNSSELKTACKRHELYVSFQDLGWQDWIIAPKGYAANYCDGECSFPLNAHMNATNHAIVQTL VHLMNPEYVPKPCCAPTKLNAISVLYFDDNSNVILKKYRNMVVRACGCH | 58 |
| BMP6 RK-KR ADHL long | VSSASDYNSSELKTACKRHELYVSFQDLGWQDWIIAPKGYAANYCDGECSFPLADHLNATNHAIVQTL VHLMNPEYVPKPCCAPTKLNAISVLYFDDNSNVILKKYRNMVVRACGCH | 59 |
| BMP6A RK-KR | SASSRRRQQSRNRSTQSQDVARVSSASDYNSSELKTACKRHELYVSFQDLGWQDWIIAPKGYAANYCD GECSFPLADHLNSTNHAIVQTLVNSVNPEYVPKPCCAPTKLNAISVLYFDDNSNVILKKYRNMVVRAC GCH | 60 |
| BMP6 ADHL long | SASSRRRQQSRNRSTQSQDVARVSSASDYNSSELKTACRKHELYVSFQDLGWQDWIIAPKGYAANYCD GECSFPLADHLNATNHAIVQTLVHLMNPEYVPKPCCAPTKLNAISVLYFDDNSNVILKKYRNMVVRAC GCH. | 61 |
| BMP6 RK-KR ADHL | SASSRRRQQSRNRSTQSQDVARVSSASDYNSSELKTACKRHELYVSFQDLGWQDWIIAPKGYAANYCD GECSFPLADHLNATNHAIVQTLVHLMNPEYVPKPCCAPTKLNAISVLYFDDNSNVILKKYRNMVVRAC GCH. | 62 |

TABLE 7-continued

| NAME | SEQUENCE | SEQ ID NO |
|---|---|---|
| BMP6 RK-KR long | SASSRRRQQSRNRSTQSQDVARVSSASDYNSSELKTACKRHELYVSFQDLGWQDWIIAPKGYAANYCDGECSFPLNAHMNATNHAIVQTLVHLMNPEYVPKPCCAPTKLNAISVLYFDDNSNVILKKYRNMVVRACGCH | 63 |
| BMP6B-RK-KR | SASSRRRQQSRNRSTQSQDVARVSSASDYNSSELKTACKRHELYVSFQDLGWQDWIIAPKGYAANYCHGECPFPLADHLNSTNHAIVQTLVNSVNSKIPKACCVPTKLNAISVLYFDDNSNVILKKYRNMVVRACGCH | 64 |
| BMP9E2 | REKRSAGAGSHCQKTSLRVNFEDIGWDSWIIAPKEYEAYECHGECPFPLADHLNSTNHAIVQTLVNSVNSKIPKACCVPTKLSPISVLYKDDMGVPTLKYHYEGMSVAECGCR | 65 |
| BMP9E6 | SAGAGSHCQKTSLRVNFEDIGWDSWIIAPKEYEAYECDGECSFPLNAHMNATNHAIVQTLVHLMNPEYVPKPCCAPTKLSPISVLYKDDMGVPTLKYHYEGMSVAECGCR | 66 |
| BMP6-Short | VSSASDYNSSELKTACRKHELYVSFQDLGWQDWIIAPKGYAANYCDGECSFPLNAHMNATNHAIVQTLVHLMNPEYVPKPCCAPTKLNAISVLYFDDNSNVILKKYRNMVVRACGCH | 67 |
| BMP6-SA | VSSASDYNSSELKTACRKHELYVSFQDLGWQDWIIAPKGYAANYCDGECSFPLNAAMNATNHAIVQTLVHLMNPEYVPKPCCAPTKLNAISVLYFDDNSNVILKKYRNMVVRACGCH | 68 |
| BMP6-SL | VSSASDYNSSELKTACRKHELYVSFQDLGWQDWIIAPKGYAANYCDGECSFPLNAHLNATNHAIVQTLVHLMNPEYVPKPCCAPTKLNAISVLYFDDNSNVILKKYRNMVVRACGCH | 69 |
| BMP-E-NR | QAKHKQRKRLKSSCKRHPLYVDFSDVGWNDWIVAPPGYHAFYCDGECSFPLNAHMNATNHAIVQTLVHLMNPEYVPKPCCAPTKLRPMSMLYYDDGQNIIKKDIQNMIVEECGCS | 70 |
| BMP-GER-NR | QAKHKQRKRLKSSCKRHPLYVDFSDVGWNDWIIAPRGYAAFYCDGECSFPLNAHMNATNHAIVQTLVHLMNPEYVPKPCCAPTKLRPMSMLYYDDGQNIIKKDIQNMIVEECGCS | 71 |
| BMP-E-NR-6 | QAKHKQRKRLKSSCKRHPLYVDFSDVGWNDWIVAPPGYHAFYCDGECSFPLNAHMNATNHAIVQTLVHLMNPEYVPKPCCAPTKLNAISVLYFDDNSNVILKKYRNMVVRACGCH | 72 |
| BMP-GER-NR-6 | QAKHKQRKRLKSSCKRHPLYVDFSDVGWNDWIIAPRGYAAFYCDGECSFPLNAHMNATNHAIVQTLVHLMNPEYVPKPCCAPTKLNAISVLYFDDNSNVILKKYRNMVVRACGCH | 73 |

Although the above listed designer BMPs comprise embodiments of the invention, the invention is not limited in any way to any specific molecules. Instead, the invention encompasses any designer BMP comprising altered receptor binding where the designer BMP comprises at least one mutation within a type II receptor binding domain A, even more preferably, the designer BMP comprises at least one further mutation within a type I receptor binding domain, most preferably, the designer BMP comprises yet another at least one further mutation within a type II receptor binding domain B.

In other embodiments, the designer BMP of the present invention comprises an amino acid sequence at least about 70%, 75%, 80%, 85%, 87%, 90%, 92%, 95%, 96%, 97%, 98%, 99% or identical to one of the sequences described above. In another embodiment, the designer BMP comprises an amino acid sequence at least about 70%, 75%, 80%, 85%, 87%, 90%, 92%, 95%, 96%, 97%, 98%, 99% or identical to the sequence of SEQ ID NOs:8-73.

In yet another embodiment, the designer BMP comprises an amino acid sequence as set forth in any one of SEQ ID NOs:8-73. In another embodiment, the amino acid sequence of the designer BMP consists of one of the sequences of SEQ ID NOs:8-73.

Further in one embodiment, the designer BMP comprises an amino acid sequence at least about 70%, 75%, 80%, 85%, 87%, 90%, 92%, 95%, 96%, 97%, 98%, 99% or identical to the sequence of SEQ ID NO:12. In another embodiment, the amino acid sequence is the sequence of SEQ ID NO:12. In yet another embodiment, the designer BMP is BMPE.

In an additional embodiment, the designer BMP comprises an amino acid sequence at least about 70%, 75%, 80%, 85%, 87%, 90%, 92%, 95%, 96%, 97%, 98%, 99% or identical to the sequence of SEQ ID NO:14. In another embodiment, the amino acid sequence is the sequence of SEQ ID NO:14. In yet another embodiment, the designer BMP is BMPG.

In another embodiment, the designer BMP comprises an amino acid sequence at least about 70%, 75%, 80%, 85%, 87%, 90%, 92%, 95%, 96%, 97%, 98%, 99% or identical to the sequence of SEQ ID NO:36. In another embodiment, the amino acid sequence is the sequence of SEQ ID NO:36. In yet another embodiment, the designer BMP is BMPGE.

In another embodiment, the designer BMP comprises an amino acid sequence at least about 70%, 75%, 80%, 85%, 87%, 90%, 92%, 95%, 96%, 97%, 98%, 99% or identical to the sequence of SEQ ID NO:37. In another embodiment, the amino acid sequence is the sequence of SEQ ID NO:37. In yet another embodiment, the designer BMP is BMPGER.

A designer BMP of the invention may comprise a fragment of any one of the sequences described above. In an embodiment, a designer BMP fragment may comprise a fragment of at least an uninterrupted 20, 22, 24, 25, 26, 27, 28, 30, 32, 33, 34, 35, 36, 37, 38, 40, 41, 43, 44, 45, 47, 50, 53, 54, 56, 58, 60, 62, 66, 68, 70, 71, 74, 77, 80, 83, 85, 88, 90, 91, 93, 95, 97, 99, 100, 102, 105, 108, 110, 112, 115, 117, 119, 120, 121, 122, or 125 amino acid sequence from the sequence of any one of the sequences of SEQ ID NOs:8-73.

It is well known in the art that BMPs are often heterogeneous with respect to the amino and/or carboxyl termini of the protein. That is, the present invention comprises a designer BMP comprising an amino acid deletion/truncation at the amino and/or carboxyl terminus comprising a deletion of at least 10 amino acid residues, preferably, 9 amino acid residues, even more preferably, 8 amino acid residues, yet more preferably, 7 amino acid residues, preferably 6 amino acid residues, even more preferably, 5 amino acid residues, preferably 4 amino acid residues, more preferably 3 amino acid residues, even more preferably 2 amino acid residues, and most preferably 1 amino acid reside from the C and or N terminus of the designer BMP.

In another embodiment, the invention comprises a designer BMP protein comprising an amino acid sequence of any one of the sequences of SEQ ID NO:8-73 and further comprising a deletion/truncation from the amino and/or carboxyl termini of the protein. In another embodiment, the invention comprises a designer BMP protein derived from a BMP protein comprising an amino acid sequence of any of the sequences of SEQ ID NOs:8-73, wherein the protein comprises an amino acid deletion/truncation at the amino and/or carboxyl terminus comprising a deletion of at least 10 amino acid residues, preferably, 9 amino acid residues, even more preferably, 8 amino acid residues, yet more preferably, 7 amino acid residues, preferably 6 amino acid residues, even more preferably, 5 amino acid residues, preferably 4 amino acid residues, more preferably 3 amino acid residues, even more preferably 2 amino acid residues, and most preferably 1 amino acid reside from the C and or N terminus of the designer BMP protein amino acid sequence.

Structural Design of BMPs with Altered Receptor Affinity Mediated by Glycosylation The data disclosed herein demonstrate that BMP2 homodimers produced in *E. coli* (referred to herein as "*E. coli* BMP2"), which are not glycosylated, are less active than glycosylated BMP2 produced in mammalian cells, such as CHO cells (referred to herein as "CHO BMP2"). In addition, data disclosed herein further demonstrate that *E. coli* produced BMP6 homodimers are essentially non-functional compared with BMP6 homodimers produced in mammalian cell culture.

The data disclosed herein demonstrate that there are significant variations in the crystal structure of *E. coli* BMP2 compared with CHO BMP2 in the type I receptor binding region.

Figure 3:
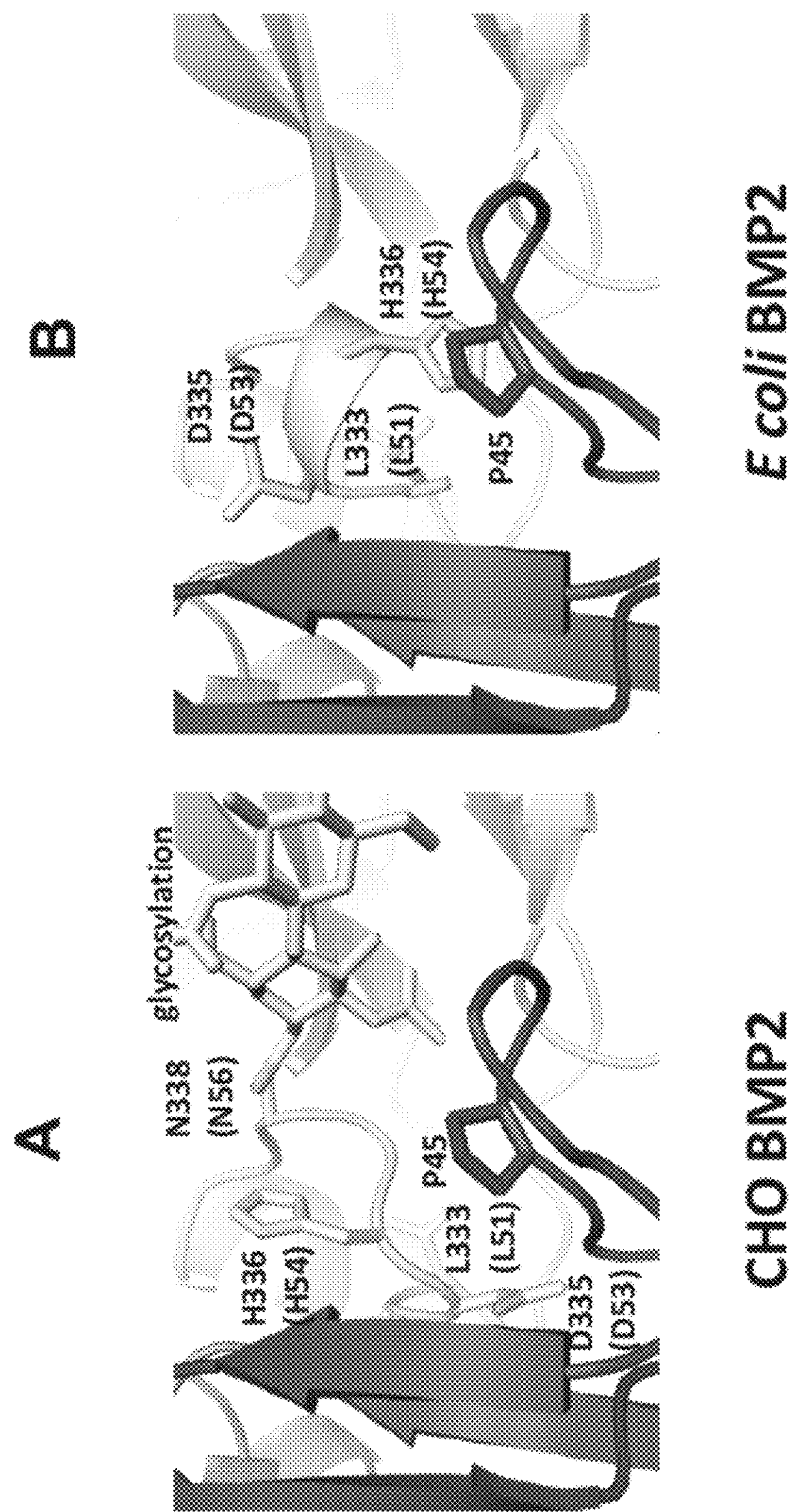
FIG. 3, comprising panels A and B, is an diagram of a structural model showing the position of the histidine doorstop (H54) in human BMP2 produced in Chinese Hamster Ovary (CHO) (FIG. 3A) and *E. coli* cells (FIG. 3B).

In one embodiment, the designer BMP comprises an altered conformation mediated by glycosylation thereby affecting a binding motif that. In turn, mediates altered binding to a type I receptor. This is based on the present discovery that in mammalian (e.g., CHO) cell produced wild type BMP2, D53 points towards the receptor interface while the H54 points away from the receptor. This is in contrast to *E. coli*-produced BMP2 where the D53 residue points away from the receptor interface and the H54 residue lines up toward the receptor, stacking against a proline reside as illustrated in FIG. 3, apparently acting as a "doorstop." In addition, the data disclosed herein demonstrate for the first time that CHO-produced BMP6, which is fully glycosylated and active, also comprises a histidine residue pointing toward the incoming receptor, i.e., a histidine "doorstop."

Without wishing to be bound by any particular theory, the data disclosed herein suggest, for the first time, that moving a "doorstop" residue away from the receptor interface, can mediate increased binding between the BMP ligand and its receptor. The data further demonstrate that the doorstop residue may be either mutated itself to remove the doorstop or other residues may be mutated to shift the position of the doorstop residue. Further, the data disclosed herein further demonstrate that other residues may be mutated to provide a "glycan tether" which then, in turn, can orient a glycan such that the tethering of the glycan will reorient the doorstop residue.

Therefore, in some embodiments, a designer BMP can be produced by incorporating at least one amino acid mutation that affects the glycan tether and/or removes a histidine doorstop structure thereby providing a designer BMP with altered receptor binding.

In summary, in some embodiments, the designer BMPs of the invention may comprise at least one mutation in the type I and/or type II binding domains of BMPs that confer altered type I and/or type II receptor binding. In one embodiment, the BMP sequence is engineered to alter the receptor affinity of BMPs in order to alter and improve the receptor binding and/or osteogenic activity of the engineered or "designer" BMP. In one embodiment, this engineering involves identifying the residues involved in type I and type II receptor binding and replacing them to create designer BMP molecules that show, among other things, higher affinity to both type I and type II receptors than the parental BMP from which the designer is derived.

In other embodiments, the designer BMPs of the invention comprise mutations that create a new arginine "glycan tether" or destroy an existing one to reshape the type I receptor binding domain. That is, the mutation to an arginine in the position two residues C-terminal from the first cysteine, equivalent to R16 of BMP2, appears to cause the glycan chain to be "tethered" onto the BMP surface and consequently alter the conformation of the pre-helical loop region compared with the wild type BMP that lacks the mutation. In other embodiments, the designer BMP of the invention may comprise at least one mutation that alters, creates or destroys (abolishes) the "doorstop" residue that blocks type I receptor from further engagement with BMP. That is, the mutation of H54 in the designer BMP, or a corresponding equivalent residue thereof, that is oriented in such a way that it impedes or increases interaction of the designer BMP with a type I receptor.

In some embodiments, the amino acid mutation affects the conformation of the designer BMP such that the mutation mediates the creation and or abolishment of an arginine "glycan tether" otherwise present in the corresponding wild type BMP. In some embodiments, the mutation mediates an altered conformation which creates or removes/abolishes a histidine doorstop conformation in the designer BMP where such doorstop conformation is either not present or active, respectively, in the corresponding wild type BMP.

Therefore, the skilled artisan, once armed with the teachings provided herein, would appreciate that the presence or absence of an arginine "glycan tether" and/or a histidine "doorstop" in a TGFβ superfamily member may be assessed using any method known in the art for the structural analysis of proteins, including, but not limited to, the methods exemplified herein. Once the presence of a "doorstop" residue has been identified, then at least one mutation can be introduced into the molecule to reorient the histidine away from the receptor binding interface. Alternatively, a mutation can be introduced that will create or enhance a "glycan tether" such that the inhibitory effect of the histidine "doorstop", if present, is decreased or, more preferably, eliminated.

In one embodiment, where the TGF superfamily member is BMP2, the mutation that removes the histidine doorstop is substitution of another amino acid for H54. In some embodiments, the H54 is replaced with alanine, glycine, serine, or threonine.

Although the present invention discloses such "doorstop"-removing mutations for BMP2, the skilled artisan would understand, based on the knowledge in the art, how to identify corresponding mutations for other TGFβ superfamily members and readily produce mutants lacking a "doorstop," i.e., removing or reorienting a residue that would otherwise interfere with receptor binding by facing or projecting into the binding interface. The effects of the mutation on protein conformation can be determined using any art-recognized method for the structural analysis of proteins such as, but not limited to, those disclosed herein. Alternatively, mutations that can remove the doorstop and increase ligand binding to the type I receptor can be identified in silico using computer modeling methods available in the art. Therefore, the present invention encompasses the design of TGFβ superfamily members having improved binding with the type I receptor in that they lack a histidine "doorstop" residue that would otherwise be present in the receptor interface.

The present invention further provides the skilled artisan with the understanding of how to identify mutations for other TGFβ family members that would generate or destroy the arginine glycan tether. Mutations that add the arginine glycan tether to a protein lacking the tether are contemplated by the instant invention. Therefore, the present invention encompasses the design of TGFβ superfamily members having improved binding with the type I receptor in that they contain an arginine glycan tether that alters the conformation of the type I receptor binding domain.

In some embodiments, the removal of the histidine doorstop thereby removing the requirement of a glycan tether, provides a designer BMP that can be produced without glycosylation while maintaining biological activity. For example, designer BMPs may be produced in cells with glycosylation activity that differs from mammalian cells or is not present, such as bacterial cells, yeast cells, insect cells, or slime mold cells. In particular embodiments, the designer BMPs may be produced in *E. coli* and maintain biological activity.

Thus, in some embodiments, the invention provides methods for designing and producing BMPs that can be produced in cells either lacking glycosylation or comprising altered glycosylation such that an altered glycan is produced which differs from that produced by a mammalian cell. That is, the present invention encompasses methods for introducing a mutation that removes a doorstop residue that would otherwise impair or inhibit receptor binding. The skilled artisan would understand once provided with the teachings of the invention that a doorstop residue that impinges upon the receptor-ligand interface may be mutated to entirely remove the residue or other mutations can be introduced such that the residue is oriented away from the interface. Such other mutations include, but are not limited to, providing a glycan tether that will alter the conformation of a glycan and thereby alter the conformation of the ligand such that the doorstop residue is orientated away from the binding interface.

Nucleic Acids Encoding Designer BMPs

The invention also includes nucleic acids encoding designer the BMPs described herein. Nucleic acids encoding the designer BMPs described herein can be prepared according to a wide plethora of methods known in the art.

In one, nucleic acids encoding designer BMPs are prepared by total gene synthesis, or by site-directed mutagenesis of a nucleic acid encoding wild type or modified BMPs. Methods including template-directed ligation, recursive FOR, cassette mutagenesis, site-directed mutagenesis or other techniques that are well known in the art may be utilized (see for example Strizhov et al., *Proc. Natl. Acad. Sci. USA* 93:15012-15017 (1996): Prodromou and Perl, *Prot. Eng.* 5: 827-829 (1992); Jayaraman and Puccini, *Biotechniques* 12: 392-398 (1992): and Chalmers et al., *Biotechniques* 30: 249-252 (2001)).

Thus, embodiments of the present invention can comprise nucleic acid molecules that encode the designer BMPs of the present invention. In certain embodiments, the invention provides a nucleic acid molecule that encodes for one of the amino acid sequences of SEQ ID NOs:8 to 66.

In other embodiments, the nucleic acid molecule encodes a designer BMP protein that comprises an amino acid sequence at least 70%, 75%, 80%, 85%, 87%, 90%, 92%, 93%, 94%, 95%, 96%, 97%, 98%, 99% identical to the amino acid sequence of SEQ ID NO:12. In some embodiments, the nucleic molecule encodes a designer BMP protein that comprises the amino acid sequence of SEQ ID NO:12. In another embodiment, the nucleic acid molecule encodes the amino acid sequence of BMPE as set forth in Table 8.

In other embodiments, the nucleic acid molecule encodes a designer BMP protein that comprises an amino acid sequence at least 70%, 75%, 80%, 85%, 87%, 90%, 92%, 93%, 94%, 95%, 96%, 97%, 98%, 99% identical to the amino acid sequence of SEQ ID NO:14. In some embodiments, the nucleic molecule encodes a designer BMP protein that comprises the amino acid sequence of SEQ ID NO:14. In another embodiment, the nucleic acid molecule encodes the amino acid sequence of BMPG as set forth in Table 8.

In other embodiments, the nucleic acid molecule encodes a designer BMP protein that comprises an amino acid sequence at least 70%, 75%, 80%, 85%, 87%, 90%, 92%, 93%, 94%, 95%, 96%, 97%, 98%, 99% identical to the amino acid sequence of SEQ ID NO:36. In some embodiments, the nucleic acid molecule encodes a designer BMP protein that comprises the amino acid sequence of SEQ ID NO:36. In another embodiment, the nucleic acid molecule encodes the amino acid sequence of BMPGE as set forth in Table 8.

In other embodiments, the nucleic acid molecule encodes a designer BMP protein that comprises an amino acid sequence at least 70%, 75%, 80%, 85%, 87%, 90%, 92%, 93%, 94%, 95%, 96%, 97%, 98%, 99% identical to the amino acid sequence of SEQ ID NO:37. In some embodiments, the nucleic acid molecule encodes a designer BMP protein that comprises the amino acid sequence of SEQ ID NO:37. In another embodiment, the nucleic acid molecule encodes the amino acid sequence of BMPGER as set forth in Table 8.

Exemplary nucleotide sequences encoding designer BMPs are set forth in Table 8, below. Table 8 shows the name of the protein encoded and the nucleotide sequence encoding that protein. In general, the mature protein coding sequence begins at nucleotide 847 of the sequences listed below.

TABLE 8

| NAME | SEQUENCE | SEQ ID NO |
|---|---|---|
| BMP-A | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG | 74 |

TABLE 8-continued

| NAME | SEQUENCE | SEQ ID NO |
|---|---|---|
| | CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>AGGGCTATGCTGCCAATTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTCAGTGCTATCTCGATGCTGTACCTTGACGAGAATGAAAAGGTTGTATTAAAGAACTATC<br>AGGACATGGTTGTGGAGGGTTGTGGGTGTCGCTGA | |
| BMP-B | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAAAGCTAAATGCCATCTCGGTTCTTTACTTTGATGACAACTCCAATGTCATTTTAAAGAACTATC<br>AGGACATGGTTGTGGAGGGTTGTGGGTGTCGCTGA | 75 |
| BMP-C | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>AGGGCTATGCTGCCAATTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAAAGCTAAATGCCATCTCGGTTCTTTACTTTGATGACAACTCCAATGTCATTTTAAAGAACTATC<br>AGGACATGGTTGTGGAGGGTTGTGGGTGTCGCTGA | 76 |
| BMP-D | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCCACGGAGAATGCCCTTTTCCACTCAACGCACACATGAATGCAACC<br>AACCACGCGATTGTGCAGACCTTGGTTCACCTTATGAACTCTAAGATTCCTAAGGCATGCTGTGTCCC<br>GACAGAACTCAGTGCTATCTCGATGCTGTACCTTGACGAGAATGAAAAGGTTGTATTAAAGAACTATC<br>AGGACATGGTTGTGGAGGGTTGTGGGTGTCGCTGA | 77 |
| BMP-E | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG | 78 |

TABLE 8-continued

| NAME | SEQUENCE | SEQ ID NO |
|---|---|---|
| | GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCGATGGAGAATGCTCCTTCCCACTCAACGCACACATGAATGCAACC<br>AACCACGCGATTGTGCAGACCTTGGTTCACCTTATGAACCCCGAGTATGTCCCCAAACCGTGCTGTGC<br>GCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTGA | |
| BMP-F | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>AGGGCTATGCTGCCTTTTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTCAGTGCTATCTCGATGCTGTACCTTGACGAGAATGAAAAGGTTGTATTAAAGAACTATC<br>AGGACATGGTTGTGGAGGGTTGTGGGTGTCGCTGA | 79 |
| BMP-G | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>AGGGCTATGCTGCCTTTTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTCAATGCCATCTCGGTTCTTTACTTTGATGACAACTCCAATGTCATTTTAAAGAACTATC<br>AGGACATGGTTGTGGAGGGTTGTGGGTGTCGCTGA | 80 |
| BMP-H | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCTCCCA<br>AGGGGTATCACGCCTTTTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTCAATGCTATCTCGGTTCTGTACTTTGACGAGAATTCCAATGTTGTATTAAAGAAATATC<br>AGGACATGGTTGTGAGAGGTTGTGGGTGTCGCTGA | 81 |
| BMP-I | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT | 82 |

TABLE 8-continued

| NAME | SEQUENCE | SEQ ID NO |
|---|---|---|
| | TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACGAGCTGTATGTGAGTTTCCAAGACCTGGGATGGCAGGACTGGATCATTGCACCCA<br>AGGGCTATGCTGCCAATTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTAAATGCCATCTCGGTTCTTTACTTTGATGACAACTCCAATGTCATTCTGAAAAAATACA<br>GGAATATGGTTGTAAGAGCTTGTGGGTGTCGCTGA | |
| BMP-J | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCTCCCA<br>AGGGGTATCACGCCTTTTACTGCGATGGAGAATGCTCCTTCCCACTCAACGCACACATGAATGCAACC<br>AACCACGCGATTGTGCAGACCTTGGTTCACCTTATGAACCCCGAGTATGTCCCCAAACCGTGCTGTGC<br>GCCGACAGAACTCAATGCTATCTCGGTTCTGTACTTTGACGAGAATTCCAATGTTGTATTAAAGAAAT<br>ATCAGGACATGGTTGTGAGAGGTTGTGGGTGTCGCTGA | 83 |
| BMP-K | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCCACGGAGAATGCCCTTTTCCTCTGGCTGATCATCTGAACTCCACT<br>AAACATGCCATTGTTCAGACGTTGGTCAACTCTGTTAACTCTAAGATTCCTAAGGCATGCTGTGTCCC<br>GACAGAACTCAGTGCTATCTCGATGCTGTACCTTGACGAGAATGAAAAGGTTGTATTAAAGAACTATC<br>AGGACATGGTTGTGGAGGGTTGTGGGTGTCGCTAG | 84 |
| BMP-T | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCCACGGAGAATGCCCTTTTCCTCTGGCTGATCATCTGAACTCCACT<br>ACTCATGCCATTGTTCAGACGTTGGTCAACTCTGTTAACTCTAAGATTCCTAAGGCATGCTGTGTCCC<br>GACAGAACTCAGTGCTATCTCGATGCTGTACCTTGACGAGAATGAAAAGGTTGTATTAAAGAACTATC<br>AGGACATGGTTGTGGAGGGTTGTGGGTGTCGCTAG | 85 |
| BMP-AP | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA | 86 |

TABLE 8-continued

| NAME | SEQUENCE | SEQ ID NO |
|---|---|---|
| | GGGCATCCTCTCCACAAAAGAGAAAAACGTCAAGCCAAACACAAACAGCGGAAACGCCTTAAGTCCAG | |
| | CTGTAAGAGACACCCTTTGTACGTGGACTTCAGTGACGTGGGGTGGAATGACTGGATTATTGCACCCC | |
| | CGGGCTATGCTGCCAATTACTGCCACGGAGAATGCCCTTTTCCTCTGGCTGATCATCTGAACTCCACT | |
| | AATCATGCCATTGTTCAGACGTTGGTCAACTCTGTTAACTCTAAGATTCCTAAGGCATGCTGTGTCCC | |
| | GACAGAACTCAGTGCTATCTCGATGCTGTACCTTGACGAGAATGAAAAGGTTGTATTAAAGAACTATC | |
| | AGGACATGGTTGTGGAGGGTTGTGGGTGTCGCTGA | |
| BMP-AR | ATGGTGGCCGGGACCCGCTGTCTTCTAGCGTTGCTGCTTCCCCAGGTCCTCCTGGGCGGCGCGGCTGG | 87 |
| | CCTCGTTCCGGAGCTGGGCCGCAGGAAGTTCGCGGCGGCGTCGTCGGGCCGCCCCTCATCCCAGCCCT | |
| | CTGACGAGGTCCTGAGCGAGTTCGAGTTGCGGCTGCTCAGCATGTTCGGCCTGAAACAGAGACCCACC | |
| | CCCAGCAGGGACGCCGTGGTGCCCCCCTACATGCTAGACCTGTATCGCAGGCACTCAGGTCAGCCGGG | |
| | CTCACCCGCCCCAGACCACCGGTTGGAGAGGGCAGCCAGCCGAGCCAACACTGTGCGCAGCTTCCACC | |
| | ATGAAGAATCTTTGGAAGAACTACCAGAAACGAGTGGGAAAACAACCCGGAGATTCTTCTTTAATTTA | |
| | AGTTCTATCCCCACGGAGGAGTTTATCACCTCAGCAGAGCTTCAGGTTTTCCGAGAACAGATGCAAGA | |
| | TGCTTTAGGAAACAATAGCAGTTTCCATCACCGAATTAATATTTATGAAATCATAAAACCTGCAACAG | |
| | CCAACTCGAAATTCCCCGTGACCAGACTTTTGGACACCAGGTTGGTGAATCAGAATGCAAGCAGGTGG | |
| | GAAAGTTTTGATGTCACCCCCGCTGTGATGCGGTGGACTGCACAGGGACACGCCAACCATGGATTCGT | |
| | GGTGGAAGTGGCCCACTTGGAGGAGAAACAAGGTGTCTCCAAGAGACATGTTAGGATAAGCAGGTCTT | |
| | TGCACCAAGATGAACACAGCTGGTCACAGATAAGGCCATTGCTAGTAACTTTTGGCCATGATGGAAAA | |
| | GGGCATCCTCTCCACAAAAGAGAAAAACGTCAAGCCAAACACAAACAGCGGAAACGCCTTAAGTCCAG | |
| | CTGTAAGAGACACCCTTTGTACGTGGACTTCAGTGACGTGGGGTGGAATGACTGGATTATTGCACCCA | |
| | GGGGCTATGCTGCCAATTACTGCCACGGAGAATGCCCTTTTCCTCTGGCTGATCATCTGAACTCCACT | |
| | AATCATGCCATTGTTCAGACGTTGGTCAACTCTGTTAACTCTAAGATTCCTAAGGCATGCTGTGTCCC | |
| | GACAGAACTCAGTGCTATCTCGATGCTGTACCTTGACGAGAATGAAAAGGTTGTATTAAAGAACTATC | |
| | AGGACATGGTTGTGGAGGGTTGTGGGTGTCGCTGA | |
| BMP-AK | ATGGTGGCCGGGACCCGCTGTCTTCTAGCGTTGCTGCTTCCCCAGGTCCTCCTGGGCGGCGCGGCTGG | 88 |
| | CCTCGTTCCGGAGCTGGGCCGCAGGAAGTTCGCGGCGGCGTCGTCGGGCCGCCCCTCATCCCAGCCCT | |
| | CTGACGAGGTCCTGAGCGAGTTCGAGTTGCGGCTGCTCAGCATGTTCGGCCTGAAACAGAGACCCACC | |
| | CCCAGCAGGGACGCCGTGGTGCCCCCCTACATGCTAGACCTGTATCGCAGGCACTCAGGTCAGCCGGG | |
| | CTCACCCGCCCCAGACCACCGGTTGGAGAGGGCAGCCAGCCGAGCCAACACTGTGCGCAGCTTCCACC | |
| | ATGAAGAATCTTTGGAAGAACTACCAGAAACGAGTGGGAAAACAACCCGGAGATTCTTCTTTAATTTA | |
| | AGTTCTATCCCCACGGAGGAGTTTATCACCTCAGCAGAGCTTCAGGTTTTCCGAGAACAGATGCAAGA | |
| | TGCTTTAGGAAACAATAGCAGTTTCCATCACCGAATTAATATTTATGAAATCATAAAACCTGCAACAG | |
| | CCAACTCGAAATTCCCCGTGACCAGACTTTTGGACACCAGGTTGGTGAATCAGAATGCAAGCAGGTGG | |
| | GAAAGTTTTGATGTCACCCCCGCTGTGATGCGGTGGACTGCACAGGGACACGCCAACCATGGATTCGT | |
| | GGTGGAAGTGGCCCACTTGGAGGAGAAACAAGGTGTCTCCAAGAGACATGTTAGGATAAGCAGGTCTT | |
| | TGCACCAAGATGAACACAGCTGGTCACAGATAAGGCCATTGCTAGTAACTTTTGGCCATGATGGAAAA | |
| | GGGCATCCTCTCCACAAAAGAGAAAAACGTCAAGCCAAACACAAACAGCGGAAACGCCTTAAGTCCAG | |
| | CTGTAAGAGACACCCTTTGTACGTGGACTTCAGTGACGTGGGGTGGAATGACTGGATTATTGCACCCA | |
| | AGGGCTATGCTGCCAATTACTGCCACGGAGAATGCCCTTTTCCTCTGGCTGATCATCTGAACTCCACT | |
| | AAACATGCCATTGTTCAGACGTTGGTCAACTCTGTTAACTCTAAGATTCCTAAGGCATGCTGTGTCCC | |
| | GACAGAACTCAGTGCTATCTCGATGCTGTACCTTGACGAGAATGAAAAGGTTGTATTAAAGAACTATC | |
| | AGGACATGGTTGTGGAGGGTTGTGGGTGTCGCTGA | |
| BMP-AT | ATGGTGGCCGGGACCCGCTGTCTTCTAGCGTTGCTGCTTCCCCAGGTCCTCCTGGGCGGCGCGGCTGG | 89 |
| | CCTCGTTCCGGAGCTGGGCCGCAGGAAGTTCGCGGCGGCGTCGTCGGGCCGCCCCTCATCCCAGCCCT | |
| | CTGACGAGGTCCTGAGCGAGTTCGAGTTGCGGCTGCTCAGCATGTTCGGCCTGAAACAGAGACCCACC | |
| | CCCAGCAGGGACGCCGTGGTGCCCCCCTACATGCTAGACCTGTATCGCAGGCACTCAGGTCAGCCGGG | |
| | CTCACCCGCCCCAGACCACCGGTTGGAGAGGGCAGCCAGCCGAGCCAACACTGTGCGCAGCTTCCACC | |
| | ATGAAGAATCTTTGGAAGAACTACCAGAAACGAGTGGGAAAACAACCCGGAGATTCTTCTTTAATTTA | |
| | AGTTCTATCCCCACGGAGGAGTTTATCACCTCAGCAGAGCTTCAGGTTTTCCGAGAACAGATGCAAGA | |
| | TGCTTTAGGAAACAATAGCAGTTTCCATCACCGAATTAATATTTATGAAATCATAAAACCTGCAACAG | |
| | CCAACTACGAAATTCCCCGTGACCAGACTTTTGGACACCAGGTTGGTGAATCAGAATGCAAGCAGGTGG | |
| | GAAAGTTTTGATGTCACCCCCGCTGTGATGCGGTGGACTGCACAGGGACACGCCAACCATGGATTCGT | |
| | GGTGGAAGTGGCCCACTTGGAGGAGAAACAAGGTGTCTCCAAGAGACATGTTAGGATAAGCAGGTCTT | |
| | TGCACCAAGATGAACACAGCTGGTCACAGATAAGGCCATTGCTAGTAACTTTTGGCCATGATGGAAAA | |
| | GGGCATCCTCTCCACAAAAGAGAAAAACGTCAAGCCAAACACAAACAGCGGAAACGCCTTAAGTCCAG | |
| | CTGTAAGAGACACCCTTTGTACGTGGACTTCAGTGACGTGGGGTGGAATGACTGGATTATTGCACCCA | |
| | AGGGCTATGCTGCCAATTACTGCCACGGAGAATGCCCTTTTCCTCTGGCTGATCATCTGAACTCCACT | |
| | ACTCATGCCATTGTTCAGACGTTGGTCAACTCTGTTAACTCTAAGATTCCTAAGGCATGCTGTGTCCC | |
| | GACAGAACTCAGTGCTATCTCGATGCTGTACCTTGACGAGAATGAAAAGGTTGTATTAAAGAACTATC | |
| | AGGACATGGTTGTGGAGGGTTGTGGGTGTCGCTGA | |
| BMP-DP | ATGGTGGCCGGGACCCGCTGTCTTCTAGCGTTGCTGCTTCCCCAGGTCCTCCTGGGCGGCGCGGCTGG | 90 |
| | CCTCGTTCCGGAGCTGGGCCGCAGGAAGTTCGCGGCGGCGTCGTCGGGCCGCCCCTCATCCCAGCCCT | |
| | CTGACGAGGTCCTGAGCGAGTTCGAGTTGCGGCTGCTCAGCATGTTCGGCCTGAAACAGAGACCCACC | |
| | CCCAGCAGGGACGCCGTGGTGCCCCCCTACATGCTAGACCTGTATCGCAGGCACTCAGGTCAGCCGGG | |
| | CTCACCCGCCCCAGACCACCGGTTGGAGAGGGCAGCCAGCCGAGCCAACACTGTGCGCAGCTTCCACC | |
| | ATGAAGAATCTTTGGAAGAACTACCAGAAACGAGTGGGAAAACAACCCGGAGATTCTTCTTTAATTTA | |
| | AGTTCTATCCCCACGGAGGAGTTTATCACCTCAGCAGAGCTTCAGGTTTTCCGAGAACAGATGCAAGA | |
| | TGCTTTAGGAAACAATAGCAGTTTCCATCACCGAATTAATATTTATGAAATCATAAAACCTGCAACAG | |
| | CCAACTCGAAATTCCCCGTGACCAGACTTTTGGACACCAGGTTGGTGAATCAGAATGCAAGCAGGTGG | |
| | GAAAGTTTTGATGTCACCCCCGCTGTGATGCGGTGGACTGCACAGGGACACGCCAACCATGGATTCGT | |
| | GGTGGAAGTGGCCCACTTGGAGGAGAAACAAGGTGTCTCCAAGAGACATGTTAGGATAAGCAGGTCTT | |
| | TGCACCAAGATGAACACAGCTGGTCACAGATAAGGCCATTGCTAGTAACTTTTGGCCATGATGGAAAA | |
| | GGGCATCCTCTCCACAAAAGAGAAAAACGTCAAGCCAAACACAAACAGCGGAAACGCCTTAAGTCCAG | |

TABLE 8-continued

| NAME | SEQUENCE | SEQ ID NO |
|---|---|---|
| | CTGTAAGAGACACCCTTTGTACGTGGACTTCAGTGACGTGGGGTGGAATGACTGGATTGTGGCTCCCC<br>CGGGGTATCACGCCTTTTACTGCCACGGAGAATGCCCTTTTCCACTCAACGCACACATGAATGCAACC<br>AACCACGCGATTGTGCAGACCTTGGTTCACCTTATGAACCCCTCTAAGATTCCTAAGGCATGCTGTGT<br>CCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTGA | |
| BMP-E9 | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCAAGGGCGGCTGCTTCTTCCCCTTGGCTGACGATGTGACGCCGACG<br>AAACACGCTATCGTGCAGACCCTGGTGCATCTCAAGTTCCCCACAAAGGTGGGCAAGGCCTGCTGTGT<br>CCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTAG | 91 |
| BMP-E10 | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCCGTGGTGTTTGTAACTACCCCCTGGCAGAGCATCTCACACCCACA<br>AAGCATGCAATTATCCAGGCCTTGGTCCACCTCAAGAATTCCCAGAAAGCTTCCAAAGCCTGCTGTGT<br>CCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTAG | 92 |
| BMP-EK | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCGATGGAGAATGCTCCTTCCCACTCAACGCACACATGAATGCAACC<br>AAACACGCGATTGTGCAGACCTTGGTTCACCTTATGAACCCCGAGTATGTCCCCAAACCGTGCTGTGC<br>GCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTGA | 93 |
| BMP-ET | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC | 94 |

TABLE 8-continued

| NAME | SEQUENCE | SEQ ID NO |
|---|---|---|
| | CGGGGTATCACGCCTTTTACTGCGATGGAGAATGCTCCTTCCCACTCAACGCACACATGAATGCAACC<br>ACCCACGCGATTGTGCAGACCTTGGTTCACCTTATGAACCCCGAGTATGTCCCCAAACCGTGCTGTGC<br>GCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTGA | |
| BMP-R | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCA<br>GGGGGTATCACGCCTTTTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTCAGTGCTATCTCGATGCTGTACCTTGACGAGAATGAAAAGGTTGTATTAAAGAACTATC<br>AGGACATGGTTGTGGAGGGTTGTGGGTGTCGCTAG | 95 |
| BMP-G5 | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCC<br>CGGGGTATCACGCCTTTTACTGCGAGGGGCTGTGCGAGTTCCCATTGCGCTCCCACCTGGAGCCCACG<br>AATCATGCAGTCATCCAGACCCTGATGAACTCCATGGACCCCGAGTCCACACCACCCACCTGCTGTGT<br>CCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTAG | 96 |
| BMP-ER | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTGTGGCTCCCA<br>GGGGGTATCACGCCTTTTACTGCGATGGAGAATGCTCCTTCCCACTCAACGCACACATGAATGCAACC<br>AACCACGCGATTGTGCAGACCTTGGTTCACCTTATGAACCCCGAGTATGTCCCCAAACCGTGCTGTGC<br>GCCGACAGAACTCAGTGCTATCTCGATGCTGTACCTTGACGAGAATGAAAAGGTTGTATTAAAGAACT<br>ATCAGGACATGGTTGTGGAGGGTTGTGGGTGTCGCTGA | 97 |
| BMP-GP | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCC<br>CGGGCTATGCTGCCTTTTACTGCCACGGAGAATGCCCTTTTCCTCTGGCTGATCATCTGAACTCCACT | 98 |

TABLE 8-continued

| NAME | SEQUENCE | SEQ ID NO |
|---|---|---|
| | AATCATGCCATTGTTCAGACGTTGGTCAACTCTGTTAACTCTAAGATTCCTAAGGCATGCTGTGTCCC<br>GACAGAACTCAATGCCATCTCGGTTCTTTACTTTGATGACAACTCCAATGTCATTTTAAAGAACTATC<br>AGGACATGGTTGTGGAGGGTTGTGGGTGTCGCTGA | |
| BMP-GR | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>GGGGCTATGCTGCCTTTTACTGCCACGGAGAATGCCCTTTTCCTCTGGCTGATCATCTGAACTCCACT<br>AATCATGCCATTGTTCAGACGTTGGTCAACTCTGTTAACTCTAAGATTCCTAAGGCATGCTGTGTCCC<br>GACAGAACTCAATGCCATCTCGGTTCTTTACTTTGATGACAACTCCAATGTCATTTTAAAGAACTATC<br>AGGACATGGTTGTGGAGGGTTGTGGGTGTCGCTGA | 99 |
| BMP-GK | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>AGGGCTATGCTGCCTTTTACTGCCACGGAGAATGCCCTTTTCCTCTGGCTGATCATCTGAACTCCACT<br>AAACATGCCATTGTTCAGACGTTGGTCAACTCTGTTAACTCTAAGATTCCTAAGGCATGCTGTGTCCC<br>GACAGAACTCAATGCCATCTCGGTTCTTTACTTTGATGACAACTCCAATGTCATTTTAAAGAACTATC<br>AGGACATGGTTGTGGAGGGTTGTGGGTGTCGCTGA | 100 |
| BMP-GT | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCACCCA<br>AGGGCTATGCTGCCTTTTACTGCCACGGAGAATGCCCTTTTCCTCTGGCTGATCATCTGAACTCCACT<br>ACTCATGCCATTGTTCAGACGTTGGTCAACTCTGTTAACTCTAAGATTCCTAAGGCATGCTGTGTCCC<br>GACAGAACTCAATGCCATCTCGGTTCTTTACTTTGATGACAACTCCAATGTCATTTTAAAGAACTATC<br>AGGACATGGTTGTGGAGGGTTGTGGGTGTCGCTGA | 101 |
| BMP-GE | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGCCAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCATCCATCCCCACCGAAGAGTTCATCACCTCCGCCGAGCTGCAGGTGTTCCGCGAGCAGATGCAGGA<br>CGCCCTGGGCAACAACTCCTCCTTCCACCACCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCAAGCGGCACCCCCTGTACGTGGACTTCTCCGACGTGGGCTGGAACGACTGGATCATTGCCCCCA<br>AGGGCTACGCCGCCTTCTACTGCGACGGCGAGTGCTCCTTCCCCCTGAACGCCCACATGAACGCCACC<br>AACCACGCCATCGTGCAGACCCTGGTGCACCTGATGAACCCCGAGTACGTGCCCAAGCCTTGTTGCGC | 102 |

TABLE 8-continued

| NAME | SEQUENCE | SEQ ID NO |
|---|---|---|
| | CCCCACCGAGCTGAACGCCATCTCCGTGCTGTACTTCGACGACAACTCCAACGTGATCCTGAAGAACT ACCAGGACATGGTGGTCGAAGGCTGCGGCTGTAGATGA | |
| BMP-GER | ATGGTGGCTGGCACCAGATGTCTGCTGGCCCTGCTGCTGCCCCAGGTGCTGCTGGGCGGAGCTGCTGG ACTGGTGCCCGAGCTGGGCAGAAGAAAGTTCGCCGCTGCCTCCTCTGGCCGGCCTTCCAGCCAGCCTT CCGACGAGGTGCTGTCCGAGTTCGAGCTGCGGCTGCTGTCCATGTTCGGCCTGAAGCAGCGGCCCACC CCTTCTAGGGACGCCGTGGTGCCCCCCTACATGCTGGACCTGTACCGGCGGCACTCCGGCCAGCCTGG ATCTCCTGCCCCCGACCACAGACTGGAAAGAGCCGCCTCCCGGGCCAACACCGTGCGGTCTTTCCACC ACGAGGAATCCCTGGAAGAACTGCCCGAGACATCCGGCAAGACCACCCGGCGGTTCTTTTTCAACCTG TCATCCATCCCCACCGAAGAGTTCATCACCTCCGCCGAGCTGCAGGTGTTCCGCGAGCAGATGCAGGA CGCCCTGGGCAACAACTCCTCCTTCCACCACCGGATCAACATCTACGAGATCATCAAGCCCGCCACCG CCAACTCCAAGTTCCCCGTGACCCGGCTGCTGGACACCCGGCTGGTGAACCAGAACGCCTCCAGATGG GAGTCCTTCGACGTGACCCCTGCCGTGATGAGATGGACCGCCCAGGGCCACGCCAACCACGGCTTTGT GGTGGAAGTGGCCCACCTGGAAGAGAAGCAGGGCGTGTCCAAGCGGCACGTGCGGATCTCTCGGTCCC TGCACCAGGACGAGCACAGCTGGTCCCAGATCCGGCCCCTGCTGGTGACATTCGGCCACGATGGCAAG GGCCACCCCCTGCACAAGAGAGAGAAGCGGCAGGCCAAGCACAAGCAGCGGAAGCGGCTGAAGTCCTC CTGCAAGCGGCACCCCCTGTACGTGGACTTCTCCGACGTGGGCTGGAACGACTGGATYRTKGCYCCCA GGGGSTAYSMCGCCTTYTACTGCGACGGCGAGTGCTCCTTCCCCCTGAACGCCCACATGAACGCCACC AACCACGCCATCGTGCAGACCCTGGTGCACCTGATGAACCCCGAGTACGTGCCCAAGCCTTGTTGCGC CCCCACCGAGCTGAACGCCATCTCCGTGCTGTACTTCGACGACAACTCCAACGTGATCCTGAAGAACT ACCAGGACATGGTGGTCGAAGGCTGCGGCTGTAGATGA | 103 |
| BMP-JP | ATGGTGGCCGGGACCCGCTGTCTTCTAGCGTTGCTGCTTCCCCAGGTCCTCCTGGGCGGCGCGGCTGG CCTCGTTCCGGAGCTGGGCCGCAGGAAGTTCGCGGCGGCGTCGTCGGGCCGCCCCTCATCCCAGCCCT CTGACGAGGTCCTGAGCGAGTTCGAGTTGCGGCTGCTCAGCATGTTCGGCCTGAAACAGAGACCCACC CCCAGCAGGGACGCCGTGGTGCCCCCCTACATGCTAGACCTGTATCGCAGGCACTCAGGTCAGCCGGG CTCACCCGCCCCAGACCACCGGTTGGAGAGGGCAGCCAGCCGAGCCAACACTGTGCGCAGCTTCCACC ATGAAGAATCTTTGGAAGAACTACCAGAAACGAGTGGGAAAACAACCCGGAGATTCTTCTTTAATTTA AGTTCTATCCCCACGGAGGAGTTTATCACCTCAGCAGAGCTTCAGGTTTTCCGAGAACAGATGCAAGA TGCTTTAGGAAACAATAGCAGTTTCCATCACCGAATTAATATTTATGAAATCATAAAACCTGCAACAG CCAACTCGAAATTCCCCGTGACCAGACTTTTGGACACCAGGTTGGTGAATCAGAATGCAAGCAGGTGG GAAAGTTTTGATGTCACCCCCGCTGTGATGCGGTGGACTGCACAGGGACACGCCAACCATGGATTCGT GGTGGAAGTGGCCCACTTGGAGGAGAAACAAGGTGTCTCCAAGAGACATGTTAGGATAAGCAGGTCTT TGCACCAAGATGAACACAGCTGGTCACAGATAAGGCCATTGCTAGTAACTTTTGGCCATGATGGAAAA GGGCATCCTCTCCACAAAAGAGAAAAACGTCAAGCCAAACACAAACAGCGGAAACGCCTTAAGTCCAG CTGTAAGAGACACCCTTTGTACGTGGACTTCAGTGACGTGGGGTGGAATGACTGGATTATTGCTCCCC CGGGGTATCACGCCTTTTACTGCGATGGAGAATGCTCCTTCCCACTCAACGCACACATGAATGCAACC AACCACGCGATTGTGCAGACCTTGGTTCACCTTATGAACCCCGAGTATGTCCCCAAACCGTGCTGTGC GCCGACAGAACTCAATGCTATCTCGGTTCTGTACTTTGACGAGAATTCCAATGTTGTATTAAAGAAAT ATCAGGACATGGTTGTGAGAGGTTGTGGGTGTCGCTGA | 104 |
| BMP-JR | ATGGTGGCCGGGACCCGCTGTCTTCTAGCGTTGCTGCTTCCCCAGGTCCTCCTGGGCGGCGCGGCTGG CCTCGTTCCGGAGCTGGGCCGCAGGAAGTTCGCGGCGGCGTCGTCGGGCCGCCCCTCATCCCAGCCCT CTGACGAGGTCCTGAGCGAGTTCGAGTTGCGGCTGCTCAGCATGTTCGGCCTGAAACAGAGACCCACC CCCAGCAGGGACGCCGTGGTGCCCCCCTACATGCTAGACCTGTATCGCAGGCACTCAGGTCAGCCGGG CTCACCCGCCCCAGACCACCGGTTGGAGAGGGCAGCCAGCCGAGCCAACACTGTGCGCAGCTTCCACC ATGAAGAATCTTTGGAAGAACTACCAGAAACGAGTGGGAAAACAACCCGGAGATTCTTCTTTAATTTA AGTTCTATCCCCACGGAGGAGTTTATCACCTCAGCAGAGCTTCAGGTTTTCCGAGAACAGATGCAAGA TGCTTTAGGAAACAATAGCAGTTTCCATCACCGAATTAATATTTATGAAATCATAAAACCTGCAACAG CCAACTCGAAATTCCCCGTGACCAGACTTTTGGACACCAGGTTGGTGAATCAGAATGCAAGCAGGTGG GAAAGTTTTGATGTCACCCCCGCTGTGATGCGGTGGACTGCACAGGGACACGCCAACCATGGATTCGT GGTGGAAGTGGCCCACTTGGAGGAGAAACAAGGTGTCTCCAAGAGACATGTTAGGATAAGCAGGTCTT TGCACCAAGATGAACACAGCTGGTCACAGATAAGGCCATTGCTAGTAACTTTTGGCCATGATGGAAAA GGGCATCCTCTCCACAAAAGAGAAAAACGTCAAGCCAAACACAAACAGCGGAAACGCCTTAAGTCCAG CTGTAAGAGACACCCTTTGTACGTGGACTTCAGTGACGTGGGGTGGAATGACTGGATTATTGCTCCCA GGGGGTATCACGCCTTTTACTGCGATGGAGAATGCTCCTTCCCACTCAACGCACACATGAATGCAACC AACCACGCGATTGTGCAGACCTTGGTTCACCTTATGAACCCCGAGTATGTCCCCAAACCGTGCTGTGC GCCGACAGAACTCAATGCTATCTCGGTTCTGTACTTTGACGAGAATTCCAATGTTGTATTAAAGAAAT ATCAGGACATGGTTGTGAGAGGTTGTGGGTGTCGCTGA | 105 |
| BMP-JK | ATGGTGGCCGGGACCCGCTGTCTTCTAGCGTTGCTGCTTCCCCAGGTCCTCCTGGGCGGCGCGGCTGG CCTCGTTCCGGAGCTGGGCCGCAGGAAGTTCGCGGCGGCGTCGTCGGGCCGCCCCTCATCCCAGCCCT CTGACGAGGTCCTGAGCGAGTTCGAGTTGCGGCTGCTCAGCATGTTCGGCCTGAAACAGAGACCCACC CCCAGCAGGGACGCCGTGGTGCCCCCCTACATGCTAGACCTGTATCGCAGGCACTCAGGTCAGCCGGG CTCACCCGCCCCAGACCACCGGTTGGAGAGGGCAGCCAGCCGAGCCAACACTGTGCGCAGCTTCCACC ATGAAGAATCTTTGGAAGAACTACCAGAAACGAGTGGGAAAACAACCCGGAGATTCTTCTTTAATTTA AGTTCTATCCCCACGGAGGAGTTTATCACCTCAGCAGAGCTTCAGGTTTTCCGAGAACAGATGCAAGA TGCTTTAGGAAACAATAGCAGTTTCCATCACCGAATTAATATTTATGAAATCATAAAACCTGCAACAG CCAACTCGAAATTCCCCGTGACCAGACTTTTGGACACCAGGTTGGTGAATCAGAATGCAAGCAGGTGG GAAAGTTTTGATGTCACCCCCGCTGTGATGCGGTGGACTGCACAGGGACACGCCAACCATGGATTCGT GGTGGAAGTGGCCCACTTGGAGGAGAAACAAGGTGTCTCCAAGAGACATGTTAGGATAAGCAGGTCTT TGCACCAAGATGAACACAGCTGGTCACAGATAAGGCCATTGCTAGTAACTTTTGGCCATGATGGAAAA GGGCATCCTCTCCACAAAAGAGAAAAACGTCAAGCCAAACACAAACAGCGGAAACGCCTTAAGTCCAG CTGTAAGAGACACCCTTTGTACGTGGACTTCAGTGACGTGGGGTGGAATGACTGGATTATTGCTCCCA AGGGGTATCACGCCTTTTACTGCGATGGAGAATGCTCCTTCCCACTCAACGCACACATGAATGCAACC AAACACGCGATTGTGCAGACCTTGGTTCACCTTATGAACCCCGAGTATGTCCCCAAACCGTGCTGTGC | 106 |

TABLE 8-continued

| NAME | SEQUENCE | SEQ ID NO |
|---|---|---|
| | GCCGACAGAACTCAATGCTATCTCGGTTCTGTACTTTGACGAGAATTCCAATGTTGTATTAAAGAAAT<br>ATCAGGACATGGTTGTGAGAGGTTGTGGGTGTCGCTGA | |
| BMP-JT | ATGGTGGCCGGGACCCGCTGTCTTCTAGCGTTGCTGCTTCCCCAGGTCCTCCTGGGCGGCGCGGCTGG<br>CCTCGTTCCGGAGCTGGGCCGCAGGAAGTTCGCGGCGGCGTCGTCGGGCCGCCCCTCATCCCAGCCCT<br>CTGACGAGGTCCTGAGCGAGTTCGAGTTGCGGCTGCTCAGCATGTTCGGCCTGAAACAGAGACCCACC<br>CCCAGCAGGGACGCCGTGGTGCCCCCCTACATGCTAGACCTGTATCGCAGGCACTCAGGTCAGCCGGG<br>CTCACCCGCCCCAGACCACCGGTTGGAGAGGGCAGCCAGCCGAGCCAACACTGTGCGCAGCTTCCACC<br>ATGAAGAATCTTTGGAAGAACTACCAGAAACGAGTGGGAAAACAACCCGGAGATTCTTCTTTAATTTA<br>AGTTCTATCCCCACGGAGGAGTTTATCACCTCAGCAGAGCTTCAGGTTTTCCGAGAACAGATGCAAGA<br>TGCTTTAGGAAACAATAGCAGTTTCCATCACCGAATTAATATTTATGAAATCATAAAACCTGCAACAG<br>CCAACTCGAAATTCCCCGTGACCAGACTTTTGGACACCAGGTTGGTGAATCAGAATGCAAGCAGGTGG<br>GAAAGTTTTGATGTCACCCCCGCTGTGATGCGGTGGACTGCACAGGGACACGCCAACCATGGATTCGT<br>GGTGGAAGTGGCCCACTTGGAGGAGAAACAAGGTGTCTCCAAGAGACATGTTAGGATAAGCAGGTCTT<br>TGCACCAAGATGAACACAGCTGGTCACAGATAAGGCCATTGCTAGTAACTTTTGGCCATGATGGAAAA<br>GGGCATCCTCTCCACAAAAGAGAAAAACGTCAAGCCAAACACAAACAGCGGAAACGCCTTAAGTCCAG<br>CTGTAAGAGACACCCTTTGTACGTGGACTTCAGTGACGTGGGGTGGAATGACTGGATTATTGCTCCCA<br>AGGGGTATCACGCCTTTTACTGCGATGGAGAATGCTCCTTCCCACTCAACGCACACATGAATGCAACC<br>ACCCACGCGATTGTGCAGACCTTGGTTCACCTTATGAACCCCGAGTATGTCCCCAAACCGTGCTGTGC<br>GCCGACAGAACTCAATGCTATCTCGGTTCTGTACTTTGACGAGAATTCCAATGTTGTATTAAAGAAAT<br>ATCAGGACATGGTTGTGAGAGGTTGTGGGTGTCGCTGA | 107 |
| BMP-A9 | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGACAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCCTCCATCCCCACCGAAGAGTTCATCACCTCCGCCGAGCTGCAGGTGTTCCGCGAGCAGATGCAGGA<br>CGCCCTGGGCAACAACTCCTCCTTCCACCATCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCAAGCGGCACCCCCTGTACGTGGACTTCTCCGACGTGGGCTGGAACGACTGGATCATTGCCCCCA<br>AAGAGTACGAGGCCTACGAGTGCCACGGCGAGTGCCCTTTCCCCCTGGCCGACCACCTGAACTCCACC<br>AACCACGCCATCGTGCAGACCCTGGTGAACTCCGTGAACAGCAAGATCCCCAAGGCCTGCTGCGTGCC<br>CACCGAGCTGTCCGCCATCTCCATGCTGTACCTGGACGAGAACGAGAAGGTGGTGCTGAAGAACTACC<br>AGGACATGGTGGTCGAAGGCTGCGGCTGTCGGTGA | 108 |
| BMP-B9 | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGACAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCCTCCATCCCCACCGAAGAGTTCATCACCTCCGCCGAGCTGCAGGTGTTCCGCGAGCAGATGCAGGA<br>CGCCCTGGGCAACAACTCCTCCTTCCACCATCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCAAGCGGCACCCCCTGTACGTGGACTTCTCCGACGTGGGCTGGAACGACTGGATCGTGGCCCCTC<br>CCGGCTACCACGGCGAGTGCCCTTTCCCCCTGGCCGACCACCTGAACTCCACCAACCACGCCATCGTG<br>CAGACCCTGGTGAACTCCGTGAACAGCAAGATCCCCAAGGCCTGCTGCGTGCCCACCGAGCTGTCCCC<br>CATCTCCGTGCTGTACAAGGACGACATGGGCGTGCCCACCCTGAAGAACTACCAGGACATGGTGGTCG<br>AAGGCTGCGGCTGTCGGTGA | 109 |
| BMP-E9B | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGACAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCCTCCATCCCCACCGAAGAGTTCATCACCTCCGCCGAGCTGCAGGTGTTCCGCGAGCAGATGCAGGA<br>CGCCCTGGGCAACAACTCCTCCTTCCACCATCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCAAGCGGCACCCCCTGTACGTGGACTTCTCCGACGTGGGCTGGAACGACTGGATCGTGGCCCCTC<br>CCGGCTACCACGCCTTCTACTGCGACGGCGAGTGCTCCTTCCCCCTGAACGCCCACATGAACGCCACC<br>AACCACGCCATCGTGCAGACCCTGGTGCACCTGATGAACCCCGAGTACGTGCCCAAGCCCTGCTGCGC | 110 |

TABLE 8-continued

| NAME | SEQUENCE | SEQ ID NO |
|---|---|---|
| | CCCCACCGAGCTGTCCCCCATCTCCGTGCTGTACAAGGACGACATGGGCGTGCCCACCCTGAAGAACT<br>ACCAGGACATGGTGGTCGAAGGCTGCGGCTGTCGGTGA | |
| BMP-G9 | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGACAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCCTCCATCCCCACCGAAGAGTTCATCACCTCCGCCGAGCTGCAGGTGTTCCGCGAGCAGATGCAGGA<br>CGCCCTGGGCAACAACTCCTCCTTCCACCATCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCAAGCGGCACCCCCTGTACGTGGACTTCTCCGACGTGGGCTGGAACGACTGGATCATCGCCCCTA<br>AGGAGTACGAGGCCTACGAGTGCCACGGCGAGTGCCCTTTCCCCCTGGCCGACCACCTGAACTCCACC<br>AACCACGCCATCGTGCAGACCCTGGTGAACTCCGTGAACAGCAAGATCCCCAAGGCCTGCTGCGTGCC<br>CACCGAGCTGTCCCCCATCTCCGTGCTGTACAAGGACGACATGGGCGTGCCCACCCTGAAGAACTACC<br>AGGACATGGTGGTCGAAGGCTGCGGCTGTCGGTGA | 111 |
| BMP-929 | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGACAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCCTCCATCCCCACCGAAGAGTTCATCACCTCCGCCGAGCTGCAGGTGTTCCGCGAGCAGATGCAGGA<br>CGCCCTGGGCAACAACTCCTCCTTCCACCATCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCCAGAAAACCTCCCTGCGGGTGAACTTCGAGGATATCGGCTGGGACTCCTGGATCATCGCCCCTA<br>AGGAGTACGAGGCCTACGAGTGCCACGGCGAGTGCCCTTTCCCCCTGGCCGACCACCTGAACTCCACC<br>AACCACGCCATCGTGCAGACCCTGGTGAACTCCGTGAACAGCAAGATCCCCAAGGCCTGCTGCGTGCC<br>CACCAAGCTGTCCCCCATCTCCGTGCTGTACAAGGACGACATGGGCGTGCCCACCCTGAAGTACCACT<br>ACGAGGGCATGTCCGTCGCCGAGTGCGGCTGTCGGTGA | 112 |
| BMP-969 | ATGGTGGCTGGCACCAGATGTCTGCTGGCCCTGCTGCTGCCCCAGGTGCTGCTGGGCGGAGCTGCTGG<br>ACTGGTGCCCGAGCTGGGCAGAAGAAAGTTCGCCGCTGCCTCCTCTGGCCGGCCTTCCAGCCAGCCTT<br>CCGACGAGGTGCTGTCCGAGTTCGAGCTGCGGCTGCTGTCCATGTTCGGCCTGAAGCAGCGGCCCACC<br>CCTTCTAGGGACGCCGTGGTGCCCCCCTACATGCTGGACCTGTACCGGCGGCACTCCGGACAGCCTGG<br>ATCTCCTGCCCCCGACCACAGACTGGAAAGAGCCGCCTCCCGGGCCAACACCGTGCGGTCTTTCCACC<br>ACGAGGAATCCCTGGAAGAACTGCCCGAGACATCCGGCAAGACCACCCGGCGGTTCTTTTTCAACCTG<br>TCCTCCATCCCCACCGAAGAGTTCATCACCTCCGCCGAGCTGCAGGTGTTCCGCGAGCAGATGCAGGA<br>CGCCCTGGGCAACAACTCCTCCTTCCACCATCGGATCAACATCTACGAGATCATCAAGCCCGCCACCG<br>CCAACTCCAAGTTCCCCGTGACCCGGCTGCTGGACACCCGGCTGGTGAACCAGAACGCCTCCAGATGG<br>GAGTCCTTCGACGTGACCCCTGCCGTGATGAGATGGACCGCCCAGGGCCACGCCAACCACGGCTTTGT<br>GGTGGAAGTGGCCCACCTGGAAGAGAAGCAGGGCGTGTCCAAGCGGCACGTGCGGATCTCTCGGTCCC<br>TGCACCAGGACGAGCACAGCTGGTCCCAGATCCGGCCCCTGCTGGTGACATTCGGCCACGATGGCAAG<br>GGCCACCCCCTGCACAAGAGAGAGAAGCGGCAGGCCAAGCACAAGCAGCGGAAGCGGCTGAAGTCCTC<br>CTGCCAGAAAACCTCCCTGCGGGTGAACTTCGAGGATATCGGCTGGGACTCCTGGATCATCGCCCCTA<br>AGGAGTACGAGGCCTACGAGTGCGACGGCGAGTGCTCCTTCCCCCTGAACGCCCACATGAACGCCACC<br>AACCACGCCATCGTGCAGACCCTGGTGCACCTGATGAACCCCGAGTACGTGCCCAAGCCCTGCTGCGT<br>CCCCACCAAGCTGTCCCCCATCTCCGTGCTGTACAAGGACGACATGGGCGTGCCCACCCTGAAGTACC<br>ACTACGAGGGCATGTCCGTCGCCGAGTGCGGCTGTCGGTGA | 113 |
| BMP-QAK no SAGA | ATGTGTCCTGGCGCTCTGTGGGTGGCCCTGCCTCTGCTGTCTCTGCTGGCCGGCAGCCTGCAGGGCAA<br>GCCTCTGCAGTCCTGGGGCAGAGGCTCCGCTGGCGGCAATGCTCACAGCCCTCTGGGAGTGCCTGGCG<br>GCGGACTGCCCGAGCACACCTTCAACCTGAAGATGTTCCTGGAAAACGTGAAGGTGGACTTCCTGCGG<br>TCCCTGAACCTGTCCGGCGTGCCCAGCCAGGACAAGACCCGGGTGGAACCCCCCCAGTACATGATCGA<br>CCTGTACAACCGGTACACCTCCGACAAGTCCACCACCCCCGCCTCCAACATCGTGCGGTCCTTCAGCA<br>TGGAAGATGCCATCTCCATTACCGCCACCGAGGACTTCCCATTTCAGAAGCACATCCTGCTGTTCAAC<br>ATCTCCATCCCCCGGCACGAGCAGATCACCAGAGCCGAGCTGCGGCTGTACGTGTCCTGCCAGAACCA<br>CGTGGACCCCTCCCACGACCTGAAGGGCTCCGTGGTGATCTACGACGTGCTGGACGGCACCGACGCCT<br>GGGACTCCGCTACCGAGACAAAGACCTTCCTGGTGTCCCAGGATATCCAGGACGAGGGCTGGGAGACA<br>CTGGAAGTGTCCTCCGCCGTGAAGAGATGGGTGCGATCCGACTCCACCAAGTCCAAGAACAAGCTGGA<br>AGTGACCGTGGAATCCCACCGGAAGGGCTGCGACACCCTGGACATCTCCGTGCCCCCTGGCTCCCGGA<br>ACCTGCCCTTCTTCGTGGTGTTCTCCAACGACCACTCCTCCGGCACCAAAGAGACACGGCTGGAACTG<br>AGAGAGATGATCTCCCACGAGCAGGAATCCGTCCTGAAGAAGCTGTCCAAGGACGGCTCCACCGAGGC<br>CGGCGAGTCCTCTCACGAAGAGGACACCGACGGCCACGTGGCAGCTGGCTCTACCCTGGCCAGACGGA<br>AGCGGCAGGCCAAGCACAAGCAGCGGAAGCGGCTGAAGTCCAGCTGCCAGAAAACCTCCCTGAGAGTG<br>AACTTCGAGGACATCGGCTGGGACAGCTGGATCATTGCCCCCAAAGAGTACGAGGCCTACGAGTGCAA<br>GGGCGGCTGCTTCTTCCCCCTGGCCGACGACGTGACCCCCACCAAGCACGCCATCGTGCAGACCCTGG | 114 |

TABLE 8-continued

| NAME | SEQUENCE | SEQ ID NO |
|---|---|---|
| | TGCACCTGAAGTTCCCCACCAAAGTGGGCAAGGCCTGCTGCGTGCCCACCAAGCTGTCCCCCATCAGC<br>GTGCTGTACAAGGACGACATGGGCGTGCCAACCCTGAAGTACCACTACGAGGGCATGTCCGTGGCCGA<br>GTGTGGCTGCCGGTGA | |
| BMP-QAKSAGAC | ATGTGTCCTGGCGCTCTGTGGGTGGCCCTGCCTCTGCTGTCTCTGCTGGCCGGCAGCCTGCAGGGCAA<br>GCCTCTGCAGTCCTGGGGCAGAGGCTCCGCTGGCGGCAATGCTCACAGCCCTCTGGGAGTGCCTGGCG<br>GCGGACTGCCCGAGCACACCTTCAACCTGAAGATGTTCCTGGAAAACGTGAAGGTGGACTTCCTGCGG<br>TCCCTGAACCTGTCCGGCGTGCCCAGCCAGGACAAGACCCGGGTGGAACCCCCCCAGTACATGATCGA<br>CCTGTACAACCGGTACACCTCCGACAAGTCCACCACCCCCGCCTCCAACATCGTGCGGTCCTTCAGCA<br>TGGAAGATGCCATCTCCATTACCGCCACCGAGGACTTCCCATTTCAGAAGCACATCCTGCTGTTCAAC<br>ATCTCCATCCCCCGGCACGAGCAGATCACCAGAGCCGAGCTGCGGCTGTACGTGTCCTGCCAGAACCA<br>CGTGGACCCCTCCCACGACCTGAAGGGCTCCGTGGTGATCTACGACGTGCTGGACGGCACCGACGCCT<br>GGGACTCCGCTACCGAGACAAAGACCTTCCTGGTGTCCCAGGATATCCAGGACGAGGGCTGGGAGACA<br>CTGGAAGTGTCCTCCGCCGTGAAGAGATGGGTGCGATCCGACTCCACCAAGTCCAAGAACAAGCTGGA<br>AGTGACCGTGGAATCCCACCGGAAGGGCTGCGACACCCTGGACATCTCCGTGCCCCCTGGCTCCCGGA<br>ACCTGCCCTTCTTCGTGGTGTTCTCCAACGACCACTCCTCCGGCACCAAAGAGACACGGCTGGAACTG<br>AGAGAGATGATCTCCCACGAGCAGGAATCCGTCCTGAAGAAGCTGTCCAAGGACGGCTCCACCGAGGC<br>CGGCGAGTCCTCTCACGAAGAGGACACCGACGGCCACGTGGCAGCTGGCTCTACCCTGGCCAGACGGA<br>AGCGGCAGGCCAAGCACAAGCAGCGGAAGCGGCTGAAGTCCAGCTCCGCTGGCGCAGGCTCCCACTGC<br>CAGAAAACCTCCCTGAGAGTGAACTTCGAGGACATCGGCTGGGACAGCTGGATCATTGCCCCCAAAGA<br>GTACGAGGCCTACGAGTGCAAGGGCGGCTGCTTCTTCCCCCTGGCCGACGACGTGACCCCCACCAAGC<br>ACGCCATCGTGCAGACCCTGGTGCACCTGAAGTTCCCCACCAAAGTGGGCAAGGCCTGCTGCGTGCCC<br>ACCAAGCTGTCCCCCATCAGCGTGCTGTACAAGGACGACATGGGCGTGCCAACCCTGAAGTACCACTA<br>CGAGGGCATGTCCGTGGCCGAGTGTGGCTGCCGGTGA | 115 |
| BMP-GEP | ATGTGTCCTGGCGCTCTGTGGGTGGCCCTGCCTCTGCTGTCTCTGCTGGCCGGCAGCCTGCAGGGCAA<br>GCCTCTGCAGTCCTGGGGCAGAGGCTCCGCTGGCGGCAATGCTCACAGCCCTCTGGGAGTGCCTGGCG<br>GCGGACTGCCCGAGCACACCTTCAACCTGAAGATGTTCCTGGAAAACGTGAAGGTGGACTTCCTGCGG<br>TCCCTGAACCTGTCCGGCGTGCCCAGCCAGGACAAGACCCGGGTGGAACCCCCCCAGTACATGATCGA<br>CCTGTACAACCGGTACACCTCCGACAAGTCCACCACCCCCGCCTCCAACATCGTGCGGTCCTTCAGCA<br>TGGAAGATGCCATCTCCATTACCGCCACCGAGGACTTCCCATTTCAGAAGCACATCCTGCTGTTCAAC<br>ATCTCCATCCCCCGGCACGAGCAGATCACCAGAGCCGAGCTGCGGCTGTACGTGTCCTGCCAGAACCA<br>CGTGGACCCCTCCCACGACCTGAAGGGCTCCGTGGTGATCTACGACGTGCTGGACGGCACCGACGCCT<br>GGGACTCCGCTACCGAGACAAAGACCTTCCTGGTGTCCCAGGATATCCAGGACGAGGGCTGGGAGACA<br>CTGGAAGTGTCCTCCGCCGTGAAGAGATGGGTGCGATCCGACTCCACCAAGTCCAAGAACAAGCTGGA<br>AGTGACCGTGGAATCCCACCGGAAGGGCTGCGACACCCTGGACATCTCCGTGCCCCCTGGCTCCCGGA<br>ACCTGCCCTTCTTCGTGGTGTTCTCCAACGACCACTCCTCCGGCACCAAAGAGACACGGCTGGAACTG<br>AGAGAGATGATCTCCCACGAGCAGGAATCCGTCCTGAAGAAGCTGTCCAAGGACGGCTCCACCGAGGC<br>CGGCGAGTCCTCTCACGAAGAGGACACCGACGGCCACGTGGCAGCTGGCTCTACCCTGGCCAGACGGA<br>AGCGGCAGGCCAAGCACAAGCAGCGGAAGCGGCTGAAGTCCAGCTCCGCTGGCGCAGGCTCCCACTGC<br>CAGAAAACCTCCCTGAGAGTGAACTTCGAGGACATCGGCTGGGACAGCTGGATCATTGCCCCCAAAGA<br>GTACGAGGCCTACGAGTGCAAGGGCGGCTGCTTCTTCCCCCTGGCCGACGACGTGACCCCCACCAAGC<br>ACGCCATCGTGCAGACCCTGGTGCACCTGAAGTTCCCCACCAAAGTGGGCAAGGCCTGCTGCGTGCCC<br>ACCAAGCTGTCCCCCATCAGCGTGCTGTACAAGGACGACATGGGCGTGCCAACCCTGAAGTACCACTA<br>CGAGGGCATGTCCGTGGCCGAGTGTGGCTGCCGGTGA | 116 |
| BMP6-SA | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCAACGCAGCCATGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 117 |
| BMP6-SL | ATGCCGGGGCTGGGGCGGAGGGCGCAGTGGCTGTGCTGGTGCTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGGAGAGGCAGCA | 118 |

TABLE 8-continued

| NAME | SEQUENCE | SEQ ID NO |
|---|---|---|
| | GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCAACGCACACCTGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | |
| BMP6-A | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCRCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGGAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGATAAGCAGCCCTTCATGGTGGCTTTCTT<br>CAAAGTGAGTGAGGTCCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCTCTGGCTGATCATCTGA<br>ACTCCACTAATCATGCCATTGTGCAGACCTTGGTTAACTCTGTTAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 119 |
| BMP6-B | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGATAAGCAGCCCTTCATGGTGGCTTTCTT<br>CAAAGTGAGTGAGGTCCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCAT<br>TGCACCCAAGGGCTATGCTGCCAATTACTGTCACGGAGAATGCCCTTTTCCTCTGGCTGATCATCTGA<br>ACTCCACTAATCATGCCATTGTGCAGACCTTGGTTAACTCTGTTAACTCTAAGATTCCTAAGGCATGC<br>TGTGTCCCAACTAAGCTAAATGCCATCTCGGTTCTTTACTTTGATGACAACTCCAATGTCATTCTGAA<br>AAAATACAGGAATATGGTTGTAAGAGCTTGTGGATGCCACTAA | 120 |
| BMP6-C | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT | 121 |

TABLE 8-continued

| NAME | SEQUENCE | SEQ ID NO |
|---|---|---|
| | CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCGT<br>GGCTCCTCCGGGGTATCACGCCTTTTACTGTGATGGAGAATGCTCCTCCCCACTCAACGCACACATGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | |
| BMP6-D | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCGT<br>GGCTCCTCCGGGGTATCACGCCTTTTACTGTGATGGAGAATGCTCCTTCCCACTCAACGCACACATGA<br>ATGCAACCAACCACGCGATTGTGCAGACCTTGGTTCACCTTATGAACCCCGAGTATGTCCCCAAACCG<br>TGCTGTGCGCCAACTGAACTCAGTGCTATCTCGATGCTGTACCTTGACGAGAATGAAAAGGTTGTACT<br>GAAAAAATACAGGAATATGGTTGTAAGAGCTTGTGGATGCCACTAA | 122 |
| BMP6-ADHL | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCGCCGATCACCTGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 123 |
| BMP6-RK-KR | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA | 124 |

TABLE 8-continued

| NAME | SEQUENCE | SEQ ID NO |
|---|---|---|
| | ATCGCTCTACCCAGTCCCAGGACGTGGCGCGGGTCTCCAGTGCTTCAGATTACAACAGCAGTGAATTG<br>AAAACAGCCTGCAAGAGGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCAACGCACACATGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | |
| BMP6-<br>RK-KR<br>ADHL<br>long | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAAGAGGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCGCCGATCACCTGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 125 |
| BMP6-A<br>RK-KR | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCRCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGATAAGCAGCCCTTCATGGTGGCTTTCTT<br>CAAAGTGAGTGAGGTCCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGGAGTGAATTG<br>AAAACAGCCTGCAAGAGGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCTCTGGCTGATCATCTGA<br>ACTCCACTAATCATGCCATTGTGCAGACCTTGGTTAACTCTGTTAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 126 |
| BMP6-<br>ADHL<br>long | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAGGAAGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCGCCGATCACCTGA<br>ATGCAACCAACCACGCGATTGTGCAGACCTTGGTTCACCTTATGAACCCCGAGTATGTCCCCAAACCG | 127 |

TABLE 8-continued

| NAME | SEQUENCE | SEQ ID NO |
|---|---|---|
| | TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | |
| BMP6-RK-KR ADHL | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAAGAGGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCGCCGATCACCTGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 128 |
| BMP6-RK-KR long | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGACAAGCAGCCCTTCATGGTGGCTTTCTT<br>CAAAGTGAGTGAGGTGCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAAGAGGCATGAGCTGTATGTGAGTTTCCAAGACCTGGGATGGCAGGACTGGATCAT<br>TGCACCCAAGGGCTATGCTGCCAATTACTGTGATGGAGAATGCTCCTTCCCACTCAACGCACACATGA<br>ATGCAACCAACCACGCGATTGTGCAGACCTTGGTTCACCTTATGAACCCCGAGTATGTCCCCAAACCG<br>TGCTGTGCGCCAACTAAGCTAAATGCCATCTCGGTTCTTTACTTTGATGACAACTCCAATGTCATTCT<br>GAAAAAATACAGGAATATGGTTGTAAGAGCTTGTGGATGCCACTAA | 129 |
| BMP6-B-RK-KR | ATGCCGGGGCTGGGGCGGAGGGCGCAGTGGTCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC<br>CCCCGAGCCGCAGGCCTGGTGGGCAGAGACGGCCCTTACGATAAGCAGCCCTTCATGGTGGCTTTCTT<br>CAAAGTGAGTGAGGTCCACGTGCGCACCACCAGGTCAGCCTCCAGCCGGCGCCGACAACAGAGTCGTA<br>ATCGCTCTACCCAGTCCCAGGACGTGGCGCGGGTCTCCAGTGCTTCAGATTACAACAGCAGTGAATTG<br>AAAACAGCCTGCAAGAGGCATGAGCTGTATGTGAGTTTCCAAGACCTGGGATGGCAGGACTGGATCAT<br>TGCACCCAAGGGCTATGCTGCCAATTACTGTCACGGAGAATGCCCTTTTCCTCTGGCTGATCATCTGA<br>ACTCCACTAATCATGCCATTGTGCAGACCTTGGTTAACTCTGTTAACTCTAAGATTCCTAAGGCATGC<br>TGTGTCCCAACTAAGCTAAATGCCATCTCGGTTCTTTACTTTGATGACAACTCCAATGTCATTCTGAA<br>AAAATACAGGAATATGGTTGTAAGAGCTTGTGGATGCCACTAA | 130 |
| BMP9-E2 | ATGTGTCCTGGCGCTCTGTGGGTGGCCCTGCCTCTGCTGTCTCTGCTGGCCGGCAGCCTGCAGGGCAA<br>GCCTCTGCAGTCCTGGGGCAGAGGCTCCGCTGGCGGCAATGCTCACAGCCCTCTGGGAGTGCCTGGCG | 131 |

TABLE 8-continued

| NAME | SEQUENCE | SEQ ID NO |
|---|---|---|
| | GCGGACTGCCCGAGCACACCTTCAACCTGAAGATGTTCCTGGAAAACGTGAAGGTGGACTTCCTGCGG<br>TCCCTGAACCTGTCCGGCGTGCCCAGCCAGGACAAGACCCGGGTGGAACCCCCCCAGTACATGATCGA<br>CCTGTACAACCGGTACACCTCCGACAAGTCCACCACCCCCGCCTCCAACATCGTGCGGTCCTTCAGCA<br>TGGAAGATGCCATCTCCATTACCGCCACCGAGGACTTCCCATTTCAGAAGCACATCCTGCTGTTCAAC<br>ATCTCCATCCCCCGGCACGAGCAGATCACCAGAGCCGAGCTGCGGCTGTACGTGTCCTGCCAGAACCA<br>CGTGGACCCCTCCCACGACCTGAAGGGCTCCGTGGTGATCTACGACGTGCTGGACGGCACCGACGCCT<br>GGGACTCCGCTACCGAGACAAAGACCTTCCTGGTGTCCCAGGATATCCAGGACGAGGGCTGGGAGACA<br>CTGGAAGTGTCCTCCGCCGTGAAGAGATGGGTGCGATCCGACTCCACCAAGTCCAAGAACAAGCTGGA<br>AGTGACCGTGGAATCCCACCGGAAGGGCTGCGACACCCTGGACATCTCCGTGCCCCCTGGCTCCCGGA<br>ACCTGCCCTTCTTCGTGGTGTTCTCCAACGACCACTCCTCCGGCACCAAAGAGACACGGCTGGAACTG<br>AGAGAGATGATCTCCCACGAGCAGGAATCCGTCCTGAAGAAGCTGTCCAAGGACGGCTCCACCGAGGC<br>CGGCGAGTCCTCTCACGAAGAGGACACAGACGGCCACGTGGCAGCTGGCTCTACCCTGGCCAGACGGA<br>AGCGGTCCGCCGGAGCTGGCTCCCACTGCCAGAAAACCTCCCTGAGAGTGAACTTCGAGGACATCGGC<br>TGGGACAGCTGGATCATTGCCCCCAAAGAGTACGAGGCCTACGAGTGCCACGGCGAGTGCCCCTTCCC<br>CCTGGCCGACCACCTGAACTCCACCAACCACGCCATCGTGCAGACCCTGGTGAACTCCGTGAACTCCA<br>AAATCCCCAAGGCCTGCTGCGTGCCCACCAAGCTGTCCCCCATCAGCGTGCTGTACAAGGACGACATG<br>GGCGTGCCAACCCTGAAGTACCACTACGAGGGCATGTCCGTGGCCGAGTGTGGCTGCCGGTGA | |
| BMP9-E6 | ATGTGTCCTGGCGCTCTGTGGGTGGCCCTGCCTCTGCTGTCTCTGCTGGCCGGCAGCCTGCAGGGCAA<br>GCCTCTGCAGTCCTGGGGCAGAGGCTCCGCTGGCGGCAATGCTCACAGCCCTCTGGGAGTGCCTGGCG<br>GCGGACTGCCCGAGCACACCTTCAACCTGAAGATGTTCCTGGAAAACGTGAAGGTGGACTTCCTGCGG<br>TCCCTGAACCTGTCCGGCGTGCCCAGCCAGGACAAGACCCGGGTGGAACCCCCCCAGTACATGATCGA<br>CCTGTACAACCGGTACACCTCCGACAAGTCCACCACCCCCGCCTCCAACATCGTGCGGTCCTTCAGCA<br>TGGAAGATGCCATCTCCATTACCGCCACCGAGGACTTCCCATTTCAGAAGCACATCCTGCTGTTCAAC<br>ATCTCCATCCCCCGGCACGAGCAGATCACCAGAGCCGAGCTGCGGCTGTACGTGTCCTGCCAGAACCA<br>CGTGGACCCCTCCCACGACCTGAAGGGCTCCGTGGTGATCTACGACGTGCTGGACGGCACCGACGCCT<br>GGGACTCCGCTACCGAGACAAAGACCTTCCTGGTGTCCCAGGATATCCAGGACGAGGGCTGGGAGACA<br>CTGGAAGTGTCCTCCGCCGTGAAGAGATGGGTGCGATCCGACTCCACCAAGTCCAAGAACAAGCTGGA<br>AGTGACCGTGGAATCCCACCGGAAGGGCTGCGACACCCTGGACATCTCCGTGCCCCCTGGCTCCCGGA<br>ACCTGCCCTTCTTCGTGGTGTTCTCCAACGACCACTCCTCCGGCACCAAAGAGACACGGCTGGAACTG<br>AGAGAGATGATCTCCCACGAGCAGGAATCCGTCCTGAAGAAGCTGTCCAAGGACGGCTCCACCGAGGC<br>CGGCGAGTCCTCTCACGAAGAGGACACAGACGGCCACGTGGCAGCTGGCTCTACCCTGGCCAGACGGA<br>AGCGGTCCGCCGGAGCTGGCTCCCACTGCCAGAAAACCTCCCTGAGAGTGAACTTCGAGGACATCGGC<br>TGGGACAGCTGGATCATTGCCCCCAAAGAGTACGAGGCCTACGAGTGCGACGGCGAGTGCTCCTTCCC<br>CCTGAACGCCCACATGAACGCCACCAACCACGCCATCGTGCAGACCCTGGTGCACCTGATGAACCCCG<br>AGTACGTGCCCAAGCCCTGCTGCGCCCCCACCAAGCTGTCCCCCATCAGCGTGCTGTACAAGGACGAC<br>ATGGGCGTGCCAACCCTGAAGTACCACTACGAGGGCATGTCCGTGGCCGAGTGTGGCTGCCGGTGA | 132 |
| BMP6-Short | ATGCCGGGGCTGGGGCGGAGGGCGCAGTGGCTGTGCTGGTGGTGGGGGCTGCTGTGCAGCTGCTGCGGG<br>CCCCCGCCGCTGCGGCCGCCCTTGCCCGCTGCCGCGGCCGCCGCCGCCGGGGGGCAGCTGCTGGGGGA<br>CGGCGGGAGCCCCGGCCGCACGGAGCAGCCGCCGCCGTCGCCGCAGTCCTCCTCGGGCTTCCTGTACC<br>GGCGGCTCAAGACGCAGGAGAAGCGGGAGATGCAGAAGGAGATCTTGTCGGTGCTGGGGCTCCCGCAC<br>CGGCCCCGGCCCCTGCACGGCCTCCAACAGCCGCAGCCCCCGGCGCTCCGGCAGCAGGAGGAGCAGCA<br>GCAGCAGCAGCAGCTGCCTCGCGGAGAGCCCCCTCCCGGGCGACTGAAGTCCGCGCCCCTCTTCATGC<br>TGGATCTGTACAACGCCCTGTCCGCCGACAACGACGAGGACGGGGCGTCGGAGGGGGAGAGGCAGCAG<br>TCCTGGCCCCACGAAGCAGCCAGCTCGTCCCAGCGTCGGCAGCCGCCCCCGGGCGCCGCGCACCCGCT<br>CAACCGCAAGAGCCTTCTGGCCCCCGGATCTGGCAGCGGCGGCGCGTCCCCACTGACCAGCGCGCAGG<br>ACAGCGCCTTCCTCAACGACGCGGACATGGTCATGAGCTTTGTGAACCTGGTGGAGTACGACAAGGAG<br>TTCTCCCCTCGTCAGCGACACCACAAAGAGTTCAAGTTCAACTTATCCCAGATTCCTGAGGGTGAGGT<br>GGTGACGGCTGCAGAATTCCGCATCTACAAGGACTGTGTTATGGGGAGTTTTAAAAACCAAACTTTTC<br>TTATCAGCATTTATCAAGTCTTACAGGAGCATCAGCACAGAGACTCTGACCTGTTTTTGTTGGACACC<br>CGTGTAGTATGGGCCTCAGAAGAAGGCTGGCTGGAATTTGACATCACGGCCACTAGCAATCTGTGGGT<br>TGTGACTCCACAGCATAACATGGGGCTTCAGCTGAGCGTGGTGACAAGGGATGGAGTCCACGTCCACC<br>CCCGAGCCGCAGGCCTGGTGGGCAGAGACGGCCCTTACGATAAGCAGCCCTTCATGGTGGCTTTCTTC<br>AAAGTGAGTGAGGTCCACGTGCGCACCACCAGGTCAGCCTCCAGCCGGCGCCGACAACAGAGTCGTAA<br>TCGCTCTACCCAGTCCCAGGACGTGGCGCGGGTCTCCAGTGCTTCAGATTACAACAGCAGTGAATTGA<br>AAACAGCCTGCAGGAAGCATGAGCTGTATGTGAGTTTCCAAGACCTGGGATGGCAGGACTGGATCATT<br>GCACCCAAGGGCTATGCTGCCAATTACTGTGATGGAGAATGCTCCTTCCCACTCAACGCACACATGAA<br>TGCAACCAACCACGCGATTGTGCAGACCTTGGTTCACCTTATGAACCCCGAGTATGTCCCCAAACCGT<br>GCTGTGCGCCAACTAAGCTAAATGCCATCTCGGTTCTTTACTTTGATGACAACTCCAATGTCATTCTG<br>AAAAAATACAGGAATATGGTTGTAAGAGCTTGTGGATGCCACTAA | 133 |
| BMP6-SA | ATGCCGGGGCTGGGGCGGAGGGCGCAGTGGCTGTGCTGGTGGTGGGGGCTGCTGTGCAGCTGCTGCGG<br>GCCCCCGCCGCTGCGGCCGCCCTTGCCCGCTGCCGCGGCCGCCGCCGCCGGGGGGCAGCTGCTGGGGG<br>ACGGCGGGAGCCCCGGCCGCACGGAGCAGCCGCCGCCGTCGCCGCAGTCCTCCTCGGGCTTCCTGTAC<br>CGGCGGCTCAAGACGCAGGAGAAGCGGGAGATGCAGAAGGAGATCTTGTCGGTGCTGGGGCTCCCGCA<br>CCGGCCCCGGCCCCTGCACGGCCTCCAACAGCCGCAGCCCCCGGCGCTCCGGCAGCAGGAGGAGCAGC<br>AGCAGCAGCAGCAGCTGCCTCGCGGAGAGCCCCCTCCCGGGCGACTGAAGTCCGCGCCCCTCTTCATG<br>CTGGATCTGTACAACGCCCTGTCCGCCGACAACGACGAGGACGGGGCGTCGGAGGGGGAGAGGCAGCA<br>GTCCTGGCCCCACGAAGCAGCCAGCTCGTCCCAGCGTCGGCAGCCGCCCCCGGGCGCCGCGCACCCGC<br>TCAACCGCAAGAGCCTTCTGGCCCCCGGATCTGGCAGCGGCGGCGCGTCCCCACTGACCAGCGCGCAG<br>GACAGCGCCTTCCTCAACGACGCGGACATGGTCATGAGCTTTGTGAACCTGGTGGAGTACGACAAGGA<br>GTTCTCCCCTCGTCAGCGACACCACAAAGAGTTCAAGTTCAACTTATCCCAGATTCCTGAGGGTGAGG<br>TGGTGACGGCTGCAGAATTCCGCATCTACAAGGACTGTGTTATGGGGAGTTTTAAAAACCAAACTTTT<br>CTTATCAGCATTTATCAAGTCTTACAGGAGCATCAGCACAGAGACTCTGACCTGTTTTTGTTGGACAC<br>CCGTGTAGTATGGGCCTCAGAAGAAGGCTGGCTGGAATTTGACATCACGGCCACTAGCAATCTGTGGG<br>TTGTGACTCCACAGCATAACATGGGGCTTCAGCTGAGCGTGGTGACAAGGGATGGAGTCCACGTCCAC | 134 |

TABLE 8-continued

| NAME | SEQUENCE | SEQ ID NO |
|---|---|---|
| | CCCCGAGCCGCAGGCCTGGTGGGCAGAGACGGCCCTTACGATAAGCAGCCCTTCATGGTGGCTTTCTT CAAAGTGAGTGAGGTCCACGTGCGCACCACCAGGTCAGCCTCCAGCCGGCGCCGACAACAGAGTCGTA ATCGCTCTACCCAGTCCCAGGACGTGGCGCGGGTCTCCAGTGCTTCAGATTACAACAGCAGTGAATTG AAAACAGCCTGCAGGAAGCATGAGCTGTATGTGAGTTTCCAAGACCTGGGATGGCAGGACTGGATCAT TGCACCCAAGGGCTATGCTGCCAATTACTGTGATGGAGAATGCTCCTTCCCACTCAACGCAGCCATGA ATGCAACCAACCACGCGATTGTGCAGACCTTGGTTCACCTTATGAACCCCGAGTATGTCCCCAAACCG TGCTGTGCGCCAACTAAGCTAAATGCCATCTCGGTTCTTTACTTTGATGACAACTCCAATGTCATTCT GAAAAAATACAGGAATATGGTTGTAAGAGCTTGTGGATGCCACTAA | |
| MBP6-SL | ATGCCGGGGCTGGGGCGGAGGGCGCAGTGGCTGTGCTGGTGGTGGGGGCTGCTGTGCAGCTGCTGCGG GCCCCCGCCGCTGCGGCCGCCCTTGCCCGCTGCCGCGGCCGCCGCCGCCGGGGGGCAGCTGCTGGGGG ACGGCGGGAGCCCCGGCCGCACGGAGCAGCCGCCGCCGTCGCCGCAGTCCTCCTCGGGCTTCCTGTAC CGGCGGCTCAAGACGCAGGAGAAGCGGGAGATGCAGAAGGAGATCTTGTCGGTGCTGGGGCTCCCGCA CCGGCCCCGGCCCCTGCACGGCCTCCAACAGCCGCAGCCCCCGGCGCTCCGGCAGCAGGAGGAGCAGC AGCAGCAGCAGCAGCTGCCTCGCGGAGAGCCCCCTCCCGGGCGACTGAAGTCCGCGCCCCTCTTCATG CTGGATCTGTACAACGCCCTGTCCGCCGACAACGACGAGGACGGGGCGTCGGAGGGGGGAGAGGCAGCA GTCCTGGCCCCACGAAGCAGCCAGCTCGTCCCAGCGTCGGCAGCCGCCCCCGGGCGCCGCGCACCCGC TCAACCGCAAGAGCCTTCTGGCCCCCGGATCTGGCAGCGGCGGCGCGTCCCCACTGACCAGCGCGCAG GACAGCGCCTTCCTCAACGACGCGGACATGGTCATGAGCTTTGTGAACCTGGTGGAGTACGACAAGGA GTTCTCCCCTCGTCAGCGACACCACAAAGAGTTCAAGTTCAACTTATCCCAGATTCCTGAGGGTGAGG TGGTGACGGCTGCAGAATTCCGCATCTACAAGGACTGTGTTATGGGGAGTTTTAAAAACCAAACTTTT CTTATCAGCATTTATCAAGTCTTACAGGAGCATCAGCACAGAGACTCTGACCTGTTTTTGTTGGACAC CCGTGTAGTATGGGCCTCAGAAGAAGGCTGGCTGGAATTTGACATCACGGCCACTAGCAATCTGTGGG TTGTGACTCCACAGCATAACATGGGGCTTCAGCTGAGCGTGGTGACAAGGGATGGAGTCCACGTCCAC CCCCGAGCCGCAGGCCTGGTGGGCAGAGACGGCCCTTACGATAAGCAGCCCTTCATGGTGGCTTTCTT CAAAGTGAGTGAGGTCCACGTGCGCACCACCAGGTCAGCCTCCAGCCGGCGCCGACAACAGAGTCGTA ATCGCTCTACCCAGTCCCAGGACGTGGCGCGGGTCTCCAGTGCTTCAGATTACAACAGCAGTGAATTG AAAACAGCCTGCAGGAAGCATGAGCTGTATGTGAGTTTCCAAGACCTGGGATGGCAGGACTGGATCAT TGCACCCAAGGGCTATGCTGCCAATTACTGTGATGGAGAATGCTCCTTCCCACTCAACGCACACCTCA ATGCAACCAACCACGCGATTGTGCAGACCTTGGTTCACCTTATGAACCCCGAGTATGTCCCCAAACCG TGCTCTGCGCCAACTAAGCTAAATGCCATCTCGGTTCTTTACTTTGATGACAACTCCAATGTCATTCT GAAAAAATACAGGAATATGGTTGTAAGAGCTTGTGGATGCCACTAA | 135 |
| BMP-E-NR | ATGGTGGCCGGGACCCGCTGTCTTCTAGCGTTGCTGCTTCCCCAGGTCCTCCTGGGCGGCGCGGCTGG CCTCGTTCCGGAGCTGGGCCGCAGGAAGTTCGCGGCGGCGTCGTCGGGCCGCCCCTCATCCCAGCCCT CTGACGAGGTCCTGAGCGAGTTCGAGTTGCGGCTGCTCAGCATGTTCGGCCTGAAACAGAGACCCACC CCCAGCAGGGACGCCGTGGTGCCCCCCTACATGCTAGACCTGTATCGCAGGCACTCAGGTCAGCCGGG CTCACCCGCCCCAGACCACCGGTTGGAGAGGGCAGCCAGCCGAGCCAACACTGTGCGCAGCTTCCACC ATGAAGAATCTTTGGAAGAACTACCAGAAACGAGTGGGAAAACAACCCGGAGATTCTTCTTTAATTTA AGTTCTATCCCCACGGAGGAGTTTATCACCTCAGCAGAGCTTCAGGTTTTCCGAGAACAGATGCAAGA TGCTTTAGGAAACAATAGCAGTTTCCATCACCGAATTAATATTTATGAAATCATAAAACCTGCAACAG CCAACTCGAAATTCCCCGTGACCAGACTTTTGGACACCAGGTTGGTGAATCAGAATGCAAGCAGGTGG GAAAGTTTTGATGTCACCCCCGCTGTGATGCGGTGGACTGCACAGGGACACGCCAACCATGGATTCGT GGTGGAAGTGGCCCACTTGGAGGAGAAACAAGGTGTCTCCAAGAGACATGTTAGGATAAGCAGGTCTT TGCACCAAGATGAACACAGCTGGTCACAGATAAGGCCATTGCTAGTAACTTTTGGCCATGATGGAAAA GGGCATCCTCTCCACAAAAGAGAAAAACGTCAAGCCAAACACAAACAGCGGAAACGCCTTAAGTCCAG CTGTAAGAGACACCCTTTGTACGTGGACTTCAGTGACGTGGGGTGGAATGACTGGATTGTGGCTCCCC CGGGGTATCACGCCTTTTACTGCGATGGAGAATGCTCCTTCCCACTCAACGCACACATGAATGCAACC AACCACGCGATTGTGCAGACCTTGGTTCACCTTATGAACCCCGAGTATGTCCCCAAACCGTGCTGTGC GCCCACCAAGCTGAGACCCATGTCCATGTTGTACTATGATGATGGTCAAAACATCATCAAAAAGGACA TTCAGAACATGATCGTGGAGGAGTGTGGGTGCTCATAG | 136 |
| BMP-GER-NR | ATGGTGGCTGGCACCAGATGTCTGCTGGCCCTGCTGCTGCCCCAGGTGCTGCTGGGCGGAGCTGCTGG ACTGGTGCCCGAGCTGGGCAGAAGAAAGTTCGCCGCTGCCTCCTCTGGCCGGCCTTCCAGCCAGCCTT CCGACGAGGTGCTGTCCGAGTTCGAGCTGCGGCTGCTGTCCATGTTCGGCCTGAAGCAGCGGCCCACC CCTTCTAGGGACGCCGTGGTGCCCCCCTACATGCTGGACCTGTACCGGCGGCACTCCGGCCAGCCTGG ATCTCCTGCCCCCGACCACAGACTGGAAAGAGCCGCCTCCCGGGCCAACACCGTGCGGTCTTTCCACC ACGAGGAATCCCTGGAAGAACTGCCCGAGACATCCGGCAAGACCACCCGGCGGTTCTTTTTCAACCTG TCATCCATCCCCACCGAAGAGTTCATCACCTCCGCCGAGCTGCAGGTGTTCCGCGAGCAGATGCAGGA CGCCCTGGGCAACAACTCCTCCTTCCACCACCGGATCAACATCTACGAGATCATCAAGCCCGCCACCG CCAACTCCAAGTTCCCCGTGACCCGGCTGCTGGACACCCGGCTGGTGAACCAGAACGCCTCCAGATGG GAGTCCTTCGACGTGACCCCTGCCGTGATGAGATGGACCGCCCAGGGCCACGCCAACCACGGCTTTGT GGTGGAAGTGGCCCACCTGGAAGAGAAGCAGGGCGTGTCCAAGCGGCACGTGCGGATCTCTCGGTCCC TGCACCAGGACGAGCACAGCTGGTCCCAGATCCGGCCCCTGCTGGTGACATTCGGCCACGATGGCAAG GGCCACCCCCTGCACAAGAGAGAGAAGCGGCAGGCCAAGCACAAGCAGCGGAAGCGGCTGAAGTCCTC CTGCAAGCGGCACCCCCTGTACGTGGACTTCTCCGACGTGGGCTGGAACGACTGGATCATTGCCCCCA GGGGCTACGCCGCCTTCTACTGCGACGGCGAGTGCTCCTTCCCCCTGAACGCCCACATGAACGCCACC AACCACGCCATCGTGCAGACCCTGGTGCACCTGATGAACCCCGAGTACGTGCCCAAGCCTTGTTGCGC CCCCACCAAGCTGAGACCCATGTCCATGTTGTACTATGATGATGGTCAAAACATCATCAAAAAGGACA TTCAGAACATGATCGTGGAGGAGTGTGGGTGCTCATAG | 137 |
| BMP-E-NR-6 | ATGGTGGCCGGGACCCGCTGTCTTCTAGCGTTGCTGCTTCCCCAGGTCCTCCTGGGCGGCGCGGCTGG CCTCGTTCCGGAGCTGGGCCGCAGGAAGTTCGCGGCGGCGTCGTCGGGCCGCCCCTCATCCCAGCCCT CTGACGAGGTCCTGAGCGAGTTCGAGTTGCGGCTGCTCAGCATGTTCGGCCTGAAACAGAGACCCACC CCCAGCAGGGACGCCGTGGTGCCCCCCTACATGCTAGACCTGTATCGCAGGCACTCAGGTCAGCCGGG CTCACCCGCCCCAGACCACCGGTTGGAGAGGGCAGCCAGCCGAGCCAACACTGTGCGCAGCTTCCACC ATGAAGAATCTTTGGAAGAACTACCAGAAACGAGTGGGAAAACAACCCGGAGATTCTTCTTTAATTTA | 138 |

TABLE 8-continued

| NAME | SEQUENCE | SEQ ID NO |
|---|---|---|
| | AGTTCTATCCCCACGGAGGAGTTTATCACCTCAGCAGAGCTTCAGGTTTTCCGAGAACAGATGCAAGA TGCTTTAGGAAACAATAGCAGTTTCCATCACCGAATTAATATTTATGAAATCATAAAACCTGCAACAG CCAACTCGAAATTCCCCGTGACCAGACTTTTGGACACCAGGTTGGTGAATCAGAATGCAAGCAGGTGG GAAAGTTTTGATGTCACCCCCGCTGTGATGCGGTGGACTGCACAGGGACACGCCAACCATGGATTCGT GGTGGAAGTGGCCCACTTGGAGGAGAAACAAGGTGTCTCCAAGAGACATGTTAGGATAAGCAGGTCTT TGCACCAAGATGAACACAGCTGGTCACAGATAAGGCCATTGCTAGTAACTTTTGGCCATGATGGAAAA GGGCATCCTCTCCACAAAAGAGAAAAACGTCAAGCCAAACACAAACAGCGGAAACGCCTTAAGTCCAG CTGTAAGAGACACCCTTTGTACGTGGACTTCAGTGACGTGGGGTGGAATGACTGGATTGTGGCTCCCC CGGGGTATCACGCCTTTTACTGCGATGGAGAATGCTCCTTCCCACTCAACGCACACATGAATGCAACC AACCACGCGATTGTGCAGACCTTGGTTCACCTTATGAACCCCGAGTATGTCCCCAAACCGTGCTGTGC GCCAACTAAGCTAAATGCCATCTCGGTTCTTTACTTTGATGACAACTCCAATGTCATTCTGAAAAAAT ACAGGAATATGGTTGTAAGAGCTTGTGGATGCCACTAA | |
| BMP-GER-NR-6 | ATGGTGGCTGGCACCAGATGTCTGCTGGCCCTGCTGCTGCCCCAGGTGCTGCTGGGCGGAGCTGCTGG ACTGGTGCCCGAGCTGGGCAGAAGAAAGTTCGCCGCTGCCTCCTCTGGCCGGCCTTCCAGCCAGCCTT CCGACGAGGTGCTGTCCGAGTTCGAGCTGCGGCTGCTGTCCATGTTCGGCCTGAAGCAGCGGCCCACC CCTTCTAGGGACGCCGTGGTGCCCCCCTACATGCTGGACCTGTACCGGCGGCACTCCGGCCAGCCTGG ATCTCCTGCCCCCGACCACAGACTGGAAAGAGCCGCCTCCCGGGCCAACACCGTGCGGTCTTTCCACC ACGAGGAATCCCTGGAAGAACTGCCCGAGACATCCGGCAAGACCACCCGGCGGTTCTTTTTCAACCTG TCATCCATCCCCACCGAAGAGTTCATCACCTCCGCCGAGCTGCAGGTGTTCCGCGAGCAGATGCAGGA CGCCCTGGGCAACAACTCCTCCTTCCACCACCGGATCAACATCTACGAGATCATCAAGCCCGCCACCG CCAACTCCAAGTTCCCCGTGACCCGGCTGCTGGACACCCGGCTGGTGAACCAGAACGCCTCCAGATGG GAGTCCTTCGACGTGACCCCTGCCGTGATGAGATGGACCGCCCAGGGCCACGCCAACCACGGCTTTGT GGTGGAAGTGGCCCACCTGGAAGAGAAGCAGGGCGTGTCCAAGCGGCACGTGCGGATCTCTCGGTCCC TGCACCAGGACGAGCACAGCTGGTCCCAGATCCGGCCCCTGCTGGTGACATTCGGCCACGATGGCAAG GGCCACCCCCTGCACAAGAGAGAGAAGCGGCAGGCCAAGCACAAGCAGCGGAAGCGGCTGAAGTCCTC CTGCAAGCGGCACCCCCTGTACGTGGACTTCTCCGACGTGGGCTGGAACGACTGGATCATTGCCCCCA GGGGCTACGCCGCCTTCTACTGCGACGGCGAGTGCTCCTTCCCCCTGAACGCCCACATGAACGCCACC AACCACGCCATCGTGCAGACCCTGGTGCACCTGATGAACCCCGAGTACGTGCCCAAGCCTTGTTGCGC CCCAACTAAGCTAAATGCCATCTCGGTTCTTTACTTTGATGACAACTCCAATGTCATTCTGAAAAAAT ACAGGAATATGGTTGTAAGAGCTTGTGGATGCCACTAA | 139 |

In other embodiments, the nucleic acid molecule encoding a designer BMP comprises a nucleic acid sequence at least 40%, 50%, 60%, 65%, 70%, 75%, 80%, 85%, 87%, 90%, 92%, 93%, 94%, 95%, 96%, 97%, 98%, 99% identical to one of the nucleic acid sequences set forth in SEQ ID NOs:74-139 or a fragment thereof. In other embodiments, the nucleic acid molecule encoding a designer BMP comprises a nucleic acid sequence at least 40%, 50%, 60%, 65%, 70%, 75%, 80%, 85%, 87%, 90%, 92%, 93%, 94%, 95%, 96%, 97%, 98%, 99% identical to one of the nucleic acid sequences set forth in Table 8 or a fragment thereof. In another embodiment, the nucleic acid molecule encoding a designer BMP comprises the nucleic acid sequence of any sequence set forth in SEQ ID NOs:74-139. In yet another embodiment, the nucleic acid molecule consists of the nucleic acid sequence of any one of the nucleic acid sequences of SEQ ID NOs:74-139.

In another embodiment, the nucleic acid molecule encoding a designer BMP comprises a nucleic acid sequence at least 40%, 50%, 60%, 65%, 70%, 75%, 80%, 85%, 87%, 90%, 92%, 93%, 94%, 95%, 96%, 97%, 98%, 99% identical to the nucleic acid sequence of SEQ ID NO:78, or a fragment thereof. In another embodiment, the nucleic acid molecule encoding a designer BMP comprises the nucleic acid sequence of SEQ ID NO:78. In yet another embodiment, the nucleic acid molecule consists of the nucleic acid sequence of SEQ ID NO:78 encoding BMPE.

In another embodiment, the nucleic acid molecule encoding a designer BMP comprises a nucleic acid sequence at least 40%, 50%, 60%, 65%, 70%, 75%, 80%, 85%, 87%, 90%, 92%, 93%, 94%, 95%, 96%, 97%, 98%, 99% identical to the nucleic acid sequence of SEQ ID NO:80, or a fragment thereof. In another embodiment, the nucleic acid molecule encoding a designer BMP comprises the nucleic acid sequence of SEQ ID NO:80. In yet another embodiment, the nucleic acid molecule consists of the nucleic acid sequence of SEQ ID NO:80 encoding BMPG.

In another embodiment, the nucleic acid molecule encoding a designer BMP comprises a nucleic acid sequence at least 40%, 50%, 60%, 65%, 70%, 75%, 80%, 85%, 87%, 90%, 92%, 93%, 94%, 95%, 96%, 97%, 98%, 99% identical to the nucleic acid sequence of SEQ ID NO:102, or a fragment thereof. In another embodiment, the nucleic acid molecule encoding a designer BMP comprises the nucleic acid sequence of SEQ ID NO:102. In yet another embodiment, the nucleic acid molecule consists of the nucleic acid sequence of SEQ ID NO:102 encoding BMPGE.

In another embodiment, the nucleic acid molecule encoding a designer BMP comprises a nucleic acid sequence at least 40%, 50%, 60%, 65%, 70%, 75%, 80%, 85%, 87%, 90%, 92%, 93%, 94%, 95%, 96%, 97%, 98%, 99% identical to the nucleic acid sequence of SEQ ID NO:103, or a fragment thereof. In another embodiment, the nucleic acid molecule encoding a designer BMP comprises the nucleic acid sequence of SEQ ID NO:103. In yet another embodiment, the nucleic acid molecule consists of the nucleic acid sequence of SEQ ID NO:103 encoding BMPGER.

Methods of Producing Designer BMPs

BMPs are naturally expressed as pro-proteins comprising a long prodomain, one or more cleavage sites, and a mature domain. This pro-protein is then processed by the cellular machinery to yield a, typically, dimeric mature BMP molecule. In some embodiments, the designer BMPs are produced in a similar manner. The prodomain is believed to play a role in the folding and processing of BMPs. Furthermore, in some BMPs, the prodomain may noncovalently bind to the mature protein and act as a solubility enhancer, chaperone, or inhibitor. In some embodiments, BMPs may be produced as mature domains produced directly from or refolded from inclusion bodies. In other embodiments, the BMPs are produced via chemical synthesis or any other known method for protein production.

In one embodiment, the designer BMP is producing using chemical synthesis methods such as, but not limited to, synthetic methods well-known in the art.

In some embodiments, nucleic acids encoding designer BMPs are prepared by total gene synthesis or by site directed mutagenesis of a nucleic acid encoding a wild type, designer, or variant BMP. Methods include template directed ligation, PCR, cassette mutagenesis, site-directed mutagenesis, restriction enzyme digestion and ligation, or other techniques that are well known in the art (see, e.g., Prodromou et al., Protein Eng 5:827-9 (1992); Jayaraman et al., Biotechniques 12:392-8 (1992); Chalmers et al., Biotechniques 30:249-52 (2001); and Sambrook and Russell. In: Molecular Cloning, A Laboratory Approach, Cold Spring Harbor Press, Cold Spring Harbor, N.Y. (2001)).

In some embodiments, an expression vector that comprises a gene encoding a designer BMP is prepared. Numerous types of appropriate expression vectors and suitable regulatory sequences for a variety of host cells are known in the art. The expression vectors may contain transcriptional and translational regulatory sequences including by not limited to promoter sequences, ribosomal binding sites, transcriptional terminator signals, polyadenylation signals, and enhancer or activator sequences. In some embodiments, the regulatory sequences include a promoter and transcriptional start and stop sequences. In addition, the expression vector may comprise additional elements, such as two replication systems to allow it to be maintained in two organisms. The expression vectors may be extrachromasomal vectors or vectors that integrate into a host cell's genome. In some embodiments, the expression vector contains at least one sequence homologous to a host cell's genome to promote integration into the genome. Constructs for integrating vectors are well known in the art. In some embodiments, the expression vector comprises a selectable marker gene to allow the selection of a stably transformed host cell. Selection marker genes are well known in the art and will vary with the host cell used.

The expression vector may include a secretory leader sequence or signal peptide sequence that provides for secretion of the designer BMP from the host cell. Suitable secretory leader sequences and signal peptides are known in the art.

Nucleic acids encoding designer BMPs may be introduced into host cells either alone or in combination with an expression vector so that the designer BMP is expressed from the nucleic acid. The method of introduction is largely dictated by the host cell type. Exemplary methods of transfection/transformation include $CaPO_4$ precipitation, liposome fusion, electroporation, viral infection, dextran-mediated transfection, polybrene-mediated transfection, protoplast fusion, direct microinjection, and other methods known in the art. Nucleic acids encoding designer BMPs may stable integrate into the host cell genome or may exist transiently or stably in the cytoplasm.

Appropriate host cells for expressing designer BMPs include any cell suitable for expressing wild type or native BMPs, including, but not limited to yeast, bacteria, archaebacteria, fungi, insect, and animal cells. In some embodiments the host cell is *Saccharomyces cerevisiae* or *Escheria coli*. In some embodiments, the host cell is a mammalian cell such as 293 (e.g., 293-T and 293-EBNA), BHK, CHO (e.g., CHOK1 and DG44), COS, Jurkat, NIH3T3, or C2C12 cells. Other suitable cells may be found in the ATCC catalog. Designer BMPs may be produced in more complex organisms, including but not limited to plants and animals. In one embodiment, the cells may be additionally genetically engineered, i.e., to contain exogenous nucleic acids other than the expression vector comprising the designer BMP nucleic acid.

In some embodiments, designer BMPs are produced by culturing a host cell transformed with an expression vector containing a nucleic acid encoding a designer BMP under the appropriate conditions to induce or cause expression of the designer BMP. The conditions appropriate for designer BMP expression are the same conditions known to be appropriate for expressing native or wild type BMPs. These conditions will vary with the choice of expression vector and host cell, and may be easily ascertained by one skilled in the art through routine experimentation.

In some embodiments, the designer BMPs may be purified or isolated after expression. Standard purification methods include electrophoretic, molecular, immunological, and chromatographic techniques, including ion exchange, hydrophobic, affinity, and reverse-phase HPLC chromatography, and chromatofocusing. General guidance in suitable purification techniques may be found in Scopes. In: *Protein Purification*, Springer-Verlag, NY, 3rd Ed. (1994). The degree of purification necessary will vary depending on the desired use, and in some instances no purification will be necessary.

Purification from bacterial cells may result in the expression of BMPs in inclusion bodies and a subsequent step of refolding in a CHAPS/High salt system. Purification from mammalian cells may involve a two-step purification via Cellufine-Sulfate and Reversed Phase chromatography columns.

In some embodiments, the designer BMPs may be modified covalently or non-covalently. Covalent modifications may be introduced to a protein by reacting targeted amino acid residues of the protein with an organic derivatizing agent capable of reacting with selected side chains or terminal residues. Optimal sites for modification can be chosen using a variety of criteria, including but not limited to visual inspection, structural analysis, sequence analysis, and molecular simulation.

In some embodiments, designer BMPs may be labeled with at least one element, isotope, or chemical compound. The label may be an isotopic label, such as a radioactive or heavy isotope. In some embodiments, the label may be an immune label such as an antibody or antigen. In some embodiments, the label may be a colored or fluorescent label, such as fluorescein. In some embodiments, the label may be biotin, a tag (e.g., FLAG, Myc, His).

The designer BMPs may be derivatized with bifunctional agents to crosslink a designer BMP to a support matrix or surface for use in purifying antibodies or proteins that bind to the proteins or to detect binding in screening assays. Commonly used crosslinking agents include but are not limited to 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane. Other modifications include deamidation of glutaminyl and asparaginyl residues to the corresponding glutamyl and aspartyl residues, respectively, hydroxylation of praline and lysine, phosphorylation of hydroxyl groups of seryl or threonyl residues, methylation of the amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group. Such derivatization may improve the solubility, absorption, transport across the blood brain barrier, serum half-life, and the like. Modifications of designer BMPs may alternatively eliminate or attenuate any possible undesirable side effect of the protein. Moieties capable of mediating such effects are disclosed, for example, in Remington's Pharmaceutical Sciences, 16th ed., Mack Publishing Co., Easton, Pa. (1980).

Another type of covalent modification of designer BMPs comprises linking the protein to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337. A variety of coupling chemistries may be used to achieve PEG attachment, as is well known in the art.

In another embodiment, the designer BMP comprises linking the protein via a CovX-body linker to a CovX-body antibody such as, but not limited to, the CovX-bodies described in U.S. Pat. No. 5,733,757, and US Patent Publication No. US 2009/0098130. Such CovX-bodies may exhibit improved characteristics, including, but not limited to, improved stability and extended serum half-life.

Methods of Assaying Receptor Binding Activity of Designer BMPs

The receptor binding activity of designer BMPs may be assessed using any methods used for assessing the activity of wild type BMPs.

The affinity of designer BMPs for one or more BMP receptors can be determined by receptor binding assays. For example, affinities for ALK-2, ALK-3, ALK-6, ActRII, ActRIIb, or BMPRII can be determined. Suitable binding assays include, but are not limited to ELISA, fluorescence anisotropy and intensity, scintillation proximity assays (SPA), Biacore (Pearce et al., *Biochemistry* 38:81-89 (1999)), DELFIA assays, and AlphaScreen™ (commercially available from PerkinElmer; Bosse R., Illy C, and Chelsky D (2002)).

In some embodiments, Biacore or surface plasmon resonance assays are used. See, for example, McDonnell, *Curr. Opin. Chem. Biol.* 5:572-577 (2001). Biacore experiments have been used previously to characterize binding of TGF-β isoforms to their receptors (De Crescenzo et al., J. Biol. Chem., 276: 29632-29643 (2001); De Crescenzo et al., J. Mol. Biol. 328: 1173-1183) (2003).

In other embodiments, a plate-based Direct Binding Assay is used to determine the affinity of one or more modified BMPs for one or more BMP receptors. This method is a modified sandwich ELISA in which BMP is captured using an anti-BMP monoclonal antibody and then detected using a BMP receptor-Fc fusion protein.

In other embodiments, AlphaScreen™ assays (Bosse R. et al., Principles of AlphaScreen™, PerkinElmer Literature Application Note Ref #4069, hypertext transfer protocol site: lifesciences.perkinelmer.com/Notes/S4069-0802.pdf (2002)) can be used to characterize receptor and inhibitor binding. Fluorescence assays may also be used to characterize receptor and inhibitor binding. For example, either BMP2 or a BMP2 receptor or inhibitor may be labeled with a fluorescent dye (for examples of suitable dyes, see the Molecular Probes catalog). Additionally, scintillation proximity assays (SPA) can be used to determine receptor binding affinity. For example, BMP receptor-Fc fusions may be bound to protein A coated SPA beads or flash-plate and treated with S35-labeled BMP; the binding event results in production of light.

In a particular embodiment, the KD of a specific BMP mutant to a Type I or Type II receptor can be determined by using receptor extracellular domain fusions to a human IgG-Fc. The receptor can be bound to an octet sensor using anti-human-IgG-Fc sensors and the BMP can bind the receptor extra-cellular domain in solution to determine Kon and Koff rates. The Octet systems utilize proprietary BioLayer Interferometry (BLI) to enable real-time, label-free analysis of biomolecular interactions and to provide information on affinity, kinetics and concentration. As proteins bind the Octet sensor the light passing through the sensor has a wavelength shift that can be measured with a spectrophotometer. The rate of the shift is measured as the analyte binds the sensor and when it loses binding.

Methods of Assaying Osteogenic Activity of Designer BMP

The osteogenic activity of designer BMPs may be assessed using any methods used for assessing the activity of wild type BMPs.

BMPs promote the growth and differentiation of a number of types of cells. Differentiation may be monitored using, for example, luminescence reporters for alkaline phosphatase or calorimetric reagents such as Alcian Blue or PNPP (Asahina et al. (1996) Exp. Cell Res., 222:38-47; Inada et al. (1996) Biochem. Biophys. Res. Commun. 222:317-322; Jortikka et al. (1998) Life Sci. 62:2359-2368; Cheng et al. (2003) J. Bone Joint Surgery 95A:1544-1582).

The rat limb bud cartilage differentiation assay may also be used to monitor activity in primary cells. In alternative embodiments, reporter gene or kinase assays may be used. Since BMPs activate the JAK-STAT signal transduction pathway, a BMP responsive cell line containing a STAT-responsive reporter such as GFP or luciferase may be used (Kusanagi et (2000) Mol Biol. Cell., 11:555-565). For example, BMP activity in kidney cells may be determined using cell-based assays; see for example Wang and Hirschberg (2004) J. Biol. Chem., 279:23200-23206.

Osteogenic activity may be measured in cell based assays such as alkaline phosphatase, BRE-luciferase, or Alizarin red mineralization, all of which are described in Isaacs et al., *Mol. Endocrinol.* 24:1469-1477 (2010).

Osteogenic activity may also be measured in vivo, via rat ectopic bone assays or mammalian bone growth models. In some embodiments, osteogenic activity measured in non-human primate models. These models are described in Isaacs et al. *Mol. Endocrinol.* 24:1469-1477 (2010).

Methods for evaluating bone mass and quality are known in the art and include, but are not limited to X-ray diffraction; DXA; DEQCT; pQCT; chemical analysis, density fractionation, histophotometry, histomorphometry, and histochemical analysis described, for example, in Lane et al., *J. Bone Min. Res.* 18:2105-2115 (2003). One assay for determining cortical bone density is the MicroCT assay. Following pQCT measurement, the microCT evaluation can be performed, for example, using a Scanco mCT40 (Scanco Medical AG) on a femur.

Any known or later developed in vitro or in vivo method for assessing bone growth/density/strength may be used to assess the osteogenic activity of the designer BMPs of the invention.

Pharmaceutical Compositions

Designer BMPs of the present invention may be formulated for administration to a mammal, preferably a human in need thereof as part of a pharmaceutical composition. The composition can be administered by any suitable means, e.g., parenterally, orally or locally. Where the designed BMPs is to be administered locally, as by injection, to a desired tissue site, or systemically, such as by intravenous, subcutaneous, intramuscular, intraorbital, ophthalmic, intraventricular, intracranial, intracapsular, intraspinal, intracistemal, intraperitoneal, buccal, rectal, vaginal, intranasal or aerosol administration, the composition preferably comprises an aqueous solution. The solution preferably is physiologically acceptable, such that administration thereof to a mammal does not adversely affect the mammal's normal electrolyte and fluid volume balance. The aqueous solution thus can comprise, e.g., normal physiologic saline (0.9% NaCl, 0.15M), pH 7-7.4.

Useful solutions for oral or parenteral systemic administration can be prepared by any of the methods well known in the pharmaceutical arts, described, for example, in "Remington's Pharmaceutical Sciences" (Gennaro, A., ed., Mack Pub., 1990, the disclosure of which is incorporated herein by reference). Formulations can include, for example, polyalkylene glycols such as polyethylene glycol, oils of vegetable origin, hydrogenated naphthalenes, and the like. Formulations for direct administration, in particular, can include glycerol and other compositions of high viscosity.

Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the designer BMPs in vivo. Other potentially useful parenteral delivery systems for the present designer BMPs can include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate or deoxycholate, or oily solutions for administration in the form of nasal drops or as a gel to be applied intranasally.

Alternatively, the designer BMPs of the invention, including designer BMP2 and BMP6, identified as described herein may be administered orally. For example, liquid formulations of designer BMPs can be prepared according to standard practices such as those described in "Remington's Pharmaceutical Sciences" (supra). Such liquid formulations can then be added to a beverage or another food supplement for administration. Oral administration can also be achieved using aerosols of these liquid formulations. Alternatively, solid formulations prepared using art-recognized emulsifiers can be fabricated into tablets, capsules or lozenges suitable for oral administration.

Optionally, the designer BMPs can be formulated in compositions comprising means for enhancing uptake of the protein by a desired tissue. For example, tetracycline and diphosphonates (bisphosphonates) are known to bind to bone mineral, particularly at zones of bone remodeling, when they are provided systemically in a mammal. Accordingly, such components can be used to enhance delivery of the present designer BMPs to bone tissue. Alternatively, an antibody or portion thereof that binds specifically to an accessible substance specifically associated with the desired target tissue, such as a cell surface antigen, also can be used. If desired, such specific targeting molecules can be covalently bound to the present designer BMP, e.g., by chemical crosslinking or by using standard genetic engineering techniques to create, for example, an acid labile bond such as an Asp-Pro linkage. Useful targeting molecules can be designed, for example, according to the teachings of U.S. Pat. No. 5,091,513.

It is contemplated also that some of the designer BMPs may exhibit the highest levels of activity in vivo when combined with carrier matrices, i.e., insoluble polymer matrices. See for example, U.S. Pat. No. 5,266,683 the disclosure of which is incorporated by reference herein. Currently preferred carrier matrices are xenogenic, allogenic or autogenic in nature. It is contemplated, however, that synthetic materials comprising polylactic acid, polyglycolic acid, polybutyric acid, derivatives and copolymers thereof may also be used to generate suitable carrier matrices. Preferred synthetic and naturally derived matrix materials, their preparation, methods for formulating them with the designer BMPs of the invention, and methods of administration are well known in the art and so are not discussed in detailed herein. See for example, U.S. Pat. No. 5,266,683.

In certain embodiments, the designer BMPs can be administered to the mammal in need thereof either alone or in combination with another substance known to have a beneficial effect on tissue morphogenesis. Examples of such substances (herein, cofactors) include substances that promote tissue repair and regeneration and/or inhibit inflammation or fibrosis. Examples of useful cofactors for stimulating bone tissue growth in osteoporotic individuals, for example, include but are not limited to, vitamin D3, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents, analgesics and anesthetics.

Designer BMPs are preferably formulated into pharmaceutical compositions by admixture with pharmaceutically acceptable, nontoxic excipients and carriers. As noted above, such compositions can be prepared for systemic, e.g., parenteral, administration, particularly in the form of liquid solutions or suspensions; for oral administration, particularly in the form of tablets or capsules; or intranasally, particularly in the form of powders, nasal drops or aerosols. Where adhesion to a tissue surface is desired, the composition can comprise a fibrinogen-thrombin dispersant or other bioadhesive such as is disclosed, for example, in PCT US91/09275, the disclosure of which is incorporated herein by reference. The composition then can be painted, sprayed or otherwise applied to the desired tissue surface.

When administered, the pharmaceutical composition of this invention is typically delivered in a pyrogen-free, physiologically acceptable form. Further, the composition may desirably be encapsulated or injected in a viscous form for delivery to the site of bone cartilage or tissue damage. Local administration may be suitable for wound healing and tissue repair. Preferably for bone and/or cartilage formation, the composition includes a matrix capable of delivering BMP protein to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the designer BMP compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the designer BMP protein. These factors include, without limitation, the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution. The addition of other known growth factors, such as IGF I (insulin like growth factor I), to the final composition, may also effect the dosage. Progress can be monitored by periodic assessment of bone growth and/or repair. One method of assessing bone growth or repair is by x-ray imaging and/or CT scanning, among many art-recognized methods.

The compositions can be formulated for parenteral or oral administration to humans or other mammals in therapeutically effective amounts, e.g., amounts which provide appropriate concentrations of the designer BMPs to target tissue for a time sufficient to induce the desired effect. Preferably, the present compositions alleviate or mitigate the mammal's need for a morphogen-associated biological response, such as maintenance of tissue-specific function or restoration of tissue-specific phenotype to senescent tissues (e.g., osteopenic bone tissue) or the inhibition or reversal of a fibrotic response in a tissue.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of a disease, tissue loss or defect, the overall health status of the particular patient, the relative biological efficacy of the compound selected, the formulation of the compound, the presence and types of excipients in the formulation, and the route of administration.

In general terms, the compounds of this invention may be provided in an aqueous physiological buffer solution containing about 0.1 to 10% w/v compound for parenteral administration. Typical doses ranges are from about 10 ng/kg to about 1 g/kg of body weight per day; with a preferred dose range being from about 0.1 mg/kg to 100 mg/kg of body weight.

Therapeutic Uses

Designer BMPs may be used for any indication that wild type BMPs are useful for or for any method in which a TGFβ superfamily member can be used. Designer BMPs are capable of inducing the developmental cascade of bone and cartilage morphogenesis and to induce or mediate Smad signaling pathways. Designer BMPs induce greater bone augmentation and repair, including, but not limited to, production of greater bone mass, bone stiffness and bone density that corresponding wild type BMP. Accordingly, designer BMPs may be used to induce bone formation in a tissue. Also, designer BMPs may be used to induce proliferation of bone and cartilage in a variety of locations in the body. For example, designer BMPs may be used to repair joints such as knee, elbow, ankle, and finger. For example, designer BMPs may be useful for regenerating cartilage in patients suffering from arthritis or other cartilage degenerating diseases. Further, designer BMPs are indicated for treating tears in cartilage due to injury. In addition, designer BMPs are useful for inducing bone growth in patients. For example, designer BMPs are indicated for use in treating patients suffering from bone fractures or breaks, osteoporosis, or patients in need of spinal fusion or for repair of the spine, vertebrae or the like.

In another embodiment, the invention includes a method of bone augmentation and/or repair. Thus, the invention encompasses administering a therapeutically effective amount of a designer BMP to a site where it mediates detectable bone augmentation or repair.

In another embodiment, the invention includes a method of inducing or increasing Smad expression. The method comprises contacting a cell comprising Smad mediated expression pathway with a designer BMP of the invention.

Designer BMPs are capable of inducing the developmental cascade of bone morphogenesis and tissue morphogenesis for a variety of tissues in mammals different from bone or bone cartilage. This morphogenic activity includes the ability to induce proliferation and differentiation of progenitor cells, and the ability to support and maintain the differentiated phenotype through the progression of events that results in the formation of bone, cartilage, non-mineralized skeletal or connective tissues, and other adult tissues.

For example, designer BMPs may be used for treatment to prevent loss of and/or increase bone mass in metabolic bone diseases. General methods for treatment to prevent loss of and/or increase bone mass in metabolic bone diseases using osteogenic proteins are disclosed in U.S. Pat. No. 5,674,844, the disclosures of which are hereby incorporated by reference. Designer BMPs may also be administered to replace or repair bone or cartilage at injury sites such as bone breaks, bone fractures, and cartilage tears. Designer BMPs of the present invention may be used for periodontal tissue regeneration. General methods for periodontal tissue regeneration using osteogenic proteins are disclosed in U.S. Pat. No. 5,733,878, the disclosures of which are hereby incorporated by reference.

Designer BMPs may be used for liver regeneration. General methods for liver regeneration using osteogenic proteins are disclosed in U.S. Pat. No. 5,849,686, the disclosures of which are hereby incorporated by reference. Designer BMPs may be used for treatment of chronic renal failure. General methods for treatment of chronic renal failure using osteogenic proteins are disclosed in U.S. Pat. No. 6,861,404, the disclosures of which are hereby incorporated by reference. Designer BMPs may be used for enhancing functional recovery following central nervous system ischemia or trauma. General methods for enhancing functional recovery following central nervous system ischemia or trauma using osteogenic proteins are disclosed in U.S. Pat. No. 6,407,060, the disclosures of which are hereby incorporated by reference.

Designer BMPs may be used for inducing dendritic growth. General methods for inducing dendritic growth using osteogenic proteins are disclosed in U.S. Pat. No. 6,949,505, the disclosures of which are hereby incorporated by reference.

Designer BMPs may be used for inducing neural cell adhesion. General methods for inducing neural cell adhesion using osteogenic proteins are disclosed in U.S. Pat. No. 6,800,603, the disclosures of which are hereby incorporated by reference.

Designer BMPs may be used for treatment and prevention of Parkinson's disease. General methods for treatment and prevention of Parkinson's disease using osteogenic proteins are disclosed in U.S. Pat. No. 6,506,729, the disclosures of which are hereby incorporated by reference.

It is within skills of an ordinary artisan to modify the general methods using the modified BMPs of the present invention for various therapeutic uses described above.

Exemplary embodiments of therapeutic applications of the modified BMPs of the present invention are further described below.

Designer BMPs may be used to repair diseased or damaged mammalian tissue. The tissue to be repaired is preferably assessed, and excess necrotic or interfering scar tissue removed as needed, by surgical, chemical, ablating or other methods known in the medical arts. The designer BMPs then may be provided directly to the tissue locus as part of a sterile, biocompatible composition, either by surgical implantation or injection. Alternatively, a sterile, biocompatible composition containing modified BMP-stimulated progenitor cells may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. For some tissues, it is envisioned that systemic provision of the modified BMPs will be sufficient.

Designer BMPs may be used to prevent or substantially inhibit scar tissue formation following an injury. If a designer BMP is provided to a newly injured tissue locus, it can induce tissue morphogenesis at the locus, preventing the aggregation of migrating fibroblasts into non-differentiated connective tissue. The designer BMP preferably is provided as a sterile pharmaceutical preparation injected into the tissue locus within five hours of the injury.

For example, the designer BMPs may be used for protein-induced morphogenesis of substantially injured liver tissue following a partial hepatectomy. Variations on this general protocol may be used for other tissues. The general method involves excising an essentially nonregenerating portion of a tissue and providing the modified BMP, preferably as a soluble pharmaceutical preparation to the excised tissue locus, closing the wound and examining the site at a future date. Like bone, liver has a potential to regenerate upon injury during post-fetal life.

As another example, designer BMPs can also be used to induce dentinogenesis. To date, the unpredictable response of dental pulp tissue to injury is a basic clinical problem in dentistry. Using standard dental surgical procedures, small areas (e.g., 2 mm) of dental pulps can be surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

The designer BMPs of the invention may be used to treat fibrosis. The fibrosis may be located in various parts of the body and can be of a particular kind, for example, the fibrosis may be located; in the kidney, for example, fibrosis as observed in glomerulonephritis, diabetic nephropathy, allograft rejection, and HIV nephropathy; in the liver, for example, cirrhosis, and veno-occlusive disease; in the lung, for example, idiopathic fibrosis (and autoimmune fibrosis); in the skin, for example, systemic sclerosis, keloids, scars, and eosinophilia-myalgia syndrome; in the central nervous system, for example, intraocular fibrosis; in the cardiovascular system, for example, vascular restenosis; in the nose, for example, nasal polyposis; in bone or bone marrow; in an endocrine organ; and in the gastrointestinal system.

In one embodiment, a designer BMP having the binding characteristics of BMP7, or useful modification thereof (extended half life, increase binding affinity for a same or different receptor compared with wild type WET, resistance to inhibition by a BMP7 antagonist, such as, but not limited to, Noggin, and the like) may be useful to treat, ameliorate or reverse fibrosis. That is, as reviewed recently in Weiskirchen et al., 2009, Frontiers in Biosci. 14:4992-5012, TGF$\beta_1$ mediates a cascade leading to increased fibrosis, including, but not limited to, epithelial-to-mesenchymal transition. The fibrosis-inducing effects of TGF$\beta_1$ may be inhibited or reversed by BMP7. See also Loureiro et al., 2010, Nephrol. Dial. Transplant. 25:1098-1108. Further, certain fribotic conditions may also be treated or ameliorated by administration of BMP4 (see Pegorier et al., 2010, Resp. Res. 11:85). Therefore, the invention encompasses a designer BMP either based on a BMP7 framework and/or incorporating the type I and type II mutations disclosed elsewhere herein, to alter receptor binding and provide a potential useful therapeutic for treatment of fibrosis in a patient in need thereof.

A fibrotic disorder may be induced by a number of causes including: chemotherapy, for example, pulmonary fibrosis resulting from bleomycin, chlorambucil, cyclophsphamide, methotrexate, mustine, or procarbazine treatment; radiation exposure whether accidental or purposeful as in radiation therapy, for example, interstitial lung disease (ILD) resulting from radiation; environmental or industrial factors or pollutants such as chemicals, fumes, metals, vapors, gases, etc., for example. ILD resulting from asbestos or coal dust; a drug or a combination of drugs, for example, antibiotics (e.g. penicillins, sulfonamides, etc.), cardiovascular drugs (e.g., hydralazine, beta blockers, etc.). CNS drugs (phenyloin, chlorpromazine, etc.) anti-inflammatory drugs (e.g., gold salts, phenylbutazone, etc.), etc. can cause ILD; an immune reaction disorder, for example, chronic graft-versus-host disease with dermal fibrosis: disease states such as aspiration pneumonia which is a known cause of ILD, and parasite induced fibrosis; and wounds, for example, blunt trauma, surgical incisions, battlefield wounds, etc., as in penetrating injuries of the CNS.

In a particular embodiment, designer BMPs with improved binding to type I receptor ALK2, such as BMPE, may be used to treat diseases related to ALK2.

Kits

The invention includes various kits which comprise a therapeutically effective amount of a designer BMP of the invention, along with an applicator and instructional materials which describe use of the designer BMP to perform the methods of the invention. Although exemplary kits are described below, the contents of other useful kits will be apparent to the skilled artisan in light of the present disclosure. Each of these kits is included within the invention.

The invention includes a kit for treatment to prevent loss of and/or increase bone mass in a metabolic bone disease in a patient in need thereof. The kit includes a designer BMP of the invention. The kit further comprises an applicator, including, but not limited to, a syringe, a bone cement mixing device, and the like, for administration of the components of the kit to a patient. Further, the kit comprises an instructional material setting forth the pertinent information for the use of the kit to treat or prevent bone mass and/or increase bone mass in the patient.

More preferably, the kit comprises at least one designer BMP selected from an antibody having an amino acid sequence selected from the amino acid sequence of SEQ ID NOs:8-73, even more preferably, the designer BMP comprises the amino acid sequence of SEQ ID NO:12, SEQ ID NO:14, SEQ ID NO:36 and SEQ ID NO:37. Preferably, the designer BMP is BMPE, BMPG, BMPGE and BMPGER.

The kit can comprise any number of additional therapeutic agents for treatment to prevent bone loss and/or increase bone mass. Such agents are set forth previously and include therapeutic compounds, cytokines, vitamins, other members of the TGFβ superfamily, among many others.

The invention also relates to an article of manufacture (e.g., dosage form adapted for i.v. or oral administration) comprising a designer BMP in the amount effective to prevent bone loss and/or increase bone mass (e.g., more than 10 mg/kg, at least 15 mg/kg, or 15 mg/kg). In certain embodiments, the article of manufacture comprises a container or containers comprising a designer BMP and a label and/or instructions for use to treat or prevent bone loss and/or increase bone mass.

The invention also includes a kit to treat or prevent fibrosis in a tissue or organ in a patient in need thereof. The kit includes a designer BMP of the invention. The kit further comprises an applicator, including, but not limited to, a syringe or device for delivering the protein, a mixing device, and the like, for administration of the components of the kit to a patient. Further, the kit comprises an instructional material setting forth the pertinent information for the use of the kit to treat or prevent fibrosis in the patient.

More preferably, the kit comprises at least one designer BMP selected from a protein having an amino acid sequence selected from the amino acid sequence of SEQ ID NOs:8-73, even more preferably, the designer BMP comprises the amino acid sequence of SEQ ID NO:12, SEQ ID NO:14, SEQ ID NO:36 and SEQ ID NO:37. Preferably, the designer BMP is BMPE, BMPG, BMPGE or BMPGER.

The kit can comprise any number of additional therapeutic agents for treatment to prevent bone loss and/or increase bone mass or treat or prevent fibrosis. Such agents are set forth previously and include therapeutic compounds, cytokines, vitamins, other members of the TGFβ superfamily, among many others.

The invention also relates to an article of manufacture (e.g., dosage form adapted for i.v. or oral administration) comprising a designer BMP in the amount effective to prevent bone loss and/or increase bone mass or to treat or prevent fibrosis (e.g., more than 1 mg/kg, at least 10 mg/kg, at least 15 mg/kg, or 15 mg/kg). In certain embodiments, the article of manufacture comprises a container or containers comprising a designer BMP and a label and/or instructions for use to treat or prevent bone loss and/or increase bone mass or to treat or prevent fibrosis.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Production and Purification of Designer BMP Proteins

Production Using Mammalian Cell Culture

Recombinant host CHO cells producing and secreting wild type and designer BMPs were generated using standard recombinant DNA procedures. Conditioned medium was generated from adherent cell cultures. Briefly, CHO cells were seeded in medium containing 10% dFBS and allowed to grow to near confluence for 3-4 days. After this growth phase, growth medium was discarded and the cells were rinsed once with PBS-CMF and subsequently switched to a serum-free medium supplemented with 200 ug/ml dextran sulfate, 2 mM sodium butyrate, and 10 mM HEPES. Cells were then cultured for 7 days at a temperature of 31° C. Conditioned medium was harvested and clarified by using sterilizing 0.2 uM filtration. Conditioned medium was stored at −20° C. until purification.

Purification of Designer BMPs

Figure 5:
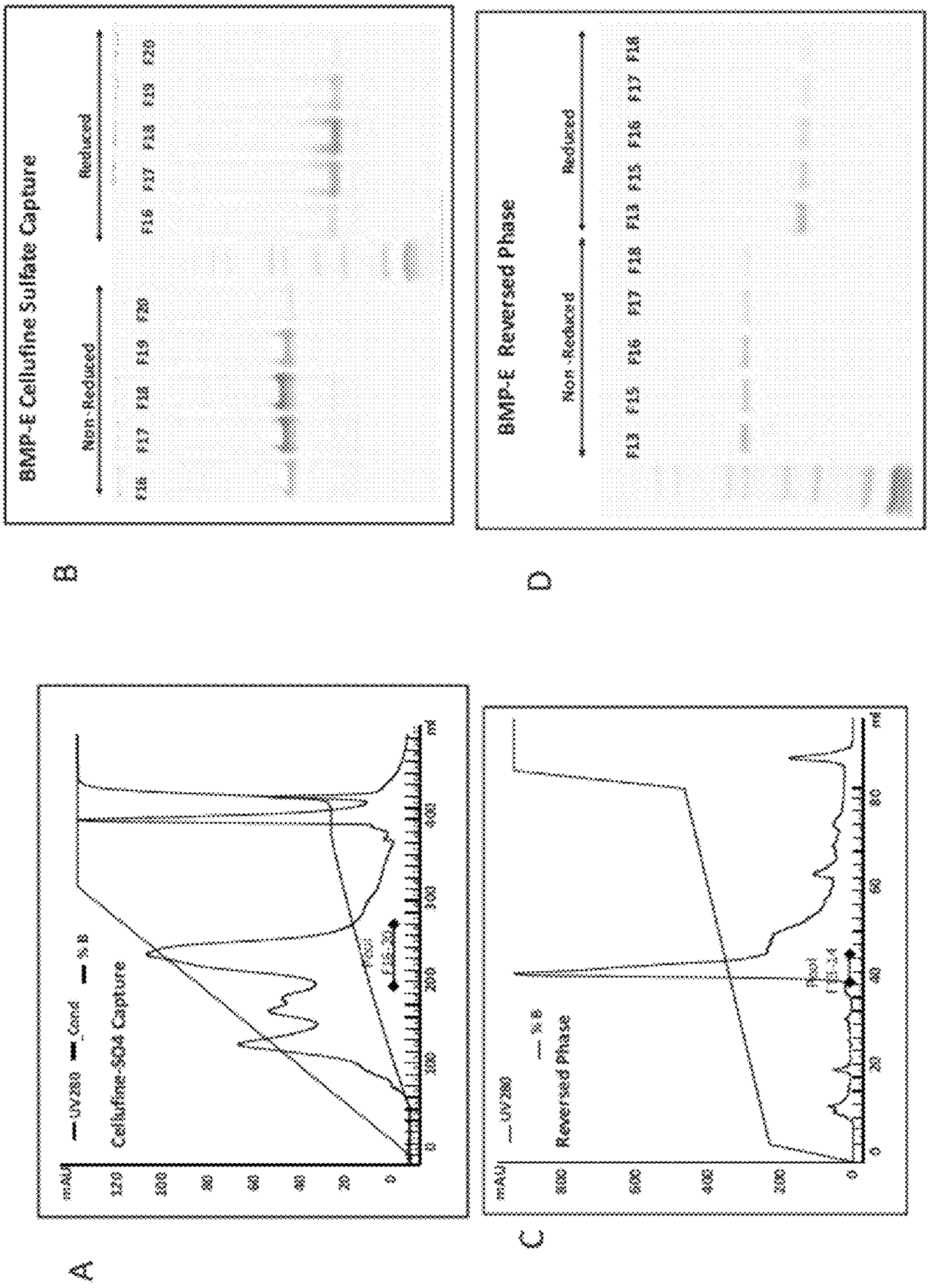
FIG. 5, comprising panels A-D, shows various steps in the process for purification of BMPs and designer BMPs.

In order to purify the novel designer BMP molecules from CHO cell conditioned media the BMPs were captured by two steps of conventional chromatography and the results are shown in FIG. 5, comprising panels A-D. Only the details of the purification of BMPE are shown herein since all of the other novel designer BMPs were purified in an essentially similar manner.

Figure 6:
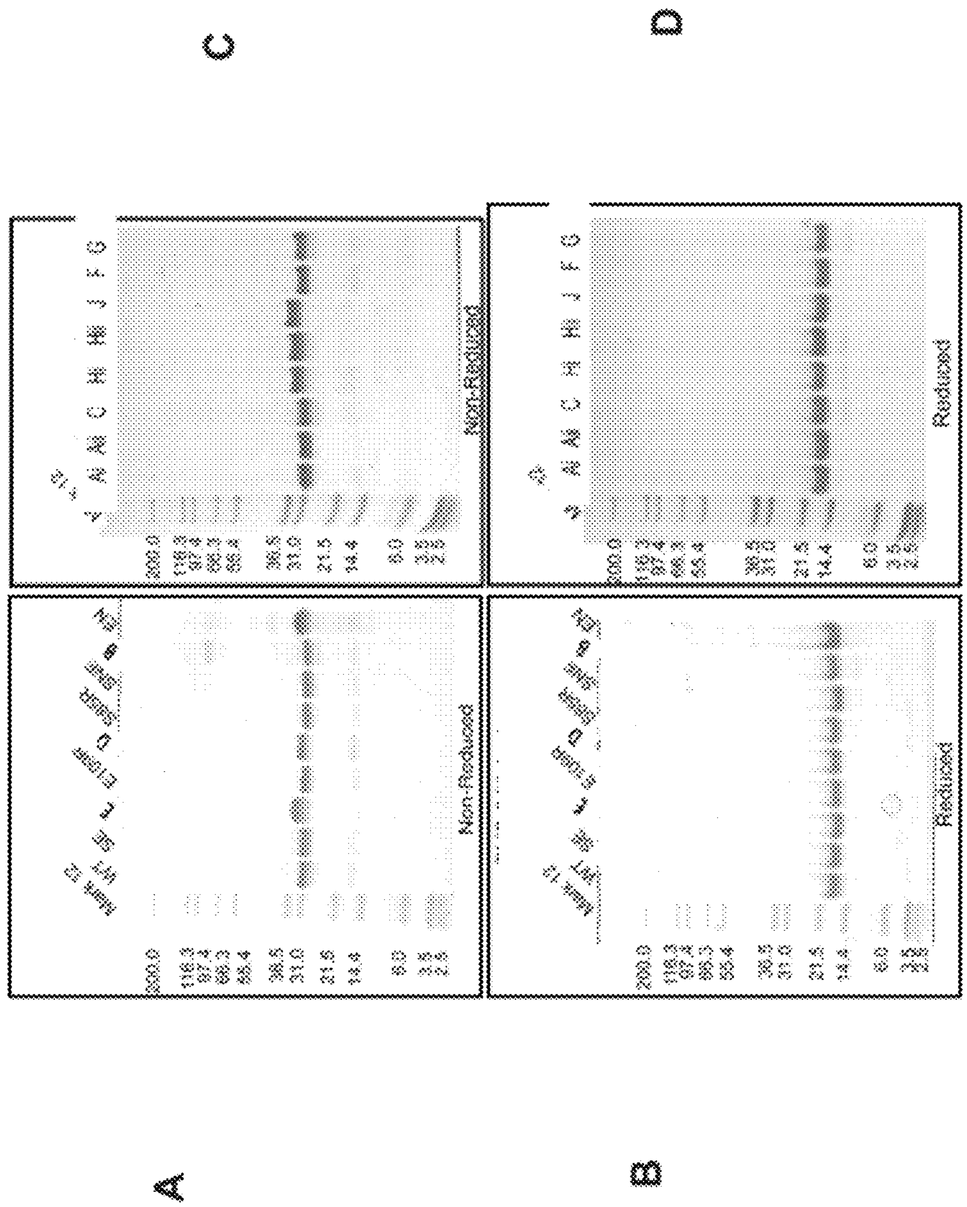
FIG. 6, comprising panels A-D, show images of Coomassie-stained SDS-PAGE protein gels showing purified BMP2 wild type and various mutants as indicated along the top of each gel image. The gels were run under either non-reducing (FIGS. 6A and 6B) and reducing (FIGS. 6C and 6D) conditions.

CHO conditioned medium (CHO CM) (pH adjusted to 8.0 with 1.0 M Tris, pH 8.0) was loaded onto a Cellufine Sulfate column (65 ml, 2.6×12.3 cm) that was equilibrated with 20 mM MES pH 8.0. The column was washed with 10 column volumes (CV) of 20 mM Tris, pH 8.0, 10 CV 50 mM MES pH 5.6 and 10 CV of Buffer A (6.0 M Urea, 50 mM MES, pH 5.6). The BMPs were eluted with a linear 0-1.0 M NaCl gradient over 5 CV (Buffer B=6.0 M Urea, 50 mM MES, 1.0 M NaCl, pH 5.6). Upon application of a sodium chloride gradient, a broad peak between conductivities of 30 and 45 mS/cm characteristic of BMP2 was observed (FIG. 5A). Fractions were analyzed by Coomassie stained SDS-PAGE gels and BMP containing fractions were pooled. BMPs in fractions were identified as reducible dimers on SDS-PAGE Non-Reduced gels (left panel of FIG. 5B). The BMP pools from the Cellufine Sulfate chromatography step were further purified by preparative Reverse Phase HPLC on a 10×250 mm Vydac 15 μm C8 Column (Solvent A=0.1% TFA, Solvent B=90% acetonitrile, 0.1% TFA), with BMP eluting with approximately 32% acetonitrile. A tracing of the Reversed Phase chromatography step is shown in FIG. 5C. The protein was concentrated and acetonitrile was removed using a speedvac and the concentrate was formulated into MFR-169 buffer via dialysis. The purified BMPs were characterized by SDS-PAGE, A280 and LAL Assay (endotoxins). A photograph of an Non-Reduced SDS-PAGE gel (left side of FIG. 5D) and a Reduced SDS-PAGE gel (right side of FIG. 5D) showing the same gel fractions (F13 through F18) is shown. A total of 16 BMP designer proteins were purified to essentially the same levels of purity and expression/purification yields ranging from 0.3-1.4 mg/L CM and the results are shown in FIG. 6 showing photographs (FIG. 6). Briefly, wild type BMP2 (WT) and designer BMPs BMPSE, BMPE, E109R, BMPD, BMP S85R, BMP SNE, BMPB, and BMP-EN are shown in photographs of a non-reduced gel (FIG. 6A) and a reduced SDS-PAGE (FIG. 6B), and designer BMPs ai (variant of BMPA), aii (variant of BMPA), c (BMPC), hi (variant of BMPI), hii, i, f, and g are shown in photographs of a non-reduced SDS-PAGE (FIG. 6C) and reduced SDS-PAGE (FIG. 6D).

Example 2

Figure 7:
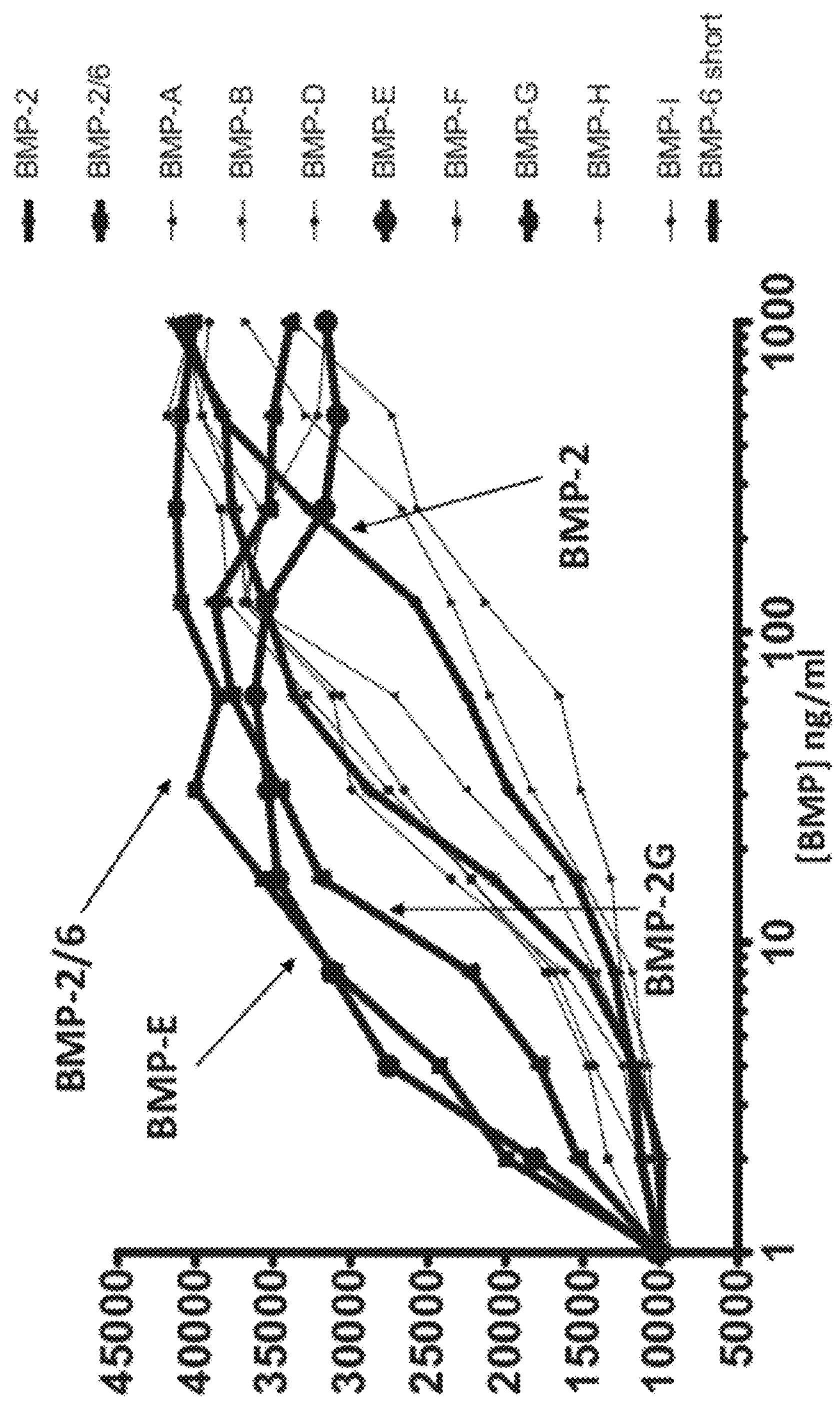
FIG. 7 shows alkaline phosphatase assay results in C2C12 pre-myoblasts comparing the osteogenic activity of wild type BMP2 and BMP2/6 heterodimer to the various designer BMPs ea indicated in the graph legend.

Osteogenic Activity of Designer BMPs Demonstrated Using In Vitro and In Vivo Assays Alkaline Phosphatase Assay Approximately 8000 C2C12 cells/well in a 96-well plate were treated with the indicated BMP ant the dose indicated. Twenty-four hours post-treatment, the plates were processed to measure alkaline phosphatase which is an art-recognized assay for osteogenic activity. The culture medium was removed, and the plates were washed twice with calcium/magnesium-free PBS. 50 μl of 4-Methylumbelliferyl phosphate (4-MUP Liquid Alkaline Phosphatase Substrate; Sigma cat. #M3168) was added to each well, and the plates were incubated in the dark at 37° C. for 15 minutes. Fluorescence was measured on a Victor luminometer (settings: excitation at 355 nM; emission at 4601 nM; CW lamp energy at 1120), 1 second per well. After the reading was complete, 50 μl of 2× protein assay lysis buffer (200 mM Tris-HCl, pH 9.8/0.4% Triton X-100) was added to each well and the protein concentration was determined using the BCA Protein assay (Pierce) following the manufacturer's microplate procedure. The alkaline phosphatase measurements were then normalized to the total protein concentration (i.e., fluorometric units per microgram of protein). As shown by the graph in FIG. 7, C2C12 muscle pre-myoblast cells treated with multiple designer BMP molecules showed significantly increased Alkaline Phosphatase activity, as a marker of osteoblast differentiation, compared to treatment with wild type BMP2 (heavy line with small circles). Designer BMPs exhibiting increased AP activity compared with WT BMP2 included designers BMPA, BMPF, BMPG, and BMPE. Surprisingly, designer BMPE demonstrated equivalent activity to that of the wild type BMP2/6 heterodimer (heavy line with squares), which is known to bind both the type I receptors of BMP2 and type II receptors of BMP6 with high affinity. Designer BMPE is the result of introduction of the low affinity type I binding region of BMP6 into BMP2. The extremely high activity of the designer BMPE molecule was extremely surprising since it was predicted that BMPE would have low affinity binding to both type I and type II receptors. Interestingly, the other designer BMP molecules, designer BMPA, designer BMPF, and designer BMPG, have regions of wild type BMP6 that bind the type II (high affinity) receptors of BMP6 which have been introduced into BMP2 (see FIG. 1B), and these designer BMPs showed increased activity compared to BMP2, but not as high as that of wild type BMP2/6 heterodimer (FIG. 7).

BRE-Luciferase Assay

C2C12 cells stably expressing the BMP-response-element luciferase reporter (element is from the Id1 promoter) were plated at 8000 cells/well of a 96 well and treated with the indicated BMP and dose. 48 hours post treatment, the cells were lysed and luciferase activity was read using the Promega Dual-Glo assay kit.

Figure 8:
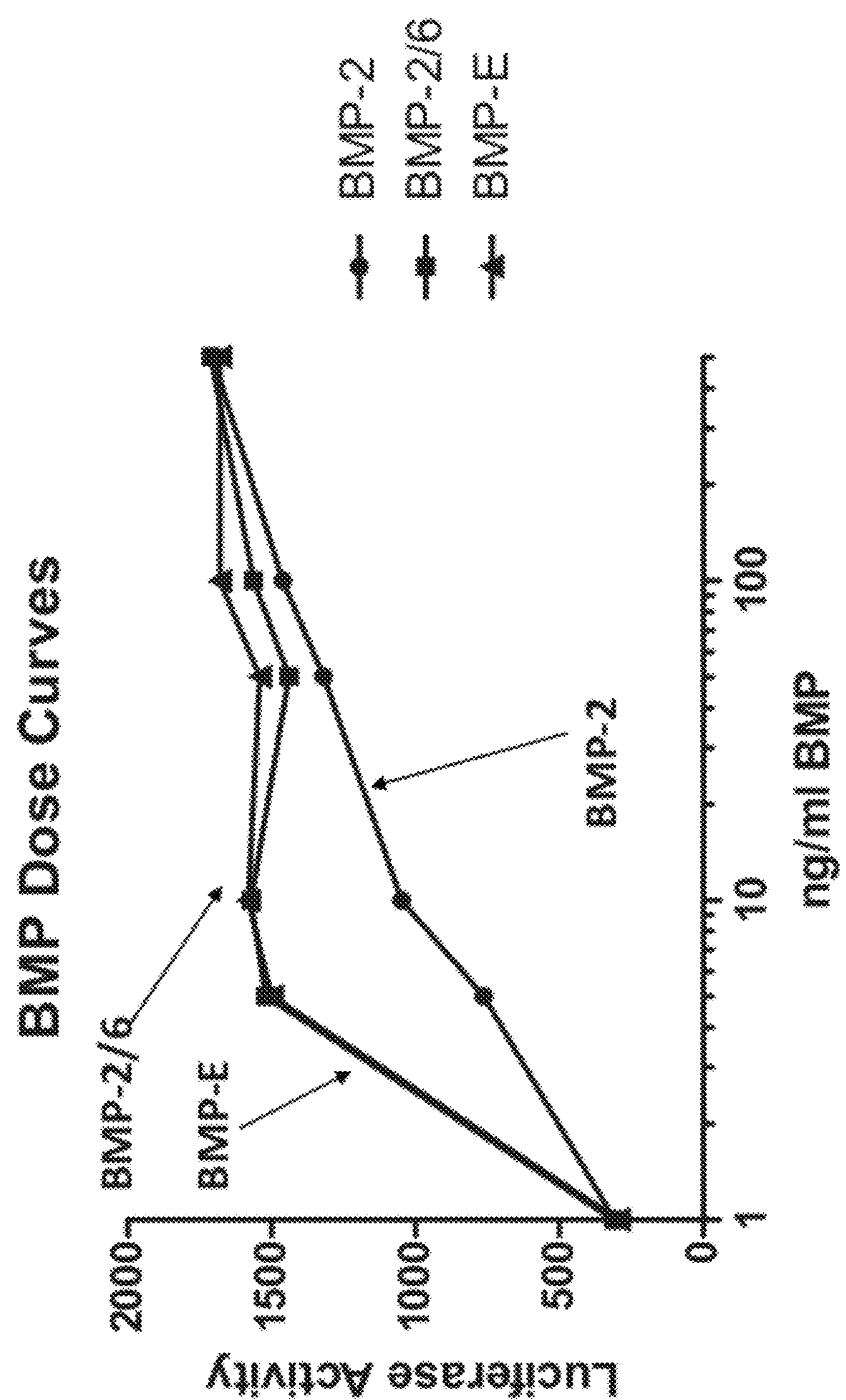
FIG. 8 shows the results of a C2C12 BMP-Response Element luciferase (BRE-luciferase) assay indicative of Smad activity showing stronger signaling by BMPE compared to BMP2 and equivalent signaling to BMP2/6.

The data disclosed herein demonstrated that not only was the activity of BMPE equivalent to that of BMP-2/6 in an alkaline phosphatase assay, it was also equivalent in a BRE-luciferase assay in C2C12 cells as shown in FIG. 8. Further, BMPE demonstrated approximately 10-20 fold greater activity in the BRE-luciferase assay compared with wild type BMP-2 (FIG. 8). Thus, the results observed in the BRE-luciferase (BRE-luc) assay correlated strongly with those obtained in the Alkaline Phosphatase (Alk-phos) activity assay in this same cell type (compare FIG. 7 and FIG. 8). Results from both the Alk-phos and BRE-luc assays are also shown in Table 10 for wild type BMP2 and the indicated designer BMPs.

Without wishing to be bound by any particular theory, these data suggest that the addition of ALK-2 as a high affinity receptor for BMPE could be the reason for its increased osteogenic activity. This is because an ALK-2 mutation has been found to cause fibrodysplasia ossificans progressiva (FOP), a disease where young children develop inappropriate ectopic bone formation. Thus, mutation of ALK-2 binding is associated with increased osteogenesis and may be correlated to the increased osteogenic activity of BMPE. Thus, BMPE is a new class of BMP molecule with high affinity for the type I receptors ALK-2, 3, and 6.

Alizarin Red Staining for Cell Mineralization

C2C12 cells were plated in 6-well tissue culture plates at a density of $4\times10^4$ cells/cm$^2$ and incubated overnight at 37° C. inside a 5% $CO_7$/95% humidified air incubator. After the recovery period, the culture medium was replaced with freshly prepared osteogenic differentiation medium: Growth Medium containing 50 ug/ml L-ascorbic acid phosphate (L-Ascorbic Acid Phosphate Magnesium Salt n-Hydrate; WAKO Pure Chemical Industries; Cat. No. 013-12061); β-glycerol phosphate (β-Glycerol phosphate Disodium salt, 10 mM Pentahydrate; Fluka BioChemica Cat. No. 50020); and 100 nM Menadione sodium bisulfite (Vitamin K3; Sigma Cat. No. M2518). The indicated BMP was added to the appropriate wells at the desired concentration. The plates were incubated at 37° C. for approximately 15 days, with medium replacement every 2 to 3 days. The cells were stained with the Alizarin Red stain following the standard published protocols.

As shown in Table 9, below, designer BMPE induced mineralization of C3H10T-1/2 mouse mesenchymal stem cells to a far greater extent than corresponding wild type BMP2 as indicated by alizarin red staining. That is, as more fully discussed below, at doses where wild type BMP-2 was unable to induce mineralization of the C3H10T-1/2 cells (5, 25, 50, and 100 ng/ml) BMPE homodimer induced strong mineralization similar to that of the BMP-2/6 heterodimer all as shown in Table 9. Thus, the alizarin red staining assay results further correlate the results obtained in the Alk-phos and BRE-luc assays as disclosed previously herein.

TABLE 9

| Treatment | BMP2 | BMP2/6 | BMPE |
|---|---|---|---|
| 5 ng/ml | – | – | – |
| 25 ng/ml | – | ++ | + |
| 50 ng/ml | – | ++++ | ++ |
| 100 ng/ml | – | ++++ | +++ |

Rat Intramuscular Ectopic Bone Assay

Figure 9:
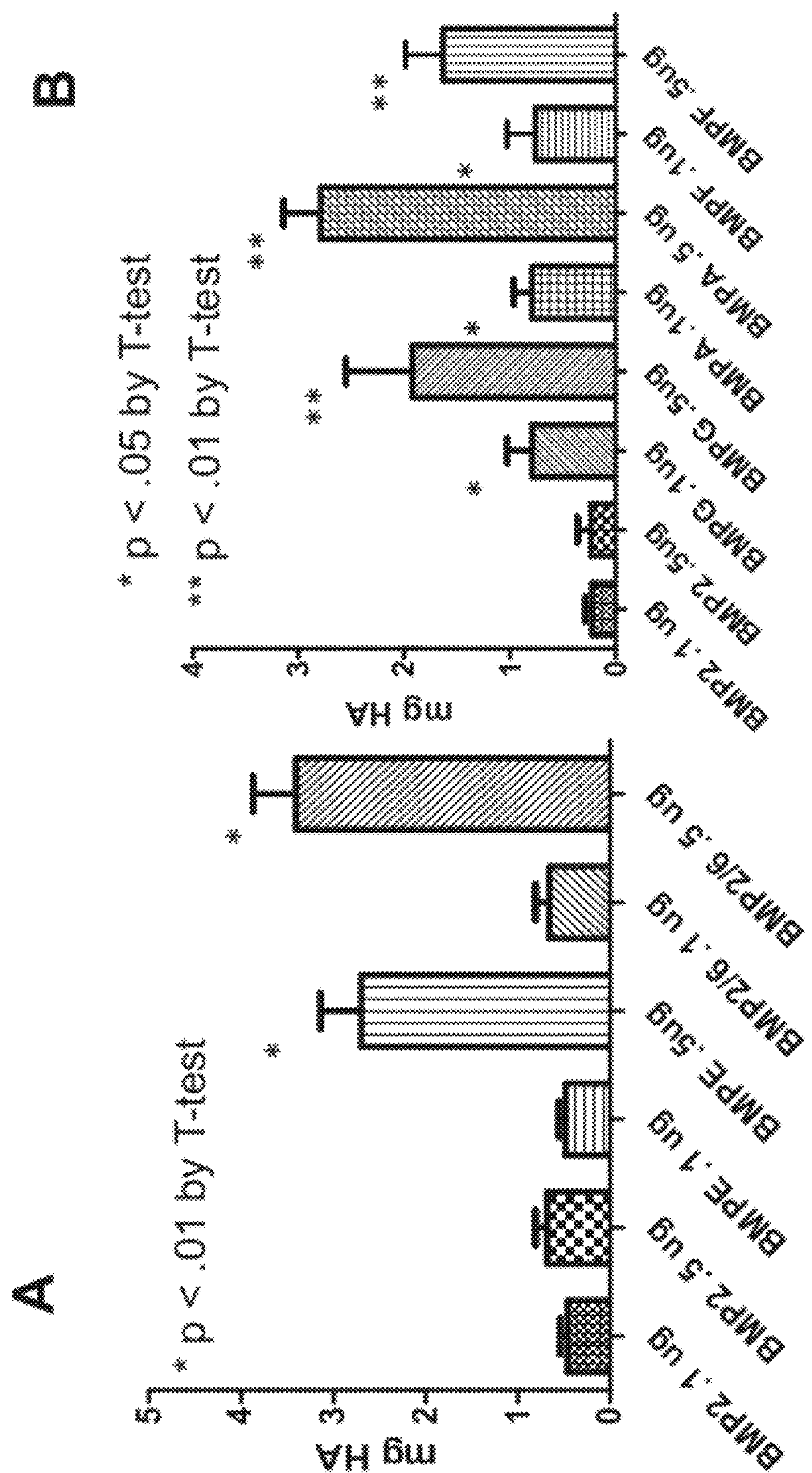
FIG. 9, comprising panels A and B, shows the ectopic bone formation mediated by various BMPs.

To determine whether the stronger osteogenic activity observed in vitro by the designer BMPs corresponded to similar increased activity in vivo, rat ectopic bone formation assays were performed. Briefly, an ACS (absorbable collagen sponge) impregnated with the indicated total amount of designer BMP in 160 microliters of buffer was implanted into the hamstring of 8 week old male Long Evans rats. More specifically, three 8 mm biopsy punched ACS discs were sutured together with non-resorbable silk sutures. The sponges were wetted with 160 microliters of the BMP solution containing the amount of BMP indicated in the chart in FIG. 9 (i.e., 0.1 μg or 0.5 μg). The wetted sponges were equilibrated at room temperature for 20 minutes. The sponges were then surgically placed into the hamstrings of each rat bilaterally. Each BMP (wild type and designer molecules) was placed into both limbs of 4 rats. Two weeks post implantation, the animals were sacrificed and the hamstrings were dissected, placed in 10% formalin and scanned by μCT (Scanco Inc.) to determine the amount of ectopic bone present. The amount of hydroxyapatite in milligrams (mg HA) present in the limbs of the treated animals is shown in FIG. 9, FIG. 9A shows the results for BMP2, BMPE and BMP2/6 heterodimer. FIG. 9B shows the results for BMP2, BMPG, BMPA, and BMPF. For each of the designer BMPs, ectopic bone was formed at doses at which wild type BMP2 was unable to form a detectable bone mass. In a head-to-head comparison of wild type BMP2 with designer BMPE was able to induce ectopic bone to the same extent as wild type BMP2/6 heterodimer, closely matching the results obtained in the in vitro experiments disclosed previously. Designer BMPs BMPG, BMPA, and BMPF also demonstrated significantly higher ectopic bone formation compared to wild type BMP2 (FIG. 9B). Results from this assay are shown in FIG. 9 and also presented in Table 10.

TABLE 10

| Name | Alk-phos | BRE-luc | Rat ectopic bone formation |
|---|---|---|---|
| BMP2WT | ++ | ++ | ++ |
| BMPA | ++++ | ++++ | ++++ |
| BMPB | ++ | ++ | ++ |
| BMPC | ++ | ++ | ++ |
| BMPD | ++ | ++ | ++ |
| BMPE | ++++++ | ++++++ | ++++++ |
| BMPF | ++++ | ++++ | ++++ |
| BMPG | +++++ | +++++ | +++++ |
| BMPH | ++ | ++ | ++ |
| BMPI | +++ | +++ | +++ |
| BMPJ | + | + | + |
| BMPD-P | ++ | ++ | ++ |
| BMP6-short | ++++ | ++++ | ++++ |

Example 3

BMP Receptor Binding

To further elucidate the mechanism of increased osteogenic activity of the designer BMPs, binding kinetic analysis of each of the designer BMPs with a panel of BMP receptors was performed using the Octet system (ForteBio, Menlo Park, Calif.). The Octet QK analysis was performed at degrees in TBS with 0.1% Tween-20. Samples were agitated at 1000 rpm. Anti-Human IgG Octet tips were saturated with 10 ug/mL of each receptor-human-IgG1-Fc fusion protein for 20 min, which typically resulted in capture levels of the receptor that are saturated within a row of eight tips. Each BMP was prepared as a sevenfold serial dilution (typically 200-3 nM in singlicate) plus buffer blanks. Each Receptor/BMP binding pair was run at least in duplicate. Association was monitored for 10 min and dissociation was followed for 30 into buffer alone. Kinetic parameters (kon and koff) and affinities (KD) were calculated using the Octet Data Analysis software 6.0 using a partial binding 1:1 model following manufacturer's instructions.

The data set forth in Table 12 show that wild type BMP2 and BMP6 proteins each demonstrated the expected high affinity binding to type I (ALK-3 and ALK-6) and type II receptors (ActRIIA, ActRIIB, and BMPRII), respectively. The wild type BMP2/6 heterodimer exhibited high affinity binding to both groups of type I and type II receptors, as did designer BMPG, which the type II binding domains A and B of BMP2 have been replaced by the domains of wild type BMP6. Designer BMPE showed similar affinity as wild type BMP2 for the type II receptors as expected since no mutations were made in the type II binding regions. Unexpectedly, designer BMPE maintained high affinity binding for the type I receptors ALK-3 and ALK-6 with the type I binding domain of BMP6 which has been substituted in place for that of BMP2, while also unexpectedly binding the type I receptor ALK-2 with a KD of 2 nm. Thus, BMPE surprisingly gained a very high affinity binding for ALK-2 not observed in either WT BMP2 or WT BMP6.

TABLE 12

| Receptor | BMP-2 (nM) | BMP-6 (nM) | BMP-2/6 (nM) | BMPE | BMPG |
|---|---|---|---|---|---|
| ALK2 | >1000 | >1000 | 250 | 2 | <1000 |
| ALK3 | 1 | 11 | 2 | 3 | 1 |
| ALK6 | 1 | 20 | 0.5 | 1 | 1 |
| ACTR IIA | 53 | 3 | 2.5 | 40 | 2 |
| ACTR IIB | 8 | 0.5 | 1 | 6 | 0.5 |
| BMPR IIA | 62 | 4 | 3 | 82 | 4 |

As shown in Table 13, combining the mutations of BMPG and BMPE, comprising either praline or arginine at amino acid residue 36 (P36R) relative to the amino acid sequence of wild type BMP2 as set forth in SEQ. ID NO:1, to produce BMP-GEP (also referred to as BMPGE P36) and BMP-GER (also referred to as BMPGE P36R), respectively, produced designer BMPs which demonstrated high affinity, low nM KDs, for all type I and Type II BMP receptors including ALK-2.

TABLE 13

| Receptor | BMP-2 | BMP-6 | BMP-2/6 | BMP-E | BMP-G | BMP-GER |
|---|---|---|---|---|---|---|
| ALK2 | >1000 | 700 | 250 | 2 | >1000 | 2 |
| ALK3 | 1 | 11 | 2 | 3 | 1 | 2 |
| ALK6 | 1 | 20 | 0.5 | 1 | 1 | 1 |
| ACTRIIA | 53 | 3 | 2.5 | 40 | 2 | 2 |
| ATRIIB | 8 | 0.5 | 1 | 6 | 0.5 | 0.5 |
| BMPRIIA | 62 | 4 | 3 | 82 | 4 | 3.5 |

Thus, the data disclosed herein demonstrate novel designer BMPs, such as, but not limited to, BMP-GER and BMP-GEP, which combine the attributes of BMP-G and BMP-E such that these novel designer BMPs demonstrate high affinity binding to a wide repertoire of both type I and type II receptors, including, but not limited to, ALK2, ALK3, ALK6, ActRIIA, ActRIIB and BMPRIIA. The data further demonstrated that replacing the proline at residue number 36 of the amino acid sequence of WT BMP2 (SEQ ID NO:1) to arginine produced a designer BMP that was as effective as an otherwise identical BMP where the amino acid was not replaced. These novel osteogenic BMPs as exemplified by BMP-GER, provide high levels of biologic activity thus allowing lower dosing and, in some cases, more rapid osteogenic response, strongly suggesting that these molecules would provide highly effective therapeutics.

Example 4

In Vivo Osteogenic Activity in Non-Human Primates

NHP Fibula Osteotomy Model

To further assess the potential therapeutic potential of the novel designer BMPs of the invention, the activity of designer BMPE and BMPG was compared to that of wild type BMP2 in an NHP (non-human primate) fibula osteotomy model.

A mid-diaphyseal osteotomy of the fibula was performed bilaterally with the 1-mm blade of an oscillating saw in adult male Cynomolgus monkeys (*Macaca fascicularis*) with a mean body weight (and standard deviation) of 7.5±0.2 kg and an age range of seven to ten years. A small intramedullary Kirschner wire was added to the previously described fibular osteotomy model to maintain alignment of the proximal and distal bone ends for more uniform torsional biomechanical testing. The two major advantages of this model are the ability to utilize a bilateral study design as a result of the low morbidity of the procedure and the ability to remove a 6 to 8-cm segment of the fibula containing the osteotomy site for subsequent biomechanical and histological evaluation without having to sacrifice the animal. A 500 μL solution of 0.5 mg/ml of either wild type or designer BMP was added to a 30 mm×15 mm ACS sponge. The sponge was wrapped around the defect following surgery. An approximately 2 mm fracture of the fibula of each limb of a skeletally mature NHP was wrapped in an ACS sponge comprising either a designer BMP molecule at 0.5 mg/ml dose (250 μg total delivered) or the same amount of wild type BMP2 in the contralateral limb. Thus, each animal received wild type BMP in one limb and a designer BMP in the contralateral limb.

Figure 10A:
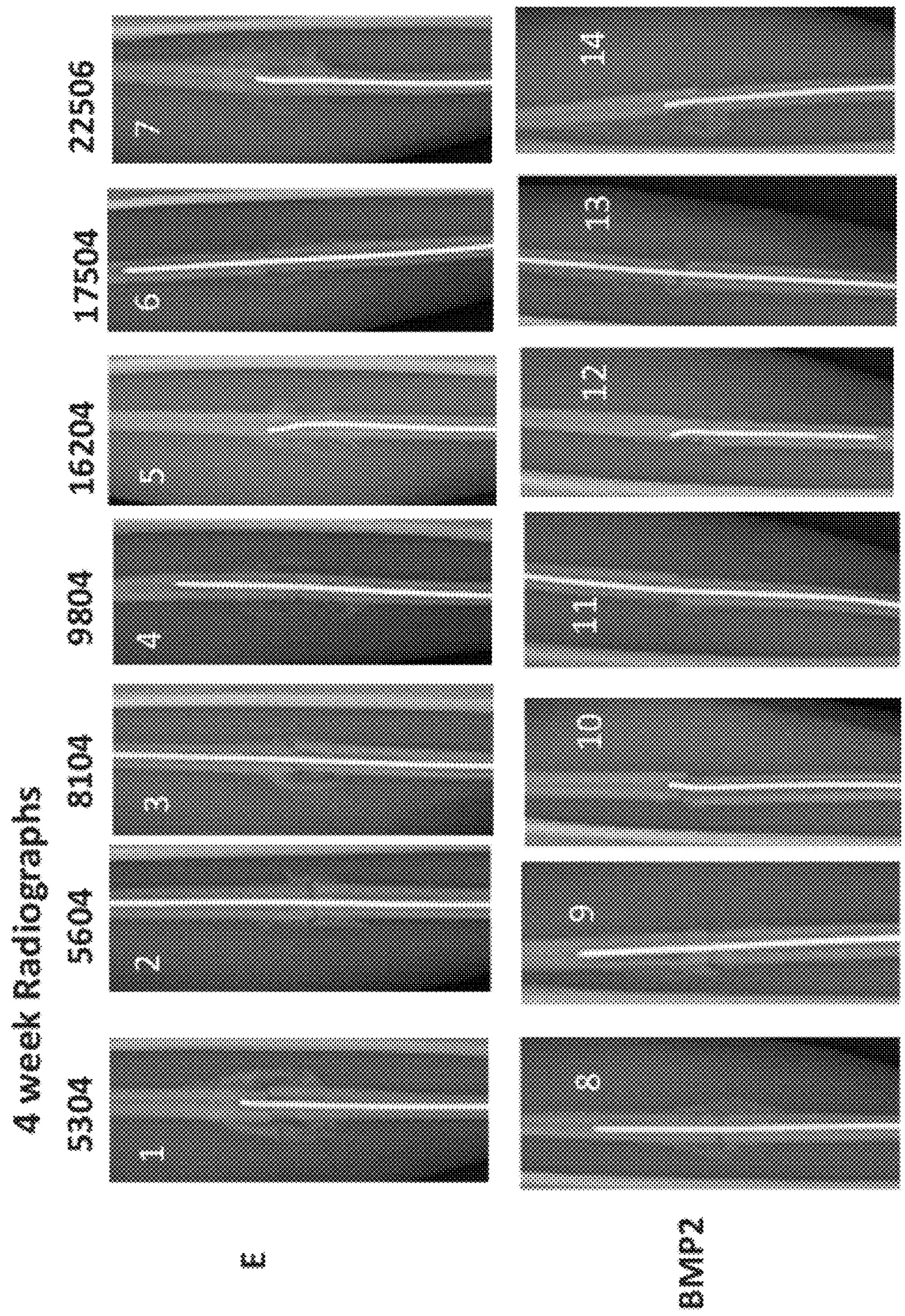
FIGS. 10A and 10B show the radiographs for the NHPs indicated at the top of each diagram showing the effects of BMPE compared with BMP2 wild type at 4 weeks and 8 weeks, respectively.
Figure 10B:
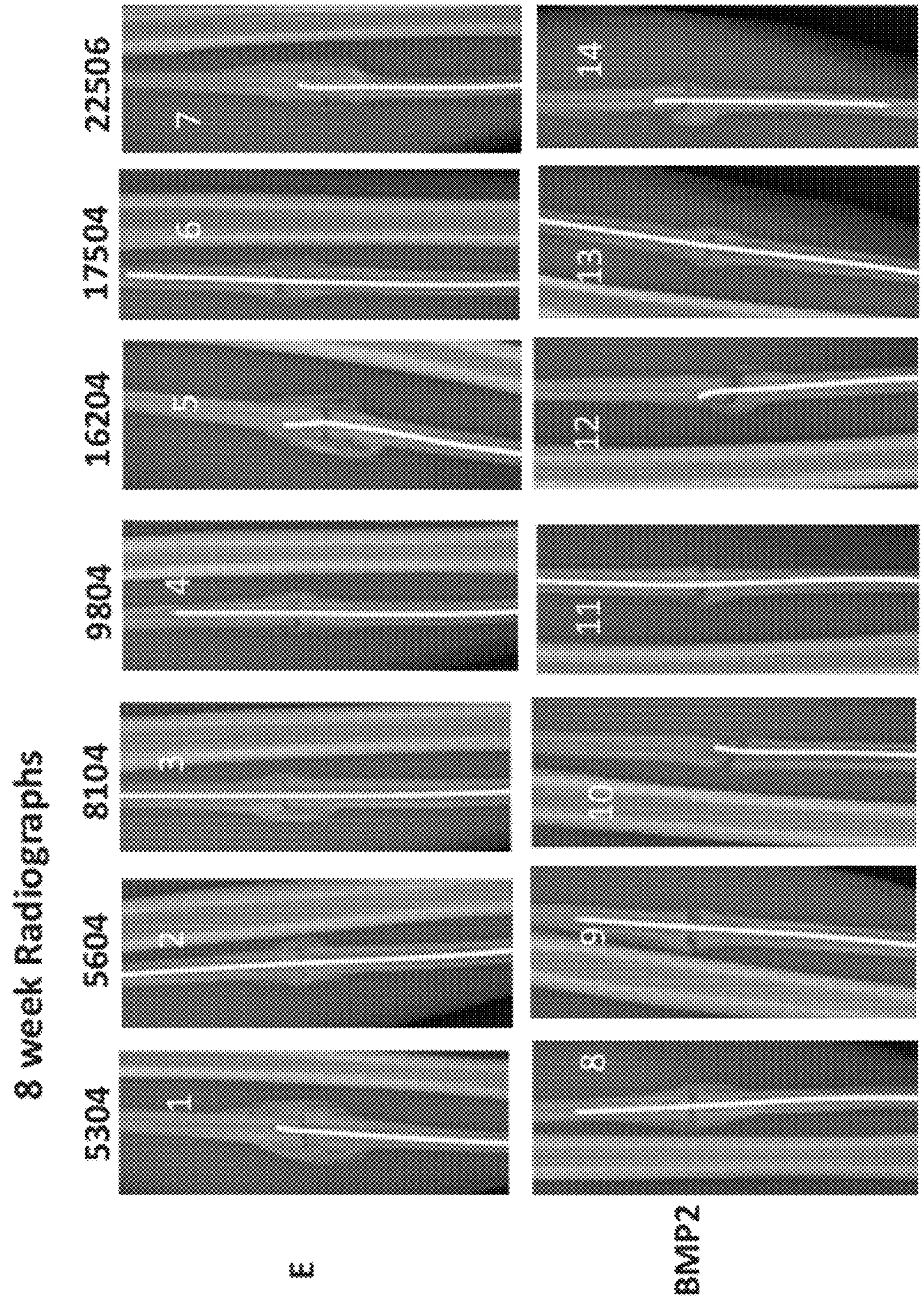
Figure 10C:
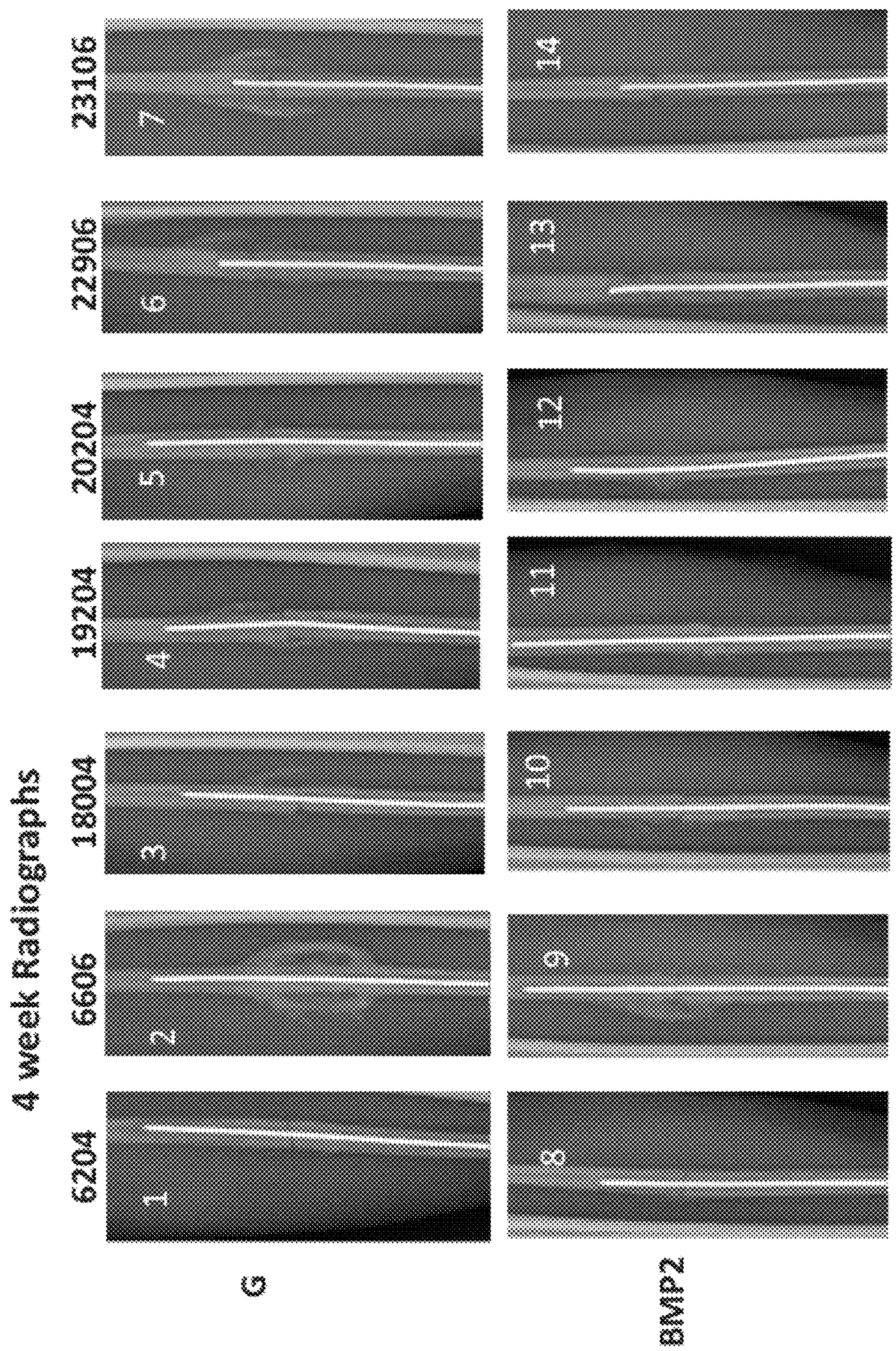
FIGS. 10C and 10D show the radiographs for the NHPs indicated at the top of each diagram showing the effects of BMPG compared with BMP2 wild type at 4 weeks and 8 weeks, respectively.
Figure 10D:
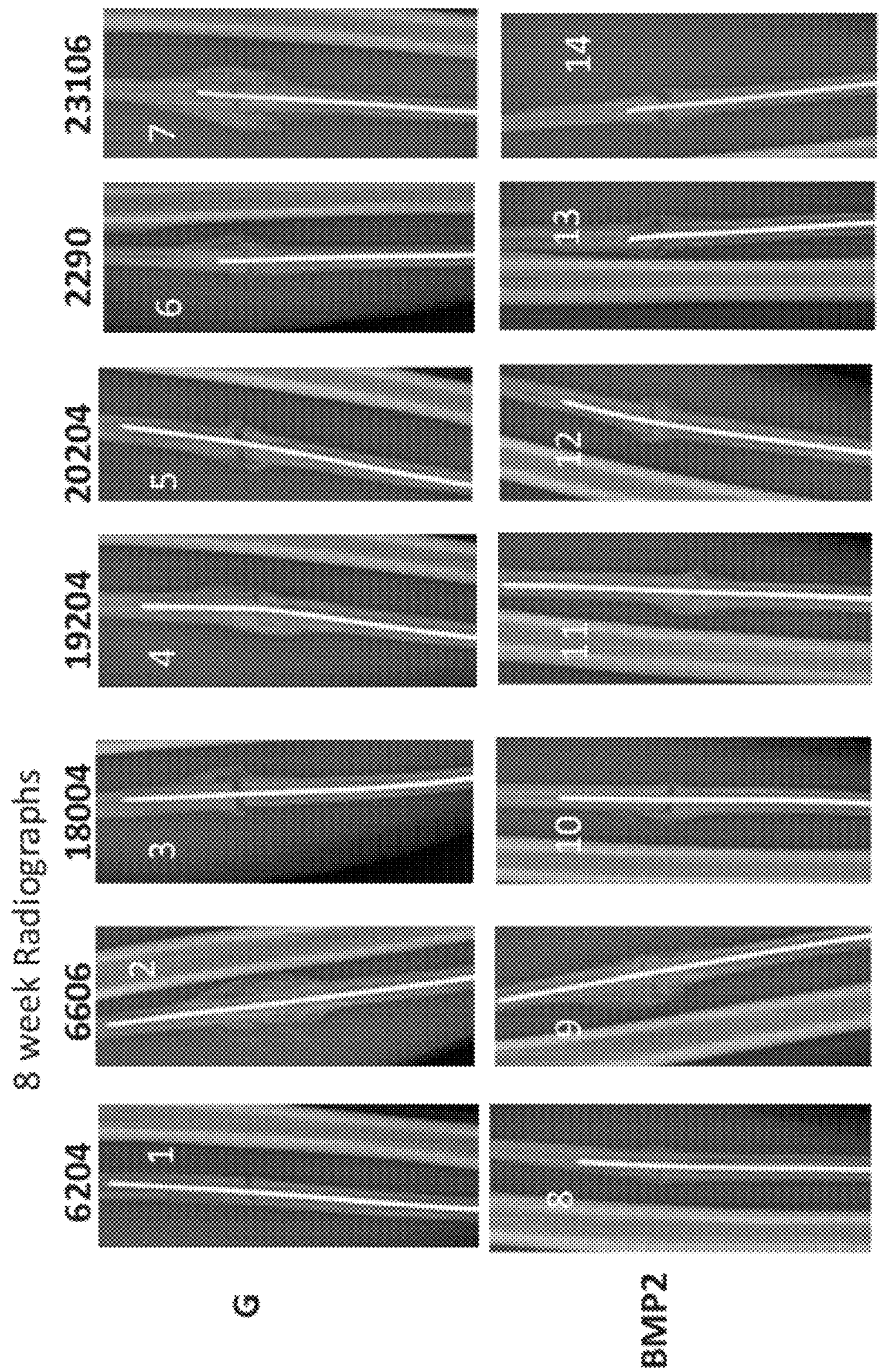

In this model, designer BMPE and BMPG were chosen since each represents a different class of designer molecule; designer BMPG shows high affinity for both type I and type II receptors while BMPE binds the type I receptor ALK-2 with high affinity in addition to binding type I receptors ALK-3 and ALK-6 with high affinity. Radiographs were obtained every 2 weeks to compare the healing of the limbs treated with the designer BMP molecule compared with the healing of the contralateral limb treated with wild type BMP2 in each animal. As shown in FIGS. 10A-10C, the data, which include seven animals from each group, demonstrated that the callus formed earlier and more robustly in the limbs treated with each designer BMP (BMPE shown in FIG. 10A and BMPG shown in FIG. 10B-10C) molecule compared to that with bone formation observed in the limb treated with wild type BMP2.

Figure 11:
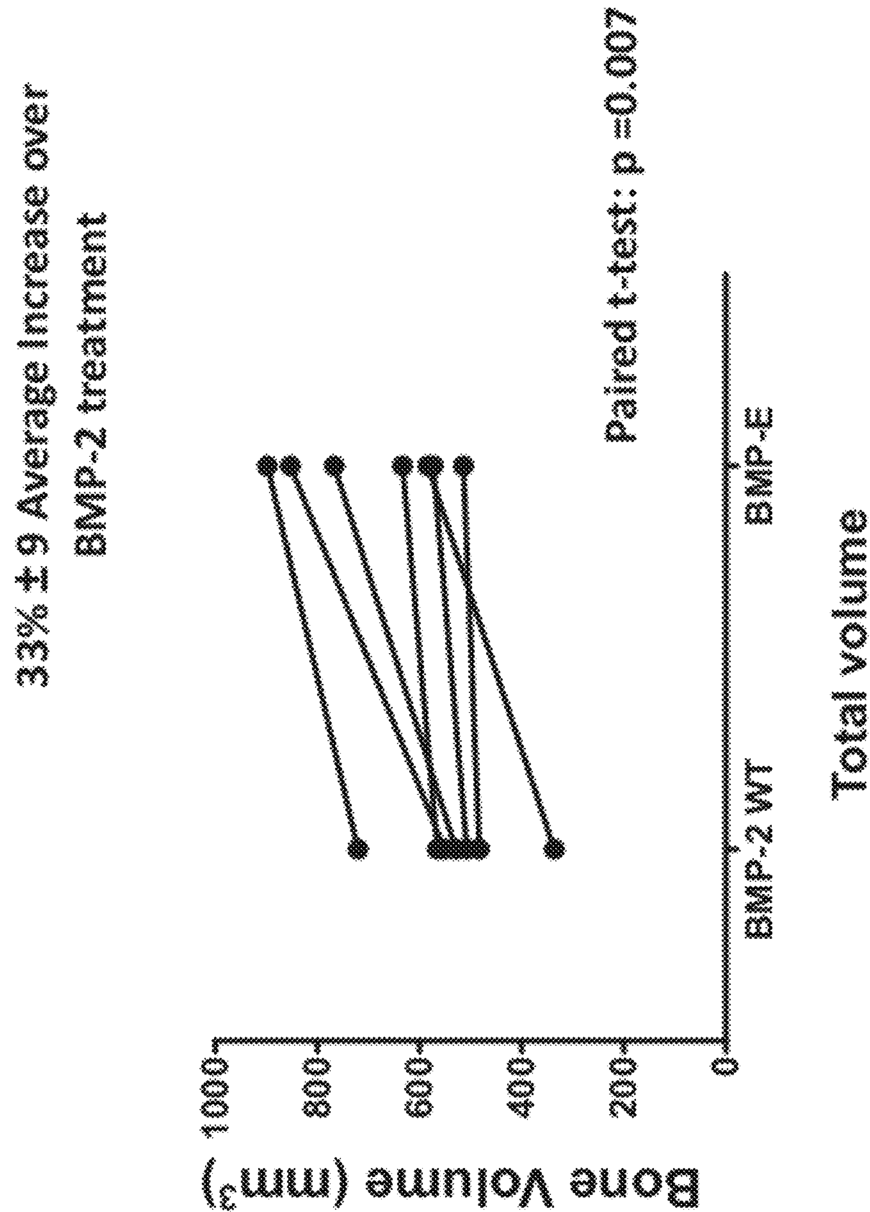
FIG. 11 is a graph showing the bone volume of the limbs treated with BMP-E versus contralateral limbs treated with BMP-2.
Figure 12:
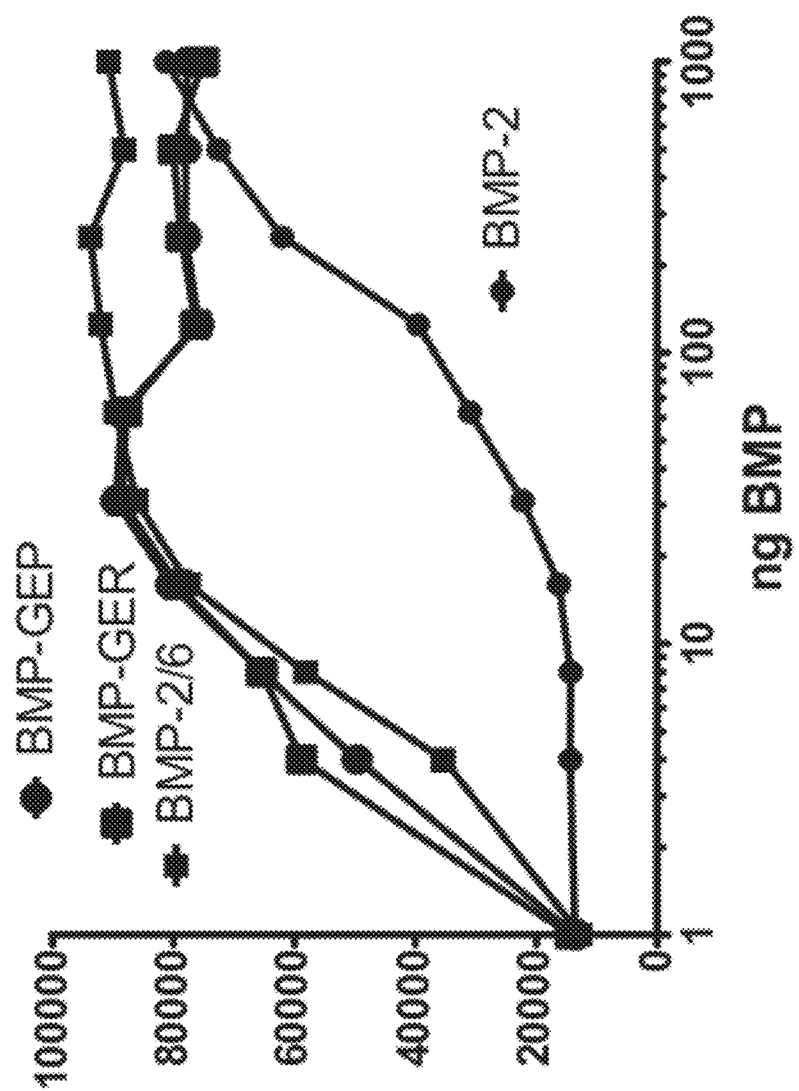
FIG. 12 is a graph showing results of an alkaline phosphatase assay in C2C12 pre-myoblasts comparing the osteogenic activity of wild type BMP2 and BMP-GER, BMP-GEP, and BMP2/6 heterodimer.

Tables 14 and 15, below, set forth data providing quantitative assessments of the difference in bone mass and bone volume observed between limbs treated with wild type BMP2 and limbs treated with designer BMPE. As shown in FIG. 11, BMPE administration resulted in an average of a 33% increase in bone volume (mm$^3$) when compared with bone volume increase in wild type BMP2 treated limbs. This μCT analysis included all the native bone where there was callus, accordingly, BMP-E was much more robust than BMP-2 in the same animals.

TABLE 14

| Bone Mass (mg HA) | | | |
|---|---|---|---|
| NHP | Left - BMPE | Right - WT BMP2 | % increase vs. R |
| 5304 | 721.2298 | 609.3317 | 18% |
| 5604 | 561.4103 | 489.706 | 15% |
| 8104 | 511.4216 | 313.4301 | 63% |
| 9804 | 524.7777 | 474.0646 | 11% |
| 16204 | 714.6123 | 536.7611 | 33% |
| 17504 | 431.5738 | 406.1264 | 6% |
| 22506 | 625.7583 | 466.0707 | 34% |
| | | average | 26% |
| | | std dev | 20% |
| | | std error | 7.40% |
| | | paired t-test | p = .0040 |

TABLE 15

| Bone volume (mm3) | | | |
|---|---|---|---|
| NHP | Left - BMPE | Right - WT BMP2 | % increase vs. R |
| 5304 | 897.4342 | 720.0308 | 25% |
| 5604 | 632.8525 | 564.9525 | 12% |
| 8104 | 583.9513 | 338.0737 | 74% |
| 9804 | 573.0165 | 507.0014 | 13% |
| 16204 | 852.58689 | 551.2446 | 55% |
| 17504 | 514.226 | 482.9475 | 6% |
| 22506 | 766.8873 | 528.5033 | 45% |
| | | average | 33% |
| | | std dev | 25% |
| | | std error | 9.60% |
| | | paired t-test | p = .0070 |

Replacement of P36 Relative to Wild Type BMP2 with Arginine Did not Affect Activity of BMPGE Proline at position 36 relative to the amino acid sequence of wild type BMP2 as set forth in SEQ ID NO:1 is purportedly important in conferring Noggin resistance and providing increased osteogenic activity to wild type BMP2 (see, e.g., WO 2009/086131). Therefore, to assess the effect of replacing P36 with a non-conserved amino acid substitution on the novel activity of BMPGE, P36 of BMPGEP was mutated to argininine to produce BMPGER and osteogenic activity of the two designer molecules was assessed in vitro. The data disclosed herein in FIG. 12 demonstrate that replacing P36 with arginine (P36R) did not affect the binding affinity of the novel BMP-GE designer BMPs and both BMPGEP and BMPGER were as active as BMP2/6 heterodimer.

BMP-GER has In Vivo Activity Comparable to BMP2/6 Heterodimer

Figure 14:
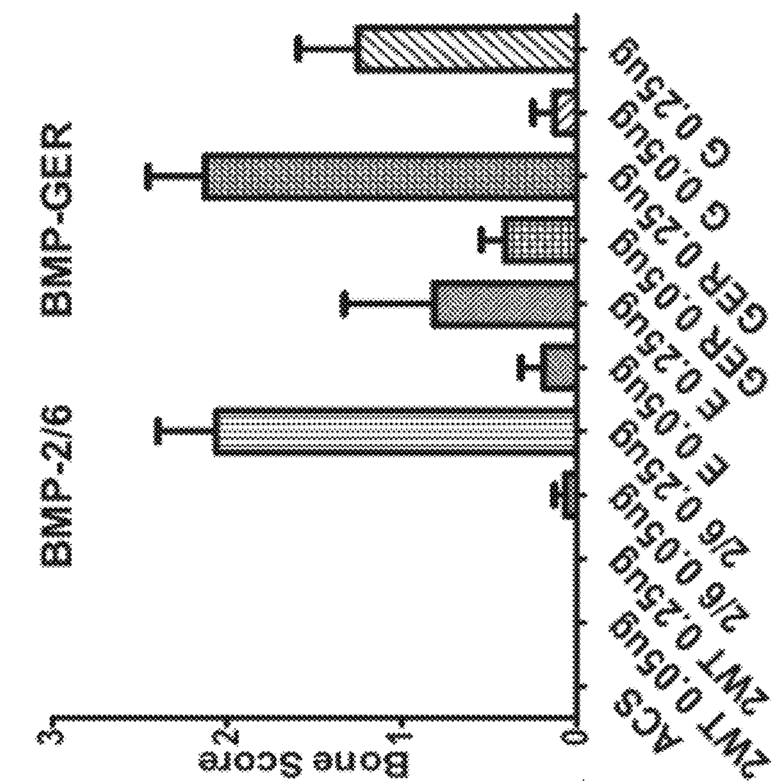
FIG. 14 is a graph showing the amount of ectopic bone (calculated as milligrams of hydroxyapatite) as determined by μCT analysis for each limb which was implanted with the indicated BMP (BMP-2, BMP-2/6, BMP-E, BMP-GER, and BMP-6) at the dose indicated (0.05 or 0.25 μg). These are the results from an experiment separate from that shown in FIG. 13.
Figure 13:
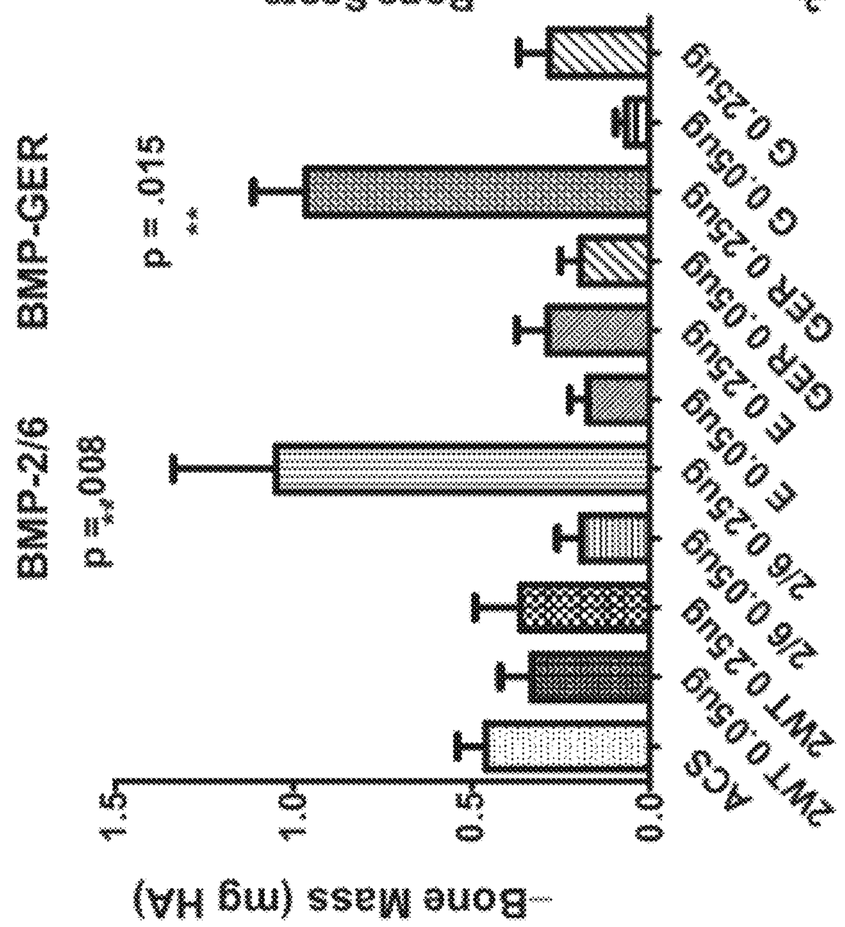
FIG. 13 is a graph showing the amount of ectopic bone (calculated as milligrams of hydroxyapatite) as determined by μCT analysis for each limb which was implanted with the indicated BMP (BMP-2, BMP-2/6, BMP-E, BMP-GER, and BMP-6) at the dose indicated (0.05 or 0.25 μg).

As shown in FIGS. 13 and 14, rat ectopic experiments show that BMP-GER is as potent as BMP-2/6 at driving the formation of ectopic bone at the very low dose of 0.25 ug total BMP when all molecules are delivered on an ACS sponge. FIG. 13 shows that only BMP-2/6 and BMP-GER, but not BMPE or BMPG, were significantly more active than BMP-2 at this low dose when the milligrams of HA formed in the ectopic were quantified by μCT analysis.

The same samples were demineralized and scored for bone formation (Bone Score) by histology and these results are shown in FIG. 14. By this method of scoring, at the low dose of 0.25 ug delivered BMP-2 has no bone formation, and BMP-GER and 2/6 had the highest score. BMP-G and BMP-E were also significantly more potent than BMP-2 but not as active as BMP-GER.

Figure 15:
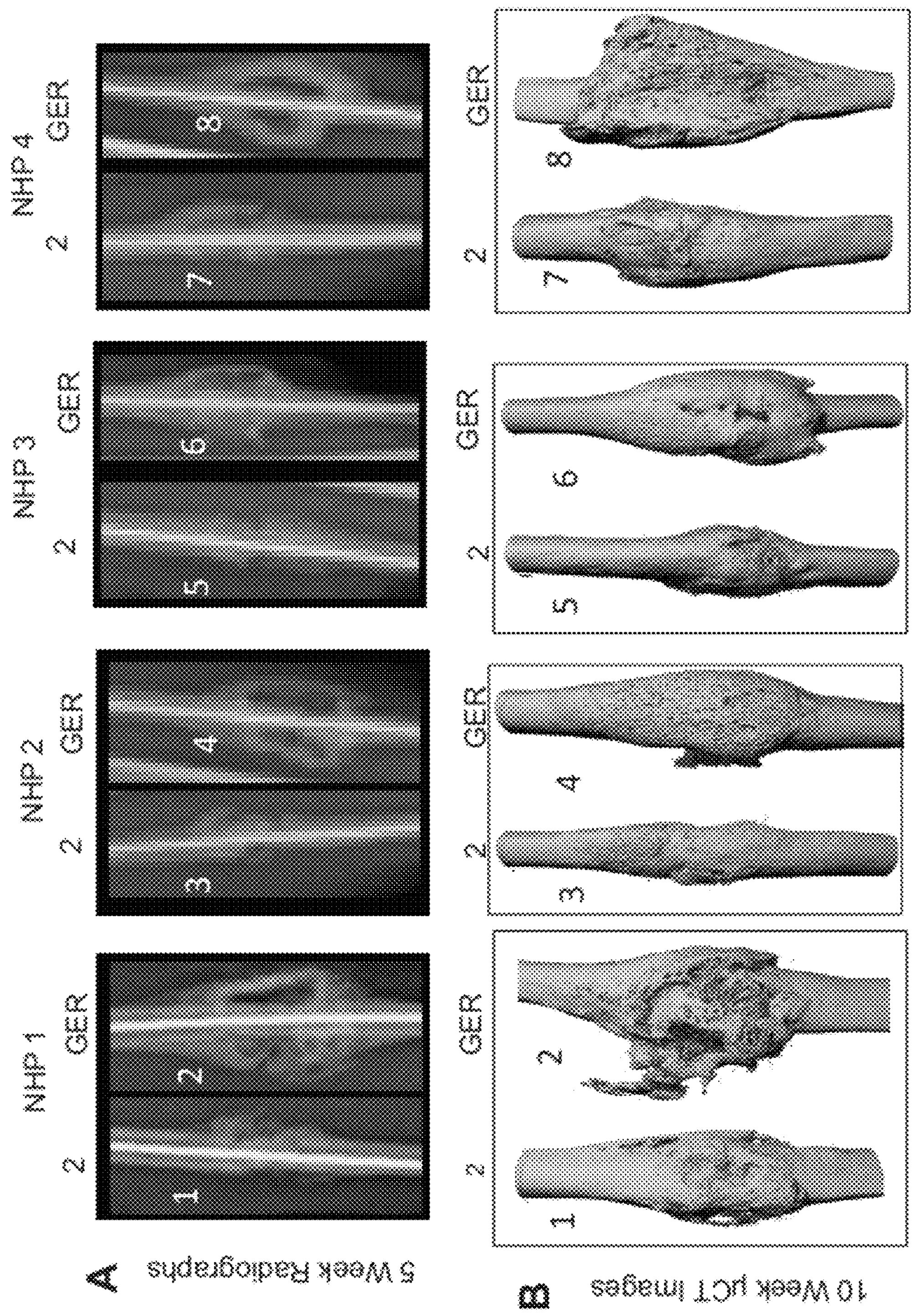
FIG. 15, comprising panels A and B, shows images of radiographs and μCT images showing the results of a non-human primate (NHP) fibula wedge osteotomy model at 5 and 10 weeks.
Figure 16:
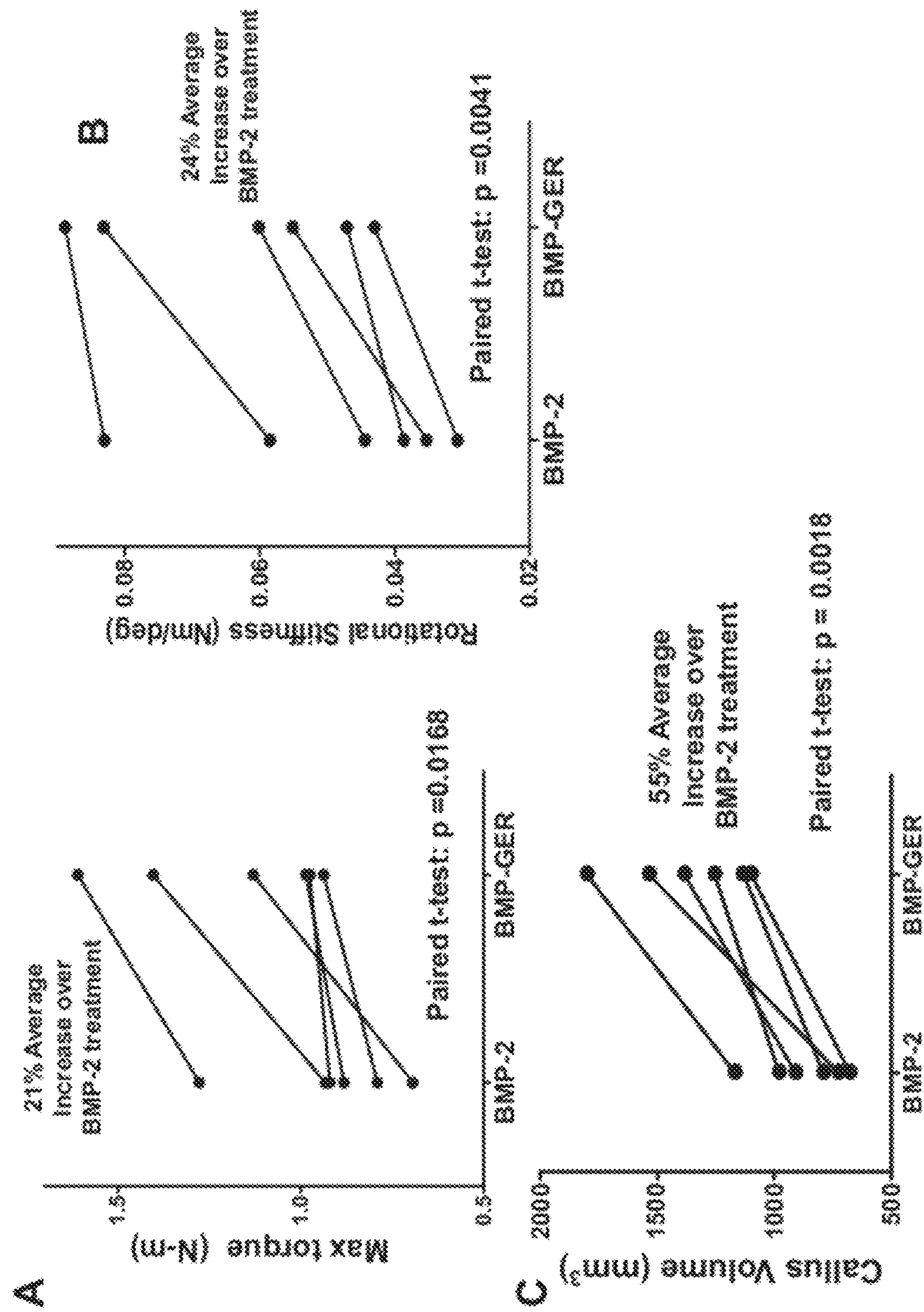
FIG. 16, comprising panels A-C, shows graphs illustrating the strength (FIG. 16A), stiffness (FIG. 16B), and callus bone volume (FIG. 16C) of the BMP-GER treated limbs versus the BMP-2 treated contralateral limbs.

Comparison of BMP-GER with BMP-2 in In Vivo Models of Osteogenesis and Tissue Repair FIGS. 15 and 16 show the results of a severe NHP fibula osteotomy model comparing the activity of BMP-2 and BMP-GER. In this model a wedge with and approximate width of 4-6 mm was removed for each fibula of the NHP and put back in place and held with a titanium pin. The defect was then wrapped with an ACS sponge containing 250 ug total BMP at a dose of 0.5 mg/ml. In each NHP BMP-2 was placed in one limb and BMP-GER was placed in the contralateral limb. FIG. 15A shows photographs of radiographs taken at 5 weeks showing the defect in 4 of the 6 animals. The BMP-GER limbs showed significantly more robust bone formation than those with BMP-2. FIG. 15B (bottom panel of the figure) shows μCT images of the fibulas of the same 4 animals following their sacrifice at week 10. As can be seen, the amount of bone formed is much more robust in the BMP-GER limbs than in the contralateral limbs treated with BMP2.

FIG. 16A-C shows the analysis of these limbs comparing the strength, stiffness, and callus bone volume comparing the BMP-2 and BMP-GER treated limbs from each animal. On average the BMP-GER treated limbs required 21% more torque to break (FIG. 16A), were 24% more stiff (FIG. 16B), and the calluses were on average 55% larger (FIG. 16C) than the contra lateral BMP-2 treated limb. All of these comparisons had a p value of less than 0.01 by pairwise analysis. These data show that BMP-GER induced fracture repair and bone formation significantly earlier and more robustly than BMP-2 in the same animal.

BMP-GER Induced Bone Formation in an NHP Model Equivalently to BMP-2 at a 3 Fold Lower Dose.

Figure 17A:
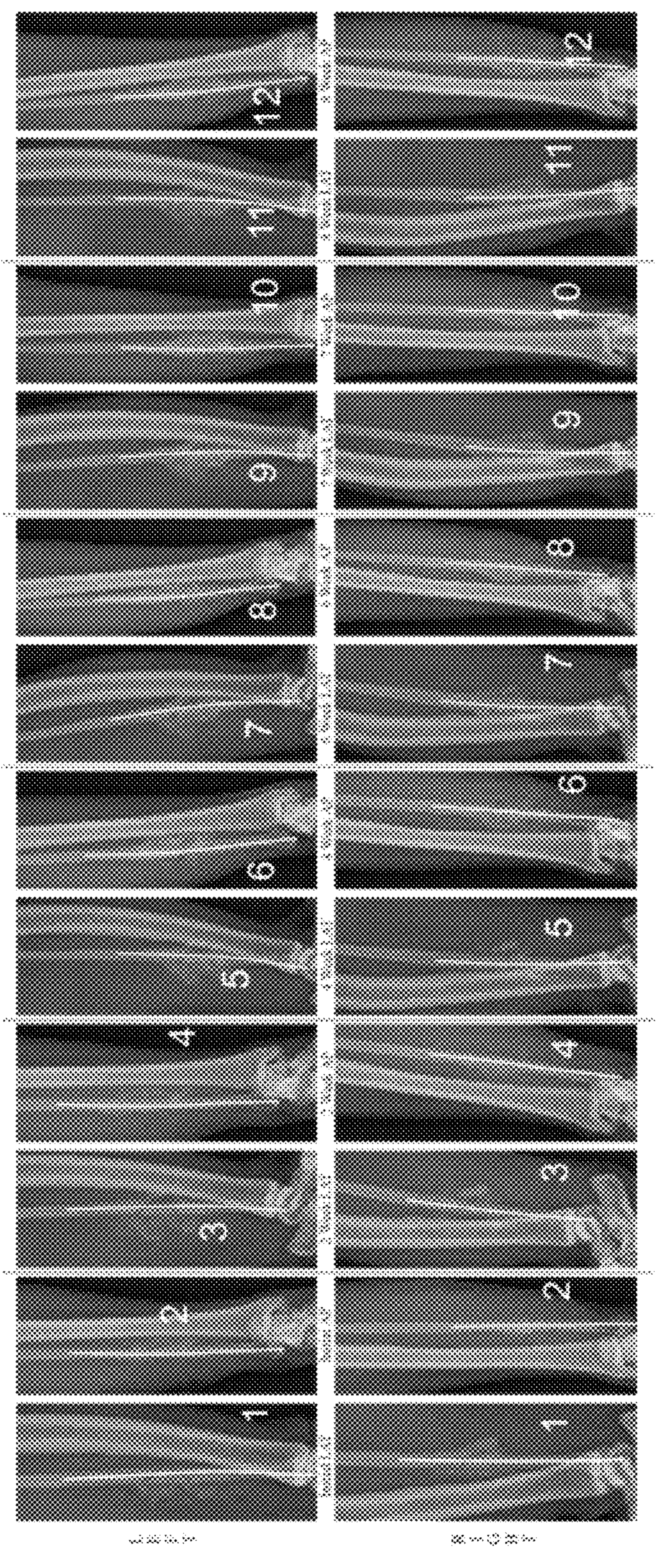
FIG. 17A, upper panel, shows results for NHP number 1 left arm treated with 05 mg/ml GER as follows; panels 1 and 2 show LAT (lateral) and AP (anterior-posterior) images, respectively, at the initial time point; panels 3 and 4 show LAT and AP images, respectively, at 2 weeks; panels 5 and 6 show LAT and AP images, respectively, at 4 weeks; panels 7 and 8 show LAT and AP images, respectively, at 6 weeks; panels 9 and 10 show LAT and AP images; respectively, at 7 weeks; panels 11 and 12 show LAT and AP images; respectively, at 8 weeks.
Figure 17B:
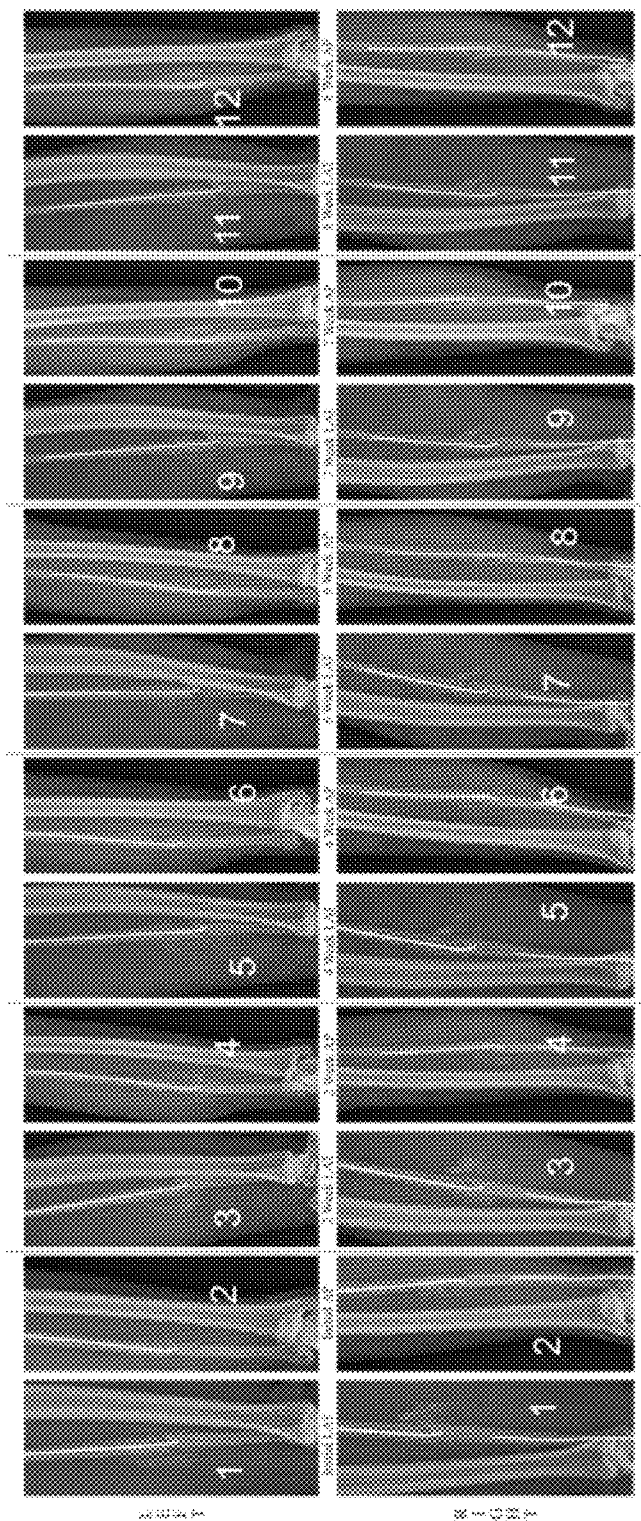
FIG. 17B shows the radiographic the results for NHP number 2 as described for NHP #1 in FIG. 17A.
Figure 17C:
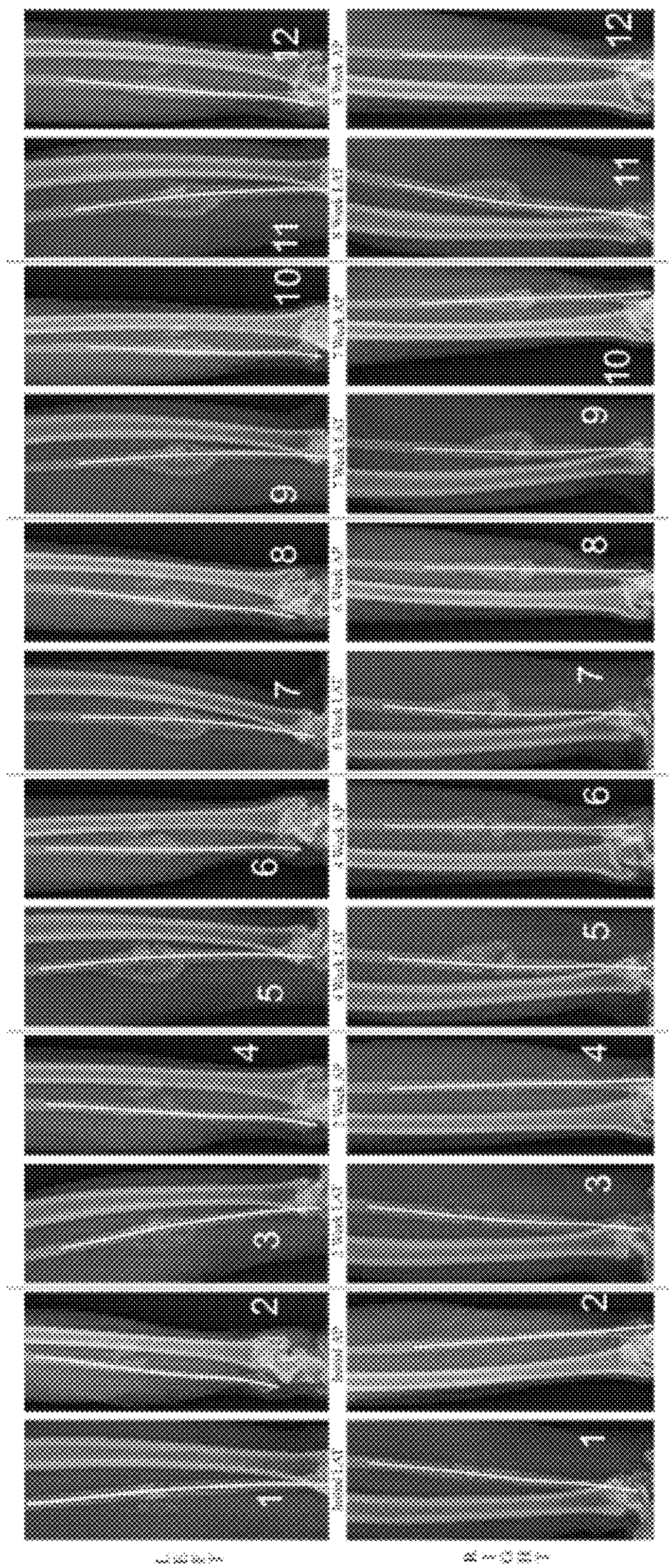
FIG. 17C sets out the results for NHP number 3 as described for NHP #1 in FIG. 17A.

To further assess the effectiveness of BMPE bone formation in NHP, the ability of BMPE to induce osteogenesis in a wedge defect assay was compared to that of BMP2. FIG. 17A-C shows radiographs of the bone formation following the wedge defect model in three non-human primates where 1.5 mg/ml of BMP-2 was used in one limb and only 0.5 mg/ml of BMP-GER was used in the other limb using a calcium phosphate cement based carrier. Radiographically, the healing and bone formation were equivalent for each of the animals whether the treatment was with the high dose of BMP-2 or the lower dose of BMP-GER. Thus, even at one-third the dose, BMPE was equivalent to BMP2 in inducing bone formation, demonstrating the greatly increased activity of this designer BMP compared with wild type BMP2.

Example 5

BMP Structural Analysis

Crystallization BMP-2 and BMP-6

Purified, fully-glycosylated wild type BMP2/6 heterodimer, wild type BMP2/2 homodimer, and wild type BMP6/6 homodimer, each produced in mammalian cells, were concentrated to 6-10 mg/ml in 10 mM sodium acetate (pH 3.5), and crystallization attempts were performed using a "mosquito" automated robotic setup at 18° C. (TTP LabTech Inc., Cambridge, Mass.). Initial crystallization hits were obtained for each dimer and the conditions were subsequently optimized to acquire crystals of good diffraction quality.

Crystals of wild type BMP2/6, BMP2/2 and BMP6/6 were transiently cryoprotected and frozen in liquid nitrogen prior to X-ray diffraction data collection at the synchrotron sources (ID beamline of Advanced Photon Source SER-CAT). Data were processed and scaled using programs Mosflm/Scala to deduce correct crystal lattice type and to integrate/scale data. The resolution and unit cell parameters are listed as follows: BMP2/6 belongs to the space group of $P4_32_12$ with two copies of the heterodimer per asymmetric unit; it diffracted to 2.8 Å in one direction and 3.0 Å in the other two, with a unit cell of a=b=105.23 Å, c=188.73 Å, α=β=γ=90°. BMP2/2 belongs to the space group of $P3_1$ with two copies of the homodimer per asymmetric unit; it diffracted to 2.7 Å with a unit cell of a=b=62.74 Å, c=126.35 Å, α=β=90°, γ=120°. BMP6/6 belongs to the space group of $P3_121$ with one copy of the homodimer per asymmetric unit; diffracted to 2.6 Å with a unit cell of a=b=97.40 Å, c=85.64 Å, α=β=90°, γ=120°. Due to anisotropic diffracting nature of BMP2/6 crystals, the data was ellipsoidally truncated and anisotropically scaled to preserve contribution of high-resolution data.

The structures of CHO BMP2/6, BMP2/2, and BMP6/6 were determined by molecular replacement method with program Phaser, using *E coli* BMP2 (PDB accession: 1REW) and *E. coli*/BMP6 (PDB accession: 2R52) as search models. After correct molecular replacement solutions were obtained and space groups confirmed. Phaser-calculated electron density maps were used to evaluate the quality of the search models, and regions in question (especially areas involving type I and type II receptor binding) were stripped from the original model for rebuilding in order to avoid model bias.

The structural models went through rigid-body refinement, followed by simulated annealing, positional and temperature factor refinement. Stripped areas were rebuilt using omit maps, and the processes were repeated along with TLS refinement until the refinement stabilized. The final refinement statistics are as follows: For BMP2/6, Rw/Rf=0.2231/0.2775, rmsd bonds=0.008, rmsd angles=1.545; For BMP2/2, Rw/Rf=0.2114/0.2659, rmsd bonds=0.005, rmsd angles=0.982; For BMP6/6, Rw/Rf=0.2170/0.2510, rmsd bonds=0.006, rmsd angles=1.182. All three structures are in very good geometry based on Procheck results.

The CHO BMP2/6 crystal structure revealed extensive glycosylation. In particular, the prehelical loop of CHO-produced BMP2, which is an important binding motif for type I receptors, is different from the corresponding region of *E. coli*-produced and refolded BMP2. In the presence of glycosylation, the CHO BMP2 loop has a uniquely "loopy" conformation when compared to the same region in bacterially refolded BMP2, which is more helical (Keller et al., *Nat Struct Mol Biol* 11:481-488 (2004)). The data demonstrated that the D53 of CHO-produced BMP2 points towards the receptor interface, while the H54 points away from the receptor as shown in FIG. 3A. In *E. coli* BMP2, the D53 points away from the receptor and the H54 lines up toward the receptor (referred to herein as a "histidine doorstop"), stacking against a proline residue (P45) on the BMP2 type I receptor Alk3 as shown in FIG. 3B (H54 is alternatively labeled H336). Without wishing to be bound by any particular theory, this stacking could prevent the type I receptor from fully binding to *E. coli* refolded BMP2, explaining the reduced binding activity of *E. coli* BMP2 when compared with CHO BMP2. This structural feature is illustrated in FIG. 3A-B. In this figure, histidine 54 (H54) is numbered as H336, asparagine 56 (N56) is labeled N338, and P45 of ALK3 is shown in darker gray.

Figure 4:
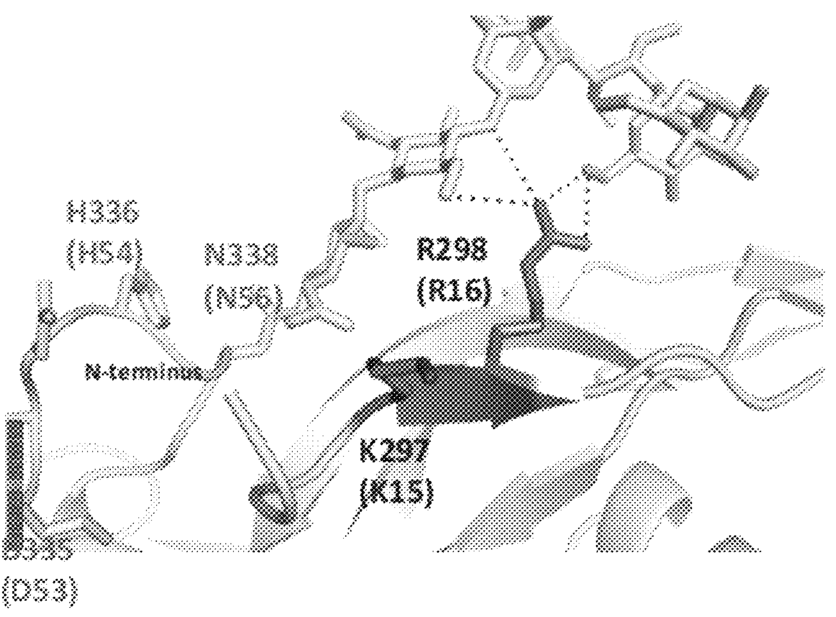
FIG. 4, comprising panels A and B, is a diagram illustrating the location of the glycan tether and potential histidine (His) doorstop.

As illustrated in FIG. 4, fully glycosylated CHO BMP6 also has this "doorstop" histidine residue pointing into the receptor binding site. This doorstop His structural motif is a common structural feature among BMPs (excluding CHO BMP2) (see, e.g., Keller et al., *Nat. Struct Mol Biol* 11:481-8 (2004); Kotzsch et al., *EMBO J* 28:937-47 (2009). Without wishing to be bound by any particular theory, it may be that a specific glycan of CHO BMP2 is linked though extensive hydrogen bonding with arginine 16 ("the glycan tether" also designated as R298). This glycan tether is illustrated in FIG. 4A and its interaction with the glycan is depicted using dotted lines between the glycan and this tether R298 which is also referred to herein as R16. Thus, without wishing to be bound by any particular theory, the glycan tether may serve to stabilize the conformation of the pre-helical loop of the BMP2 molecule such that the histidine doorstop, if otherwise present, is instead oriented away from the type I receptor interface thereby allowing the ligand to contact the receptor to a greater extent than in the presence of the histidine doorstop. In other words, the re-orientation of the histidine doorstop as observed in CHO BMP2 is most likely to be the consequence of glycan tethering. Without wishing to be bound by any particular theory, the data disclosed herein suggest that where the histidine doorstop is present, removal of the doorstop in the absence of glycosylation (i.e., by introducing a mutation that changes the orientation of the His away from the receptor interface) increases binding of the BMP ligand with the type I receptor.

Designer BMPE, which contains a low affinity type II binding domain of BMP2 and a low affinity type I binding domain similar to that of BMP6, shows (1) increased osteogenic activity in both in vitro and in vivo assays; and (2) has an unexpected gain of function to bind Alk2, a type I receptor, despite the presence of a low affinity type I receptor binding domain. Without wishing to be bound by any particular theory, it may be that this surprising discovery is mediated by multiple hydrogen bonds formed between the glycan moieties and the R16 (the "glycan tether") in the type I receptor-binding domain of BMPE. This tethering interaction may mediate a structural rearrangement at the pre-helical region of the BMPE molecule that presents a proper binding surface for Alk2 by positing H54 (the "doorstop") away from the interface thereby allowing closer interaction between the BMP and the receptor. In contrast, as illustrated in FIG. 4B, BMP6, which also has a low affinity type I binding domain similar to that of BMPE, does not bind Alk2 because its "glycan tether" (R413) which would be needed to tether its glycan moieties, is shifted in location when compared to the BMPE tether (R298/R16). Thus, in BMP6, the glycan is not tethered and the doorstop (H454) is not positioned away from the ligand-receptor interface. The "glycan tether" appears to be a phenomenon unique to wild type glycosylated BMP2 (as exemplified by BMP2 produced in CHO cells), and structural remodeling of the prehelical loop of BMPs by introducing (or removing) "glycan tether" can now be used, for the first time, to modulate type I receptor-binding ability of other BMPs. Therefore, one skilled in the art, now armed with the teachings provided herein, would understand how to mutate the BMP in order to position the doorstop away from the receptor interface by introducing mutations that swing the H54 away or by affecting the glycan tether so that tethering mediates the shift in H54 and would further appreciate that these teachings can be used to design a BMP with increased (or decreased if mutations are introduced to swing H54 into the doorstop position) binding to its receptor or to create designer BMPs with gain-of-function mutations such that they bind to novel receptors that they did previously bind. As more fully set forth below, the present invention demonstrates how to use this novel doorstop/tether design method to design improved osteogenic proteins. Thus, the present invention provides a novel method for rational design of improved osteogenic proteins comprising altered receptor binding.

Figure 18:
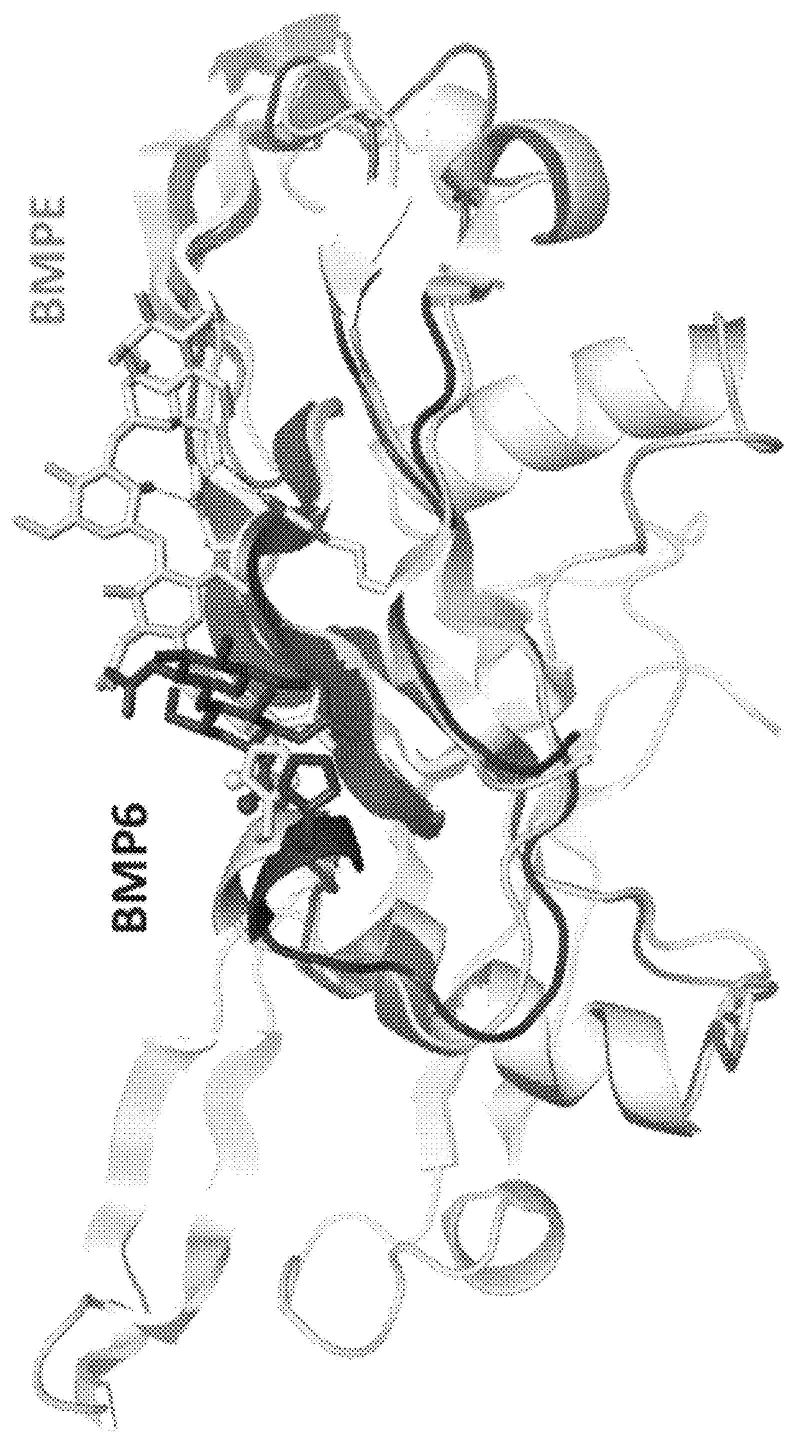
FIG. 18 is a diagram of a structural model showing representations and comparison of the crystal structures BMP-E and BMP-6 WT. The differences in the length of the glycan resolved is highlighted showing that the glycan for BMPE that is resolved is much longer than that for BMP6. This indicates that the BMPE glycan is more conformationally constrained than that of BMP6 such that more of the glycan can be rendered in this model. The histidine doorstop residues for both BMPE and BMP6 are shown in similar non-doorstop configurations. Also, the arginine glycan "tether" stabilizing the BMPE glycan is shown by dotted lines representing the interactions of the arginine with the glycan.
Figure 19:
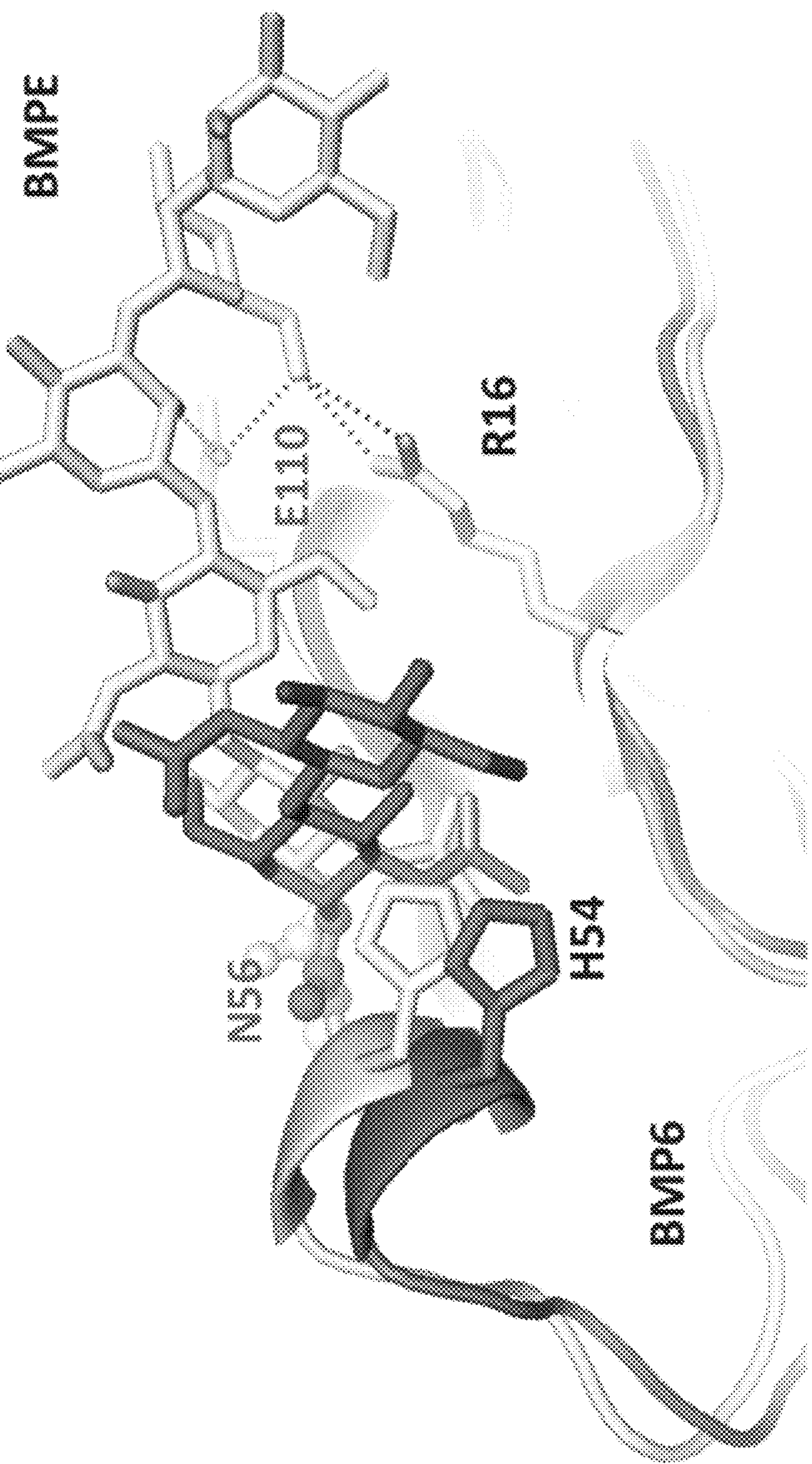
FIG. 19 is a closer view of the histidine doorstop and arginine tether of the BMPE and BMP6 comparison shown in FIG. 18. This image shows the similar conformation of the H54 histidine residue of BMPE and the equivalent histidine BMP6 both in the non-doorstop position. The image also shows the R16 tethering (via interactions of the BMPE glycan such that the glycan is more rigid and therefore more is rendered by the model compared to the more "floppy" and less constrained glycan of BMP6 such that less of the BMP6 glycan is visualized in this model. The diagram of this model also shows the similar positioning of asparagine N56 of BMPE showing N-linked attachment of the glycan and the equivalent and similarly positioned asparagine of BMP6. The diagram also illustrates the potential additional glycan tethering interaction of BMPE E110 shown by dotted lines between the amino acid residue and the distal end of the glycan. The differences in the length of the glycan resolved is highlighted showing that less of the darker BMP6 glycan can be resolved compared with the lighter shaded longer glycan rendered for BMPE indicating that the BMPE glycan is more conformationally constrained and thus more is rendered upon structural analysis.

In order to more fully understand what drives the BMP-E and BMP-GER binding to ALK-2, and to further elucidate this novel mechanism of affecting receptor binding using the doorstop/glycan tether, the crystal structure of BMP-E was solved and compared to that of BMP-2 and BMP-6. The key structural findings are shown in FIGS. 18 and 19. As illustrated in FIG. 18 BMP-E maintains the ordered sugar of BMP-2 while maintaining the central helical structure of BMP-6. The structure shown in FIG. 18 demonstrates that BMP-E, and presumably BMP-GER, is different from both BMP-2 and BMP-6 in the critical region of type I receptor binding. FIG. 19 is a blow-up comparing the area surrounding the potential His doorstop of BMPE (light gray) and BMP6 (dark gray). The diagram demonstrates the similarity of the alignment of the histidine and asparagine in both molecules and also shows the difference in glycan positioning and demonstrating the tethering of the BMPE glycan by R16 (the tether) which also causes a more rigid conformation of the glycan such that a longer glycan is rendered for BMPE by the analysis compared with the shorter glycan rendered for BMP6 (in dark gray).

Figure 20:
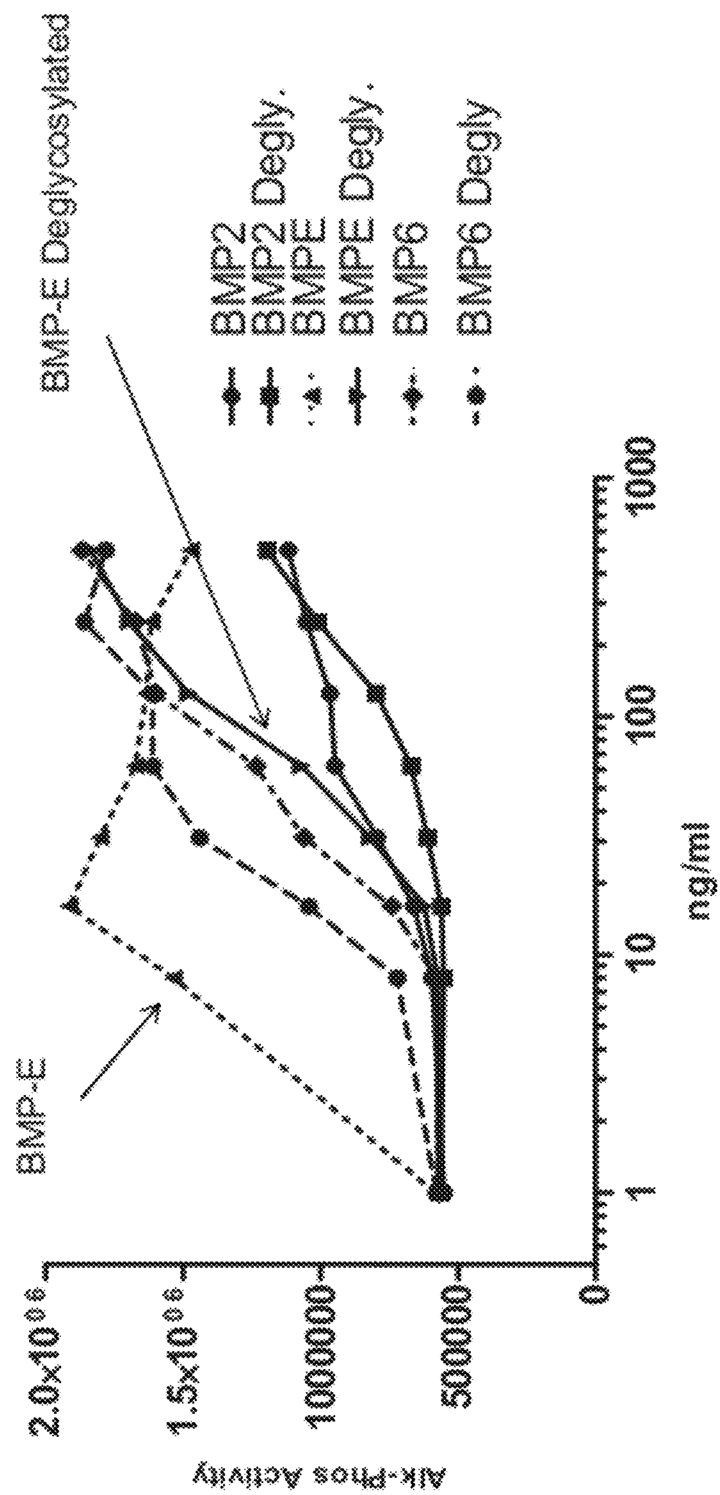
FIG. 20 is a graph showing the results of an alkaline phosphatase assay using C2C12 pre-myoblasts comparing the osteogenic activity of BMP-2, BMPE and BMP-6 with their Endo-H treated deglycosylated (Degly.) counterparts.

In order to determine if the glycan of BMP-E is driving the interaction with ALK-2 and its higher activity, BMP-2. BMP-6, and BMP-E were treated with Endo H to clip the sugar down to two GlcNac units. The binding affinity of BMP-E for AlK-2 decreased to 400 nM whereas it's affinity for ALK-3 and ALK-6 were still in the 3-6 nM range showing the intact carbohydrate is extremely important for this interaction. The activity of this deglycosylated mutant also decreased significantly. As shown in FIG. 20, in this experiment the Endo H treated deglycosylated BMP-E activity shifts to the right and is almost equivalent to BMP-6 WT. The EC-50 shifts from 3 nM to approximately 50 nM. These data show that the carbohydrate of BMP-E is essential for its activity, and this should translate to BMP-GER since it has the exact same region of BMP-6 substituted into BMP-2 with only the finger domains differing. Since the carbohydrate is essential for increased receptor binding and osteogenic activity, these results indicate indicates that production of BMP-E or BMP-GER in *E. coli*, or any other system lacking glycosylation, would not produce a BMP with activity superior to BMP-2 WT.

Crystallization BMP-E and BMP-GER

Purified, fully-glycosylated BMP-E, was concentrated to 8.7 mg/ml in 25 mM sodium acetate (pH 3.5), and crystallization attempts were performed using a "mosquito" automated robotic setup at 18° C. (TTP LabTech Inc., Cambridge, Mass.). Initial crystallization hits were obtained for each dimer and the conditions were subsequently optimized to acquire crystals of good diffraction quality.

Crystals of BMP-E were transiently cryoprotected and frozen in liquid nitrogen prior to X-ray diffraction data collection at the synchrotron sources (ID beamline of Advanced Photon Source SER-CAT). Data were processed and scaled using programs Mosflm/Scala in the CCP4 package to deduce correct crystal lattice type and to integrate/scale data. The resolution and unit cell parameters are listed as follows: BMPE belongs to the space group of $P4_32_12$ with two copies of the BMPE in each asymmetric unit; it diffracted to 2.7 Å, with a unit cell of a=b=67.78 Å, c=148.01 Å, $\alpha=\beta=\gamma=90°$.

The structure of BMPE was determined by molecular replacement method with program Phaser, using fully glycosylated CHO BMP2 and BMP6, both determined at Pfizer, as search models. After correct molecular replacement solutions were obtained and space groups confirmed, Phaser-calculated electron density maps were used to evaluate the quality of the search models, and regions in question (especially areas around type I receptor binding and glycosylation) were stripped from the original model for rebuilding in order to avoid model bias.

The structural model of BMPE went through rigid-body refinement, followed by simulated annealing, positional and temperature factor refinement using program Phenix. Stripped areas were rebuilt using omit maps, and the processes were repeated along with TLS refinement until the refinement stabilized. The final refinement statistics are: Rw/Rf=0.2252/0.2840, rmsd bonds=0.006, rmsd angles=0.935. The structure is in very good geometry based on Procheck results.

Figure 21:
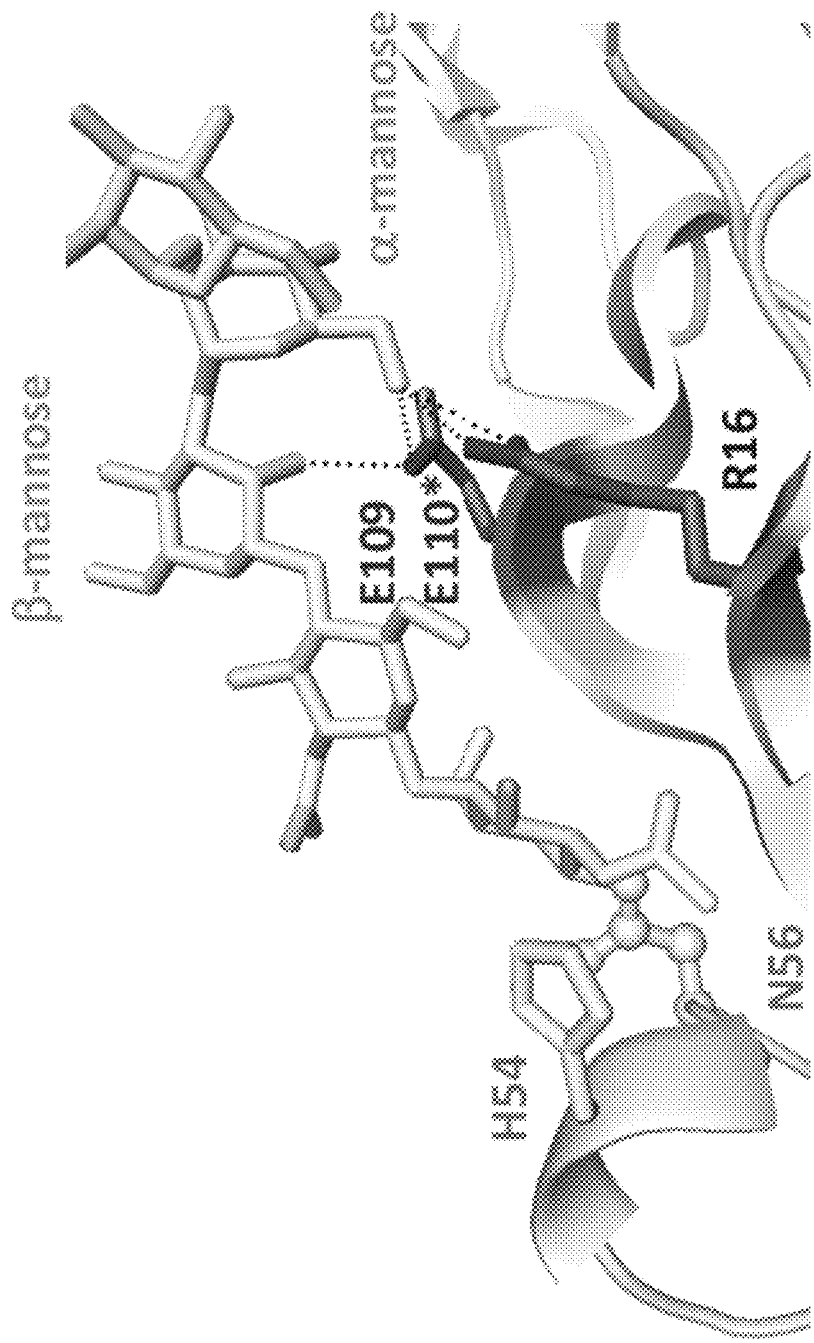
FIG. 21 is a diagram illustrating the structural model of BMPE showing the location of the glycan tether at R16 and illustrating the stabilizing interactions between the arginine (R16) and glutamic acid (E110 corresponding to E109 BMP2) residues. The diagram shows that R16 and E110 both form multiple hydrogen bonds with the third (β-mannose) and fourth (α-mannose) glycan moieties. The diagram also shows the position of H54 potential "doorstop" and asparagine 56 (N56) which provides the N-linked attachment site of the glycan.

BMPE, a designer molecule wherein residues 44-80 of BMP2 replaced by the corresponding region from BMP6, maintains the overall framework of BMP2 while possessing the Type I receptor-binding segment of BMP6. As shown in FIG. 21, the crystal structure revealed that the grafted segment still retains a similar conformation as in BMP6, forming a small helix in the pre-helical loop within which the "doorstop" H54 points toward the receptor. However, without wishing to be bound by any particular theory, it may be that due to the presence of "glycan tethers" at R16 and E110* (E109 of BMP-2), both of which form multiple hydrogen bonds with the third and forth glycan moieties (β-mannose and α-mannose, respectively), the extended glycosylation chain is attached to the protein surface, exactly as seen in CHO BMP2. The tethering of glycan chain also dislocated the pre-helical loop by about 2 Å in reference to the overall framework. Without wishing to be bound by any particular theory, it may be that the surprising discovery that the BMP6-like pre-helical loop combined with the BMP2-like glycosylation present a binding epitope for the Alk2 receptor, which does not normally interact with either BMP2 or BMP6. Deglycosylation renders BMPE incapable of binding to Alk2, which underscores the importance of glycosylation in mediating Alk2 recognition for BMPE.

Example 6

Noggin Resistance

Figure 22:
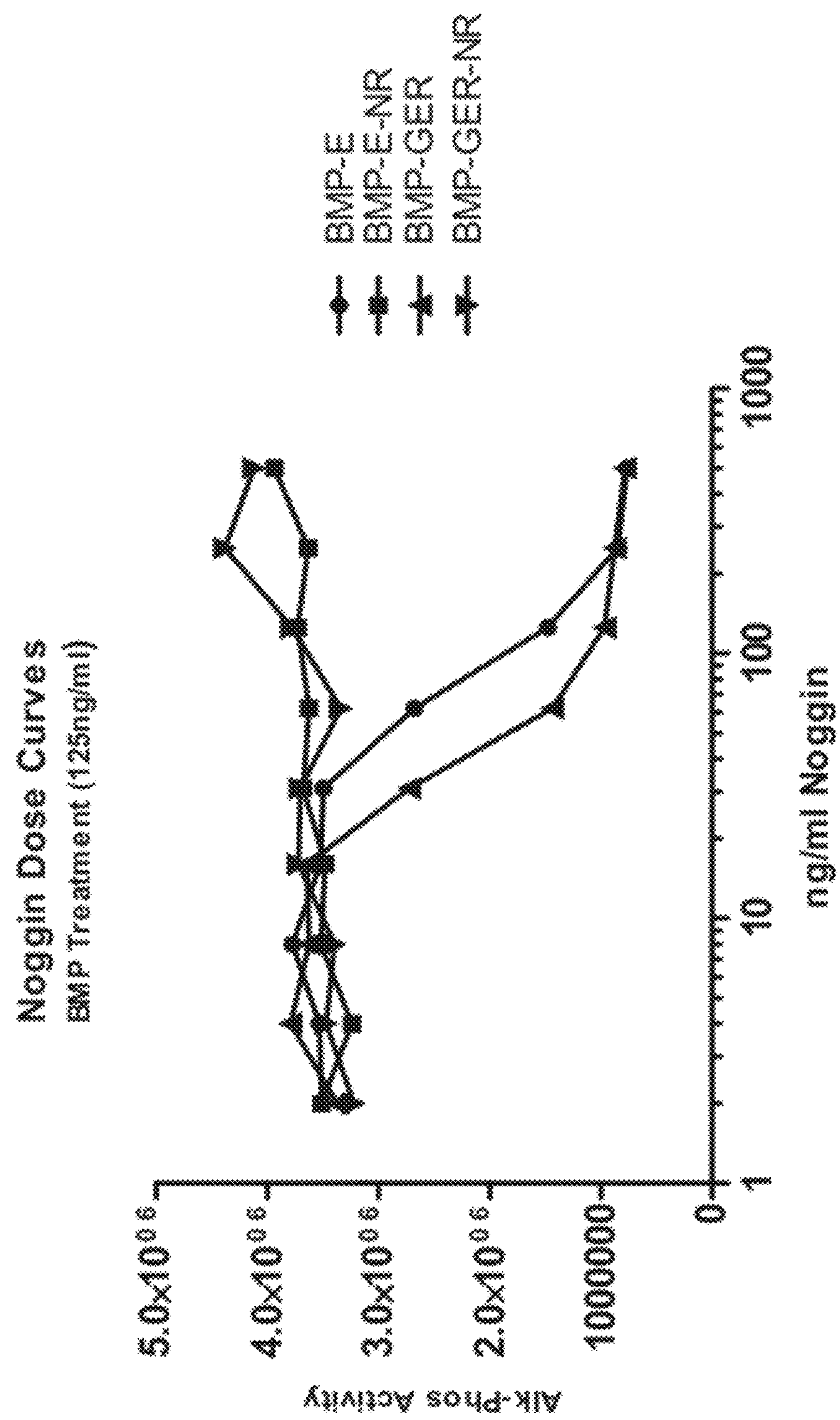
FIG. 22 is a graph showing the results of an alkaline phosphatase assay using C2C12 pre-myoblasts comparing the osteogenic activity of BMP-E, with BMP-E-NR, BMP-GER and BMP-GER-NR in the presence of increasing doses of Noggin—a natural inhibitor of BMP-2. The data demonstrate that BMP-GER-NR comprising sequences derived from activin was not inhibited by Noggin even at high concentrations but that BMP-GER was sensitive to Noggin inhibition. Thus, addition of sequences derived from activin caused BMP-GER to become Noggin resistant (NR). These results demonstrate that at least in this in vitro assay, BMP-GER and BMPE, which are Noggin sensitive, become Noggin resistant (NR) upon replacement of the C-terminal region of the protein with sequences derived from activin.

In order to investigate if resistance to the secreted BMP inhibitor Noggin would increase the activity of BMP-GER or BMP-E, these potential therapeutic molecules were further modified to potentially increase their resistance to Noggin. Recently, it was demonstrated that in *E. coli*-produced proteins, incorporation of a C-terminal portion of activin-A into wild type BMP2 increased resistance to Noggin inhibition. See WO 2010/099219 at, e.g., FIGS. 15 and 16. Therefore, to determine whether the novel designer proteins disclosed herein could be improved even further by incorporation of activin-A sequences, the Noggin resistance (NR) amino acid sequences were substituted into BMP-E (SEQ ID NO:12) and BMP-GER (SEQ ID NO:37) to produce BMP-E-NR (SEQ ID NO:70) and BMP-GER-NR (SEQ ID NO:71). As shown in FIG. 22 BMP-E-NR and BMP-GER-NR have equivalent in vitro activity in an Alkaline phosphate activity assay compared with BMP-E and BMP-GER and are completely resistant to Noggin while BMP-E and BMP-GER are sensitive to Noggin.

To understand the potential basis for the Noggin resistance demonstrated in vitro by BMPE-NR and BMP-GER-NR, the binding affinity of these molecules for the type II activin receptor ActRIIB was assessed. As shown in Table 16, below, activin-A is unable to bind Noggin but the Noggin resistant BMP-E-NR and BMP-GER-NR bind Noggin, but not as strongly as BMP-2, BMP-E, or BMP-GER. These data also show that the Noggin resistant BMPs bind the type II BMP receptor ActRIIB with extremely high affinity that is even higher than that of BMP-GER. Without wishing to be bound by any particular theory, these data suggests that BMP-GER-NR and BMP-E-NR are resistant to Noggin due to their much higher affinity for the BMP type II receptors than that of Noggin and are therefore able to bind BMP receptors even in the presence of high amounts of Noggin.

TABLE 16

| | ActRIIb affinity (nM) |
|---|---|
| BMP-E | 9.00 |
| BMP-E-NR | 0.50 |
| BMP-GER | 2.00 |
| BMP-GER-NR | 0.07 |
| | Noggin Affinity |
| BMP-E | 1.00 |
| BMP-E-NR | 6.00 |
| BMP-GER | 4.00 |
| BMP-GER-NR | 7.50 |
| | ActRIIb on rate (K on) with equal molar ration of noggin* |
| BMP-E | no binding |
| BMP-E-NR | no binding |
| BMP-GER | 1.00E+03 |
| BMP-GER-NR | 1.00E+06 |

*little to no change in on rate with up to 10 fold molar excess of Noggin

Figures 23, 24:
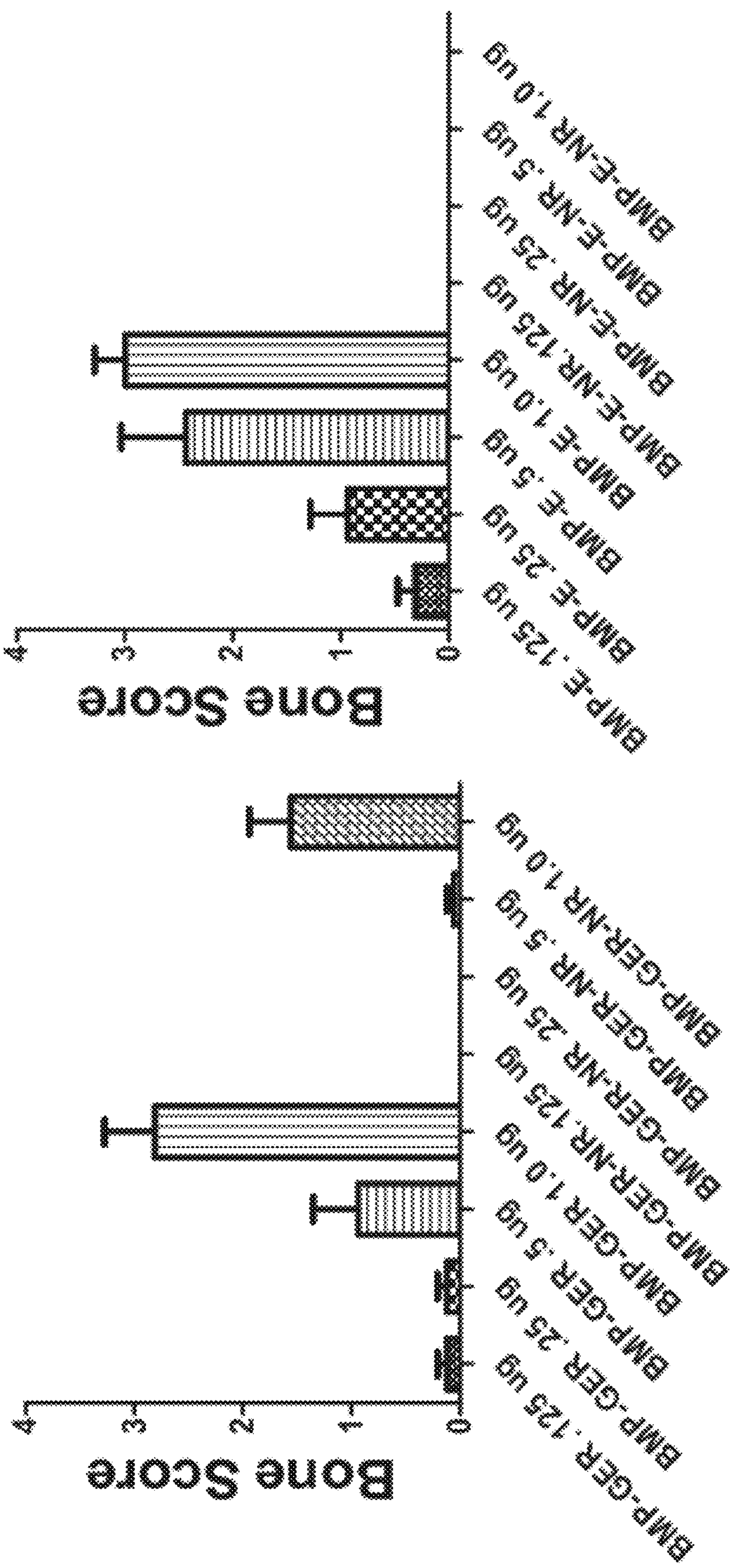
FIG. 23 is a graph showing the bone score as determined by immunohistochemistry (IHC) for rat ectopic implants treated with the indicated BMP at the specified dose. The data show that the bone forming activity of BMP-GER was greatly decreased when the C-terminal sequence of the molecule was replaced with a sequence derived from activin (NR). Thus, the data demonstrate that BMP-GER-NR was much less active than BMP-GER in vivo.
FIG. 24 is a graph showing the bone score as determined by immunohistochemistry (IHC) for rat ectopic implants treated with the indicated BMP at the specified dose. The data show that the bone forming activity of BMP-E was greatly decreased, indeed, it was completely abrogated, when the C-terminal sequence of the molecule was replaced with a sequence derived from activin (NR).

Although the BMP-E and BMP-GER molecules comprising the Noggin resistant portions of activin-A demonstrated Noggin resistance in vitro, these results did not correlate to improved in vivo activity. That is, when the osteogenic activity of these BMP-E-NR and BMP-GER-NR was compared with that of BMP-E and BMP-GER in a rat ectopic assay, the NR molecules were much less potent. This data is shown in FIGS. 23 and 24. More specifically, the Bone Score for BMP-GER and BMP-GER-NR was compared and, at all concentrations tested (0.125 μg, 0.25 μg, 0.5 μg, and 1.0 μg), BMP-GER greatly outperformed BMP-GER-NR as shown in FIG. 23. Similarly, FIG. 24 demonstrates that BMP-E produced a much higher Bone Score compared with BMP-E-NR in this in vivo assay. Thus, for both BMP-E and BMP-GER the purportedly Noggin resistant versions were much less potent in vivo than their NR (Noggin resistant) counterparts, and in the case of BMP-E, almost all in vivo activity was lost due to incorporation of sequences of activin-A (see FIG. 24 comparing BMP-E-NR with BMP-E).

These data demonstrate that incorporation of sequences potentially conferring Noggin resistance, while increasing binding for certain type II receptors (e.g., ActRIIB), did not increase in vivo osteogenic activity of the designer BMP.

Further, although the addition of Noggin did not improve the osteogenic activity of the designer BMPs in vivo, indeed, it appeared to decrease their in vivo activity, the novel designer BMPs of the invention demonstrate greatly increased osteogenic characteristics compared with wild type BMP and provide potential novel therapeutics for a wide variety of applications even without demonstrating Noggin resistance in vitro. Therefore, the designer BMPs of the invention provide remarkable novel potential therapeutics demonstrating a greatly improved clinical profile for, among other uses, bone augmentation and repair.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A designer osteogenic protein comprising the amino acid sequence of any one of SEQ ID NOs: 36, 37, and 50.

2. A method of producing the protein of claim 1, the method comprising introducing a nucleic acid encoding the protein into a host cell, culturing the cell under conditions where the protein is produced, and purifying the protein.

3. An isolated nucleic acid molecule comprising a nucleotide sequence encoding the designer osteogenic protein of claim 1.

4. A method of treating a bone disease associated with bone loss in a patient in need thereof, the method comprising administering an effective amount of a designer osteogenic protein of claim 1 to said patient, thereby treating bone disease in said patient.

5. A method of inducing bone formation in a tissue, said method comprising contacting said tissue with a designer osteogenic protein of claim 1, thereby inducing bone formation in said tissue.

6. A designer osteogenic protein comprising the amino acid sequence of SEQ ID NO: 36.

7. A designer osteogenic protein comprising the amino acid sequence of SEQ ID NO: 50.

8. A designer osteogenic protein comprising the amino acid sequence of SEQ ID NO: 37.

9. A designer osteogenic protein comprising the amino acid sequence of SEQ ID NO: 71.

10. A designer osteogenic protein comprising the amino acid sequence of SEQ ID NO: 73.

* * * * *